United States Patent
Møller et al.

(10) Patent No.: US 10,434,162 B2
(45) Date of Patent: Oct. 8, 2019

(54) **PROTEINS AND NUCLEIC ACIDS USEFUL IN VACCINES TARGETING *KLEBSIELLA PNEUMONIAE***

(71) Applicant: Evaxion Biotech ApS, København K (DK)

(72) Inventors: Niels Iversen Møller, København K (DK); Andreas Holm Mattsson, København K (DK)

(73) Assignee: Evaxion Biotech ApS, København K (DK)

( * ) Notice: Subject to any disclaimer, the term of this patent is extended or adjusted under 35 U.S.C. 154(b) by 0 days.

(21) Appl. No.: 15/542,580

(22) PCT Filed: Jan. 12, 2016

(86) PCT No.: PCT/EP2016/050468
§ 371 (c)(1),
(2) Date: Jul. 10, 2017

(87) PCT Pub. No.: WO2016/113252
PCT Pub. Date: Jul. 21, 2016

(65) Prior Publication Data
US 2019/0015496 A1    Jan. 17, 2019

(30) Foreign Application Priority Data
Jan. 12, 2015   (EP) .................................... 15150819

(51) Int. Cl.
| | | |
|---|---|---|
| *C07K 14/26* | (2006.01) | |
| *C07K 16/12* | (2006.01) | |
| *A61K 38/03* | (2006.01) | |
| *A61K 38/16* | (2006.01) | |
| *A61K 39/108* | (2006.01) | |
| *C12N 15/79* | (2006.01) | |
| *G01N 33/569* | (2006.01) | |
| *C12N 15/70* | (2006.01) | |
| *C12N 15/75* | (2006.01) | |

(52) U.S. Cl.
CPC .......... *A61K 39/0266* (2013.01); *A61K 38/03* (2013.01); *A61K 38/164* (2013.01); *C07K 14/26* (2013.01); *C07K 16/12* (2013.01); *C12N 15/79* (2013.01); *G01N 33/56916* (2013.01); *C07K 2317/24* (2013.01); *C07K 2317/54* (2013.01); *C07K 2317/55* (2013.01); *C07K 2317/622* (2013.01); *C12N 15/70* (2013.01); *C12N 15/75* (2013.01); *G01N 2333/26* (2013.01); *G01N 2469/20* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,684,611 A | 8/1987 | Schilperoot et al. |
| 4,800,159 A | 1/1989 | Mullis et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,843,650 A | 12/1998 | Segev |
| 5,846,709 A | 12/1998 | Segev |
| 5,846,783 A | 12/1998 | Wu et al. |
| 5,849,497 A | 12/1998 | Steinman |
| 5,849,546 A | 12/1998 | Sousa et al. |
| 5,849,547 A | 12/1998 | Cleuziat et al. |
| 5,858,652 A | 1/1999 | Laffler et al. |
| 5,866,366 A | 2/1999 | Kallender |
| 5,871,986 A | 2/1999 | Boyce |
| 5,916,776 A | 6/1999 | Kumar |
| 5,922,574 A | 7/1999 | Minter |

(Continued)

FOREIGN PATENT DOCUMENTS

| | | |
|---|---|---|
| GB | 2202328 | 9/1988 |
| WO | WO9409699 | 5/1994 |

(Continued)

OTHER PUBLICATIONS

Lederman et al (Molecular Immunology 28:1171-1181, 1991) (Year: 1991).*
Li et al (Proc. Natl. Acad. Sci. USA 77:3211-3214, 1980) (Year: 1980).*
Carpenter, J., "Klebsiella pulmonary infections: Occurrence at one medical center and review", Rev. Infect. Dis., vol. 12(4), pp. 672-682, (1990) Abstract.
Sahly, H. et al, "Clinical, bacteriological, and serological aspects of Klebsiella infections and their spondylarthropathic sequelae", Clinical and Diagnostic Laboratory Immunology, vol. 4(4), pp. 393-399, (Jul. 1997).

(Continued)

*Primary Examiner* — Padmavathi Baskar
(74) *Attorney, Agent, or Firm* — McHale & Slavin, P.A.

(57) ABSTRACT

The present invention relates to proteins and nucleic acids derived from *Klebsiella pneumonia* as well as therapeutic and diagnostic uses of the proteins and nucleic acids.

8 Claims, 3 Drawing Sheets

Figure 1:
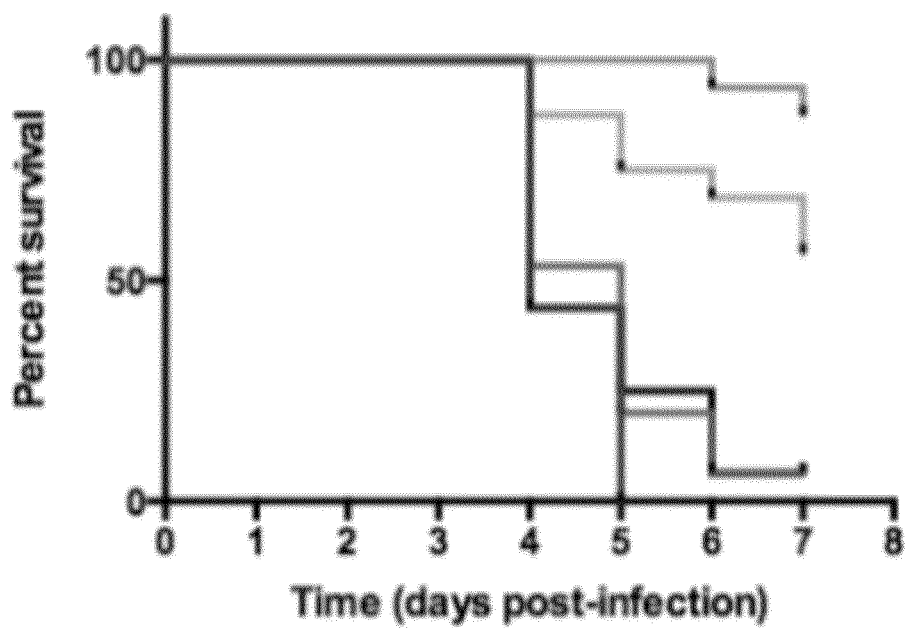

Specification includes a Sequence Listing.

(56) References Cited

U.S. PATENT DOCUMENTS

| | | |
|---|---|---|
| 5,925,565 A | 7/1999 | Berlioz et al. |
| 5,928,905 A | 7/1999 | Stemmer et al. |
| 5,928,906 A | 7/1999 | Koster et al. |
| 5,932,451 A | 8/1999 | Wang et al. |
| 5,935,818 A | 8/1999 | Israeli et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,981,274 A | 11/1999 | Tyrrell et al. |
| 5,994,624 A | 11/1999 | Trolinder et al. |

FOREIGN PATENT DOCUMENTS

| | | |
|---|---|---|
| WO | WO9506128 | 3/1995 |
| WO | WO9820734 | 5/1998 |

OTHER PUBLICATIONS

Schwimmbeck, P. et al, "Klebsiella pneumoniae and HLA B27-associated diseases of Reiter's Syndrome and ankylosing spondylitis", Molecular Mimicry. DOI: 10.1007/978-3-642-74594-2_4, (1989).

Watanakunakorn, C. et al, "Klebsiella baceremia: a review of 196 episodes during a decade (1980-1989)", Scand. J. of Infect. Dis., vol. 23(4), pp. 399-405, (Jul. 2009) Abstract.

Tang, L. et al, "Klebsiella ozaenae meningitis: report of two cases and review of their literature", Infection, vol. 22(1), pp. 58-61, (Jan.-Feb. 1994) Abstract.

Sirot, D., "Extended-spectrum plasmid-mediated beta-lactamases", J. Antimicrob. Chemother., Supplement A., pp. 19-34, (Jul. 1995) Sirot.

Cameron, D. et al, "Metabolic engineering of propanediol pathways", Bioltechnol. Prog., vol. 14(1), pp. 116-125, (Jan.-Feb. 1998) Abstract.

Kohler, G. et al, "Continuous cultures of fused cells secreting antibody of predefined specificity", Nature, vol. 256, pp. 495-497, (Aug. 1975).

Robinson, H. et al, "DNA vaccines", Seminars in Immunology, vol. 9(5), pp. 271-283, (Oct. 1997) Abstract.

Donnelly, J. et al, "DNA vaccines", Annu. Rev. Immunol., vol. 15, pp. 617-648, (1997) Abstract.

Wu, K. et al, "Genome sequencing and comparative analysis of Klebsiella pneumoniae NTUH-K2044, a strain liver abscess and meningitis", J. of Bacteriology, vol. 191(14), pp. 4492-4501, (Jul. 2009).

* cited by examiner

SEQUENCE LISTING

<160> NUMBER OF SEQ ID NOS: 102

<210> SEQ ID NO 1
<211> LENGTH: 94
<212> TYPE: PRT
<213> ORGANISM: Klebsiella pneumoniae

<400> SEQUENCE: 1

Met Lys Lys Leu Ala Leu Leu Ser Ala Val Met Thr Leu Gly Met Ser
1               5                   10                  15

Ser Trp Ala Phe Ala Ala Asp Asn Pro Pro Pro Pro Glu Lys Gly
            20                  25                  30

Ala Gln His Gln Gly Lys Pro Pro Val Lys Asn Gly Gln His Glu Gly
        35                  40                  45

Lys Gln Ala Gln Tyr Asn Arg Lys Gln Pro Gln Arg Asp Gly Lys Gln
    50                  55                  60

Pro Gln His Asp Gly Lys Gln Pro Gln His Asn Gly Lys Gln Pro Pro
65                  70                  75                  80

Lys Gly Ser Glu His Ser Gly Lys Pro Leu Pro Pro Lys Ala
                85                  90

<210> SEQ ID NO 2
<211> LENGTH: 117
<212> TYPE: PRT
<213> ORGANISM: Klebsiella pneumoniae

<400> SEQUENCE: 2

Met Lys Arg Tyr Ala Thr Ala Leu Leu Phe Cys Thr Leu Ser Leu Thr
1               5                   10                  15

Ser Leu Ala Ala Arg Ala Asp Ile Ile Asp Asp Ala Ile Gly Asn Ile
            20                  25                  30

Gln Gln Ala Ile Asn Asp Ala Tyr Asn Pro Gly Ser Ser Arg Ser Asp
        35                  40                  45

Asp Asp Asp Arg Tyr Asp Asp Asp Gly Arg Tyr Asp Asp Gly Arg Tyr

```
                    50                  55                  60
Gln Gly Ser Arg Gln Gln Ser Arg Asp Ser Gln Arg Gln Tyr Asp Glu
 65                  70                  75                  80

Arg Gln Arg Gln Leu Asp Glu Arg Arg Gln Leu Asp Glu Arg Gln
                 85                  90                  95

Arg Gln Leu Asp Arg Asp Arg Gln Leu Glu Ser Asp Gln Arg Arg
                100                 105                 110

Leu Asp Asp Ser Tyr
            115

<210> SEQ ID NO 3
<211> LENGTH: 119
<212> TYPE: PRT
<213> ORGANISM: Klebsiella pneumoniae

<400> SEQUENCE: 3

Met Phe Arg Ser Leu Ile Leu Ala Ala Val Leu Leu Ala Ala Gly Pro
 1               5                  10                  15

Leu Val Ala Asn Ala Gly Glu Ile Thr Leu Leu Pro Ser Val Lys Leu
                20                  25                  30

Gln Ile Gly Asp Arg Asp Asn Tyr Gly Asn Tyr Trp Asp Gly Gly Ser
            35                  40                  45

Trp Arg Asp Arg Asp Tyr Trp Arg Arg His Tyr Glu Trp Arg Asp Asn
 50                  55                  60

Arg Trp His Arg His Asp Asn Gly Trp His Lys Gly Trp Tyr Lys Gly
 65                  70                  75                  80

Arg Asp Lys Ala Trp Glu Arg Gly Tyr Arg Ala Gly Trp Asn Asp Arg
                 85                  90                  95

Asp Asp His Arg Gly Gly Trp Gly Arg Gly Pro Gly Gly Arg Gly His
                100                 105                 110

Gly His Gly His Gly His His
            115

<210> SEQ ID NO 4
<211> LENGTH: 120
<212> TYPE: PRT
<213> ORGANISM: Klebsiella pneumoniae

<400> SEQUENCE: 4

Met Lys Glu Ile Gly Leu Pro Leu Leu Leu Thr Ala Leu Ala Ser
 1               5                  10                  15

Pro Ala Phe Ala Ala Asp Cys Gln Pro Asn Gly Ile Gly Gly Ser Phe
                20                  25                  30

Cys Ile Asn Asp Asp Gly Thr Thr Thr Asp Thr Val Pro Asn Glu Val
            35                  40                  45

Asn Gly Met Asp Thr Tyr Ser Asn Asn Gly Gly Tyr Thr Ser Ser Leu
 50                  55                  60

Pro Asp Arg Ser Gly Ala Asp Glu Ala Leu Glu Gly Ser Ser Leu Ser
 65                  70                  75                  80

Thr Gln Gln Gly Val Gly Ser Gly Gln Ser Asp Ser Ala Leu Ala Gly
                 85                  90                  95

Arg Asp Trp His Ser Pro Ala Asn Leu Asn Asp Gly Ala Ala Thr Ser
                100                 105                 110

Ser Met Ser Leu Leu Asp Lys Pro
            115                 120
```

-continued

```
<210> SEQ ID NO 5
<211> LENGTH: 121
<212> TYPE: PRT
<213> ORGANISM: Klebsiella pneumoniae

<400> SEQUENCE: 5

Met Asn Met Lys Lys Leu Thr Thr Leu Leu Thr Ala Thr Leu Gly
1               5                   10                  15

Leu Ala Ser Gly Ala Ala Leu Ala Ala Asp Thr Gly Ala Gln Ser Asn
            20                  25                  30

Asn Gly Gln Ala Asn Ser Ser Ala Asp Ala Gly Gln Val Ala Pro Asp
        35                  40                  45

Ala Arg Glu Asn Val Ala Pro Asn Asn Val Asp Asn Ser Gln Ile Asn
    50                  55                  60

Ser Gly Ser Gly Gly Thr Thr Gly Ser Thr Met Thr Gln Asp Asn Met
65                  70                  75                  80

Ser Ser Asn Glu Val His Lys Asn Ser Met Cys Lys Asp Gly Arg Cys
                85                  90                  95

Pro Asp Thr Gly Lys Lys Leu Asp Asn Gly Gly Asn Thr Thr Gln Asp
            100                 105                 110

Asn Ser Lys Thr Asp Gly Thr Thr Gln
        115                 120

<210> SEQ ID NO 6
<211> LENGTH: 122
<212> TYPE: PRT
<213> ORGANISM: Klebsiella pneumoniae

<400> SEQUENCE: 6

Met Lys His Arg Ile Ala Leu Leu Val Leu Thr Ser Leu Ser Ala
1               5                   10                  15

Ser Ala Leu Ala Ala Ser Pro Cys Gln Glu Lys Glu Gln Asp Ile Gln
            20                  25                  30

Arg Glu Ile Ser Tyr Ala Glu Lys His His Asn Gln Ser Arg Ile Asp
        35                  40                  45

Gly Leu Asn Thr Ala Leu Arg Gln Val Arg Glu Asn Cys Ser Asp Ser
    50                  55                  60

Lys Leu Lys Ala Asp His Gln Gln Lys Ile Ala Lys Gln Arg Glu Glu
65                  70                  75                  80

Ile Ala Glu Arg Gln Arg Asp Leu Gln Glu Ala Arg Lys Lys Gly Asp
                85                  90                  95

Ala Asp Lys Ile Asn Lys Arg Gln His Lys Leu Asn Glu Ala Gln Gln
            100                 105                 110

Glu Leu Lys Thr Leu Glu Ser Arg Asp Tyr
        115                 120

<210> SEQ ID NO 7
<211> LENGTH: 141
<212> TYPE: PRT
<213> ORGANISM: Klebsiella pneumoniae

<400> SEQUENCE: 7

Met Arg Leu Ile Thr Arg His Val Arg Glu Asp Ile Met Lys Lys Ala
1               5                   10                  15

Met Ile Ala Leu Ser Ala Ile Leu Val Ala Ala Pro Val Phe Ala Ala
            20                  25                  30

Thr Thr His Ala Thr Asp Asp Thr Val Ala Ala Ala Asn Ala Asn Ala
        35                  40                  45
```

Asn Thr Ala Lys Glu Lys Leu His Gln Ala Gln His Glu Gly Glu Glu
        50                  55                  60

Gln Gln Leu Lys Ala Lys His Ala Ala Glu Gly Lys Gln Asp Ser Val
65                  70                  75                  80

Gly Ser Gln Val Ser Glu Gly Ala Gln Lys Thr Trp Asn Lys Thr Lys
                85                  90                  95

Glu Gly Thr Glu Lys Gly Trp Asp Lys Thr Lys Glu Val Ser Glu Lys
            100                 105                 110

Gly Trp Asn Ala Thr Lys Ser Gly Ala Glu Lys Gly Trp Asp Lys Thr
        115                 120                 125

Lys Thr Gly Ala Glu Glu Leu Lys Asn Lys Val Thr Glu
    130                 135                 140

<210> SEQ ID NO 8
<211> LENGTH: 151
<212> TYPE: PRT
<213> ORGANISM: Klebsiella pneumoniae

<400> SEQUENCE: 8

Met Lys Lys Met Ile Ser Leu Ala Val Ile Leu Ser Cys Val Leu Ser
1               5                   10                  15

Val Pro Ala Phe Ala Asp Gly Pro Asn Asp Gly His Arg Pro Glu Gln
            20                  25                  30

Pro Thr Val Trp Gln Asn Gly Pro Asp His Asp Gly His Ala Pro Gln
        35                  40                  45

Gly Gly Pro Asp Ala His His Gln Gly Asp His Asp Gln Arg Gly Pro
    50                  55                  60

Asp Arg Asp Gly His Asp Lys Arg Asp Leu Ala Arg His Glu Gln Asp
65                  70                  75                  80

His Phe Ala Trp Arg Gly Asn Asp Phe Arg Lys Gly His Pro Ala Pro
                85                  90                  95

Ala Pro Phe Arg Gly Asp Glu Tyr Arg Val Arg Asp Trp Ser Asp Arg
            100                 105                 110

Gly Leu Pro Pro Pro Pro Glu Gly His His Trp Ser Tyr Ile Asp Gly
        115                 120                 125

Asn Tyr Val Leu Ile Ala Ala Ala Thr Gly Ile Ile Thr Ser Ile Leu
    130                 135                 140

Val Ser Gly Ala Leu Gly His
145                 150

<210> SEQ ID NO 9
<211> LENGTH: 168
<212> TYPE: PRT
<213> ORGANISM: Klebsiella pneumoniae

<400> SEQUENCE: 9

Met Lys Lys Pro Thr Ser Ala Thr Arg Gly Lys Ser Gly Arg Lys Ser
1               5                   10                  15

Arg Glu Glu Leu Asn Gln Glu Ala Arg Asp Arg Lys Arg Gln Lys Lys
            20                  25                  30

His Arg Gly His Ala Ala Gly Ser Arg Ala Asn Gly Gly Asp Ala Ala
        35                  40                  45

Ser Ala Gly Lys Lys Gln Arg Gln Ala Gln Asp Pro Arg Val Gly Ser
    50                  55                  60

Lys Lys Pro Ile Pro Leu Gly Val Ser Glu Ser Ser Val Pro Ala Pro
65                  70                  75                  80

```
Lys Gln His Lys Pro Lys Ser Glu Lys Pro Met Leu Ser Pro Gln Ala
                 85                  90                  95

Glu Leu Glu Leu Leu Glu Asn Asp Glu Arg Leu Asp Ala Leu Leu Glu
            100                 105                 110

Arg Leu Glu Glu Gly Gly Thr Leu Asn Ala Glu Glu Gln Ser Trp Val
        115                 120                 125

Asp Ala Lys Leu Asp Arg Ile Asp Glu Leu Met Gln Gln Leu Gly Leu
    130                 135                 140

Ser Tyr Asp Asp Glu Asp Glu Glu Glu Glu Arg Gln Glu Asp Met
145                 150                 155                 160

Met Arg Leu Leu Lys Gly Gly Asn
                165
```

<210> SEQ ID NO 10
<211> LENGTH: 229
<212> TYPE: PRT
<213> ORGANISM: Klebsiella pneumoniae

<400> SEQUENCE: 10

```
Met Ala Ser Lys Phe Gln Asn Arg Leu Val Gly Thr Ile Val Leu Val
1               5                   10                  15

Ala Leu Gly Val Ile Ile Leu Pro Gly Leu Leu Asp Gly Gln Lys Lys
            20                  25                  30

His Tyr Gln Asp Glu Phe Ala Ala Ile Pro Leu Val Pro Lys Pro Gly
        35                  40                  45

Asp Arg Asp Glu Pro Asp Met Leu Pro Ala Ala Thr Gln Ala Leu Pro
    50                  55                  60

Ser Gln Pro Pro Glu Gly Ala Ala Glu Glu Val Arg Ala Gly Asp Ala
65                  70                  75                  80

Ala Ala Pro Ser Leu Asp Pro Ser Arg Ile Pro Val Asn Ser Asn Ser
                85                  90                  95

Phe Asp Asp Val Gln Glu Pro Val Val Ala Ala Lys Pro Gln Pro Lys
            100                 105                 110

Pro Gln Pro Lys Pro Gln Pro Gln Gln Ala Ser Thr Pro Thr Pro
        115                 120                 125

Pro Pro Ala Lys Pro Gln Gln Gln Pro Gln Gln Gln Ala Ala
    130                 135                 140

Leu Pro Ala Pro Thr Gly Lys Ala Tyr Val Val Gln Leu Gly Ala Leu
145                 150                 155                 160

Lys Asn Ala Asp Lys Val Asn Glu Ile Val Gly Lys Leu Arg Ala Ser
                165                 170                 175

Gly Phe Lys Val Tyr Thr Ser Pro Ser Thr Pro Val Gln Gly Lys Ile
            180                 185                 190

Thr Arg Ile Leu Val Gly Pro Asp Ala Ser Lys Asp Lys Leu Lys Gly
        195                 200                 205

Gln Leu Gly Asp Leu Gln Gln Ile Ser Gly Leu Ser Gly Val Val Met
    210                 215                 220

Gly Phe Thr Pro Asn
225
```

<210> SEQ ID NO 11
<211> LENGTH: 322
<212> TYPE: PRT
<213> ORGANISM: Klebsiella pneumoniae

<400> SEQUENCE: 11

Met Ala Gln Arg Asp Tyr Val Arg Arg Ser Gln Pro Ala Ser Ser Arg
1               5                   10                  15

Arg Lys Lys Ser Thr Thr Arg Ser Ser Arg Asn Lys Gln Ser Ser Leu
                20                  25                  30

Pro Ala Ile Ser Pro Ala Met Val Ala Ile Ala Ala Ala Val Leu Val
            35                  40                  45

Ala Phe Ile Gly Gly Leu Tyr Phe Ile Thr His His Lys Lys Glu Glu
50                  55                  60

Ala Glu Ala Met Gln Asn Arg Gln Ala Ala Gly Asn Gly Leu Pro Pro
65                  70                  75                  80

Lys Pro Glu Glu Arg Trp Arg Tyr Ile Lys Glu Leu Glu Ser Arg Gln
                85                  90                  95

Pro Gly Val Arg Ala Pro Thr Glu Pro Thr Ala Gly Gly Glu Val Met
            100                 105                 110

Lys Pro Glu Gln Leu Thr Asp Glu Gln Arg Gln Leu Leu Ala Gln Met
        115                 120                 125

Gln Ala Asp Met Arg Gln Gln Pro Thr Gln Leu Thr Glu Val Pro Trp
130                 135                 140

Asn Glu Gln Thr Pro Ala Gln Arg Gln Gln Thr Leu Gln Arg Gln Arg
145                 150                 155                 160

Leu Ala Gln Gln Gln Gln Ala Gln Gln Gln Trp Ala Gln Thr
                165                 170                 175

Gln Ala Gln Thr Val Gln Gln Pro Pro Arg Val Gln Gln Pro Lys
            180                 185                 190

Pro Val Gln Gln Gln Pro Lys Gln Thr Ala Ser Asn Gln Gln Pro
        195                 200                 205

Tyr Gln Asp Leu Leu Gln Thr Pro Ala His Thr Asn Thr Thr Gln Pro
210                 215                 220

Arg Thr Gln Ala Ala Ala Pro Val Thr Arg Val Glu Glu Ala Pro Lys
225                 230                 235                 240

Thr Thr Ala Glu Lys Lys Asp Asp Arg Ser Trp Met Ile Gln Cys Gly
                245                 250                 255

Ser Phe Lys Gly Ala Glu Gln Ala Glu Thr Val Arg Ala Gln Leu Ala
            260                 265                 270

Phe Glu Gly Phe Ala Ser His Ile Thr Thr Asn Asn Gly Trp Asn Arg
        275                 280                 285

Val Val Ile Gly Pro Leu Lys Gly Lys Glu Ser Ala Asn Glu Met Ile
290                 295                 300

Thr Arg Leu Lys Met Ala Gly His Ala Asn Cys Ile Arg Leu Ala Ala
305                 310                 315                 320

Arg Gly

<210> SEQ ID NO 12
<211> LENGTH: 376
<212> TYPE: PRT
<213> ORGANISM: Klebsiella pneumoniae

<400> SEQUENCE: 12

Met Ser Ala Gly Ser Thr Lys Phe Thr Val Ser Arg Ile Ala Ala Leu
1               5                   10                  15

Ser Leu Val Ser Leu Trp Leu Ala Gly Cys Thr Asn Thr Asn Asn Pro
                20                  25                  30

Pro Ala Pro Val Ser Ser Ala Gly Gly Ala Ala Ser Ser Ser Thr Asn
            35                  40                  45

```
Ser Gly Met Leu Ile Thr Pro Pro Ser Gly Val Lys Ser Ala Pro
         50                  55                  60

Gln Ala Gln Pro Ile Gln Pro Met Gln Thr Gln Thr Ile Gln Pro Ala
 65                  70                  75                  80

Pro Val Ala Gln Glu Pro Val Gln Thr Val Asn Gly Arg Ile Val Tyr
                 85                  90                  95

Asn Arg Lys Tyr Gly Asp Ile Pro Lys Gly Ser Tyr Thr Gly Gly Ser
            100                 105                 110

Thr Tyr Thr Val Lys Arg Gly Asp Thr Leu Phe Tyr Ile Ala Trp Val
        115                 120                 125

Thr Gly Asn Asp Phe Arg Asp Leu Ala Gln Arg Asn Asn Ile Pro Ala
130                 135                 140

Pro Tyr Ala Leu Asn Val Gly Gln Val Leu Gln Val Gly Asn Ala Ser
145                 150                 155                 160

Gly Gln Pro Ile Thr Gly Glu Asn Ala Val Ser Gln Ala Ser Ala Arg
                165                 170                 175

Ala Ser Gly Gly Ala Thr Thr Ser Thr Thr Ser Ala Gln Lys Ser Thr
            180                 185                 190

Ala Val Val Ala Ser Gln Pro Thr Ile Thr Tyr Ser Glu Ser Ser Gly
        195                 200                 205

Glu Gln Ser Ala Thr Lys Met Leu Pro Asn Asn Lys Pro Ala Thr Thr
210                 215                 220

Thr Thr Thr Val Val Ala Pro Val Thr Ala Pro Thr Thr Val Ser Thr
225                 230                 235                 240

Thr Gln Pro Thr Ala Ser Ser Thr Ser Thr Ser Pro Ile Ser Ala
                245                 250                 255

Trp Arg Trp Pro Thr Asp Gly Lys Val Ile Glu Asn Phe Ser Gly Ala
            260                 265                 270

Glu Gly Gly Asn Lys Gly Ile Asp Ile Ala Gly Ser Lys Gly Gln Ala
        275                 280                 285

Ile Val Ala Thr Ala Asp Gly Arg Val Val Tyr Ala Gly Asn Ala Leu
290                 295                 300

Arg Gly Tyr Gly Asn Leu Ile Ile Ile Lys His Asn Asp Asp Tyr Leu
305                 310                 315                 320

Ser Ala Tyr Ala His Asn Asp Thr Met Leu Val Arg Glu Gln Gln Glu
                325                 330                 335

Val Lys Ala Gly Gln Lys Ile Ala Thr Met Gly Ser Thr Gly Thr Ser
            340                 345                 350

Ser Thr Arg Leu His Phe Glu Ile Arg Tyr Lys Gly Lys Ser Val Asn
        355                 360                 365

Pro Leu Gln Tyr Leu Pro Gln Arg
370                 375

<210> SEQ ID NO 13
<211> LENGTH: 382
<212> TYPE: PRT
<213> ORGANISM: Klebsiella pneumoniae

<400> SEQUENCE: 13

Met Arg Lys Gln Trp Leu Gly Ile Cys Ile Ala Ala Gly Leu Leu Ala
  1               5                  10                  15

Ala Cys Ser Ser Asp Asp Val Gln Gln Lys Thr Val Ser Thr Pro Gln
             20                  25                  30

Pro Ala Val Cys Asn Gly Pro Thr Val Glu Ile Ser Gly Ala Asp Pro
```

35                  40                  45
Gln Tyr Glu Thr Pro Asn Ala Thr Ala Asn Gln Asp Tyr Glu Arg Asp
    50                  55                  60

Gly Lys Ser Tyr Lys Ile Val Gln Asp Pro Ala Asn Phe Thr Gln Ala
65                  70                  75                  80

Gly Phe Ala Ala Ile Tyr Asp Ala Glu Pro Asn Ser Asn Leu Thr Ala
                85                  90                  95

Ser Gly Glu Ala Phe Asp Pro Thr Gln Leu Thr Ala Ala His Pro Thr
            100                 105                 110

Leu Pro Ile Pro Ser Tyr Ala Arg Ile Thr Asn Leu Ala Asn Gly Arg
        115                 120                 125

Met Ile Val Val Arg Ile Asn Asp Arg Gly Pro Tyr Gly Asn Asp Arg
    130                 135                 140

Val Ile Ser Leu Ser Arg Ala Ser Ala Asp Arg Leu Asn Thr Ser Asn
145                 150                 155                 160

Asn Thr Lys Val Arg Ile Asp Pro Ile Ile Val Ala Pro Asp Gly Ser
                165                 170                 175

Leu Ser Gly Pro Gly Met Ala Cys Thr Thr Val Ala Lys Gln Thr Tyr
            180                 185                 190

Ala Leu Pro Ala Arg Pro Asn Leu Asp Gly Asp Ala Ala Gly Met
        195                 200                 205

Ser Gln Pro Ala Pro Thr Asp Val Arg Pro Ile Ser Asn Ser Thr Leu
    210                 215                 220

Thr Pro Ala Asp Ser Val Gly Ala Pro Val Asn Ser Gly Gly Phe Leu
225                 230                 235                 240

Gly Ala Pro Thr Pro Leu Asn Asn Gly Val Leu Glu Ser Ser Glu Pro
                245                 250                 255

Ala Ala Ala Ala Ala Thr Ala Pro Ala Ala Gly Ala Thr Pro Thr Ala
            260                 265                 270

Pro Val Thr Ala Pro Gly Ser Ile Gln Gly Asn Val Val Pro Ala Ala
        275                 280                 285

Ala Thr Ala Ala Ala Gly Ala Val Ala Ala Ser Ser Ser Ala Thr
    290                 295                 300

Ser Ser Ala Ser Gly Asn Phe Val Val Gln Val Gly Ala Val Ser Asp
305                 310                 315                 320

Gln Thr Arg Ala Gln Gln Tyr Gln Gln Arg Leu Ser Gln Gln Phe Ser
                325                 330                 335

Val Pro Gly Arg Val Met Gln Asn Gly Ala Val Trp Arg Ile Gln Leu
            340                 345                 350

Gly Pro Phe Ala Asp Lys Ala Gln Ala Ser Ala Val Gln Gln Arg Leu
        355                 360                 365

Gln Ser Glu Ala Gln Leu Gln Ser Phe Ile Thr Arg Ala Asn
    370                 375                 380

<210> SEQ ID NO 14
<211> LENGTH: 428
<212> TYPE: PRT
<213> ORGANISM: Klebsiella pneumoniae

<400> SEQUENCE: 14

Met Asp Asp Phe Lys Pro Glu Asp Asp Met Lys Ala Asp Arg Asn Asp
1               5                   10                  15

Arg Arg Ala Gly Arg Ser Arg Gln Ser Ser Glu Arg Asp Ala Asp Pro
            20                  25                  30

Gln Ile Asn Phe Asp Asp Val Asp Leu Asp Ala Asp Glu Gly Arg Pro
            35                  40                  45

Thr Arg Ala Gly Lys Ala Arg Arg Glu Arg Glu Glu Glu Glu Phe Glu
 50                  55                  60

Glu Glu Leu Asp Ala Gln Asp Glu Glu Met Leu Glu Glu Gln Pro Val
 65                  70                  75                  80

Glu Arg Arg Pro Arg Lys Arg Lys Ala Pro Ala Lys Pro Ala Ser
                 85                  90                  95

Arg Gln Tyr Ile Met Met Gly Val Gly Ile Leu Val Leu Leu Leu
                100                 105                 110

Ile Val Gly Ile Gly Ser Ala Leu Lys Ser Pro Ser Ser Ser Ser Gln
            115                 120                 125

Gln Thr Ala Ser Gly Glu Lys Ser Ile Asn Leu Ser Asp Asp Gln Ser
    130                 135                 140

Ala Ser Met Pro Ala Ala Gly Gln Asp Gln Thr Ala Ala Ala Asn Ser
145                 150                 155                 160

Thr Ser Gln Gln Asp Val Thr Val Pro Pro Ile Ala Ala Asn Pro Thr
                165                 170                 175

Gln Gly Gln Ala Ala Val Ala Pro Gln Gly Gln Gln Arg Ile Glu Val
            180                 185                 190

Gln Gly Asp Leu Asn Asn Ala Leu Thr Gln Gln Gln Gly Gln Leu Asp
    195                 200                 205

Gly Ala Val Ala Asn Ser Thr Leu Pro Thr Glu Pro Ala Thr Val Ala
210                 215                 220

Pro Ile Arg Asn Gly Ala Asn Gly Thr Ala Ala Pro Arg Gln Ala Thr
225                 230                 235                 240

Glu Arg Gln Thr Ala Ala Thr Pro Arg Pro Ala Glu Arg Lys His Thr
                245                 250                 255

Val Ile Glu Ala Lys Pro Gln Ser Lys Pro Gln Ala Val Ala Lys Thr
            260                 265                 270

Pro Val Glu Ser Lys Pro Val Gln Pro Lys His Val Glu Ser Thr Ala
    275                 280                 285

Thr Thr Ala Pro Ala Lys Thr Ser Val Ser Glu Ser Lys Pro Val Ala
290                 295                 300

Thr Ala Gln Ser Lys Pro Thr Thr Thr Ala Ala Pro Ala Ala Thr
305                 310                 315                 320

Ala Ala Ala Ala Ala Pro Ala Ala Lys Thr Gly Lys Thr Ala Gly Asp
                325                 330                 335

Val Ser Ser Met Lys Thr Ala Pro Ser Gly His Tyr Thr Leu Gln Leu
            340                 345                 350

Ser Ser Ser Ser Asn Tyr Asp Asn Leu Asn Asn Trp Ala Lys Lys Glu
    355                 360                 365

Lys Leu Asp Lys Tyr Val Val Tyr Glu Thr Ser Arg Asn Gly Gln Pro
370                 375                 380

Trp Tyr Val Leu Val Ser Gly Ile Tyr Ala Ser Lys Asp Glu Ala Lys
385                 390                 395                 400

Arg Ala Val Thr Ser Leu Pro Ala Asp Val Gln Ala Lys Asn Pro Trp
                405                 410                 415

Ala Lys Pro Leu His Gln Val Gln Ala Asp Leu Lys
            420                 425

<210> SEQ ID NO 15
<211> LENGTH: 441
<212> TYPE: PRT

<213> ORGANISM: Klebsiella pneumoniae

<400> SEQUENCE: 15

```
Met Ser Lys Ala Thr Glu Gln Asn Asp Lys Leu Lys Arg Ala Ile Ile
1               5                   10                  15
Ile Ser Val Ala Leu His Ile Ile Leu Ile Ala Leu Leu Ile Trp Ser
                20                  25                  30
Ser Phe Asp Glu His Leu Asp Ala Ser Ala Gly Gly Gly Gly Gly Ser
            35                  40                  45
Ser Ile Asp Ala Val Met Val Asp Pro Gly Ala Val Val Asn Asn Tyr
        50                  55                  60
Asn Arg Gln Gln Gln Gln Ala Ser Ala Arg Arg Ala Ala Glu Gln
65                  70                  75                  80
Arg Glu Lys Gln Ala Gln Gln Ala Glu Glu Leu Arg Glu Lys Gln
                85                  90                  95
Ala Ala Glu Gln Glu Arg Leu Lys Gln Leu Glu Gln Glu Arg Leu Gln
                100                 105                 110
Ala Gln Glu Ala Ala Lys Glu Ala Glu Gln Gln Lys Gln Ala Glu
            115                 120                 125
Glu Ala Ala Lys Ala Ala Ala Ala Lys Ala Lys Ala Asp Ala
    130                 135                 140
Gln Ala Lys Glu Ala Gln Glu Ala Ala Lys Ala Ala Ala Glu Ala
145                 150                 155                 160
Lys Ala Lys Ala Asp Ala Gln Ala Lys Ala Ala Glu Gln Ala Ala
                165                 170                 175
Lys Ala Ala Asp Ala Lys Lys Gln Ala Glu Ala Ala Ala Ala Lys
                180                 185                 190
Ala Ala Ala Glu Ala Lys Lys Gln Ala Glu Ala Glu Ala Ala Lys Ala
            195                 200                 205
Ala Ala Glu Ala Gln Lys Lys Ala Glu Ala Ala Ala Lys Lys Ala
    210                 215                 220
Gln Gln Glu Ala Glu Lys Lys Ala Gln Glu Ala Ala Lys Gln Ala
225                 230                 235                 240
Ala Ala Glu Lys Ala Ala Ala Glu Lys Ala Ala Glu Lys Ala Ala Ala
                245                 250                 255
Gln Lys Ala Ala Ala Glu Lys Ala Ala Ala Glu Lys Ala Ala Ala
                260                 265                 270
Glu Lys Ala Ala Ala Lys Ala Ala Ala Glu Lys Ala Ala
            275                 280                 285
Asp Lys Ala Ala Lys Ala Ala Ala Lys Ala Ala Ala Lys Lys
    290                 295                 300
Ala Ala Ala Ala Lys Glu Ala Asp Gly Val Asp Asn Leu Leu Gly Asp
305                 310                 315                 320
Leu Ser Ser Gly Lys Asn Ala Pro Lys Thr Gly Gly Ala Lys Gly
                325                 330                 335
Asn Asn Ala Ser Ala Ala Gly Ser Gly Asn Thr Lys Asn Ser Ala Ser
                340                 345                 350
Gly Ala Asp Ile Asn Asn Tyr Ala Gly Gln Ile Lys Ser Ala Ile Glu
            355                 360                 365
Ser Lys Phe Tyr Asp Ala Ser Ser Tyr Ala Gly Lys Thr Cys Thr Leu
    370                 375                 380
Arg Ile Lys Leu Ala Pro Asp Gly Leu Leu Leu Asn Ile Gln Ser Glu
385                 390                 395                 400
```

```
Gly Gly Asp Pro Ala Leu Cys Gln Ala Ala Leu Ala Ala Ala Arg Gln
                405                 410                 415

Ala Lys Phe Pro Lys Pro Pro Ser Gln Ala Val Tyr Glu Val Phe Lys
            420                 425                 430

Asn Ala Pro Leu Asp Phe Lys Pro Gln
            435                 440

<210> SEQ ID NO 16
<211> LENGTH: 484
<212> TYPE: PRT
<213> ORGANISM: Klebsiella pneumoniae

<400> SEQUENCE: 16

Met Phe Phe Leu Ser Ile Phe Tyr Met Glu Met Thr Lys Val Lys Leu
1               5                   10                  15

Ser Ala Leu Phe Ile Ala Leu Ile Pro Leu Leu Gly Ser Pro Val Ile
                20                  25                  30

His Ala Glu Thr Thr Ala Ala Pro Val Leu Glu Asn Arg Ala Ala Gln
            35                  40                  45

Gly Asp Ile Thr Thr Pro Gly Gly Ala Arg Arg Leu Thr Gly Asp Gln
        50                  55                  60

Thr Glu Ala Leu Arg Ala Ser Leu Ile Asn Lys Pro Ala Lys Asn Val
65                  70                  75                  80

Ile Leu Leu Ile Gly Asp Gly Met Gly Asp Ser Glu Ile Thr Ala Ala
                85                  90                  95

Arg Asn Tyr Ala Glu Gly Ala Gly Gly Phe Phe Lys Gly Ile Asp Ala
            100                 105                 110

Leu Pro Leu Thr Gly Gln Tyr Thr His Tyr Ser Leu Asp Lys Lys Thr
        115                 120                 125

Gly Lys Pro Asp Tyr Val Thr Asp Ser Ala Ala Ser Ala Thr Ala Trp
    130                 135                 140

Thr Thr Gly Val Lys Thr Tyr Asn Gly Ala Leu Gly Val Asp Ile His
145                 150                 155                 160

Glu Asn Ala His Gln Thr Ile Leu Glu Leu Ala Lys Ala Ala Gly Leu
                165                 170                 175

Ala Thr Gly Asn Val Ser Thr Ala Glu Leu Gln Asp Ala Thr Pro Ala
            180                 185                 190

Ala Leu Val Ala His Val Thr Ser Arg Lys Cys Tyr Gly Pro Thr Val
        195                 200                 205

Thr Ser Glu Lys Cys Pro Ser Asn Ala Leu Glu Lys Gly Gly Lys Gly
    210                 215                 220

Ser Ile Thr Glu Gln Leu Leu Asn Ala Arg Pro Asp Val Thr Leu Gly
225                 230                 235                 240

Gly Gly Ala Lys Thr Phe Thr Glu Thr Ala Thr Ala Gly Glu Trp Gln
                245                 250                 255

Gly Lys Thr Leu Arg Glu Gln Ala Gln Ala Arg Gly Tyr Gln Ile Val
            260                 265                 270

Thr Asp Ala Ala Ser Leu Ala Ala Ala Thr Glu Ala Ser Gln Asp Lys
        275                 280                 285

Pro Leu Leu Gly Leu Phe Ala Asp Gly Asn Met Pro Val Arg Trp Glu
    290                 295                 300

Gly Pro Lys Ala Ser Tyr His Gly Asn Ile Asp Lys Pro Pro Val Thr
305                 310                 315                 320

Cys Thr Pro Asn Pro Lys Arg Asp Ala Ser Val Pro Thr Leu Ala Gln
                325                 330                 335
```

```
Met Thr Glu Lys Ala Ile Asp Leu Leu Ser Arg Asn Glu Lys Gly Phe
            340                 345                 350

Phe Leu Gln Val Glu Gly Ala Ser Ile Asp Lys Gln Asp His Ala Ala
            355                 360                 365

Asn Pro Cys Gly Gln Ile Gly Glu Thr Val Asp Leu Asp Glu Ala Val
            370                 375                 380

Gln Lys Ala Leu Glu Phe Ala Arg Lys Asp Gly Asn Thr Leu Val Ile
385                 390                 395                 400

Val Thr Ala Asp His Ala His Ala Ser Gln Ile Ile Pro Ala Asp Ser
            405                 410                 415

Lys Ala Pro Gly Leu Thr Gln Ala Leu Asn Thr His Asp Gly Ala Val
            420                 425                 430

Met Val Met Ser Tyr Gly Asn Ser Glu Glu Ser Met Glu His Thr
            435                 440                 445

Gly Thr Gln Leu Arg Ile Ala Ala Tyr Gly Pro His Ala Ala Asn Val
            450                 455                 460

Val Gly Leu Thr Asp Gln Thr Asp Leu Phe Thr Thr Met Lys Ala Ala
465                 470                 475                 480

Leu Ser Leu Lys

<210> SEQ ID NO 17
<211> LENGTH: 535
<212> TYPE: PRT
<213> ORGANISM: Klebsiella pneumoniae

<400> SEQUENCE: 17

Met Ser Leu Pro Phe Lys Pro His Ile Ile Ala Leu Leu Cys Ser Ala
1               5                   10                  15

Gly Leu Leu Ala Ala Ala Gly Thr Leu Tyr Val Gln Ser Arg Thr Pro
            20                  25                  30

Ala Thr Ile Ala Glu Pro Pro Ala Gln Ala Pro Ala Pro Ala Ala
            35                  40                  45

Ser Thr Thr Gln Pro Val Ala Ala Thr Tyr Thr Gln Ala Gln Ile Asp
50                  55                  60

Gln Trp Val Ala Pro Ile Ala Leu Tyr Pro Asp Ser Leu Leu Ser Gln
65                  70                  75                  80

Val Leu Met Ala Ser Thr Tyr Pro Asp Asn Val Leu Gln Ala Val Gln
            85                  90                  95

Trp Ser Gln Asp Asn Pro Ala Met Lys Gly Asp Ala Ala Val Gln Ala
            100                 105                 110

Val Ala Ser Gln Pro Trp Asp Pro Ser Val Lys Ser Leu Val Ala Phe
            115                 120                 125

Pro Ala Leu Leu Ala Met Met Gly Glu Asn Pro Pro Trp Val Glu Asn
            130                 135                 140

Leu Gly Asn Ala Phe Leu Ala Gln Pro His Asp Val Met Asp Ser Val
145                 150                 155                 160

Gln Arg Leu Arg Ala Ile Ala Gln Gln Thr Gly Thr Leu Lys Ser Thr
            165                 170                 175

Pro Gln Gln Lys Val Ile Val Thr Pro Ala Ala Pro Val Ser Ala Ser
            180                 185                 190

Ser Ser Thr Ala Ala Thr Ala Thr Ala His Thr Ala Ala Pro Ala Pro
            195                 200                 205

Thr Gln Val Ile Lys Ile Glu Pro Thr Asn Pro Gln Val Val Tyr Val
            210                 215                 220
```

```
Pro Ser Tyr Asn Pro Ser Thr Val Tyr Gly Thr Trp Pro Asn Ser Ala
225                 230                 235                 240

Tyr Pro Pro Val Tyr Leu Pro Pro Pro Gly Glu Gln Phe Thr Asp
            245                 250                 255

Ser Phe Val Lys Gly Phe Gly Tyr Ser Leu Gly Val Ala Thr Thr Trp
            260                 265                 270

Ala Leu Phe Ser Ser Ile Asp Trp Asp Asp Asp His His His His
            275                 280                 285

Asp Asp Asp Tyr His His Gly Asp Tyr Ser His Asn Gly Asp Asn Ile
            290                 295                 300

Asn Ile Asn Val Asn Asn Phe Asn His Ile Thr Gly Glu Asn Leu Pro
305                 310                 315                 320

Gly Asn His Val Asn Trp Gln His Asn Pro Ala Tyr Arg Gly His Thr
                325                 330                 335

Pro Tyr Pro Asp Asn Thr Val Ala Gln Arg Phe His Gln Thr Asn Val
            340                 345                 350

Ser Gly Gly Leu Ser Ala Thr Gln His Ala Pro Val Asp Arg Glu Ala
            355                 360                 365

Gln Arg Gln Ala Ala Met Thr Gln Leu Gln His Asn Val Pro Thr Ala
370                 375                 380

Thr Ala Gly Asn Leu Ala Ala Asn Asn Ala Ser Arg Asp Ala Gln Arg
385                 390                 395                 400

Gln Ala Ala Ser Ala Gln Leu Lys Gln Ala Thr Gln Arg Ser Asn Tyr
                405                 410                 415

Arg Gly Tyr Asp Ser Thr Pro Thr Gln Gln Arg Arg Glu Ala Ala
            420                 425                 430

Lys Thr Gln Leu Lys Asn Pro Thr Pro Gln Gln Gln Arg Arg Glu
            435                 440                 445

Ala Ala Arg Ser His Glu Gln Asn Arg Thr Pro Gln Gln Gln Arg
            450                 455                 460

Arg Gln Gln Phe Gln Ser Ala Thr Pro Ala Gln Arg Gln Thr Leu
465                 470                 475                 480

Ser His Leu Arg Ala Asn Ala Leu Ser Gly Asn Glu Ser Arg Ala Pro
                485                 490                 495

Ser Trp Gln Ala Gln Gln Glu Arg Gly Leu Gln Ser Arg Gln Phe Ser
            500                 505                 510

Gly Val Asn Arg Glu Leu Arg Asp Gly Thr Arg Glu Arg Leu Ser Glu
            515                 520                 525

His His Glu Leu Arg Arg Arg
            530                 535

<210> SEQ ID NO 18
<211> LENGTH: 597
<212> TYPE: PRT
<213> ORGANISM: Klebsiella pneumoniae

<400> SEQUENCE: 18

Met Phe Lys Phe Lys Ala Ser Tyr Val Ala Leu Ala Ala Val Leu Thr
1               5                   10                  15

Ser Ser Val Val Tyr Ala Asp Pro Thr Ser Tyr Thr His Ser Ser Gly
                20                  25                  30

Ala Thr Val Ile Asp Ile Glu Lys Pro Asn Ala Ala Gly Val Ser His
            35                  40                  45

Asn Leu Tyr Arg Asp Phe Asn Val Gly Ala Asn Gly Thr Ile Leu Asn
```

-continued

```
              50                  55                  60
Asn Ser Gly Asp Asp Val Ser His Ser Thr Phe Gly Asn Ile Ala Arg
 65                  70                  75                  80

Asn Asn Asn Leu Thr Ala Gly Ser Ala Ser Val Ile Leu Asn Glu Val
                 85                  90                  95

Thr Ser Lys Asn Ala Ser Ser Leu Lys Gly Phe Ile Glu Val Asn Gly
            100                 105                 110

Gln Lys Ala Asp Val Val Ile Ala Asn Pro Asn Gly Ile Thr Cys Ser
            115                 120                 125

Gly Cys Ser Phe Val Asn Thr Asn Lys Ala Ile Leu Thr Thr Gly Lys
        130                 135                 140

Val Asn Met Thr Asp Asp Gly Ala Ile Gly Ser Tyr Thr Val Thr Gly
145                 150                 155                 160

Gly Thr Leu Thr Ile Gly Glu Asn Gly Met Asn Ala Ala Asn Gly Tyr
                165                 170                 175

Ala Val Leu Leu Ala Asp Ala Ile Asn Ile Asn Gly Lys Val Gln Ala
            180                 185                 190

Asn Asn Ala Leu Val Ser Ala Gly Asn Phe Thr Met Asp Asn Ser Ser
            195                 200                 205

Gly Ser Val Thr Ser Ala Gly Lys Lys Ala Thr Leu Ile Gln Met Thr
        210                 215                 220

Val Asn Pro Gln Tyr Ser Ile Asp Val Ser Ser Leu Gly Gly Ile Glu
225                 230                 235                 240

Ala Asn Ser Ile Ser Met Val Gly Asn Asn Ile Gly Phe Gly Val Arg
                245                 250                 255

Asn Lys Gly Ser Ile Val Ala Asn Ser Ser Leu Gln Leu Thr Ser Asn
            260                 265                 270

Gly Asn Leu Leu Asn Lys Gly Thr Ile Lys Ser Asn Gly Leu Leu Ser
            275                 280                 285

Gln Val Ala Thr Ala Ser Gly Ile Thr Asn Asp Gly Ser Ile Ala Gly
        290                 295                 300

Ala Tyr Tyr Leu Met Leu Ser Ser Gly Asp Tyr Ile Val Asn Thr Gly
305                 310                 315                 320

Ser Leu Ser Gly Gly Gln Leu Ile Ala Thr Ala Asn Gly Asn Ile Thr
                325                 330                 335

Asn Gly Asp Ser Gly Thr Met Thr Gly Thr Ser Gly Leu Ser Leu Thr
            340                 345                 350

Ser Gly Gly Lys Ile Arg Asn Glu Glu Lys Ala Ser Leu Leu Ser Asn
        355                 360                 365

Asn Gln Ile Ala Ala Thr Ala Ile Gly Asp Phe Leu Asn Glu Gly Lys
    370                 375                 380

Ile Ser Ala Lys His Thr Ser Leu Thr Phe Val Gly Asp Ser Phe Lys
385                 390                 395                 400

Asn Thr Gly Asn Ile Asn Ser Thr Gly Gln Thr Thr Ile Gln Ser Leu
                405                 410                 415

Lys Gln Asp Gly Ser Ala Asn Thr Gly Glu Ile Tyr Asn Leu Gly Asn
            420                 425                 430

Ile Thr Gly Glu Asn Ile Asn Leu Gln Thr Asn Gly Thr Leu Ala Gln
        435                 440                 445

Ser Ser Ser Gly Arg Ile Glu Ala Thr Asn Ala Ile Thr Ala His Ser
    450                 455                 460

Tyr Trp Leu Asn Gln Asn Gly Tyr Met Asn Ala Ala Asp Ile Thr Thr
465                 470                 475                 480
```

Asp His Gly Val Val Asn Asn Tyr Gly Asn Ile Thr Ala Lys Asn Ile
            485                 490                 495

Ser Ile Thr Thr Tyr Ser Asp Ile Thr Asn Glu Gly Gln Ile Ser Ser
            500                 505                 510

Thr Gly Asp Leu Thr Leu Asn Thr Lys Asn Lys Gly Ala Ile Tyr Asn
            515                 520                 525

Tyr Ser Thr Leu Ser Ala Gly Gly Asn Met Thr Leu Thr Ala Thr Lys
            530                 535                 540

Val Val Asn Gly Gly Lys Ser Cys Gly Ile Leu Gly Leu Ala Lys Cys
545                 550                 555                 560

Gly Val Gly Thr Leu Thr Ala Asp Lys Leu Val Leu Asn Ser Ser Gln
            565                 570                 575

Lys Tyr Val Ser Asp Met Gly Gly Lys Gln Tyr Phe Lys Ser Thr Glu
            580                 585                 590

Val Asn Thr Val Lys
            595

<210> SEQ ID NO 19
<211> LENGTH: 624
<212> TYPE: PRT
<213> ORGANISM: Klebsiella pneumoniae

<400> SEQUENCE: 19

Met Met Asp Asn Leu Arg Thr Ala Ala Asn Ser Val Val Leu Lys Ile
1               5                   10                  15

Ile Phe Gly Ile Ile Val Ser Phe Ile Leu Thr Gly Val Ser Gly
            20                  25                  30

Tyr Leu Ile Gly Gly Gly Lys Asn Tyr Ala Ala Lys Val Asn Gly Gln
            35                  40                  45

Glu Ile Gly Arg Gly Gln Phe Glu Asn Ala Val Ala Ser Glu Arg Asn
        50                  55                  60

Arg Met Gln Gln Gln Leu Gly Asp Gln Phe Ser Glu Leu Ala Ala Asn
65                  70                  75                  80

Glu Asn Tyr Met Lys Thr Met Arg Gln Gln Val Leu Asn Arg Leu Ile
            85                  90                  95

Asp Glu Ser Leu Leu Asp Gln Tyr Ala Arg Glu Leu Gly Leu Ser Ile
            100                 105                 110

Ser Asp Glu Gln Val Lys Gln Ala Ile Phe Gln Thr Gln Ala Phe Gln
            115                 120                 125

Thr Asn Gly Lys Phe Asp Asn Gln Arg Phe Ser Gly Ile Val Ala Gln
            130                 135                 140

Met Gly Met Thr Thr Asp Gln Tyr Ala Gln Ala Leu Arg Asn Gln Leu
145                 150                 155                 160

Thr Thr Gln Gln Leu Ile Asn Ala Ile Ala Gly Thr Asp Phe Met Leu
            165                 170                 175

Pro Gly Glu Ser Asp Gln Leu Ala Ala Leu Val Ser Gln Gln Arg Val
            180                 185                 190

Val Arg Glu Ala Thr Ile Asn Val Asn Ala Leu Ala Ala Lys Gln Thr
            195                 200                 205

Ala Ser Asp Glu Glu Ile Asn Ala Phe Trp Gln Gln Asn Gln Ala Arg
            210                 215                 220

Phe Met Ala Pro Glu Gln Phe Arg Val Ser Tyr Ile Lys Met Asp Ala
225                 230                 235                 240

Ala Ser Met Gln Glu Ser Ala Ser Asp Glu Glu Ile Gln Ser Trp Tyr

```
                245                 250                 255
Asp Gln His Lys Asp Gln Phe Thr Gln Pro Gln Arg Asn Arg Tyr Ser
            260                 265                 270

Val Ile Gln Thr Lys Thr Glu Ala Asp Ala Lys Ala Val Leu Ala Glu
            275                 280                 285

Leu Gln Lys Gly Ala Asp Phe Ala Thr Leu Ala Lys Glu Lys Ser Thr
            290                 295                 300

Asp Ile Ile Ser Ala Arg Asn Gly Gly Asp Met Gly Trp Met Glu Asp
305                 310                 315                 320

Ala Ser Thr Val Pro Glu Leu Lys Asp Ala Gly Leu Lys Glu Lys Gly
                325                 330                 335

Gln Leu Ser Gly Val Ile Lys Ser Ser Val Gly Phe Leu Val Ala Arg
                340                 345                 350

Leu Asp Asp Val Gln Pro Ala Gln Val Lys Pro Leu Ala Asp Val Arg
                355                 360                 365

Asn Asp Ile Ala Ala Lys Val Lys Gln Glu Lys Ala Leu Asp Ala Tyr
370                 375                 380

Tyr Ala Leu Gln Gln Lys Val Ser Asp Ala Ala Ser Asn Asp Asn Glu
385                 390                 395                 400

Ser Leu Ala Ser Ala Ala Gln Val Ala Gly Leu Lys Val Val Glu Thr
                405                 410                 415

Gly Trp Phe Gly Arg Asp Asn Leu Pro Glu Glu Leu Asn Phe Lys Pro
                420                 425                 430

Val Ala Asp Ala Ile Phe Asn Gly Gly Leu Val Gly Glu Asn Gly Ala
                435                 440                 445

Pro Gly Ser Asn Ser Asp Ile Ile Thr Val Asp Gly Asp Arg Ala Phe
            450                 455                 460

Val Leu Arg Ile Ser Glu His Lys Ala Glu Ala Val Lys Pro Leu Ala
465                 470                 475                 480

Glu Val Lys Ala Gln Val Ser Asp Ile Val Lys His Asn Lys Ala Glu
                485                 490                 495

Gln Gln Ala Lys Leu Glu Ala Asp Lys Leu Leu Ala Ala Leu Lys Asp
            500                 505                 510

Gly Lys Gly Asp Glu Ala Met Lys Ala Ala Gly Leu Ser Phe Gly Ala
            515                 520                 525

Pro Gln Thr Leu Ser Arg Thr Gly Gln Asp Pro Leu Ser Gln Leu Ala
            530                 535                 540

Phe Thr Leu Pro Leu Pro Gln Gln Gly Lys Pro Val Tyr Gly Val Gly
545                 550                 555                 560

Ser Asn Met Gln Gly Asp Val Val Leu Val Ala Leu Asp Glu Val Lys
                565                 570                 575

Ala Gly Ser Met Pro Glu Glu Gln Lys Ala Met Val Gln Gly Ile
            580                 585                 590

Thr Gln Asn Asn Ala Gln Ile Ala Phe Glu Ala Leu Met Ser Asn Leu
            595                 600                 605

Arg Lys Ala Ala Lys Ile Lys Leu Gly Asp Ser Ile Asp Gln Gln Gln
            610                 615                 620

<210> SEQ ID NO 20
<211> LENGTH: 657
<212> TYPE: PRT
<213> ORGANISM: Klebsiella pneumoniae

<400> SEQUENCE: 20
```

```
Met Phe Arg Leu Asn Pro Phe Ile Arg Ala Gly Leu Ser Ala Ser Val
 1               5                  10                 15

Val Ser Leu Ala Phe Pro Ala Leu Ala Asp Val Asn Glu Glu Thr Leu
             20                  25                 30

Val Val Thr Ala Ser Ala Thr Glu Gln Asn Val Lys Asp Ala Pro Ala
             35                  40                 45

Ser Ile Ser Val Ile Thr Gln Gln Asp Leu Gln Arg Lys Pro Val Gln
 50                  55                  60

Asn Leu Lys Asp Val Leu Arg Asp Val Pro Gly Val Gln Leu Thr Asn
 65                  70                  75                 80

Glu Gly Asp Asn Arg Lys Gly Val Ser Ile Arg Gly Leu Ser Ser Ser
                 85                  90                 95

Tyr Thr Leu Ile Leu Val Asp Gly Lys Arg Val Asn Ser Arg Asn Ala
             100                 105                110

Val Phe Arg His Asn Asp Phe Asp Leu Asn Trp Ile Pro Val Asp Ala
             115                 120                125

Ile Glu Arg Ile Glu Val Arg Gly Pro Met Ser Ser Leu Tyr Gly
             130                 135                140

Ser Asp Ala Leu Gly Gly Val Val Asn Ile Ile Thr Lys Lys Ile Gly
145                 150                 155                160

Gln Lys Trp Thr Gly Thr Leu Ser Ala Asp Thr Thr Ile Gln Glu His
                165                 170                 175

Arg Asp Arg Gly Asp Thr Trp Asn Gly Gln Phe Phe Thr Ser Gly Pro
                180                 185                 190

Leu Ile Asp Gly Val Leu Gly Met Lys Ala Tyr Gly Ser Leu Ala Lys
                195                 200                 205

Arg Ala Lys Asp Asp Pro Gln Ser Ser Ser Asn Ala Thr Gly Glu Thr
                210                 215                 220

Pro Arg Ile Glu Gly Phe Thr Ser Arg Asp Gly Asn Val Glu Phe Ala
225                 230                 235                240

Trp Thr Pro Asn Glu Asn His Asp Phe Thr Ala Gly Tyr Gly Phe Asp
                245                 250                 255

Arg Gln Asp Arg Asp Ser Asp Ser Leu Asp Arg Asn Arg Leu Glu Arg
                260                 265                 270

Glu Asn Tyr Ser Leu Ser His Asn Gly Arg Trp Asp Ile Gly Asn Ser
                275                 280                 285

Glu Leu Lys Phe Tyr Gly Glu Lys Val Asp Asn Lys Asn Pro Gly Gln
                290                 295                 300

Ser Gly Thr Ile Thr Ser Glu Ser Asn Ala Ile Asp Gly Lys Tyr Val
305                 310                 315                320

Leu Pro Leu Gly Met Ile Asn Gln Leu Val Thr Phe Gly Gly Glu Trp
                325                 330                 335

Arg His Asp Lys Leu Lys Asp Pro Val Asn Leu Ser Ser Gly Gly Gln
                340                 345                 350

Ser Thr Ser Ala Ser Gln Tyr Ala Leu Phe Ile Glu Asp Glu Trp Arg
                355                 360                 365

Ile Ile Glu Pro Leu Ala Leu Thr Thr Gly Ile Arg Met Asp Asp His
                370                 375                 380

Gln Thr Tyr Gly Asp His Trp Ser Pro Arg Ala Tyr Leu Val Tyr Asn
385                 390                 395                400

Ala Thr Asp Thr Val Thr Val Lys Gly Gly Trp Ala Thr Ala Phe Lys
                405                 410                 415

Ala Pro Ser Leu Leu Gln Leu Asn Pro Asp Trp Thr Thr Asn Ser Cys
```

-continued

```
                420                 425                 430
Arg Gly Ser Cys Ser Ile Val Gly Asn Pro Asp Leu Lys Pro Glu Thr
            435                 440                 445
Ser Glu Ser Phe Glu Leu Gly Leu Tyr Tyr Arg Gly Glu Gly Trp
450                 455                 460
Leu Glu Asn Val Glu Gly Ser Ile Thr Thr Phe Gln Asn Asn Val Asp
465                 470                 475                 480
Asp Met Ile Asp Val Leu Arg Thr Ser Ser Ala Ser Glu Ala Pro Gly
                485                 490                 495
Tyr Pro Asn Phe Val Gly Trp Lys Thr Val Asn Gly Lys Arg Val Pro
            500                 505                 510
Ile Phe Arg Tyr Phe Asn Val Asn Lys Ala Arg Ile Lys Gly Val Glu
        515                 520                 525
Thr Glu Val Lys Ile Pro Phe Gly Asp Glu Trp Lys Leu Thr Val Asn
    530                 535                 540
Tyr Thr Tyr Asn Asp Gly Arg Asp Leu Ser Asn Gly Asp Lys Pro
545                 550                 555                 560
Leu Gln Thr Leu Pro Phe His Thr Ala Asn Gly Thr Leu Asp Trp Lys
                565                 570                 575
Pro Leu Asp Asp Trp Ser Phe Tyr Val Thr Ala Asn Tyr Thr Gly Gln
            580                 585                 590
Gln Arg Ala Val Ser Ala Thr Gly Lys Thr Pro Gly Tyr Thr Leu
        595                 600                 605
Phe Asp Val Gly Ala Ala Trp Gln Val Thr Lys Asn Val Lys Leu Arg
    610                 615                 620
Ser Gly Val Gln Asn Val Gly Asp Lys Asp Leu Ser Arg Asp Asp Tyr
625                 630                 635                 640
Ser Tyr Thr Glu Glu Gly Arg Arg Tyr Phe Met Ala Val Asp Tyr Arg
                645                 650                 655
Phe

<210> SEQ ID NO 21
<211> LENGTH: 675
<212> TYPE: PRT
<213> ORGANISM: Klebsiella pneumoniae

<400> SEQUENCE: 21

Met Asn Arg Ala Ala Thr Leu Thr Leu Asn Ala Pro Leu Leu Met Leu
1               5                   10                  15
Val Ala Leu Ala Leu Ser Thr Pro Phe Thr Ala Gly Ala Ala Pro
            20                  25                  30
Ala Phe Leu Asp Tyr Ala Gln Gln Gln Thr Gln Ser Gln Ala Gln
        35                  40                  45
Glu Lys Asn Asp Ala Ala Ser Ala Lys Gln Thr Gln Glu Ser Arg Gln
50                  55                  60
Ser Ala Asp Asn Lys Lys Thr Gly Thr Ser Thr Ser Gln Leu Gln Lys
65                  70                  75                  80
Arg Ile Thr Ser Gln Gln Ala Ala Ile Ala Gln Lys Asp Lys Leu Ile
                85                  90                  95
Gln Gln Leu Lys Lys Gln Leu Ala Thr Pro Gln Thr Asp Thr Ala
            100                 105                 110
Gly Ala Asn Glu Gln Ala Ala Leu Asn Lys Arg Ile Asn Glu Leu Gln
        115                 120                 125
Val Ala Leu Ser Ala Ala Thr Ala Glu Lys Glu Ala Leu Ile Lys Lys
```

```
            130                 135                 140
Ala Gly Val Val Gln Asn Asn Leu Gln Gln Ser Gln Ala Ala Ala
145                 150                 155                 160

Arg Gln Gln Ile Gln Gln Leu Thr Thr Gln Ile Gln Gln Ala Glu Ala
                165                 170                 175

Glu Asn Lys Arg Leu Ser Ala Ser Phe Thr Thr Leu Asn Lys Asp Lys
                180                 185                 190

His Ala Leu Met Thr Gln Leu Ala Ala Thr Glu Lys Glu Lys Gln Ala
                195                 200                 205

Ala Leu Glu Gln Val Lys Ala Leu Asn Ala Asp Lys Gln Pro Leu Thr
            210                 215                 220

Thr Arg Leu Ala Ala Ala Glu Lys Glu Lys Gln Ala Val Leu Glu Gln
225                 230                 235                 240

Val Lys Ala Leu Asn Ala Asp Lys Gln Ser Leu Thr Ile Arg Leu Ala
                245                 250                 255

Ala Ala Glu Lys Ala Gln Gln Ala Ala Val Asp Gln Ala Lys Ala Leu
                260                 265                 270

Asn Ala Asp Lys Gln Pro Leu Ala Thr Arg Leu Ala Ala Ala Glu Lys
                275                 280                 285

Glu Lys Gln Ala Val Leu Glu Gln Val Lys Ala Leu Ser Ala Asp Lys
            290                 295                 300

Gln Ser Leu Thr Ile Arg Leu Ala Ala Glu Lys Ala Gln Gln Ala
305                 310                 315                 320

Ala Leu Asp Gln Ala Lys Ala Leu Asn Ala Asp Lys Gln Pro Leu Ala
                325                 330                 335

Thr Arg Leu Ala Ala Ala Glu Lys Glu Lys Gln Ala Val Leu Glu Gln
                340                 345                 350

Val Lys Ala Leu Asn Ala Asp Lys Gln Ser Leu Thr Ile Arg Leu Ala
                355                 360                 365

Ala Ala Glu Lys Thr Gln Gln Ala Ala Leu Asp Gln Val Lys Ala Leu
            370                 375                 380

Asn Ala Asp Lys Gln Ser Leu Ser Thr Arg Leu Ala Ala Ala Asp Lys
385                 390                 395                 400

Ala Pro His Gly Pro Ala Asn Asp Ala Ala Ala Pro Lys Asn Glu Pro
                405                 410                 415

Pro Glu Met Ala Ala Ile Val Ala Ala Tyr Arg Leu Gln Ala Asp Lys
                420                 425                 430

Asp Asn Ala Gln Leu Arg Met Lys Glu Asp Glu Ile Glu Leu Leu Arg
                435                 440                 445

Thr Gln Leu Ser Val Gln Ser Lys Thr Arg Ser Gly Glu Ser Ala Ala
            450                 455                 460

Ala Lys Leu Ser Ala Ser Gly Glu Gln Gln Ala Tyr Ala Ile Gly Ala
465                 470                 475                 480

Ser Met Gly Ser Glu Ala Leu Asn Val Leu Thr Thr Arg Arg Thr Gln
                485                 490                 495

Gly Val Thr Val Asp Ala Gly Leu Val Leu Gln Gly Ile Glu Asp Ala
                500                 505                 510

Phe Arg Gly Gln Leu Arg Leu Gly Glu Gln Glu Arg Asn Lys Ala Leu
                515                 520                 525

Phe Asp Val Ser Gln Gln Val Phe Gln Asn Leu Asn Lys Ile Glu Gln
                530                 535                 540

Lys Asn Ile Ser Ala Gly Lys Lys Tyr Gln Gln Ala Phe Ala Arg Lys
545                 550                 555                 560
```

```
Lys Asp Val Val Phe Lys Glu Gly Val Tyr Ser Arg Val Asp Tyr Leu
                565                 570                 575

Gly Lys Gly Lys Ile Ser Gly Asn Asp Leu Val Thr Val Ile Lys
            580                 585                 590

Glu Met Leu Thr Asp Gly Thr Val Ile Asn Asp Met Glu Ala Lys Asp
            595                 600                 605

Gln Ala Leu Thr Gln Lys Leu Asp Ala Tyr Pro Pro Val Phe Arg Glu
            610                 615                 620

Pro Leu Lys Arg Leu Gln Asn His Gly Ser Val Thr Leu Val Val Pro
625                 630                 635                 640

Pro Glu Lys Ala Tyr Gly Ser Lys Gly Leu Pro Pro Lys Ile Pro Pro
                645                 650                 655

Gly Ala Thr Met Val Tyr Ser Val Arg Ile Val Asp Ser Gln Pro Glu
                660                 665                 670

Pro Ala Lys
        675

<210> SEQ ID NO 22
<211> LENGTH: 701
<212> TYPE: PRT
<213> ORGANISM: Klebsiella pneumoniae

<400> SEQUENCE: 22

Met Lys Ile Leu Ser Val Arg His Ala Ala Leu Pro Ala Leu Leu Leu
1               5                   10                  15

Pro Leu Ile Ala Ala Gln Ala Ala Asp Glu Gln Thr Met Val Val
            20                  25                  30

Thr Ala Ala Pro Thr Thr Val Ser Glu Leu Asp Thr Pro Ala Ala Val
            35                  40                  45

Ser Val Val Asn Gly Asp Glu Met Arg Gln Ala Ala Pro Arg Val Asn
        50                  55                  60

Leu Ser Glu Ser Leu Gly Ala Val Pro Gly Leu Gln Val Gln Asn Arg
65                  70                  75                  80

Gln Asn Tyr Ala Gln Asp Leu Gln Leu Ser Ile Arg Gly Phe Gly Ser
                85                  90                  95

Arg Ser Thr Tyr Gly Val Arg Gly Leu Arg Ile Tyr Val Asp Gly Ile
            100                 105                 110

Pro Ala Thr Met Pro Asp Gly Gln Gly Gln Thr Ser Asn Ile Asp Ile
            115                 120                 125

Gly Ser Val Asp Thr Ile Glu Val Leu Arg Gly Pro Phe Ser Ala Leu
        130                 135                 140

Tyr Gly Asn Ser Ser Gly Gly Val Ile Asn Val Thr Ser Gln Thr Gly
145                 150                 155                 160

Thr Gln Pro Pro Thr Val Glu Ala Ser Ser Tyr Tyr Gly Ser Phe Gly
                165                 170                 175

Thr Trp His Tyr Gly Met Lys Ala Thr Gly Ala Val Gly Asp Gly Ser
                180                 185                 190

His Ala Gly Asp Val Asp Tyr Thr Val Ser Thr Asn Arg Phe Thr Thr
            195                 200                 205

His Gly Tyr Arg Asp His Ser Gly Ala Arg Lys Asn Leu Ala Asn Ala
            210                 215                 220

Arg Leu Gly Val Arg Ile Asn Asp Val Ser Lys Leu Thr Leu Leu Leu
225                 230                 235                 240

Asn Ser Val Asp Ile Lys Ala Asn Asp Ala Gly Gly Leu Thr Ala Asp
```

-continued

```
            245                 250                 255
Glu Trp Arg Asp Asn Pro Arg Gln Ser Pro Arg Gly Asp Gln Tyr Asn
            260                 265                 270

Thr Arg Lys Asn Thr Arg Gln Thr Gln Ala Gly Leu Arg Tyr Glu Arg
            275                 280                 285

Gln Leu Ser Ala Gln Asp Asp Leu Ser Val Met Met Tyr Ala Gly Glu
            290                 295                 300

Arg Glu Thr Thr Gln Phe Gln Ser Ile Pro Arg Ala Pro Gln Leu Lys
305                 310                 315                 320

Pro Ser His Ala Gly Gly Val Ile Asp Leu Thr Arg His Tyr Gln Gly
                    325                 330                 335

Ile Asp Thr Arg Leu Thr His Arg Gly Glu Leu Leu Val Pro Val Thr
                340                 345                 350

Leu Thr Ala Gly Leu Asp Tyr Glu Asn Met Ser Glu Arg Arg Lys Gly
                355                 360                 365

Tyr Glu Asn Phe Val Met Val Asn Gly Ala Pro Gln Tyr Gly Glu Gln
            370                 375                 380

Gly Ala Leu Arg Arg Asn Glu Arg Asn Leu Met Trp Asn Val Asp Pro
385                 390                 395                 400

Tyr Leu Gln Thr Gln Trp Gln Leu Thr Asp Lys Leu Ser Leu Asp Ala
                    405                 410                 415

Gly Val Arg Tyr Ser Ser Val Trp Phe Asp Ser Asn Asp Tyr Tyr Ile
                420                 425                 430

Thr Pro Gly Asn Gly Asp Asp Ser Gly Asp Ala Ser Tyr His Lys Trp
                435                 440                 445

Leu Pro Ala Gly Ser Leu Lys Tyr Ala Leu Thr Asp Ala Trp Asn Val
450                 455                 460

Tyr Leu Ser Ala Gly Arg Gly Phe Glu Thr Pro Thr Ile Asn Glu Leu
465                 470                 475                 480

Ser Tyr Arg Ser Asp Asn Gln Ser Gly Leu Asn Phe Gly Leu Lys Pro
                485                 490                 495

Ser Thr Asn Asp Thr Val Glu Ile Gly Ser Lys Thr Arg Ile Gly Asn
                500                 505                 510

Gly Leu Phe Thr Ala Ala Leu Phe Gln Thr Asn Thr Asp Asn Glu Ile
            515                 520                 525

Val Val Asp Ser Ser Gly Gly Arg Thr Ser Tyr Lys Asn Ala Gly
            530                 535                 540

Lys Thr Arg Arg Gln Gly Met Glu Leu Gly Leu Asp Gln Gln Phe Gly
545                 550                 555                 560

Glu Ser Trp Arg Leu Lys Ala Ala Trp Thr Trp Leu Asp Ala Thr Tyr
                565                 570                 575

Arg Thr Asn Val Cys Asp Asp Ala Ser Cys Asn Gly Asn Arg Ile Pro
                580                 585                 590

Gly Ile Ala Arg Asn Met Gly Tyr Ala Ser Phe Gly Tyr Gln Pro Glu
                595                 600                 605

Gln Gly Trp Tyr Ala Gly Ser Asp Ile Arg Tyr Met Ser Asp Ile Met
            610                 615                 620

Ala Asn Asp Glu Asn Thr Ala Lys Ala Pro Ser Trp Thr Val Val Gly
625                 630                 635                 640

Leu Thr Thr Gly Tyr Lys Trp Ser Tyr Gly Arg Met Asp Met Asp Leu
                    645                 650                 655

Phe Gly Arg Ile Asp Asn Leu Phe Asp Arg Glu Tyr Val Gly Ser Val
                660                 665                 670
```

```
Ile Val Asn Glu Ser Asn Gly Arg Tyr Tyr Glu Pro Ala Pro Gly Arg
        675                 680                 685

Asn Tyr Gly Ile Gly Leu Asn Leu Ala Trp Arg Phe Glu
    690                 695                 700

<210> SEQ ID NO 23
<211> LENGTH: 752
<212> TYPE: PRT
<213> ORGANISM: Klebsiella pneumoniae

<400> SEQUENCE: 23

Met Lys Tyr Thr Ser His Phe Pro Leu Gly Ile Val Ile Pro Leu Leu
1               5                   10                  15

Ala Cys Ser Val Pro Leu Gln Ala Ala Glu Asn Met Thr Glu Gln Ser
            20                  25                  30

Thr Pro Asp Glu Ser Ala Ala Thr Ala Glu Asn His Glu Glu Thr Met
        35                  40                  45

Val Ile Thr Ala Ala Arg Gln Asn Leu Gln Ala Pro Gly Val Ser Thr
    50                  55                  60

Ile Thr Ala Glu Glu Ile Arg Lys His Pro Pro Ala Arg Asp Val Ser
65                  70                  75                  80

Glu Leu Ile Arg Thr Gln Pro Gly Val Asn Leu Thr Gly Asn Ser Thr
                85                  90                  95

Ser Gly Gln Arg Gly Asn Asn Arg Gln Ile Asp Ile Arg Gly Met Gly
            100                 105                 110

Pro Glu Asn Thr Leu Val Leu Val Asp Gly Lys Pro Val Thr Ser Arg
        115                 120                 125

Asn Ser Val Arg Tyr Gly Trp Arg Gly Asp Arg Asp Ser Arg Gly Asp
    130                 135                 140

Thr Ser Trp Val Pro Ala Glu Met Ile Asp His Ile Asp Val Ile Arg
145                 150                 155                 160

Gly Pro Ala Ala Ala Arg Tyr Gly Asn Gly Ala Met Gly Gly Val Val
                165                 170                 175

Asn Ile Val Thr Lys Pro Thr Thr Arg Glu Trp His Gly Ser Trp Asn
            180                 185                 190

Thr Tyr Met Asn Ala Pro Gln His Arg Lys Glu Gly Ala Thr Lys Arg
        195                 200                 205

Thr Asn Phe Ser Leu Asn Gly Pro Leu Ser Asp Ser Val Ser Phe Asn
    210                 215                 220

Leu Trp Gly Asn Leu Ser Lys Thr Gln Ala Asp Ala Gln Asp Ile Asn
225                 230                 235                 240

Ala Gly His Glu Ala Glu Arg Thr Gly Ser Tyr Ala Gly Ser Tyr Pro
                245                 250                 255

Ala Gly Arg Glu Gly Val Val Asn Lys Asp Ile His Ser Lys Leu Arg
            260                 265                 270

Trp Glu Phe Ala Pro Met Gln Ala Leu Glu Phe Glu Ala Gly Tyr Ser
        275                 280                 285

Arg Gln Gly Asn Leu Tyr Ala Gly Asp Thr Gln Asn Thr Asn Thr Ser
    290                 295                 300

Thr Leu Val Lys Ser Met Tyr Gly Lys Glu Thr Asn Arg Leu Tyr Arg
305                 310                 315                 320

Gln Thr Tyr Gly Val Thr Trp Thr Gly Gly Trp Asp Asn Gly Val Thr
                325                 330                 335

Ser Asn Ser Tyr Ala Gln Tyr Glu His Thr Arg Asn Ser Arg Met Asp
```

```
             340                 345                 350
Glu Gly Leu Ala Gly Gly Thr Glu Gly Ile Phe Ser Ser Ser Glu Phe
             355                 360                 365

Ser Asp Ile Asp Leu Ala Asp Val Leu Leu His Ser Glu Val Asn Ile
    370                 375                 380

Pro Phe Thr Leu Gly Val Asp Gln Asn Leu Thr Leu Gly Ala Glu Trp
385                 390                 395                 400

Asn Gln Gln Arg Met Lys Asp Gly Val Ser Thr Thr Gln Ala Leu Ser
                405                 410                 415

Tyr Gly Thr Ile Asp Gly Val Ser Ala Thr Gly Arg Ser Pro Tyr Ser
            420                 425                 430

Ser Ala Glu Ile Phe Ser Leu Phe Thr Glu Asp Asn Met Ala Leu Thr
        435                 440                 445

Asp Ser Thr Met Leu Thr Pro Ala Leu Arg Phe Asp His His Ser Ile
    450                 455                 460

Val Gly Asn Asn Trp Ser Pro Ser Leu Asn Leu Ser Gln Glu Leu Thr
465                 470                 475                 480

Asp Asp Trp Thr Leu Lys Leu Gly Ile Ala Arg Ala Tyr Lys Ala Pro
                485                 490                 495

Asn Leu Tyr Gln Leu Asn Pro Asn Tyr Ile Leu Tyr Ser Asn Gly Gln
            500                 505                 510

Gly Cys Tyr Ala Ser Ser Ala Cys Tyr Leu Met Gly Asn Ser Asp
        515                 520                 525

Leu Lys Ala Glu Thr Ser Val Asn Lys Glu Ile Gly Leu Glu Tyr Lys
    530                 535                 540

His Asp Gly Tyr Gln Ala Gly Ile Thr Trp Phe Arg Asn Asp Tyr His
545                 550                 555                 560

Asn Lys Ile Glu Ser Gly Tyr Ala Ala Val Gly Thr Ala Ser Asn Gly
                565                 570                 575

Thr Thr Asn Ile Tyr Gln Trp Glu Asn Val Pro Lys Ala Leu Val Glu
            580                 585                 590

Gly Leu Glu Gly Thr Leu Asn Leu Pro Val Gly Glu Ala Val Asn Trp
        595                 600                 605

Ser Asn Asn Leu Thr Trp Met Leu Gln Ser Lys Asn Lys Thr Thr Gly
    610                 615                 620

Asp Arg Leu Ser Val Ile Pro Gln Phe Thr Leu Asn Ser Thr Leu Ser
625                 630                 635                 640

Trp Gln Val Arg Glu Asp Leu Ser Leu Gln Ser Thr Phe Thr Trp Tyr
                645                 650                 655

Gly Arg Gln Lys Pro Lys Arg Phe Asn Tyr Lys Gly Glu Ala Val Ser
            660                 665                 670

Gly Ser Glu Leu Asn Glu Val Ser Pro Tyr Ser Ile Val Gly Leu Ser
        675                 680                 685

Ala Thr Trp Asp Val Asn Lys Asn Leu Ser Phe Thr Ser Gly Ile Asp
    690                 695                 700

Asn Leu Phe Asp Ile Arg His Tyr Arg Ala Gly Asn Ala Gln Thr Thr
705                 710                 715                 720

Gly Asn Ala Thr Thr Gly Ala Tyr Leu Tyr Gly Ala Gly Ala Glu Thr
                725                 730                 735

Tyr Asn Glu Ser Gly Arg Thr Phe Phe Met Ser Val Asn Thr His Phe
            740                 745                 750
```

<210> SEQ ID NO 24

```
<211> LENGTH: 761
<212> TYPE: PRT
<213> ORGANISM: Klebsiella pneumoniae

<400> SEQUENCE: 24
```

| | | | | | | | | | | | | | | |
|---|---|---|---|---|---|---|---|---|---|---|---|---|---|---|
| Met | Glu | Lys | Asn | Ala | Ser | Leu | Pro | Phe | Gly | Ser | Phe | Asn | Ser | Leu | Ala |
| 1 | | | | 5 | | | | | 10 | | | | | 15 | |
| Leu | Phe | Thr | Gly | Leu | Cys | Leu | Gly | Ala | Ser | Pro | Ala | Ala | Gly | Ile | Ala |
| | | | 20 | | | | | 25 | | | | | 30 | | |
| Ala | Glu | Asn | Ser | Val | Lys | Asn | Ser | Glu | Glu | Thr | Leu | Val | Glu | Ala | |
| | | 35 | | | | | 40 | | | | | 45 | | | |
| Ala | Pro | Pro | Ser | Leu | Tyr | Ser | Pro | Gly | Ala | Ser | Ala | Asp | Pro | Lys | Phe |
| | 50 | | | | | 55 | | | | | 60 | | | | |
| Asn | Lys | Pro | Leu | Val | Asp | Thr | Thr | Arg | Thr | Ile | Thr | Val | Ile | Pro | Glu |
| 65 | | | | | 70 | | | | | 75 | | | | | 80 |
| Gln | Val | Ile | Lys | Asp | Gln | Gly | Val | Thr | Asn | Leu | Thr | Asp | Ala | Leu | Lys |
| | | | | 85 | | | | | 90 | | | | | 95 | |
| Asn | Val | Pro | Gly | Val | Gly | Ala | Phe | Tyr | Ala | Gly | Glu | Asn | Gly | Ser | Ser |
| | | | 100 | | | | | 105 | | | | | 110 | | |
| Thr | Thr | Gly | Asp | Ala | Ile | Phe | Met | Arg | Gly | Val | Asp | Thr | Ser | Asn | Ser |
| | | | 115 | | | | | 120 | | | | | 125 | | |
| Ile | Tyr | Val | Asp | Gly | Ile | Arg | Asp | Ile | Gly | Ser | Val | Thr | Arg | Asp | Thr |
| | 130 | | | | | 135 | | | | | 140 | | | | |
| Phe | Asn | Thr | Gln | Gln | Val | Glu | Val | Ile | Lys | Gly | Pro | Ala | Gly | Thr | Asp |
| 145 | | | | | 150 | | | | | 155 | | | | | 160 |
| Tyr | Gly | Arg | Ser | Ala | Pro | Ser | Gly | Ser | Ile | Asn | Met | Ile | Ser | Lys | Gln |
| | | | | 165 | | | | | 170 | | | | | 175 | |
| Pro | Arg | Leu | Asp | Ser | Gly | Ile | Asp | Gly | Ser | Ala | Ser | Ile | Gly | Ser | Ala |
| | | | 180 | | | | | 185 | | | | | 190 | | |
| Trp | Ser | Arg | Arg | Gly | Thr | Leu | Asp | Leu | Asn | Gln | Ala | Phe | Ser | Asp | Asn |
| | | | 195 | | | | | 200 | | | | | 205 | | |
| Ala | Ala | Phe | Arg | Leu | Asn | Leu | Met | Gly | Glu | Lys | Thr | His | Asp | Ala | Gly |
| | 210 | | | | | 215 | | | | | 220 | | | | |
| Arg | Asp | Arg | Ile | Glu | Asn | Glu | Arg | Tyr | Gly | Ile | Ala | Pro | Ser | Leu | Ala |
| 225 | | | | | 230 | | | | | 235 | | | | | 240 |
| Phe | Gly | Leu | Asp | Thr | Pro | Thr | Arg | Leu | Tyr | Leu | Asn | Tyr | Leu | His | Val |
| | | | | 245 | | | | | 250 | | | | | 255 | |
| Arg | Gln | Asn | Asn | Thr | Pro | Asp | Gly | Gly | Ile | Pro | Thr | Val | Gly | Leu | Pro |
| | | | 260 | | | | | 265 | | | | | 270 | | |
| Gly | Tyr | Ser | Ala | Pro | Ser | Pro | Lys | Tyr | Ala | Ala | Leu | Asn | Ser | Ala | Gly |
| | | | | 275 | | | | | 280 | | | | | 285 | |
| Lys | Val | Asp | Thr | Ser | Asn | Phe | Tyr | Gly | Thr | Asp | Ser | Asp | Tyr | Asp | Lys |
| | | 290 | | | | | 295 | | | | | 300 | | | |
| Ser | Thr | Thr | Asp | Ser | Gly | Thr | Leu | Arg | Phe | Glu | His | Asp | Leu | Thr | Glu |
| 305 | | | | | 310 | | | | | 315 | | | | | 320 |
| Asn | Thr | Thr | Val | Arg | Asn | Thr | Arg | Trp | Ser | Arg | Val | Lys | Gln | Glu | |
| | | | | 325 | | | | | 330 | | | | | 335 | |
| Tyr | Leu | Leu | Thr | Ala | Val | Met | Gly | Gly | Ala | Asn | Asn | Ile | Thr | Ala | Pro |
| | | | 340 | | | | | 345 | | | | | 350 | | |
| Asp | Ile | Asn | Asp | Val | Asn | Thr | Trp | Ser | Trp | Ser | Arg | Leu | Val | Asn | Thr |
| | | | | 355 | | | | | 360 | | | | | 365 | |
| Lys | Asp | Val | Ser | Asn | Arg | Ile | Leu | Thr | Asn | Gln | Thr | Asn | Ile | Thr | Ser |
| | 370 | | | | | 375 | | | | | 380 | | | | |
| Thr | Phe | Asn | Thr | Gly | Ser | Ile | Gly | His | Asp | Val | Ser | Ala | Gly | Val | Glu |

```
            385                 390                 395                 400
        Phe Thr Arg Glu Asn Gln Thr Asn Tyr Gly Val Asn Ala Arg Thr Ala
                        405                 410                 415
        Pro Ala Val Asn Leu Tyr His Pro Val Ser Asn Leu Ser Ile Gly Gly
                        420                 425                 430
        Leu Asp Arg Asn Gly Ala Asn Ala Asn Gly Gln Thr Asp Thr Phe Gly
                        435                 440                 445
        Ile Tyr Ala Phe Asp Thr Leu Thr Leu Thr Glu Arg Ile Glu Ile Asn
                        450                 455                 460
        Gly Gly Leu Arg Leu Asp Asn Tyr His Thr Lys Tyr Asp Ser Ala Thr
        465                 470                 475                 480
        Ala Cys Gly Gly Ser Arg Gly Ala Ile Ala Cys Pro Pro Gly Gln
                                485                 490                 495
        Ser Thr Gly Ser Pro Val Thr Val Asp Thr Ala Lys Ser Gly Asn
                        500                 505                 510
        Leu Val Asn Trp Lys Ala Gly Ala Leu Tyr Arg Leu Thr Glu Gln Gly
                        515                 520                 525
        Asn Val Tyr Val Asn Tyr Ala Ile Ser Gln Gln Pro Pro Gly Gly Ser
                        530                 535                 540
        Ser Phe Ala Leu Ala Ala Ser Gly Ser Gly Asn Ser Ala Asn Arg Thr
        545                 550                 555                 560
        Asp Phe Lys Pro Gln Lys Ala Lys Ser Ser Glu Leu Gly Thr Lys Trp
                        565                 570                 575
        Gln Ile Phe Asp Asn Arg Leu Leu Ser Ala Ala Leu Phe Arg Thr
                        580                 585                 590
        Asp Ile Glu Asn Glu Val Ala Ala Asn Asp Asp Gly Thr Trp Ser Gln
                        595                 600                 605
        Tyr Gly Lys Lys Arg Val Glu Gly Tyr Glu Leu Ser Ala Thr Gly Asn
                        610                 615                 620
        Leu Thr Pro Asp Trp Thr Ile Ile Ala Gly Tyr Thr Gln Gln His Ala
        625                 630                 635                 640
        Thr Val Thr Glu Gly Gln Asn Val Ala Gln Asp Gly Ser Ser Ala Leu
                        645                 650                 655
        Ala Tyr Thr Pro Lys His Ala Phe Thr Leu Trp Thr Gln Tyr Gln Ala
                        660                 665                 670
        Thr Ser Asp Leu Ser Val Gly Gly Val Arg Tyr Val Gly Ser Leu
                        675                 680                 685
        Arg Arg Gly Ser Asp Gly Ala Val Gly Thr Pro Asp His Thr Glu Gly
        690                 695                 700
        Tyr Trp Val Ala Asp Ala Lys Leu Gly Tyr Arg Val Asn Ser Asn Leu
        705                 710                 715                 720
        Asp Leu Gln Leu Asn Met Tyr Asn Leu Phe Asp Thr Asp Tyr Val Ala
                        725                 730                 735
        Ser Ile Asn Lys Ser Gly Tyr Arg Tyr His Pro Gly Glu Pro Arg Thr
                        740                 745                 750
        Phe Met Leu Thr Ala Asn Val His Phe
                        755                 760

<210> SEQ ID NO 25
<211> LENGTH: 790
<212> TYPE: PRT
<213> ORGANISM: Klebsiella pneumoniae

<400> SEQUENCE: 25
```

```
Met Ala Thr Met Tyr Lys Ser Thr Pro Ser Ala Ala Trp Cys Lys Lys
1               5                   10                  15
Arg Leu Leu Val Thr Ser Leu Phe Ala Ala Ile Tyr Gln Thr Ser Ala
            20                  25                  30
Ile Ala Ala Asp Thr Ser Ala Val Ser Gly Glu Ala Val Asp Asp Thr
        35                  40                  45
Ser Glu Gln Met Thr Val Thr Ala Pro Ala Pro Val Gln Lys Ala Gly
    50                  55                  60
Ser Glu His Ser Ile Ser Ala Arg Glu Leu Glu Asn Lys Gly Ala Asn
65                  70                  75                  80
Asp Phe Gly Ser Ile Met Arg Tyr Glu Pro Leu Ile Ser Ala Thr Gly
                85                  90                  95
Ala Ser Gly Gly Ser Gly Asn Gly Lys Ser Gly Phe Asp Arg Gly Gly
            100                 105                 110
Tyr Thr Gly Tyr Asn Ile Arg Gly Met Glu Ser Asn Arg Val Gly Ile
            115                 120                 125
Asp Val Asp Gly Ile Ala Gln Pro Asn Ala Thr Gly Arg Gly Tyr Val
        130                 135                 140
Gly Arg Ala Gly Leu Asn Thr Phe Gly Ile Gly Arg Asp Tyr Ile Asp
145                 150                 155                 160
Pro Tyr Met Tyr Gly Ser Val Asp Ile Gln Ser Gly Ala Thr Ser Thr
                165                 170                 175
Glu Thr Ala Asn Ser Ala Ile Gly Gly Asn Val Ser Phe Arg Pro Lys
            180                 185                 190
Ser Ala Asp Asp Tyr Leu Arg Pro Gly Lys Thr Ser Ala Phe Gly Tyr
            195                 200                 205
Arg Ser Gly Tyr Asp Ser Ala Asp Arg Ser Trp His Asn Gly Val Thr
210                 215                 220
Val Ala Gly Gly Asp Glu Phe Leu Arg Gly Ile Leu Val Tyr Ser Arg
225                 230                 235                 240
Arg Asp Gly Gln Glu Thr Glu Asn Asn Ser Gly Thr Val Asp Ala Tyr
                245                 250                 255
Pro Ala Asn Trp His Ser Asp Ala Phe Leu Ala Ser Gly Ile Trp Gln
            260                 265                 270
Pro Asn Asp Glu His Lys Leu Thr Ser Thr Phe Asp Tyr Tyr His Lys
            275                 280                 285
Thr Asn His Thr His Tyr Asp Thr Trp Asp Ser Ser Gly Asn Ser Thr
290                 295                 300
Ile Gly Thr Ala Asn Gln Thr Ser Gln Thr Arg Arg Trp Gly Leu Ser
305                 310                 315                 320
Leu Lys Asp Asp Trp Thr Pro Met Asn Asp Tyr Leu Asp Ser Val Ser
                325                 330                 335
Thr Lys Ile Tyr Tyr Gln His Thr Glu Ala His Asp Trp Thr Tyr Met
            340                 345                 350
Pro Asp Ser Val Thr Arg Lys Met Gln Thr Val Asn Ser Asn Tyr Asp
            355                 360                 365
Thr Asp Thr Trp Gly Leu Gln Thr Ala Leu Ala Lys Thr Leu Gly Arg
        370                 375                 380
His Asp Leu Ser Ala Gly Phe Asn Ala Ser Thr Ser Lys Thr Gln Arg
385                 390                 395                 400
Pro Phe Ser Gln Ser Pro Ile Pro Ser Val Tyr Ser Glu Ile Met Gln
                405                 410                 415
Pro Glu Ala Asp Ser Arg Ser Tyr Thr Leu Gly Gly Phe Val Gln Asp
```

420                 425                 430
Lys Ile Asn Phe Asp Leu Asp Ser His Asn Phe Ala Val Ile Pro Gly
                435                 440                 445
Val Arg Val Val His Gln Ser Thr Lys Pro Glu Asn Leu Ser Asp Leu
    450                 455                 460
Ala Ala Asn Ser Ser Val Leu Ser Glu Ser Val Ala Asn Leu Tyr
465                 470                 475                 480
Gly Lys Asn Ser Asp Thr Gln Val Leu Pro Ser Leu Thr Phe Gln Tyr
                485                 490                 495
Asp Leu Thr Pro Arg Leu Met Thr Tyr Leu Gln Tyr Gln Arg Gly Ala
                500                 505                 510
Gln Phe Pro Asn Ala Ser Gln Leu Tyr Gly Ser Trp Asn Leu Gly Ser
                515                 520                 525
Ser Tyr Ala Gly Ser Gln Gln Tyr Ala Leu Ile Gly Asn Thr Asp Leu
                530                 535                 540
Lys Thr Glu Thr Ser Asp Asn Leu Glu Trp Gly Leu Lys Gly Glu Val
545                 550                 555                 560
Thr Glu Gly Ile Thr Leu Arg Thr Ala Leu Phe Tyr Asn Ser Tyr Lys
                565                 570                 575
Asn Phe Ile Ala Tyr Thr Arg Tyr Thr Arg Ala Asn Asn Pro Gly Gln
                580                 585                 590
Phe Thr Asn Val Pro Ser Asn Ile Tyr Thr Ile Tyr Gln Ala Glu Asn
                595                 600                 605
Arg Asp Lys Ala Tyr Ile Tyr Gly Gly Glu Ile Ser Thr Lys Phe Asn
        610                 615                 620
Phe Gly Thr Trp Phe Glu Gln Val Asp Gly Leu Ser Ala Thr Leu Ala
625                 630                 635                 640
Leu Gly Tyr Ser Glu Gly Lys Ser Lys Ser Ser Tyr Ser Gly Asp Lys
                645                 650                 655
Tyr Val Asp Leu Asp Ser Val Ala Pro Met Lys Ala Ile Val Gly Val
                660                 665                 670
Ala Trp Asp Asp Pro Ala Lys Arg Tyr Gly Thr Ala Leu Thr Ala Thr
        675                 680                 685
Phe Val Lys Gly Lys Gln Ala Thr Ala Thr Asn Arg Glu Ser Tyr Ser
        690                 695                 700
Asn Ser Gly Ser Ala Ile Thr Asp Ala Ser Ser Asp Tyr Met Arg Val
705                 710                 715                 720
Pro Gly Tyr Gly Met Leu Asp Trp Thr Ala Tyr Trp Gln Val Ala Lys
                725                 730                 735
Asn Val Arg Leu Asn Gly Gly Val Tyr Asn Leu Thr Asp Arg Lys Tyr
                740                 745                 750
Trp Asp Tyr Leu Ser Ser Arg Asn Ile Glu Thr Gly Thr Asn Gln Asp
                755                 760                 765
Ala Asn Asp Lys Ala Leu Ala Val Met Pro Gly Arg Thr Trp Gln Leu
                770                 775                 780
Gly Val Asn Val Asp Phe
785                 790

<210> SEQ ID NO 26
<211> LENGTH: 809
<212> TYPE: PRT
<213> ORGANISM: Klebsiella pneumoniae

<400> SEQUENCE: 26

-continued

```
Met Ala Met Lys Lys Leu Leu Ile Ala Ser Leu Leu Phe Ser Ser Ala
1               5                   10                  15

Thr Val Tyr Gly Ala Glu Gly Phe Val Val Lys Asp Ile His Phe Glu
            20                  25                  30

Gly Leu Gln Arg Val Ala Val Gly Ala Leu Leu Ser Met Pro Val
        35                  40                  45

Arg Pro Gly Asp Thr Val Thr Asp Asp Ile Ser Asn Thr Ile Arg
    50                  55                  60

Ala Leu Phe Ala Thr Gly Asn Phe Glu Asp Val Arg Val Leu Arg Asp
65                  70                  75                  80

Gly Asp Thr Leu Leu Val Gln Val Lys Glu Arg Pro Thr Ile Ala Ser
                85                  90                  95

Ile Thr Phe Ser Gly Asn Lys Ser Val Lys Asp Asp Met Leu Lys Gln
            100                 105                 110

Asn Leu Glu Ala Ser Gly Val Arg Val Gly Glu Ser Leu Asp Arg Thr
        115                 120                 125

Thr Ile Ala Asp Ile Glu Lys Gly Leu Glu Asp Phe Tyr Tyr Ser Val
    130                 135                 140

Gly Lys Tyr Ser Ala Ser Val Lys Ala Val Val Thr Pro Leu Pro Arg
145                 150                 155                 160

Asn Arg Val Asp Leu Lys Leu Val Phe Gln Glu Gly Val Ser Ala Lys
                165                 170                 175

Ile Gln Gln Ile Asn Ile Val Gly Asn His Ala Phe Ser Thr Asp Glu
            180                 185                 190

Leu Ile Ser His Phe Gln Leu Arg Asp Glu Val Pro Trp Trp Asn Val
        195                 200                 205

Val Gly Asp Arg Lys Tyr Gln Lys Gln Lys Leu Ala Gly Asp Leu Glu
    210                 215                 220

Thr Leu Arg Ser Tyr Tyr Leu Asp Arg Gly Tyr Ala Arg Phe Asn Ile
225                 230                 235                 240

Asp Ser Thr Gln Val Ser Leu Thr Pro Asp Lys Lys Gly Ile Tyr Ile
                245                 250                 255

Thr Val Asn Ile Thr Glu Gly Asp Gln Tyr Lys Phe Ser Gly Val Gln
            260                 265                 270

Val Thr Gly Asn Leu Ala Gly His Ser Ala Glu Ile Glu Ala Leu Thr
        275                 280                 285

Lys Val Glu Pro Gly Glu Leu Tyr Asn Gly Ala Lys Val Thr Lys Met
    290                 295                 300

Glu Asn Asp Ile Lys Lys Leu Leu Gly Arg Tyr Gly Tyr Ala Tyr Pro
305                 310                 315                 320

Arg Val Gln Ser Gln Pro Glu Ile Asn Asp Ser Asp Lys Thr Val Lys
                325                 330                 335

Leu His Val Asn Val Asp Ala Gly Asn Arg Tyr Tyr Val Arg Lys Ile
            340                 345                 350

Arg Phe Glu Gly Asn Asp Thr Ser Lys Asp Ala Val Leu Arg Arg Glu
        355                 360                 365

Met Arg Gln Met Glu Gly Ala Trp Leu Gly Ser Asp Leu Val Asp Gln
    370                 375                 380

Gly Lys Asp Arg Leu Asn Arg Leu Gly Phe Phe Glu Thr Val Asp Thr
385                 390                 395                 400

Asp Thr Gln Arg Val Pro Gly Ser Pro Asp Gln Val Asp Val Val Tyr
                405                 410                 415

Lys Val Lys Glu Arg Asn Thr Gly Ser Phe Asn Phe Gly Ile Gly Tyr
```

```
            420                 425                 430
Gly Thr Glu Ser Gly Val Ser Phe Gln Ala Gly Val Gln Gln Asp Asn
        435                 440                 445
Trp Leu Gly Thr Gly Tyr Ala Val Gly Ile Asn Gly Thr Lys Asn Asp
450                 455                 460
Tyr Gln Thr Tyr Thr Glu Leu Ser Val Thr Asn Pro Tyr Phe Thr Val
465                 470                 475                 480
Asp Gly Val Ser Leu Gly Gly Arg Val Phe Tyr Asn Asp Phe Asp Ala
                485                 490                 495
Asn Asp Ala Asp Leu Ser Asp Tyr Thr Asn Lys Ser Tyr Gly Thr Asp
            500                 505                 510
Ile Thr Leu Gly Phe Pro Val Asn Glu Tyr Asn Thr Leu Arg Ala Gly
        515                 520                 525
Val Gly Tyr Val His Asn Ser Leu Ser Asn Met Gln Pro Gln Val Ala
    530                 535                 540
Met Trp Arg Tyr Leu Asn Ser Met Gly Gln Tyr Pro Asp Asn Thr Asn
545                 550                 555                 560
Asp Arg Asn Ser Phe Ser Ala Asn Asp Phe Thr Phe Asn Tyr Gly Trp
                565                 570                 575
Thr Tyr Asn Lys Leu Asp Arg Gly Phe Phe Pro Thr Glu Gly Ser Arg
            580                 585                 590
Val Asn Leu Asn Gly Lys Val Thr Ile Pro Gly Ser Asp Asn Glu Tyr
        595                 600                 605
Tyr Lys Ala Thr Leu Asp Thr Ala Thr Tyr Val Pro Ile Asp Asn Asp
    610                 615                 620
His Gln Trp Val Val Leu Gly Arg Thr Arg Phe Gly Tyr Gly Asp Gly
625                 630                 635                 640
Ile Gly Gly Lys Glu Met Pro Phe Tyr Glu Asn Phe Tyr Ala Gly Gly
                645                 650                 655
Ser Ser Thr Val Arg Gly Phe Gln Ser Asn Thr Ile Gly Pro Lys Ala
            660                 665                 670
Val Tyr Phe Pro Ala Ser Ser Arg His Asp Asp Asp Ser Tyr Asp
        675                 680                 685
Asn Glu Cys Lys Ser Thr Glu Ser Ala Pro Cys Lys Ser Asp Asp Ala
    690                 695                 700
Val Gly Gly Asn Ala Met Ala Val Ala Ser Leu Glu Leu Ile Thr Pro
705                 710                 715                 720
Thr Pro Phe Ile Ser Asp Lys Tyr Ala Asn Ser Val Arg Thr Ser Val
                725                 730                 735
Phe Trp Asp Met Gly Thr Val Trp Asp Thr His Trp Asp Ser Ser Ala
            740                 745                 750
Tyr Ala Gly Tyr Pro Asp Tyr Ser Asp Pro Ser Asn Ile Arg Met Ser
        755                 760                 765
Ala Gly Ile Ala Val Gln Trp Met Ser Pro Leu Gly Pro Leu Val Phe
    770                 775                 780
Ser Tyr Ala Gln Pro Phe Lys Lys Tyr Asp Gly Asp Lys Ala Glu Gln
785                 790                 795                 800
Phe Gln Phe Asn Ile Gly Lys Thr Trp
                805

<210> SEQ ID NO 27
<211> LENGTH: 896
<212> TYPE: PRT
<213> ORGANISM: Klebsiella pneumoniae
```

<400> SEQUENCE: 27

Met Thr Asp Val Thr Ile Lys Ala Leu Ala Ser Glu Ile Gln Thr Ser
1               5                   10                  15

Val Asp Arg Leu Ile Gln Gln Phe Ala Asp Ala Gly Ile Arg Lys Ser
            20                  25                  30

Ala Asp Asp Ser Val Thr Ser Gln Glu Lys Gln Thr Leu Leu Thr His
        35                  40                  45

Leu Asn Arg Glu His Gly Ser Ala Pro Asp Lys Leu Thr Leu Gln Arg
    50                  55                  60

Lys Thr Arg Ser Thr Leu Asn Ile Pro Gly Thr Gly Gly Lys Ser Lys
65                  70                  75                  80

Ser Val Gln Ile Glu Val Arg Lys Lys Arg Thr Phe Val Lys Arg Asp
                85                  90                  95

Pro Gln Glu Ala Glu Arg Leu Ala Ala Glu Gln Ala Gln Arg Glu
            100                 105                 110

Ala Glu Glu Gln Ala Arg Arg Glu Ala Glu Ala Ala Lys Arg Glu
            115                 120                 125

Ala Gln Leu Lys Ala Glu Arg Glu Ala Ala Gln Ala Lys Arg Glu
        130                 135                 140

Val Ala Asp Lys Ala Lys Arg Glu Ala Ala Glu Lys Asp Lys Val Ser
145                 150                 155                 160

Asn Gln His Thr Asp Glu Met Thr Lys Thr Ala Gln Ala Glu Lys Ile
                165                 170                 175

Arg Arg Glu Asn Glu Ala Ala Glu Leu Lys Arg Lys Ser Glu Glu
            180                 185                 190

Ala Arg Arg Lys Leu Glu Glu Glu Ala Arg Arg Val Ala Glu Glu Ala
            195                 200                 205

Arg Arg Met Ala Glu Glu Asn Glu Lys Asn Trp Ser Glu Thr Ser Asp
        210                 215                 220

Ser Pro Glu Asp Ser Ser Asp Tyr His Val Thr Thr Ser Gln His Ala
225                 230                 235                 240

Arg Gln Ala Glu Asp Asp Asn Asp Arg Glu Val Glu Gly Gly Arg Gly
                245                 250                 255

Arg Ser Arg Ser Ser Lys Ala Ala Arg Pro Ala Lys Lys Gly Asn Lys
            260                 265                 270

His Ala Glu Ser Lys Ala Asp Arg Glu Glu Ala Arg Ala Ala Val Arg
        275                 280                 285

Gly Gly Lys Gly Lys His Arg Lys Gly Ser Ala Leu Gln Gln Gly
    290                 295                 300

Phe Gln Lys Pro Ala Gln Ala Val Asn Arg Asp Val Val Ile Gly Glu
305                 310                 315                 320

Thr Ile Thr Val Gly Glu Leu Ala Asn Lys Met Ala Val Lys Gly Ser
                325                 330                 335

Gln Val Ile Lys Ala Met Met Lys Leu Gly Ala Met Ala Thr Ile Asn
            340                 345                 350

Gln Val Ile Asp Gln Glu Thr Ala Gln Leu Val Ala Glu Glu Met Gly
        355                 360                 365

His Lys Val Ile Leu Arg Arg Glu Asn Glu Leu Glu Glu Ala Val Met
    370                 375                 380

Ser Asp Arg Asp Thr Gly Ala Ala Ala Glu Pro Arg Ala Pro Val Val
385                 390                 395                 400

Thr Ile Met Gly His Val Asp His Gly Lys Thr Ser Leu Leu Asp Tyr

```
                    405                 410                 415
Ile Arg Ser Thr Lys Val Ala Ser Gly Glu Ala Gly Ile Thr Gln
                420                 425                 430

His Ile Gly Ala Tyr His Val Glu Thr Asp Asn Gly Met Ile Thr Phe
                435                 440                 445

Leu Asp Thr Pro Gly His Ala Ala Phe Thr Ser Met Arg Ala Arg Gly
            450                 455                 460

Ala Gln Ala Thr Asp Ile Val Val Leu Val Val Ala Ala Asp Asp Gly
465                 470                 475                 480

Val Met Pro Gln Thr Ile Glu Ala Ile Gln His Ala Lys Ala Ala Gln
                485                 490                 495

Val Pro Val Val Val Ala Val Asn Lys Ile Asp Lys Pro Glu Ala Asp
                500                 505                 510

Pro Asp Arg Val Lys Asn Glu Leu Ser Gln Tyr Gly Ile Leu Pro Glu
            515                 520                 525

Glu Trp Gly Gly Glu Ser Gln Phe Val His Val Ser Ala Lys Ala Gly
        530                 535                 540

Thr Gly Ile Asp Asp Leu Leu Asp Ala Ile Leu Leu Gln Ala Glu Val
545                 550                 555                 560

Leu Glu Leu Lys Ala Val Arg Asn Gly Met Ala Ser Gly Ala Val Ile
                565                 570                 575

Glu Ser Phe Leu Asp Lys Gly Arg Gly Pro Val Ala Thr Val Leu Val
            580                 585                 590

Arg Glu Gly Thr Leu His Lys Gly Asp Ile Val Leu Cys Gly Phe Glu
                595                 600                 605

Tyr Gly Arg Val Arg Ala Met Arg Asp Glu Leu Gly Arg Glu Val Leu
        610                 615                 620

Glu Ala Gly Pro Ser Ile Pro Val Glu Ile Leu Gly Leu Ser Gly Val
625                 630                 635                 640

Pro Ala Ala Gly Asp Glu Val Thr Val Val Arg Asp Glu Lys Lys Ala
                645                 650                 655

Arg Glu Val Ala Leu Tyr Arg Gln Gly Lys Phe Arg Glu Val Lys Leu
            660                 665                 670

Ala Arg Gln Gln Lys Ser Lys Leu Glu Asn Met Phe Ala Asn Met Thr
                675                 680                 685

Glu Gly Glu Val His Glu Val Asn Ile Val Leu Lys Ala Asp Val Gln
        690                 695                 700

Gly Ser Val Glu Ala Ile Ser Asp Ser Leu Leu Lys Leu Ser Thr Asp
705                 710                 715                 720

Glu Val Lys Val Lys Ile Ile Gly Ser Gly Val Gly Gly Ile Thr Glu
                725                 730                 735

Thr Asp Ala Thr Leu Ala Ala Ala Ser Asn Ala Ile Leu Val Gly Phe
            740                 745                 750

Asn Val Arg Ala Asp Ala Ser Ala Arg Lys Val Ile Glu Ala Glu Ser
                755                 760                 765

Leu Asp Leu Arg Tyr Tyr Ser Val Ile Tyr Asn Leu Ile Asp Glu Val
        770                 775                 780

Lys Ala Ala Met Ser Gly Met Leu Ser Pro Glu Leu Lys Gln Gln Ile
785                 790                 795                 800

Ile Gly Leu Ala Glu Val Arg Asp Val Phe Lys Ser Pro Lys Phe Gly
                805                 810                 815

Ala Ile Ala Gly Cys Met Val Thr Glu Gly Thr Ile Lys Arg His Asn
            820                 825                 830
```

```
Pro Ile Arg Val Leu Arg Asp Asn Val Val Ile Tyr Glu Gly Glu Leu
        835                 840                 845

Glu Ser Leu Arg Arg Phe Lys Asp Asp Val Asn Glu Val Arg Asn Gly
        850                 855                 860

Met Glu Cys Gly Ile Gly Val Lys Asn Tyr Asn Asp Val Arg Val Gly
865                 870                 875                 880

Asp Met Ile Glu Val Phe Glu Ile Ile Glu Ile Gln Arg Ser Ile Asp
                885                 890                 895
```

<210> SEQ ID NO 28
<211> LENGTH: 1077
<212> TYPE: PRT
<213> ORGANISM: Klebsiella pneumoniae

<400> SEQUENCE: 28

```
Met Lys Arg Met Leu Ile Asn Ala Thr Gln Gln Glu Glu Leu Arg Val
1               5                   10                  15

Ala Leu Val Asp Gly Gln Arg Leu Tyr Asp Leu Asp Ile Glu Ser Pro
                20                  25                  30

Gly His Glu Gln Lys Lys Ala Asn Ile Tyr Lys Gly Lys Ile Thr Arg
            35                  40                  45

Ile Glu Pro Ser Leu Glu Ala Ala Phe Val Asp Tyr Gly Ala Glu Arg
50                  55                  60

His Gly Phe Leu Pro Leu Lys Glu Ile Ala Arg Glu Tyr Phe Pro Ala
65                  70                  75                  80

Asn Tyr Asn Ala His Gly Arg Pro Asn Ile Lys Asp Val Leu Arg Glu
                85                  90                  95

Gly Gln Glu Val Ile Val Gln Ile Asp Lys Glu Glu Arg Gly Asn Lys
            100                 105                 110

Gly Ala Ala Leu Thr Thr Phe Ile Ser Leu Ala Gly Ser Tyr Leu Val
            115                 120                 125

Leu Met Pro Asn Asn Pro Arg Ala Gly Gly Ile Ser Arg Arg Ile Glu
        130                 135                 140

Gly Asp Asp Arg Thr Glu Leu Lys Glu Ala Leu Ala Ser Leu Glu Leu
145                 150                 155                 160

Pro Asp Gly Met Gly Leu Ile Val Arg Thr Ala Gly Val Gly Lys Ser
                165                 170                 175

Ala Glu Ala Leu Gln Trp Asp Leu Ser Phe Arg Leu Lys His Trp Glu
            180                 185                 190

Ala Ile Gln Lys Ala Ala Glu Ser Arg Pro Ala Pro Phe Leu Ile His
        195                 200                 205

Gln Glu Ser Asn Val Ile Val Arg Ala Phe Arg Asp Tyr Leu Arg Gln
    210                 215                 220

Asp Ile Gly Glu Ile Leu Ile Asp Asn Pro Lys Val Leu Glu Leu Ala
225                 230                 235                 240

Arg Gln His Ile Ala Ala Leu Gly Arg Pro Asp Phe Ser Ser Lys Ile
                245                 250                 255

Lys Leu Tyr Thr Gly Glu Ile Pro Leu Phe Ser His Tyr Gln Ile Glu
            260                 265                 270

Ser Gln Ile Glu Ser Ala Phe Gln Arg Glu Val Arg Leu Pro Ser Gly
        275                 280                 285

Gly Ser Ile Val Ile Asp Ser Thr Glu Ala Leu Thr Ala Ile Asp Ile
    290                 295                 300

Asn Ser Ala Arg Ala Thr Arg Gly Gly Asp Ile Glu Glu Thr Ala Phe
```

-continued

```
            305                 310                 315                 320
        Asn Thr Asn Leu Glu Ala Ala Asp Glu Ile Ala Arg Gln Leu Arg Leu
                        325                 330                 335

Arg Asp Leu Gly Gly Leu Ile Val Ile Asp Phe Ile Asp Met Thr Pro
                        340                 345                 350

Val Arg His Gln Arg Ala Val Glu Asn Arg Leu Arg Glu Ala Val Arg
                        355                 360                 365

Gln Asp Arg Ala Arg Ile Gln Ile Ser His Ile Ser Arg Phe Gly Leu
                        370                 375                 380

Leu Glu Met Ser Arg Gln Arg Leu Ser Pro Ser Leu Gly Glu Ser Ser
        385                 390                 395                 400

His His Val Cys Pro Arg Cys Ser Gly Thr Gly Thr Val Arg Asp Asn
                        405                 410                 415

Glu Ser Leu Ser Leu Ser Ile Leu Arg Leu Ile Glu Glu Ala Leu
                        420                 425                 430

Lys Glu Asn Thr Lys Glu Val His Ala Ile Val Pro Val Pro Ile Ala
                        435                 440                 445

Ser Tyr Leu Leu Asn Glu Lys Arg Ala Ala Val Ser Ala Ile Glu Ser
                        450                 455                 460

Arg Gln Gly Asp Val Arg Val Ile Ile Val Pro Asn Asp Glu Met Gln
        465                 470                 475                 480

Thr Pro His Tyr Ser Val Leu Arg Val Arg Lys Gly Glu Glu Thr Ser
                        485                 490                 495

Thr Leu Ser Tyr Leu Leu Pro Lys Leu His Glu Glu Met Ala Leu
                        500                 505                 510

Pro Gly Asp Asp Glu Pro Ala Glu Arg Lys Arg Pro Glu Gln Pro Ala
                        515                 520                 525

Leu Ala Ala Phe Val Met Pro Asp Ala Pro Ala Pro Met Leu Glu
                        530                 535                 540

Glu Pro Ala Ala Ala Pro Val Ala Ala Ala Ala Pro Val Ala Ala Ala
        545                 550                 555                 560

Ala Pro Ala Gln Pro Gly Leu Leu Ser Arg Phe Phe Ser Ala Leu Lys
                        565                 570                 575

Asn Ile Phe Ser Gly Ala Glu Glu Ala Lys Pro Ala Glu Val Gln Val
                        580                 585                 590

Glu Lys Lys Ala Glu Glu Lys Pro Glu Arg Gln Gln Glu Arg Arg Lys
                        595                 600                 605

Pro Arg Ala Asn Asn Arg Arg Asp Arg Asn Asp Arg Arg Asp Asn Arg
                        610                 615                 620

Asp Asn Arg Asp Asn Arg Asp Asn Arg Asp Asn Arg Asp Thr Arg Ala
        625                 630                 635                 640

Asp Asn Ala Glu Gly Arg Glu Pro Arg Glu Ser Arg Glu Glu Asn Arg
                        645                 650                 655

Arg Asn Arg Arg Glu Lys Pro Ser Gln Asn Val Glu Ala Arg Asp Val
                        660                 665                 670

Arg Gln Thr Ser Gly Asp Asp Ala Glu Lys Ala Lys Ser Arg Asp Glu
                        675                 680                 685

Gln Gln Pro Arg Arg Glu Arg Thr Arg Arg Ser Asp Asp Lys Arg
                        690                 695                 700

Gln Ala Gln Gln Glu Ala Lys Ala Gly Thr Glu Glu Pro Val Val
        705                 710                 715                 720

Gln Glu Thr Glu Gln Glu Glu Arg Val Gln Thr Leu Pro Arg Arg Lys
                        725                 730                 735
```

Pro Arg Gln Leu Ala Gln Lys Val Arg Val Glu Ser Ala Val Val Glu
            740                 745                 750

Pro Val Ala Glu Ile Val Pro Glu Ala Val Val Ala Glu Val Ile Ala
            755                 760                 765

Pro His Ser Glu Pro Val Lys Ala Glu Leu Pro Ala Gly Val Glu Ser
        770                 775                 780

Val Ala Asp Gln Asp Glu Asn Gly Glu Ser Arg Glu Ala Asn Gly Met
785                 790                 795                 800

Pro Arg Arg Ser Arg Arg Ser Pro Arg His Leu Arg Val Ser Gly Gln
            805                 810                 815

Arg Arg Arg Arg Tyr Arg Asp Glu Arg Tyr Pro Thr Gln Ser Pro Met
            820                 825                 830

Pro Leu Thr Val Ala Cys Ala Ser Pro Glu Met Ala Ser Gly Lys Val
            835                 840                 845

Trp Ile Arg Tyr Pro Val Val Arg Pro Gln Asp Gln Pro Glu Glu
        850                 855                 860

Val Gln Val Gln Asp Ala Ser Val Ala Lys Thr Val Glu Ala Val Ala
865                 870                 875                 880

Ala Pro Val Ala Val Val Glu Thr Val Thr Ala Ala Pro Val Thr Val
            885                 890                 895

Glu Pro Ala Thr Met Glu Pro Val Thr Ala Glu Pro Val Val Glu
            900                 905                 910

Pro Val Ala Ala Ala Glu Pro Leu Val Val Asp Ala Ala Glu Val Val
            915                 920                 925

Ala Pro Ala Ala Val Glu Pro Ala Pro Gln Glu Pro Val Thr Glu Ala
            930                 935                 940

Pro Ala Val Glu Ala Pro Gln Ala Ile Ala Pro Val Thr Leu Asp Ala
945                 950                 955                 960

Glu Pro Val Val Glu Pro Glu Ala Val Glu Thr Thr Pro Val Val
            965                 970                 975

Ala Ala Pro Val Glu Thr Ile Ala Pro Val Ala Glu Thr Val Glu Gln
            980                 985                 990

Ala Pro Val Thr Glu Ala Ala Pro Ala Glu Pro Val Lys Ala Glu Pro
            995                 1000                1005

Pro Val Ser Lys Pro Val Val Val Ala Gly His Arg His Ala Thr
        1010                1015                1020

Ala Pro Met Thr Arg Ala Pro Ala Pro Asp Tyr Val Pro Glu Ala
        1025                1030                1035

Pro Arg His Ser Thr Trp Val Arg Pro Pro Phe Ala Phe Glu Gly
        1040                1045                1050

Lys Gly Ala Ala Gly Gly His Ser Ala Thr His Lys Ala Thr Ala
        1055                1060                1065

Glu Pro Thr Arg Pro Gln Pro Val Glu
        1070                1075

<210> SEQ ID NO 29
<211> LENGTH: 1159
<212> TYPE: PRT
<213> ORGANISM: Klebsiella pneumoniae

<400> SEQUENCE: 29

Met Arg Lys Leu Ser Leu Ser Leu Leu Thr Leu Ser Leu Gly Val Ala
1               5                   10                  15

Leu Leu Pro Leu Ala Gln Ala Ala Thr Thr Pro Ala Gln Glu His Leu

```
            20                  25                  30
Leu Glu Gln Val Arg Leu Gly Glu Ala Ser Asn Arg Glu Asp Leu Val
         35                  40                  45
Arg Gln Ser Leu Tyr Arg Leu Glu Leu Ile Asp Pro Asn Asn Pro Glu
         50                  55                  60
Leu Ile Ala Ala Arg Met Arg Tyr Leu Leu Arg Gln Gly Asp Ala Ala
 65                  70                  75                  80
Gly Ala Gln Lys Glu Leu Glu Arg Leu Thr Lys Gln Ala Pro Asp Ser
                 85                  90                  95
Pro Glu Leu Lys Ala Ser Arg Asn Glu Met Lys Ser Asn Thr Gly Glu
                100                 105                 110
Gly Arg Gln Ala Leu Gln Ala Arg Leu Leu Gly Val Ala Gly Lys
                115                 120                 125
Val Asp Glu Ala Ile Ala Ala Tyr Glu Lys Leu Tyr Gly Gly Val Pro
        130                 135                 140
Asp Asp Val Asp Val Ala Ile Glu Tyr Trp Thr Leu Val Ala Arg Leu
145                 150                 155                 160
Pro Ala Arg His Ser Glu Gly Val Ser Gln Leu Lys Lys Leu Asn Ala
                165                 170                 175
Ser Ala Pro Gly Asn Val Ser Leu Leu Thr Ser Leu Ala Lys Gln Met
                180                 185                 190
Phe Ala Asp Asn Lys Pro Gln Glu Gly Phe Ala Tyr Leu Ala Glu Met
                195                 200                 205
Ala Arg Ser Ala Ser Gly Arg Gly Ile Ala Ala Asp Met Trp Phe Ser
        210                 215                 220
Glu Val Lys Ser Met Pro Val Ser Lys Ala Ser Val Gln Ala Leu Gln
225                 230                 235                 240
Gln Phe Leu Leu Gln Phe Pro Thr Gly Ser Val Ala Ala Asn Ala Arg
                245                 250                 255
Val Leu Leu Asp Gln Gln Gln Ala Gln Leu Gln Asp Pro Thr Phe Arg
                260                 265                 270
Ala Arg Ser Glu Gly Leu Ala Ala Val Lys Ser Gly Asn Thr Thr Gln
        275                 280                 285
Ala Val Ala Asp Leu Gln Lys Ala Val Gln Ala Asp Ser Arg Asp Ser
        290                 295                 300
Asp Ala Val Gly Ala Leu Gly Gln Ala Tyr Ser Gln Arg Gly Asp Arg
305                 310                 315                 320
Ala Arg Ala Val Ala Gln Leu Ser Lys Ala Ile Ala Met Asp Pro Asp
                325                 330                 335
Ser Pro Asn Arg Gly Lys Trp Asp Ser Leu Leu Gln Thr Asn Arg Tyr
                340                 345                 350
Trp Leu Leu Ile Lys Gln Gly Asp Asn Ala Leu Lys Ala Gly Gln Leu
        355                 360                 365
Ser Gln Ala Gln Asn Tyr Tyr Ala Gln Ala Gln Arg Val Asp Arg Thr
        370                 375                 380
Asp Ser Tyr Ala Val Leu Gly Leu Gly Asp Val Ala Ala Ala Arg Lys
385                 390                 395                 400
Glu Ala Ala Ala Ala Glu Arg Tyr Tyr Gln Gln Ala Leu Arg Leu Asp
                405                 410                 415
Arg Gly Asn Asn Leu Ala Val Arg Gly Leu Ala Asn Leu Tyr Arg Ala
                420                 425                 430
Glu Ser Pro Glu Lys Ala Ser Ala Trp Ile Ala Gly Leu Pro Pro Ala
                435                 440                 445
```

```
Gln Arg Arg Ser Ile Asp Asp Ile Glu Arg Ser Leu Thr Asn Asp Arg
    450                 455                 460

Leu Glu Lys Gln Ala Gln Ala Leu Glu Ser Gln Gly Asn Trp Ala Gln
465                 470                 475                 480

Ala Ala Glu Val Gln Arg Arg Leu Ala Leu Asp Pro Asp Ser Val
            485                 490                 495

Trp Ile Thr Tyr Arg Leu Ala Arg Asp Leu Val Ser Ala Gly Glu Arg
            500                 505                 510

Gln Glu Ala Asp Ala Leu Met Arg Thr Met Val Asn Arg Gln Pro Gln
        515                 520                 525

Asp Ala Glu Arg Val Tyr Ala Ser Gly Leu Tyr Leu Ser Gly Asn Asp
    530                 535                 540

Gln Asp Asp Leu Ala Leu Ala Gln Ile Ala Ala Leu Pro Arg Ser Ala
545                 550                 555                 560

Trp Thr Asp Asn Ile Arg Glu Leu Glu Ala Arg Leu Gln Ser Asp Arg
            565                 570                 575

Val Leu Arg Gln Ala Asn Gln Leu Arg Asp Ser Gly Asn Glu Ala Gln
            580                 585                 590

Ala Ile Ala Leu Ile Arg Gln Gln Pro Ala Ser Val Arg Tyr Asp Leu
        595                 600                 605

Thr Leu Ala Asp Trp Ala Gln Gln Arg Gly Asp Ser Gln Thr Ala Ile
    610                 615                 620

Ala Asn Tyr Gln Arg Val Leu Arg Gln Glu Ala Asp Asn Gly Asp Ala
625                 630                 635                 640

Arg Leu Gly Leu Ala Glu Val Tyr Leu Ala Glu Gly Asp Lys Pro Ala
            645                 650                 655

Ala Arg Ala Gln Val Met Gln Leu Lys Gly Ala Glu Thr Glu Ser Met
            660                 665                 670

Asn Met Gln Arg Arg Val Ala Leu Ala Arg Ala Gly Leu Gly Asp Thr
        675                 680                 685

Ala Asp Ala Gln Arg Ile Phe Asn Gln Ile Val Pro Gln Ala Lys Ala
    690                 695                 700

Gln Pro Pro Ser Met Glu Ser Ala Leu Val Leu Arg Asp Ala Ala Arg
705                 710                 715                 720

Phe Ala Thr Gln Ser Gly Ala Pro Gln Gln Ala Leu Thr His Tyr Arg
            725                 730                 735

Glu Ala Met Val Ala Ser Gly Ile Thr Pro Ala Gln Pro Gln Asp Asn
            740                 745                 750

Asp Thr Phe Thr Arg Leu Thr Arg Asn Asp Ser His Asp Asp Trp Leu
        755                 760                 765

Lys Arg Gly Ile Arg Ser Asp Ala Ala Asp Leu Tyr Arg Gln Gln Asp
    770                 775                 780

Leu Asn Val Thr Leu Glu His Asp Phe Trp Gly Ser Ser Gly Thr Gly
785                 790                 795                 800

Gly Tyr Ser Asp Leu Lys Ala His Thr Thr Met Leu Gln Met Asp Ala
            805                 810                 815

Pro Leu Ala Asp Gly Arg Met Phe Phe Arg Thr Asp Leu Val Asn Met
            820                 825                 830

Asp Ala Gly Ser Phe Ser Thr His Ser Asp Gly Ser Tyr Ser Pro Ser
        835                 840                 845

Trp Gly Thr Cys Gly Glu Ile Ala Cys Thr Ser Gly Ser Lys Asn Gln
    850                 855                 860
```

Thr Asp Ser Gly Ala Ser Val Ala Val Gly Trp Lys Asn Asp Thr Trp
865                 870                 875                 880

Ser Gly Asp Ile Gly Thr Thr Pro Met Gly Phe Asn Val Val Asp Val
            885                 890                 895

Val Gly Gly Leu Ser Tyr Ser Ser Asp Val Gly Pro Val Gly Tyr Thr
            900                 905                 910

Val Asn Val His Arg Arg Pro Ile Ser Ser Ser Leu Leu Ser Phe Gly
        915                 920                 925

Gly Gln Lys Asp Ser Ser Ser His Thr Gly Ala Thr Trp Gly Gly Val
    930                 935                 940

Arg Ala Asp Gly Gly Leu Ser Leu Ser Tyr Asp Arg Gly Glu Ala
945                 950                 955                 960

His Gly Ile Trp Ser Ser Leu Gly Ala Asp Ser Leu Thr Gly Lys Asn
            965                 970                 975

Val Ala Asp Asn Trp Arg Val Arg Trp Met Thr Gly Tyr Tyr Tyr Lys
        980                 985                 990

Val Ile Asn Glu Asn Asn Arg Arg Val Thr Val Gly Leu Asn Asn Met
    995                 1000                1005

Ile Trp His Tyr Asp Lys Asp Leu Ser Gly Tyr Thr Leu Gly Gln
    1010                1015                1020

Gly Gly Tyr Tyr Ser Pro Gln Glu Tyr Leu Ser Phe Ala Val Pro
    1025                1030                1035

Val Thr Trp Arg Gln Arg Thr Glu Asn Trp Ser Trp Glu Leu Gly
    1040                1045                1050

Gly Ser Val Ser Trp Ser His Ser Arg Thr Gln Thr Gln Ala Arg
    1055                1060                1065

Tyr Pro Leu Leu Asn Leu Ile Pro Ser Asp Tyr Arg Gln Arg Ala
    1070                1075                1080

Ser Glu Leu Thr Glu Glu Gly Ser Ser Ser His Gly Phe Gly Tyr
    1085                1090                1095

Thr Ala Arg Ala Leu Val Glu Arg Arg Val Thr Ser Asn Trp Phe
    1100                1105                1110

Val Gly Ala Ala Val Asp Ile Gln Gln Ala Lys Asp Tyr Thr Pro
    1115                1120                1125

Ser His Ala Leu Leu Tyr Val Arg Tyr Ser Ala Ala Gly Trp Gln
    1130                1135                1140

Gly Asp Leu Asp Met Pro Pro Gln Pro Leu Val Pro Tyr Ala Asp
    1145                1150                1155

Trp

<210> SEQ ID NO 30
<211> LENGTH: 1411
<212> TYPE: PRT
<213> ORGANISM: Klebsiella pneumoniae

<400> SEQUENCE: 30

Met Ser Gln Glu Tyr Thr Glu Asp Lys Glu Val Lys Leu Thr Lys Leu
1               5                   10                  15

Ser Ser Gly Arg Arg Leu Leu Glu Ala Met Leu Ile Leu Cys Ser Leu
                20                  25                  30

Phe Ala Ile Trp Leu Met Ala Ala Leu Leu Ser Phe Asn Pro Ser Asp
            35                  40                  45

Pro Ser Trp Ser Gln Thr Ala Trp His Glu Pro Ile His Asn Leu Gly
        50                  55                  60

```
Gly Ala Pro Gly Ala Trp Leu Ala Asp Thr Leu Phe Phe Ile Phe Gly
 65                  70                  75                  80

Val Met Ala Tyr Thr Ile Pro Val Ile Ile Gly Gly Cys Trp Phe
                 85                  90                  95

Ala Trp Arg His Gln Glu Asn Asp Glu Tyr Ile Asp Tyr Phe Ala Val
                100                 105                 110

Ser Leu Arg Leu Ile Gly Ala Leu Ala Leu Ile Leu Thr Ser Cys Gly
                115                 120                 125

Leu Ala Ala Ile Asn Ala Asp Asp Ile Trp Tyr Phe Ala Ser Gly Gly
                130                 135                 140

Val Ile Gly Ser Leu Leu Ser Thr Thr Leu Gln Pro Leu Leu His Ser
145                 150                 155                 160

Ser Gly Gly Thr Ile Ala Leu Leu Cys Ile Trp Ala Ala Gly Leu Thr
                165                 170                 175

Leu Phe Thr Gly Trp Ser Trp Val Ser Ile Ala Glu Lys Leu Gly Gly
                180                 185                 190

Gly Ile Leu Ser Val Leu Thr Phe Ala Ser Asn Arg Thr Arg Arg Asp
                195                 200                 205

Asp Thr Trp Val Asp Glu Gly Glu Tyr Glu Asp Glu Glu Glu Tyr
                210                 215                 220

Asp Asp Glu Glu Ala Ala Arg Pro Gln Glu Ser Arg Arg Ala Arg Ile
225                 230                 235                 240

Leu Arg Ser Ala Leu Ala Arg Arg Lys Arg Leu Ala Glu Lys Phe Thr
                245                 250                 255

Asn Pro Met Gly Arg Lys Thr Asp Ala Ala Leu Phe Ser Gly Lys Arg
                260                 265                 270

Met Asp Asp Gly Glu Glu Val Val Gln Tyr Ser Ala Ser Gly Ala Pro
                275                 280                 285

Val Ala Ala Asp Asp Val Leu Phe Ser Gly Ala Ser Ala Ala Arg Pro
                290                 295                 300

Ala Glu Asp Asp Val Leu Phe Ser Gly Ala Ser Ala Val Arg Pro Gly
305                 310                 315                 320

Asp Phe Asp Pro Tyr Asp Pro Leu Leu Asn Gly His Ser Ile Ala Glu
                325                 330                 335

Pro Val Ser Ala Ala Ala Ala Thr Ala Ala Pro Gln Ala Trp Ala
                340                 345                 350

Glu Ser Pro Val Gly His His Gly Ala Ala Pro Ala Tyr Gln Pro Glu
                355                 360                 365

Ala Ser Tyr Pro Pro Gln Gln Ala Tyr Gln Pro Glu Pro Ala Pro Phe
                370                 375                 380

Gln Gln Ala Tyr Gln Pro Glu Pro Ala Pro Phe Gln Gln Ala Tyr
385                 390                 395                 400

Gln Pro Pro Ala Gly Gln Thr Ala Pro Gln Ala Tyr Gln Pro Glu Pro
                405                 410                 415

Ala Pro Tyr Gln Gln Pro Val Tyr Asp Pro Arg Ala Gly Gln Pro Ala
                420                 425                 430

Pro Gln Ala Tyr Gln Pro Glu Pro Ala Pro Tyr Gln Gln Pro Ala Tyr
                435                 440                 445

Asp Pro Tyr Ala Gly Gln Pro Ala Pro Gln Ala Tyr Gln Pro Glu Pro
                450                 455                 460

Ala Pro Tyr Gln Gln Pro Ala Tyr Asp Pro His Ala Gly Gln Pro Ala
465                 470                 475                 480

Pro Gln Ala Tyr Gln Pro Glu Pro Ala Pro Tyr Gln Gln Pro Ala Tyr
```

-continued

```
                485                 490                 495
Asp Pro Tyr Ala Gly Gln Pro Ala Pro Gln Ala Tyr Gln Pro Glu Pro
                500                 505                 510
Ala Pro Tyr Gln Gln Pro Thr Tyr Asp Pro Tyr Ala Gly Gln Pro Ala
                515                 520                 525
Pro Gln Thr Tyr Gln Gln Pro Ala Tyr Asp Pro Asn Ala Gly Gln Pro
                530                 535                 540
Ala Pro Gln Pro Tyr Gln Pro Glu Pro Ala Ala Tyr Gln Pro Gln Ser
545                 550                 555                 560
Ala Pro Val Pro Pro Glu Pro Glu Pro Val Val Gln Glu Glu
                565                 570                 575
Val Lys Arg Pro Pro Leu Tyr Tyr Phe Glu Val Glu Glu Lys Arg
                580                 585                 590
Ala Arg Glu Arg Glu Leu Leu Ala Ser Trp Tyr Gln Pro Ile Pro Glu
                595                 600                 605
Pro Glu Ser Pro Ile Ala Thr Lys Pro Leu Thr Pro Pro Thr Thr Ala
                610                 615                 620
Ser Lys Pro Pro Val Glu Thr Val Val Ser Ala Val Ala Gly
625                 630                 635                 640
Val His Gln Ala Thr Ala Ala Ser Gly Gly Ala Ala Ala Thr Ser
                645                 650                 655
Ser Thr Ala Ala Ser Ala Ala Ala Thr Pro Leu Phe Ser Pro Ala Ser
                660                 665                 670
Ser Gly Pro Arg Val Gln Val Lys Glu Gly Ile Gly Pro Lys Leu Pro
                675                 680                 685
Arg Pro Asn Arg Val Arg Val Pro Thr Arg Arg Glu Leu Ala Ser Tyr
                690                 695                 700
Gly Ile Lys Leu Pro Ser Gln Arg Glu Ala Gln Arg Ala Arg Gln
705                 710                 715                 720
Ala Glu Arg Asp Pro His Tyr Asp Asp Glu Leu Leu Ser Asp Glu Glu
                725                 730                 735
Ala Asp Ala Met Glu Gln Asp Glu Leu Ala Arg Gln Phe Ala Ala Thr
                740                 745                 750
Gln Gln Gln Arg Tyr Gly His Arg Trp Glu Asp Asp Asn Ala Thr Asp
                755                 760                 765
Asp Asp Glu Ala Asp Ala Ala Ala Glu Ala Glu Leu Ala Arg Gln Phe
                770                 775                 780
Ala Ala Thr Gln Gln Gln Arg Tyr Ala Thr Glu Gln Pro Pro Gly Ala
785                 790                 795                 800
Asn Pro Phe Ser Pro Ala Asp Tyr Glu Phe Ser Pro Met Lys Thr Leu
                805                 810                 815
Val Asn Asp Gly Pro Ser Glu Pro Leu Phe Thr Pro Thr Pro Glu Val
                820                 825                 830
Gln Pro Gln Gln Pro Ala Gln Arg Tyr Gln Gln Pro Ala Ala Ala Pro
                835                 840                 845
Gln Gln Gly Tyr Gln Pro Ala Gln His Gln Pro Ile His His Gln Pro
                850                 855                 860
Val Pro Pro Gln Pro Gln Ser Tyr Pro Thr Ala Ser Gln Pro Val Gln
865                 870                 875                 880
Pro Gln Gln Pro Val Ala Pro Gln Gly His Gln Pro Ala Ala Pro Ala
                885                 890                 895
Pro Gln Glu Ser Leu Ile His Pro Leu Leu Met Arg Asn Gly Asp Ser
                900                 905                 910
```

```
Arg Pro Leu Gln Lys Pro Thr Thr Pro Leu Pro Ser Leu Asp Leu Leu
    915                 920                 925

Thr Pro Pro Pro Ser Glu Val Glu Pro Val Asp Thr Phe Ala Leu Glu
    930                 935                 940

Gln Met Ala Arg Leu Val Glu Ala Arg Leu Ala Asp Phe Arg Ile Lys
945                 950                 955                 960

Ala Asp Val Val Asn Tyr Ser Pro Gly Pro Val Ile Thr Arg Phe Glu
                965                 970                 975

Leu Asn Leu Ala Pro Gly Val Lys Ala Ala Arg Ile Ser Asn Leu Ser
                980                 985                 990

Arg Asp Leu Ala Arg Ser Leu Ser Thr Val Ala Val Arg Val Val Glu
                995                 1000                1005

Val Ile Pro Gly Lys Pro Tyr Val Gly Leu Glu Leu Pro Asn Lys
    1010                1015                1020

Lys Arg Gln Thr Val Tyr Leu Arg Glu Val Leu Asp Asn Ala Lys
    1025                1030                1035

Phe Arg Asp Asn Pro Ser Pro Leu Thr Val Val Leu Gly Lys Asp
    1040                1045                1050

Ile Ala Gly Asp Pro Val Val Ala Asp Leu Ala Lys Met Pro His
    1055                1060                1065

Leu Leu Val Ala Gly Thr Thr Gly Ser Gly Lys Ser Val Gly Val
    1070                1075                1080

Asn Ala Met Ile Leu Ser Met Leu Tyr Lys Ala Gln Pro Glu Asp
    1085                1090                1095

Val Arg Phe Ile Met Ile Asp Pro Lys Met Leu Glu Leu Ser Val
    1100                1105                1110

Tyr Glu Gly Ile Pro His Leu Leu Thr Glu Val Val Thr Asp Met
    1115                1120                1125

Lys Asp Ala Ala Asn Ala Leu Arg Trp Ser Val Asn Glu Met Glu
    1130                1135                1140

Arg Arg Tyr Lys Leu Met Ser Ala Leu Gly Val Arg Asn Leu Ala
    1145                1150                1155

Gly Tyr Asn Glu Lys Ile Ala Glu Ala Ala Arg Met Gly Arg Pro
    1160                1165                1170

Ile Pro Asp Pro Tyr Trp Lys Pro Gly Asp Ser Met Asp Ala Val
    1175                1180                1185

His Pro Val Leu Glu Lys Leu Pro Tyr Ile Val Val Leu Val Asp
    1190                1195                1200

Glu Phe Ala Asp Leu Met Met Thr Val Gly Lys Lys Val Glu Glu
    1205                1210                1215

Leu Ile Ala Arg Leu Ala Gln Lys Ala Arg Ala Ala Gly Ile His
    1220                1225                1230

Leu Val Leu Ala Thr Gln Arg Pro Ser Val Asp Val Ile Thr Gly
    1235                1240                1245

Leu Ile Lys Ala Asn Ile Pro Thr Arg Ile Ala Phe Thr Val Ser
    1250                1255                1260

Ser Lys Ile Asp Ser Arg Thr Ile Leu Asp Gln Gly Gly Ala Glu
    1265                1270                1275

Ser Leu Leu Gly Met Gly Asp Met Leu Tyr Ser Gly Pro Asn Ser
    1280                1285                1290

Thr Thr Pro Val Arg Val His Gly Ala Phe Val Arg Asp Gln Glu
    1295                1300                1305
```

```
Val His Ala Val Val Gln Asp Trp Lys Ala Arg Gly Arg Pro Gln
    1310                1315                1320

Tyr Val Asp Gly Ile Thr Ser Asp Ser Glu Ser Glu Gly Gly Gly
    1325                1330                1335

Gly Gly Phe Asp Gly Gly Glu Glu Leu Asp Pro Leu Phe Asp Gln
    1340                1345                1350

Ala Val Asn Phe Val Thr Glu Lys Arg Lys Ala Ser Ile Ser Gly
    1355                1360                1365

Val Gln Arg Gln Phe Arg Ile Gly Tyr Asn Arg Ala Ala Arg Ile
    1370                1375                1380

Ile Glu Gln Met Glu Ala Gln Gly Ile Val Ser Glu Gln Gly His
    1385                1390                1395

Asn Gly Asn Arg Glu Val Leu Ala Pro Pro Pro Phe Glu
    1400                1405                1410

<210> SEQ ID NO 31
<211> LENGTH: 285
<212> TYPE: DNA
<213> ORGANISM: Klebsiella pneumoniae

<400> SEQUENCE: 31
atgaagaagt tagctttact ctccgccgta atgacgcttg aatgtcgtc atgggctttt      60 gctgccgaca acccgccgcc gccgccggaa aaaggcgcgc agcatcaggg taaaccgccg    120
gtgaaaaacg gccaacacga aggtaagcaa gcgcaataca acagaaaaca gccacaacga    180
gacggcaaac agccgcagca cgacggtaaa cagccgcagc acaacggcaa gcagccgcca    240
aaagggagcg agcacagcgg gaaaccgctg ccgccgaaag cgtaa                   285

<210> SEQ ID NO 32
<211> LENGTH: 354
<212> TYPE: DNA
<213> ORGANISM: Klebsiella pneumoniae

<400> SEQUENCE: 32
atgaaacgtt acgcaaccgc actgctcttt tgcactctgt cgctgaccag cctggccgct     60
cgcgccgata ttatcgatga cgcgatcggc aatattcagc aagccattaa cgacgcctat    120
aaccccggca gcagtcgctc cgatgacgac gacagatacg atgacgatgg ccggtatgat    180
gacgggcgct atcaggggag ccgtcagcag agccgtgaca gtcagcgcca gtatgacgag    240
cggcaacgcc agctggacga gcgccgccgc cagctggatg aacgccagcg tcagctcgac    300
cgcgatcgtc gtcagttaga aagcgaccag cgtcgtctgg atgatagcta ctga          354

<210> SEQ ID NO 33
<211> LENGTH: 360
<212> TYPE: DNA
<213> ORGANISM: Klebsiella pneumoniae

<400> SEQUENCE: 33
atgttcaggt cactgattct ggcagcagta ctgctggccg cagggccact ggtcgctaac     60
gctggtgaaa tcaccctgct gccatcggta aaattacaaa taggcgatcg tgacaattac    120
ggtaactact gggacggtgg cagctggcgc gaccgtgatt actggcgtcg tcactatgaa    180
tggcgtgata accgttggca tcgtcatgac aacggctggc acaaggctgg tacaaaggc    240 agagataaag cctgggagcg cggctatcgt gctggctgga acgaccgcga tgaccaccgc    300
ggcggctggg gtcgcggccc gggcgggcgc ggtcacggtc atggacatgg ccatcactaa    360
```

<210> SEQ ID NO 34
<211> LENGTH: 363
<212> TYPE: DNA
<213> ORGANISM: Klebsiella pneumoniae

<400> SEQUENCE: 34

| | | | | | | |
|---|---|---|---|---|---|---|
| atgaaggaaa | tcggcttacc | gttattgcta | ctgaccgcgc | tggccagtcc | ggcttttgct | 60 |
| gcagactgtc | agccaaacgg | cattggcggc | tcgttttgca | ttaacgatga | cggtacgact | 120 |
| accgacacgg | tgcctaacga | agtcaacggc | atggatacgt | actcgaataa | tggcggctat | 180 |
| accagttccc | tgcccgatcg | gtcaggggcg | gatgaagcac | tggaaggttc | atcgctgtcg | 240 |
| acgcagcaag | gcgtcggcag | cggacagagc | gacagtgcgc | tggcgggtcg | cgactggcat | 300 |
| tcgcccgcca | atctgaatga | tggcgccgcc | acctccagta | tgagcctgct | ggataaaccc | 360 |
| tga | | | | | | 363 |

<210> SEQ ID NO 35
<211> LENGTH: 366
<212> TYPE: DNA
<213> ORGANISM: Klebsiella pneumoniae

<400> SEQUENCE: 35

| | | | | | | |
|---|---|---|---|---|---|---|
| atgaatatga | aaaaactgac | gacccttttg | ctcaccgcca | ccttaggtct | tgccagcggc | 60 |
| gcggccctgg | cggcagacac | cggcgcccag | tccaataatg | ccaggccaa | ctcttccgcg | 120 |
| gatgccggtc | aggtggcgcc | ggatgcccgt | gagaacgtgg | cgccgaacaa | cgtggacaat | 180 |
| agtcagatca | actctggctc | tgggggcacc | acgggctcga | cgatgaccca | ggataatatg | 240 |
| tcgagcaatg | aggtacataa | aaactcgatg | tgtaaagacg | gccgctgtcc | ggacaccggt | 300 |
| aaaaaactgg | acaacggtgg | caatacgacc | caagacaaca | gcaaaaccga | cggcaccacc | 360 |
| cagtaa | | | | | | 366 |

<210> SEQ ID NO 36
<211> LENGTH: 369
<212> TYPE: DNA
<213> ORGANISM: Klebsiella pneumoniae

<400> SEQUENCE: 36

| | | | | | | |
|---|---|---|---|---|---|---|
| atgaaacacc | gcatcgctct | gcttctggtc | ctgacttcac | ttagcgccag | cgccctagcc | 60 |
| gcctctccct | gccaggaaaa | agagcaggat | attcaacgag | agatcagcta | cgccgaaaag | 120 |
| catcataatc | aaagtcgcat | tgatgggcta | aataccgcgc | tacgtcaggt | tcgggaaaac | 180 |
| tgtagcgaca | gtaaactcaa | agccgatcat | cagcaaaaaa | ttgccaaaca | gcgggaagag | 240 |
| atcgctgaac | gtcagcgcga | tctgcaggaa | gcccggaaga | aaggcgatgc | ggacaaaatt | 300 |
| aacaaacgcc | agcataaact | caatgaagcg | caacaggagt | taaaaacgct | ggagtctcgg | 360 |
| gattactaa | | | | | | 369 |

<210> SEQ ID NO 37
<211> LENGTH: 426
<212> TYPE: DNA
<213> ORGANISM: Klebsiella pneumoniae

<400> SEQUENCE: 37

| | | | | | | |
|---|---|---|---|---|---|---|
| atgcgactca | taacacgaca | cgtgagagag | gatattatga | aaaaagcaat | gattgcgtta | 60 |
| tcggctattc | tggttgcggc | tccggttttt | gctgcgacaa | cacatgcaac | agatgatacc | 120 |
| gtcgcggcgg | cgaatgccaa | cgccaacacc | gctaaagaga | agctgcatca | ggcccagcac | 180 |

```
gagggcgaag agcagcagct gaaggcgaaa cacgccgccg aaggcaagca ggacagcgtc    240
ggcagccagg tgagcgaagg cgcgcagaaa acctggaaca agaccaaaga aggcaccgag    300
aaggggtggg ataagaccaa agaggtcagt gaaaaaggct ggaacgccac caaatccggt    360
gcggaaaagg gctgggataa aaccaaaacc ggcgccgaag agttaaaaaa taaagtgact    420
gaataa                                                              426
```

<210> SEQ ID NO 38
<211> LENGTH: 456
<212> TYPE: DNA
<213> ORGANISM: Klebsiella pneumoniae

<400> SEQUENCE: 38

```
atgaaaaaga tgatttctct ggcagtaatt ttatcctgtg tgctgagcgt cccggccttt     60
gccgatggcc cgaacgacgg ccatcgcccg gagcagccca cggtgtggca gaacggtccg    120
gaccatgacg gcatgcacc gcagggcgga cctgacgcgc atcatcaggg cgaccatgac    180
cagcgtggcc cggatcgcga cggccatgac aaacgcgatc tggcacgtca tgagcaggac    240
catttcgcct ggcgcgggaa cgatttccgc aaaggccacc cggctccggc gccgttccgt    300
ggcgatgaat atcgcgtccg cgactggagc gaccgcggcc tgccgccccc gccggaaggc    360
catcactggt cctatatcga cggtaactat gtgctgatcg ccgcggcgac cgggatcatc    420
acctcgattc tggtgagcgg cgccctcggc cactaa                             456
```

<210> SEQ ID NO 39
<211> LENGTH: 507
<212> TYPE: DNA
<213> ORGANISM: Klebsiella pneumoniae

<400> SEQUENCE: 39

```
atgaaaaaac cgacatccgc cacccgtggc aaatccggcc gcaagtcgcg tgaagagtta     60
aatcaggaag ctcgcgatcg caaacggcag aagaaacatc gtggccacgc ggcaggcagt    120
cgcgcgaacg gcggcgatgc ggcttcagcg ggtaaaaaac agcgtcaggc gcaagatccg    180
cgcgtgggta gcaaaaaacc gatcccgctg gcgtgagcg aaagcagcgt tccagctccc    240
aagcagcata accaaagag cgagaaacct atgctttcac cgcaggctga gctggagttg    300
ctggagaatg atgagcgcct ggacgcgctg ctggaacgtc tggaagaggg cggcaccctg    360
aatgctgaag agcagagctg ggtggacgcc aaactggatc gcattgatga gctgatgcag    420
cagctcggcc tctcttacga tgatgaagat gaagaagagg aagagcgtca ggaagatatg    480
atgcgtctgc tgaagggtgg aaactaa                                       507
```

<210> SEQ ID NO 40
<211> LENGTH: 690
<212> TYPE: DNA
<213> ORGANISM: Klebsiella pneumoniae

<400> SEQUENCE: 40

```
atggcgagta agtttcagaa ccgtttagtc gggacaatcg tgctggtggc gctgggggtg     60
attatcctgc cagggctgct ggacgggcag aaaaagcatt accaggatga gtttgccgcg    120
atcccgctgg taccgaaacc aggcgatcgc gatgaaccgg atatgttgcc ggcggcaacc    180
caggcgttgc cttcgcaacc gccggaaggg cggcggaag aggtgcgggc gggcgatgcc    240
gccgcgccat cgttagatcc atcgcgtatt ccggtgaaca gcaacagctt cgatgacgtt    300
```

| | |
|---|---|
| caggagccgg tggtggccgc gaaaccgcag cccaagccgc agccgaaacc gcagccgcaa | 360 |
| cagcaggcct cgacgccaac gccgccgccg gctaagccac agcagcaaca gccaccgcag | 420 |
| cagcaggcgg ccctgccggc gccgaccggc aaagcctatg tggttcagct gggcgcgttg | 480 |
| aagaacgccg ataaggtgaa tgagattgtc ggtaaactgc gggcctcggg tttcaaagtc | 540 |
| tatacgtcgc cttcgacgcc ggtacagggt aaaattaccc gcatcctcgt cggcccggat | 600 |
| gcgtcaaaag acaagctgaa aggccagctg ggcgatctgc agcagatctc cgggcttagc | 660 |
| ggggtggtga tgggcttcac cccgaactga | 690 |

<210> SEQ ID NO 41
<211> LENGTH: 969
<212> TYPE: DNA
<213> ORGANISM: Klebsiella pneumoniae

<400> SEQUENCE: 41

| | |
|---|---|
| atggcacaac gagattatgt acgccgcagc caaccggctt cttcgcggcg caaaagagc | 60 |
| acgacccgaa gctcaaggaa taagcaaagc agccttccgg cgatttcacc ggcgatggtg | 120 |
| gcgatcgcgg cggctgtgct ggtggccttt atcggtggcc tctatttcat tacgcatcat | 180 |
| aagaaagaag aagcggaagc gatgcaaaat cgccaggccg ccggcaacgg cttgccgccc | 240 |
| aaaccggaag agcgctggcg ctatattaaa gagctggaaa gccgccagcc tggcgtccgc | 300 |
| gcgccgaccg aaccgaccgc cggtggcgaa gtcatgaaac cggaacagct gaccgacgag | 360 |
| cagcgccagc tgctcgccca gatgcaggcc gatatgcgcc agcagccgac ccagctgacc | 420 |
| gaagtgccgt ggaacgaaca aacgccggcg cagcgccagc agacgcttca gcgtcagcgt | 480 |
| ttagcgcagc aacagcagca ggcgcagcag caacagtggg cgcagactca ggcgcagacc | 540 |
| gtccaacagc agccgccgcg cgttcagcag ccgaagccgg ttcagcagca acagccgaag | 600 |
| cagaccgcgt caaaccagca gccgtaccag gatctgctgc agacgccagc gcataccaat | 660 |
| accacgcagc gcgtacccca ggccgcgcg ccggtaactc gggtggaaga agcgccgaaa | 720 |
| accaccgccg agaagaaaga cgatcgtagc tggatgatcc agtgcggctc ttttaaaggc | 780 |
| gccgagcagg ccgaaaccgt ccgcgctcag ctggctttcg aagggtttgc ttcgcacatt | 840 |
| accactaaca acggctggaa ccgcgtggtt attggcccgt tgaaaggcaa agaaagcgcc | 900 |
| aacgagatga tcacccgcct gaagatggct ggacacgcga actgcattcg tctcgccgcc | 960 |
| aggggttga | 969 |

<210> SEQ ID NO 42
<211> LENGTH: 1131
<212> TYPE: DNA
<213> ORGANISM: Klebsiella pneumoniae

<400> SEQUENCE: 42

| | |
|---|---|
| atgagcgcgg gaagcaccaa atttaccgtc agccgtattg cggctctttc actggtttca | 60 |
| ctctggctgg ccgggtgtac caacaccaat aatccgcctg cgccgttag ctctgccggc | 120 |
| ggcgccgcct cttccagcac caactccggc atgctgatta cgccgccacc ctccggcgtc | 180 |
| aagtccgctc ctcaggcgca gccgattcag ccgatgcaga cccagaccat tcagccggcg | 240 |
| ccggtggcgc aggagccggt acagacggta atggccggat cgtttacaa ccgcaaatat | 300 |
| ggcgatattc cgaaaggtag ctataccggc ggcagtacct atacggtaaa acgcggcgac | 360 |
| acgctattct atatcgcctg ggtcaccggc aacgatttcc gcgacctggc gcaacgtaac | 420 |
| aatatcccgg ccccgtacgc gctgaacgtg gggcaggtac tgcaggtcgg taacgccctca | 480 |

```
ggccagccga tcaccggcga aaacgccgtt tctcaggcca gcgcaagagc gagcggcggt      540
gcgacgacca gcacaacttc tgcacaaaaa tcgaccgcgg tggttgcttc acaaccgact      600
attacgtatt ctgaatcttc aggtgaacag agtgctacca agatgttgcc taataataaa      660
ccagcgacca caaccacaac ggttgtcgcg ccggtgacgg caccaacaac ggtgagcaca      720
acccagccga ctgcaagcag tacgtcaacc agttcgccga tctcagcatg gcgctggccg      780
actgatggca aggttatcga gaactttagc ggcgcggaag gcggcaataa aggcatcgat      840
attgcaggca gtaagggaca ggctattgtc gcgaccgccg atgggcgcgt cgtctatgcc      900
ggtaacgcac tgcgcggcta cggtaatctt attatcatca aacacaacga tgattacctg      960
agtgcctacg ctcataacga taccatgctg gttcgggagc aacaggaagt caaagcgggg     1020
cagaaaatcg ctaccatggg tagcaccgga accagctcaa caagattaca ttttgaaatt     1080
cgttacaagg ggaaatccgt caacccgctg cagtacttac cgcagcgata a              1131

<210> SEQ ID NO 43
<211> LENGTH: 1149
<212> TYPE: DNA
<213> ORGANISM: Klebsiella pneumoniae

<400> SEQUENCE: 43
atgcgtaagc aatggctggg gatctgcata gcagcggggc tgctggcggc atgttcgagt       60
gatgacgtgc aacaaaaaac ggtcagtact ccacagccgg ccgtctgtaa tggcccgacg      120
gttgagatca gcggcgccga tccgcagtat gaaacgccga acgccacggc gaatcaggat      180
tatgagcgcg acggtaaaag ctacaaaatc gttcaggatc cggccaactt tactcaggcc      240
ggtttcgcgg cgatctatga cgcagaaccc aacagcaacc tgaccgccag cggcgaagcc      300
ttcgatccga ctcagttgac cgcagcgcac ccgacgctgc cgatcccgag ctacgcgcgg      360
atcactaacc ttgccaacgg acggatgatc gtcgtgcgga ttaacgatcg cggtccctat      420
ggcaacgatc gggtcatctc gctttcccgc gcatccgctg accgcctgaa cacctccaac      480
aacaccaaag tgcgcatcga ccccatcatc gtcgcgcctg acggttcgct ttccggcccg      540
gggatggcct gtaccaccgt cgccaaacag acttacgccc tgcccgcccg tccgaatctg      600
gacggtgggg acgccgctgg catgagccag cccgcgccca ctgacgttcg cccgatcagc      660
aacagcacgc tgacgccggc agacagcgtg ggcgcgccgg tgaacagcgg cggtttcctc      720
ggcgcgccga cgccccctgaa caacggcgtg ctggagagta gcgaaccagc ggcagccgcc      780
gcgacggctc ctgccgccgg cgccacgcca acagcgccag tgaccgcgcc tggctccatt      840
cagggtaatg tggtgcccgc tgcggccacc gccgcagccg ctggcgccgt ggcggcctcg      900
tcctccgcga cctccagcgc cagcggtaat tttgttgtcc aggtgggcgc agtaagcgac      960
cagacgcggg cgcagcagta tcagcagcgc ctgagccagc agtttctgt gccaggccgg     1020 gtcatgcaaa acgcgcggt ctggcgtatt cagctgggtc cctttgctga taaagcacag     1080
gccagcgccg tgcagcagcg cctgcaaagc gaagcgcagc tgcagtcctt tattactcgc     1140
gccaactaa                                                             1149

<210> SEQ ID NO 44
<211> LENGTH: 1287
<212> TYPE: DNA
<213> ORGANISM: Klebsiella pneumoniae

<400> SEQUENCE: 44
```

| | |
|---|---|
| atggatgatt tcaaaccaga agacgatatg aaagccgatc gcaacgatcg tcgtgctggt | 60 |
| cgttcccgtc agtcttccga gcgtgatgcc gatccgcaga tcaattttga cgatgttgat | 120 |
| cttgatgccg atgaaggccg tccgacgcgc gctggtaagg cccgtcgcga gcgtgaagag | 180 |
| gaagagttcg aagaagaact ggatgcgcaa gacgaggaga tgctcgaaga gcagcctgta | 240 |
| gagcgtcgtc cgcgcaagcg taaaaaagcg ccggccaaac cggcctcccg ccagtacatc | 300 |
| atgatgggtg tggggattct ggtgctgctg ctgttgatcg tgggtatcgg ttccgcactg | 360 |
| aaatcgccat catcttccag ccagcagacc gcttccggcg agaagagcat taatctgtct | 420 |
| gacgaccagt ccgccagcat gcctgctgcc ggcaggacc agactgccgc cgctaacagc | 480 |
| acctcacagc aggacgtaac ggtaccgcct attgccgcga acccgacgca gggccaggca | 540 |
| gcggttgcgc cgcagggcca gcagcgtatc gaagttcagg gcgatctgaa caatgccttg | 600 |
| acccagcagc agggccaact ggacggcgcc gtggctaact cgacgctgcc gactgaaccg | 660 |
| gctaccgtcg cgccaatccg gaatggcgcc aatggcaccg cggcgccgcg ccaggcgacc | 720 |
| gagcgtcaga cagcagcgac cccgcgtccg gctgaacgta agcataccgt tatcgaagcg | 780 |
| aagccgcagt cgaagccaca ggccgtggcg aaaacgccgg tagaatcgaa gccggtccag | 840 |
| ccgaagcatg ttgaaagcac ggcgaccacc gctccggcga aacgtccgt cagcgaaagc | 900 |
| aaaccggtgg ccaccgctca gagcaaaccg accacgacga ccgcagcgcc agcggcaacg | 960 |
| gcagctgcgg cagcgccggc agcgaagacc gggaagacgg caggtgacgt cagctcaatg | 1020 |
| aaaactgcgc cgtcgggtca ctatactctg cagctcagca gctcctctaa ctacgacaac | 1080 |
| ctcaacaact gggcgaagaa agagaagctg gataaatatg ttgtctatga aacgtcgcgt | 1140 |
| aacggccaac catggtacgt gctggtgagc ggtatctatg catcgaaaga tgaagcgaaa | 1200 |
| cgtgctgtca cctcgctgcc ggcggacgtg caggcgaaaa atccatgggc aaaaccgctg | 1260 |
| catcaggttc aggctgacct gaaataa | 1287 |

<210> SEQ ID NO 45
<211> LENGTH: 1326
<212> TYPE: DNA
<213> ORGANISM: Klebsiella pneumoniae

<400> SEQUENCE: 45

| | |
|---|---|
| atgtcaaagg caaccgaaca aaacgacaag cttaaacgag cgatcatcat ttcagtcgcg | 60 |
| ctgcacatca ttctgatcgc gctgctgatc tggagttcgt ttgacgagca tctggatgcc | 120 |
| tctgccggcg gcggcggcgg atcgtcgatt gatgccgtca tggtcgatcc ggggcggtg | 180 |
| gtaaataact ataaccgtca gcaacagcag caggccagcg cacgtcgcgc cgctgaacag | 240 |
| cgtgaaaaac aggcgcagca gcaggcgaa gagttacgtg agaaacaggc ggcggaacag | 300 |
| gaacggctga acagctcga acaggagcgg ctgcaggcgc aggaagcggc gaaagaagcg | 360 |
| aaggagcagc agaagcaggc tgaagaagcg gctgccaagg ccgccgcggc ggcaaaagcc | 420 |
| aaagcggacg cacaggcaaa agaagcgcag gaagccgctg ccaaagcggc cgccgaggcg | 480 |
| aaagcgaagg cggatgccca ggcgaaagcg gcagaacagg cggcggccaa ggcggctgct | 540 |
| gacgcgaaaa agcaggccga agccgctgca gcgaaagccg ctgccgaggc gaagaaacag | 600 |
| gcggaagctg aagcggcgaa agctgcggcc gaggcgcaga gaaagcgga gcggcggct | 660 |
| gcgaagaaag cgcaacagga gcggagaaa aaagcccagc aggaagcggc taagcaggcg | 720 |
| gcagctgaaa aagcggctgc cgaaaaagcc gctgagaaag ccgccgcgca aaagcggcc | 780 |
| gctgagaagg ccgccgccga aaagccgca gccgctgaaa agcggcggc agcgaaagcg | 840 |

```
gctgcagcag agaaggctgc agctgataaa gcggccaaag cggcagcagc aaaagccgcg    900
gcggcgaaga aagcggcggc tgcgaaagaa gcggacggcg ttgacaacct gctcggcgat    960
ctgagttctg gtaagaatgc gcctaaaaca ggcggtgggg ccaaaggaaa caatgcctcc   1020
gctgccggga gtggtaatac taaaaacagt gcctcagggg ctgatatcaa caactatgcc   1080
ggacagataa aatcggcgat tgaaagtaag ttttatgacg catcgtccta tgcgggcaaa   1140
acatgtacct tgcgtatcaa acttgctcct gacggcctgt tgttaaatat acagtccgaa   1200
ggtggtgatc ctgctctgtg ccaggccgct cttgccgcag cccgacaggc taagtttccg   1260
aaaccaccta gccaggcagt atatgaagtc ttcaaaaatg cgccactgga cttcaaacct   1320
cagtga                                                              1326
```

<210> SEQ ID NO 46
<211> LENGTH: 1455
<212> TYPE: DNA
<213> ORGANISM: Klebsiella pneumoniae

<400> SEQUENCE: 46

```
atgtttttt taagtatttt ttacatggag atgacaaaag tgaaattaag cgctctgttt     60
attgccctga ttcctctact gggctcgccg gttattcatg cagaaactac tgctgcgccg    120
gttctggaaa tcgcgctgc gcagggagat atcaccactc ctggcggcgc gcgtcgttta    180
acaggcgatc aaaccgaagc gctgcgcgcc tcgttaatca ataagccagc taaaaacgtt    240
attttgctga ttggcgatgg catgggtgat tcggaaatta ccgctgcgcg aaactatgcc    300 gaggggggcgg gcggtttctt taaaggaatt gatgctctgc cgttaaccgg gcagtacacg    360
cattattcgc tggataaaaa aaccgggaaa ccggactacg tgaccgactc ggcggcctcc    420
gccaccgcct ggaccaccgg cgtgaagact tataacggcg cgctgggcgt cgatattcat    480
gagaatgcgc atcagaccat cctcgagctg gcgaaagcgg cggggctggc caccggcaac    540
gtttccaccg ccgagctgca ggacgccacc cccgcggcgt tggtagcgca tgtgacatcg    600
cgtaaatgct acggcccgac ggtcaccagc gaaaaatgcc ccagcaatgc gctgaaaaaa    660
gggggcaaag gctccattac cgaacagctg ctgaacgccc gaccggatgt caccttgggc    720
ggcggcgcga agacctttac cgaaacggcg acggcgggcg agtggcaggg caaaaccctg    780
cgcgagcagg cgcaagcgcg cggctaccag attgtgaccg acgcggcttc tcttgccgcc    840
gcgacggaag ccagtcagga taaaccgctg ctgggactct ttgccgatgg caatatgccg    900
gtacgctggg aagggccgaa ggcgtcttat cacggtaata tcgataagcc gccggtgacc    960
tgtacgccaa acccgaagcg tgacgcctcg gtgccgacgc tggcgcagat gacggagaaa   1020
gcgattgacc tgctcagtcg caacgagaaa ggtttcttcc tgcaagtcga aggcgcttcc   1080
atcgataagc aggaccatgc ggcgaatccg tgcgccagat cggcgaaac ggttgatctt   1140 gacgaagcg tgcagaaggc gctggaattc gcgcgaaaag acgtaatac cctggtgatc   1200 gtcaccgccg accatgcgca tgccagccag atcatcccgg cggatagcaa agccccgggg   1260
ctgacccagg ctctgaacac gcacgatggc gcggtgatgg tgatgagcta cggcaactct   1320
gaggaagagt cgatggagca caccggcacc caactgcgca ttgcggccta cggtccgcat   1380
gcggctaacg tcgtaggcct gaccgatcag accgacctgt tcacgaccat gaaagctgcc   1440
ctgagtctca aataa                                                    1455
```

<210> SEQ ID NO 47

```
<211> LENGTH: 1608
<212> TYPE: DNA
<213> ORGANISM: Klebsiella pneumoniae

<400> SEQUENCE: 47
atgtcactgc cgttcaaacc ccatattatc gccctgctct gtagcgctgg cttactcgcg      60
gcggcaggaa cactctatgt gcaaagccga accccagcga cgatcgctga accgcctgcg     120
cagcaagcgc cagcgcccgc agcgtcgacg acacagccgg tggccgccac ttacacccag     180
gcgcaaattg atcagtgggt cgcccctatc gcgctctacc cggacagcct gctgtcgcag     240
gtgttgatgg cctccactta tcccgacaac gtcctgcagg cggtccagtg gtcccaggat     300
aaccccgcga tgaaagggga tgcggccgtg caggcggttg ccagccagcc gtgggaccct     360
agcgtcaaat ctcttgtcgc tttccctgcc ctgctggcga tgatgggcga gaatccgccc     420
tgggtggaaa atcttggcaa tgcgttttg gcccagccgc atgatgtgat ggattcagtg      480
cagcgcctgc gcgccattgc ccaacaaacc gggacgctga atccacaccc gcagcagaaa     540
gtgattgtca cccctgccgc accggtttca gccagcagca gcacggcagc aaccgcaacc     600
gcccacacag cggcgcctgc gcccacgcag gtcattaaaa tagagccgac caatccacag     660
gtggtctatg ttcccagcta taacccctcc accgtctatg gtacctggcc gaacagcgcc     720
tatccgccgg tctatctgcc gcccctcccc ggggagcagt ttaccgatag cttcgtcaaa     780
ggcttcgggt acagcctcgg cgtggccacc acctgggcgc tgttcagcag tatcgactgg     840
gatgatgatg accatcacca tcacgatgac gactaccacc acggcgatta ctcgcataat     900
ggcgataaca tcaatattaa tgtaaataat ttcaatcata taacaggaga aaacctgccg     960
ggaaaccacg ttaactggca gcacaatcct gcctatcgcg gacacacacc gtatcccgat    1020
aatacggtag ctcagcgctt ccatcagacc aacgtttccg gcggactgag cgcgacccaa    1080
catgcgccag tcgatcgcga agcgcagcgc caggcagcga tgacccagct gcagcataac    1140
gtaccgacgg ccacagcggg caacctggcg gcaaacaacg cctcacgcga cgcccagcgt    1200
caggcggcct cggcgcagct gaagcaagcc acccaacgca gtaattaccg cggttacgac    1260
agtacgccga cccaacagca gcgtcgcgag gcggcaaaaa cgcagctgaa aaaccccacg    1320
ccgcagcaac agcagcgtcg agaagccgcc aggagccacg agcagaaccg cacacctcag    1380
cagcagcagc gccggcagca gttccagtcc gccacgccag cccagcgtca gcagacgctc    1440
agccatctgc gcgccaacgc ccttagcggc aacgaaagcc gcgccccctc ctggcaagcg    1500
cagcaggaac gaggactgca gagccgccag ttttccggcg taaaccgcga gttacgcgat    1560
ggcaccagag aacgtctttc cgaacaccat gaactgcgtc gccgctaa                 1608

<210> SEQ ID NO 48
<211> LENGTH: 1794
<212> TYPE: DNA
<213> ORGANISM: Klebsiella pneumoniae

<400> SEQUENCE: 48
atgtttaagt ttaaggcttc ttatgtcgca ctggcggcag tattaacctc gtcggtagtt     60
tatgccgacc ccacaagcta tacgcactct tccggcgcca cggttatcga tattgaaaag    120
ccgaacgccg ccggtgtctc ccataacctg taccgcgact tcaacgtcgg cgccaatggc    180
accatcctca ataacagcgg cgatgatgtc agccacagca catttggcaa tatcgcccgc    240
aacaataatc tgaccgccgg cagcgcttcg gtgattttga acgaggtgac ctccaaaaac    300
gccagtagcc tgaagggctt tatcgaagtc aacggtcaga aagcggatgt ggtaatcgcc    360
```

-continued

```
aacccgaacg gcatcacctg ttccggctgt agctttgtta ataccaacaa ggctatcctg    420
accaccggca aggttaatat gaccgacgat ggcgctatcg gcagctatac cgtaacgggc    480
ggcaccctca ccatcggcga aaatggcatg aacgccgcca acggctatgc ggttctgctc    540
gccgacgcga tcaatatcaa cggtaaagtg caggccaaca acgccctggt cagcgcgggc    600
aacttcacca tggataacag ctctggctcg gtgacctccg ctggtaaaaa ggccacccctg   660 atccagatga cggttaaccc gcagtacagc atcgacgtca gcagccttgg cggcattgag    720
gccaacagca tcagcatggt cggcaataac atcggctttg gcgtacgtaa taaaggctct    780
atcgtcgcga atagttcgct gcagctcacc agcaacggta atctgctgaa caaaggcacg    840
atcaaaagca acggtctgct gagtcaggtc gccaccgcct cgggcatcac caatgacggt    900
agcatcgccg gcgcctatta tttaatgctc tccagtggcg attatatcgt taacaccggt    960
tctctctccg gcggccagct gattgccacc gctaacggca acatcaccaa cggcgactca   1020
ggcacgatga ccggcaccag tggattaagc ctgaccagcg gcgggaaaat ccgcaacgaa   1080
gaaaaagcct ccctgctgtc aaataaccag attgccgcca cggcaatcgg tgatttcctc   1140
aatgaaggca aaatcagcgc caaacacacc agcctgacgt ttgtcggcga cagctttaaa   1200
aacactggca atattaactc tactggccaa accaccattc agtcgcttaa acaggacggc   1260
agcgccaata cgggcgagat ctataaccctc ggcaatatca ccggcgaaaa tatcaatctg   1320
cagaccaatg gcacgctggc gcaaagcagc agtggtcgta ttgaggcaac caacgccatt   1380
accgcccaca gctactggct gaaccaaaat ggttatatga atgccgccga tatcaccacc   1440
gatcacggcg tagtgaataa ttatggcaat attactgcca aaaatatttc aatcacgacc   1500
tactcagata tcaccaacga agggcagatc agcagcaccg gcgacctgac cttaaatacc   1560
aaaaataaag gcgcgatcta caattattca accctcagcg cgggcggcaa catgacgtta   1620
accgccacca aagtggtcaa tggtggtaaa agttgcggca tactgggcct ggcgaaatgc   1680
ggcgtcggga cgttaactgc tgacaagctg gtactgaact catcgcagaa atatgttagc   1740
gacatgggtg aaaacagta tttcaagagc accgaagtca cacggtgaa ataa           1794
```

<210> SEQ ID NO 49
<211> LENGTH: 1875
<212> TYPE: DNA
<213> ORGANISM: Klebsiella pneumoniae

<400> SEQUENCE: 49

```
atgatggaca acctacgcac ggccgccaac agcgtcgtgc tcaagattat tttcggtatc     60
attatcgtct cgttcatttt gaccggggtg agtggttacc tgattggcgg tggcaaaaac    120
tatgccgcaa aagtgaatgg ccaggagatt ggccgtgggc agtttgaaaa cgccgtcgcc    180
agcgaacgta accgtatgca gcagcagctt ggcgatcaat tctccgagct ggcggcgaac    240
gaaaactaca tgaaaccat cgccagcag gtgctgaacc gcctgatcga tgagtcgctt      300
ctggatcagt atgcccgcga gctgggcctc agcatcagcg atgagcaggt gaagcaggcg    360
atcttccaga cccaggcgtt ccagacgaac ggtaagttcg acaaccagcg tttcagtggt    420
attgtcgccc agatggggat gaccaccgat cagtacgccc aggcgctgcg taaccagctg    480
accacgcagc agctgattaa cgccattgcg ggtaccgact tcatgctgcc gggcgagtcc    540
gatcagctgg cggcgctggt atctcaacag cgggtggtcc gcgaagcgac catcaacgta    600
aatgccctgg cggcaaaaca gaccgccagc gatgaggaaa tcaacgcctt ctggcagcag    660
```

-continued

| | |
|---|---|
| aatcaggccc gttttatggc gccggagcag ttccgcgtca gctacatcaa aatggatgcc | 720 |
| gccagcatgc aggagagcgc ctctgacgaa gagattcagt catggtacga ccagcacaag | 780 |
| gatcagttca ctcagccgca gcgcaaccgc tacagcgtga ttcagaccaa aactgaagcc | 840 |
| gatgcgaaag cggtactggc cgagctgcaa aaggagcgg acttcgccac gctggcgaaa | 900 |
| gaaaaatcga ccgatattat ctctgcccgc aacggtggcg atatggggtg gatggaagat | 960 |
| gcctctaccg tgcctgagct gaaagatgcc gggctgaaag agaaaggcca gctgtctggc | 1020 |
| gtgatcaaat cctcggttgg cttcctggta gctcgtctgg acgacgtcca gccggcgcag | 1080 |
| gtgaagccgc tggctgacgt gcgtaatgac attgcggcga agtgaagca ggaaaaagcg | 1140 |
| ttggatgctt actacgcgct gcagcagaag gtgagcgatg cggccagcaa cgataatgaa | 1200 |
| tcgctggcga gcgcagcgca ggtcgccggg ctgaaggtcg tagaaaccgg ctggtttggc | 1260 |
| cgcgataacc tgccggagga gctgaacttt aaaccggtcg ctgacgctat tttcaacggc | 1320 |
| ggtctggtgg gtgagaacgg cgcgccgggc agcaactccg atatcattac cgttgacggc | 1380 |
| gatcgcgctt ttgttctgcg cattagcgaa cacaaagccg aggcggtgaa gccgctggcc | 1440 |
| gaagtgaagg cacaggttag cgatatcgtt aagcacaata agcggaaca gcaggcgaaa | 1500 |
| ctggaggccg caagctgct ggcggcgctg aagacggca aaggcgatga agcgatgaag | 1560 |
| gcggctggcc tgagctttgg cgcgccgcag acgctttctc gtaccggcca ggatccgctg | 1620 |
| agccagctgg catttaccct gccgctgccg cagcaggta aaccggtcta cggcgtgggc | 1680 |
| agcaatatgc aaggcgatgt ggtgctggta gcgctggatg aggtgaaagc cggcagcatg | 1740 |
| ccggaagagc agaagaaggc catggttcag gggatcaccc agaacaatgc ccaaatcgct | 1800 |
| ttcgaagcgc tgatgagcaa cctgcgcaag gcggcgaaaa ttaagctcgg cgacagcatc | 1860 |
| gaccagcagc agtaa | 1875 |

<210> SEQ ID NO 50
<211> LENGTH: 1974
<212> TYPE: DNA
<213> ORGANISM: Klebsiella pneumoniae

<400> SEQUENCE: 50

| | |
|---|---|
| atgttcaggt taaacccttt tatccgggcg ggattgtctg cgtccgtcgt atcgttggcg | 60 |
| tttccggctc tggccgatgt gaatgaagaa acgctggtgg tgaccgcctc ggccactgaa | 120 |
| cagaatgtca agacgcgcc ggcgagcatc agcgtcatca cccaacagga tttacaacgc | 180 |
| aagcctgttc agaacctgaa agacgtgctg cgcgatgtgc ctggggtcca gctcaccaac | 240 |
| gaaggggata accgcaaggg cgttagcatc cgcggtctga gcagcagcta taccctgatc | 300 |
| ctggtcgacg gcaagcgcgt taactcgcgg aacgccgtct ccgccacaa tgacttcgac | 360 |
| cttaactgga tcccggtgga tgctattgag cgtatcgaag tggtgcgcgg cccgatgtcc | 420 |
| tccctctacg gctccgatgc gctcggtggg gtggtcaaca ttattaccaa aaaaatcggc | 480 |
| cagaaatgga ccgggacgct gagtgctgat accactattc aggagcaccg cgatcgcggg | 540 |
| gatacctgga acggccagtt cttcaccagc ggcccgctga tcgacggcgt acttggaatg | 600 |
| aaggcctacg gcagcctggc aaaacgcgcc aaggacgatc cgcagtcatc cagtaatgcc | 660 |
| accggcgaga cgccgcgcat cgagggcttc accagccgcg atggcaatgt tgaattcgcc | 720 |
| tggacgccga acgaaaacca cgattttacc gcaggctacg gctttgaccg tcaggatcgc | 780 |
| gattccgatt cccttgaccg caaccgcctt gagcgggaga actactctct gagccataac | 840 |
| ggccgctggg atatcggcaa tagcgagctc aagttctacg gcgaaaaggt ggataacaaa | 900 |

```
aatccagggc agagcgggac tattacctcg gaaagcaatg ccatcgacgg caagtatgtc    960
ctgccgctgg gcatgattaa ccagctggtg accttcggcg gcgaatggcg ccacgacaaa   1020
cttaaagatc cggtcaacct gagcagcggc ggccagtcaa cgtcggccag ccagtacgcc   1080
ctgtttatcg aagacgaatg gcgcatcatc gagccgctgg cgctgaccac cggcattcgt   1140
atggacgacc atcagaccta tggcgatcac tggagcccgc gcgcctatct ggtgtataac   1200
gccaccgata ccgtcaccgt caaaggcggc tgggcgacgg cgtttaaagc cccgtcgctg   1260
ctgcagctta accccgactg gaccaccaac tcctgccgcg gctcgtgcag catcgtcggt   1320
aacccggatc tgaaaccgga accagcgaa agcttcgagc tcggtctcta ctaccgcggg    1380
gaagagggct ggcttgaaaa tgtcgaaggc agcatcacca ccttccagaa taatgtcgac   1440
gacatgatcg acgttctgcg cacctccagc gccagcgaag cgccgggcta cccgaacttt   1500
gtcggctgga aaactgtcaa cggcaagcgc gtgccgatct tccgctattt caacgtcaac   1560
aaagcccgca tcaagggggt ggagacggag gtgaagatcc cgtttggcga tgagtggaag   1620
ctgacggtga actacaccta caacgatggt cgcgatctga gcaatggcgg cgacaaaccg   1680
ctgcagacgt gccgttcca taccgccaac ggcacgctcg actggaaacc gctgacgac    1740
tggtccttct acgtgacggc caactatacc ggccagcagc gcgcggtgag cgccaccggc   1800
aaaacgccgg gcggctacac cctgtttgac gttggcgcgg catggcaggt gaccaaaaac   1860
gtgaaactgc gctccggggt gcagaacgtg ggtgataaag atctgagccg ggacgactac   1920
agctataccg aagaaggccg tcgctacttt atggcggtgg attatcgctt ctga         1974

<210> SEQ ID NO 51
<211> LENGTH: 2028
<212> TYPE: DNA
<213> ORGANISM: Klebsiella pneumoniae

<400> SEQUENCE: 51
atgaacagag ccgccacgct gaccctcaac gcgcccctgc tgatgctcgt cgctgcgctg    60
gcgctttcaa ccccttttcac cgccggcgcc gcgccggcct tcttgatta cgcccaacag   120
caaacccagc aatctcaggc gcaagaaaaa acgatgccg caagcgcaaa acaaacacaa    180
gaaagccgcc agagcgcaga taataaaaaa accggtacca gcacctcaca attacaaaaa   240
agaatcacca gccagcaggc ggcgattgca caaaaagata gcttataca gcaattaaaa    300
aaacagcttg ccgctacgcc gcaaacggat actgccggag cgaatgagca agcggcgttg   360
aataagagaa ttaatgaatt acaggtcgcc ttaagcgccg ctactgcaga aaagaggca    420
ttaataaaaa aagcaggcgt tgtgcagaat aataatctac agcaaagcca ggccgcggcg   480
cgtcagcaga tccagcaatt aacgacgcag attcagcaag ccgaagctga aaataaacgc   540
ctcagcgcca gctttaccac gcttaataaa gataaacacg cgctaatgac ccaactggcc   600
gcaacgaaa aagagaaaca ggccgctctt gagcaggtca aagcgcttaa cgctgacaaa   660
cagccgctga cgacccggct ggccgccgcg gaaaaagaga acaggccgt cctcgagcag   720
gttaaggccc ttaacgccga taaacagtcg ctgactattc gcctcgccgc tgcggagaaa   780
gcgcagcagg ccgctgttga ccaggctaaa gcgcttaacg ctgacaaaca gccgctggct   840
acccgactgg ccgccgcgga aaaagagaaa caggccgtcc tcgagcaggt taaggccctt   900
agcgccgata gcagtcgct gactattcgc ctcgccgctg cggagaaggc gcagcaggcc   960
gctcttgacc aggctaaagc gcttaacgct gacaaacagc cgctggcgac ccggctggcc   1020
```

```
gccgcggaaa aagagaaaca ggccgtcctc gagcaggtta aagcccttaa cgccgataag    1080
cagtcgctga ctattcgcct cgccgctgcg gaaaagacgc agcaggctgc cctcgatcag    1140
gtcaaagccc ttaacgccga taaacaatcg ctgtccaccc ggctggccgc cgcggataaa    1200
gcgccgcatg gccccgctaa cgacgccgct gcgccaaaaa atgagccacc agagatggcg    1260
gccatagtgg cagcctatcg cctgcaggcg gataaagaca acgcccagct acggatgaaa    1320
gaagatgaaa tcgaactgct gagaacgcag ctttctgtac agtccaaaac gcgcagcggc    1380
gagagcgccg ccgccaaact cagcgcatcg ggagaacagc aggcttatgc gatcggcgcc    1440
tcgatgggaa gcgaggcgct caacgtcctt accacccgtc gtactcaggg agttaccgtc    1500
gacgcaggcc tggtgctgca gggcatcgaa gatgcctttc gcggccagct tcgtctcgga    1560
gagcaggaac gtaacaaggc gctgtttgat gtgtcgcagc aggttttca gaacctgaat    1620 aaaatagagc agaaaaacat cagtgccggc aagaaatatc agcaggcgtt tgcgcgcaaa    1680
aaagatgtgg tctttaaaga gggcgtctac agccgcgtcg attacctggg taaaggaaaa    1740
ataagcggta atgacctggt taccgtggtg atcaaagaga tgctgacgga cgggacggtg    1800
atcaacgata tggaagcgaa agatcaggcg cttacgcaaa agctggatgc ctatcccccg    1860
gtgtttcgcg aaccgctgaa gcgtctacag aaccacggct ccgtgacgct cgtcgtcccg    1920
cctgaaaagg cctatggcag taaaggatta ccgccaaaaa tcccgccagg cgccaccatg    1980
gtttattccg tgcggatagt agatagccaa cccgagccgg caaaatag                 2028

<210> SEQ ID NO 52
<211> LENGTH: 2106
<212> TYPE: DNA
<213> ORGANISM: Klebsiella pneumoniae

<400> SEQUENCE: 52
atgaaaatcc tgtccgtgcg tcacgccgcc ctcccggccc tgctcttgcc gctcattgcg     60
gcagcccagg ccgctgatga acaaaccatg gtggtgaccg ccgcgccaac cacggtttct    120
gaactggata ccccgccgc cgtcagcgtg gtgaatgggg atgagatgcg ccaggccgcg    180
ccgcgcgtca atctctctga atcgctgggc gccgtgccgg gcctgcaggt gcagaaccgg    240
caaaactatg cccaggatct gcagctgtcg attgcgggct ttggctcgcg ctcaacctat    300
ggcgtgcgcg gactgcgcat ctatgtggat ggcattccgg ccaccatgcc cgacggccag    360
gggcagacct caaatattga tatcggcagc gttgacacca ttgaggtgct gcgcggcccc    420
ttctctgccc tgtacggtaa ctcgtccggc ggggtgatca acgtcaccag ccagaccggc    480
acccagccgc ccaccgtgga agccagcagc tactatggca gcttcggcac ctggcactac    540
gggatgaaag ccactggcgc cgttggcgac ggcagccacg caggcgatgt ggattacacg    600
gtctcaacca atcgcttcac cacccatggc tatcgcgatc acagcggcgc gcgcaaaaat    660
ctggcgaacg cccggctggg ggtgcgcatc aacgacgtca gtaagctgac tctgctgctg    720
aatagcgtgg atatcaaagc caatgacgcc ggtggcctga ccgccgatga atggcgcgat    780
aacccgcgcc agtcgccgcg cggcgaccag tataataccc gcaagaatac ccgacagacc    840
caggccggcc tgcgctatga gcgccagctc agtgcccagg acgatctcag cgttatgatg    900
tacgctggag aacgtgaaac cactcagttc cagtcgatcc cgcgcgcgcc gcagctgaag    960
ccgagccatg ccggcggggt gatcgacctt accgtcact accaggggat cgatacccgg    1020
ctgacccatc gcggagagct gctggtgccc gtcacgctca ccgccggtct cgactacgaa    1080
aacatgagcg agcggcgcaa agggtatgaa aactttgtga tggtcaacgg cgcgccgcag    1140
```

```
tatggcgaac agggcgcgct gcgccgtaac gaacgcaacc tgatgtggaa cgtcgacccc    1200
tacctgcaga cccagtggca gctcactgac aaactctcgc tcgatgccgg ggttcgctac    1260
agctcggtat ggttcgactc gaacgactac tacatcaccc caggcaatgg cgatgacagc    1320
ggtgatgcca gctatcacaa atggctgccc gcgggctcgc tgaaatatgc cctgaccgac    1380
gcgtggaacg tctatctttc cgccggccgc ggcttcgaga cgccaaccat taacgaactc    1440
tcctaccgct ccgataacca gagcggcctc aacttcggcc tgaaaccctc caccaacgac    1500
acggtggaga tcggcagcaa gacgcggatc ggcaatgggc tgttcaccgc cgccctgttc    1560
cagaccaata ccgataatga gattgtggtc gacagcagca gcggcgggcg caccagttat    1620
aaaaacgccg gcaagacccg ccgtcagggg atggagctgg ggctggatca gcagtttggc    1680
gagagctggc gtctgaaggc ggcctggacc tggctggacg cgacctatcg cactaacgtc    1740
tgcgacgacg ccagctgcaa tggcaatcgc attccgggga tcgcgcgcaa tatgggctac    1800
gcctcctttg gctatcagcc ggagcaaggt tggtacgccg ggagcgatat tcgctatatg    1860
agcgatatca tggccaatga cgaaaacacc gccaaagcgc cctcctggac ggtggttggc    1920
ctgacgactg gctataaatg gagctacggc aggatggata tggatctgtt cggtcgcatc    1980
gacaacctgt tcgaccggga gtacgtcggg tctgtcatcg ttaacgagtc taacggacgt    2040
tactacgagc tgccccgggg acgtaactac ggcatcggcc tgaacctcgc ctggcgcttc    2100
gaataa                                                              2106

<210> SEQ ID NO 53
<211> LENGTH: 2259
<212> TYPE: DNA
<213> ORGANISM: Klebsiella pneumoniae

<400> SEQUENCE: 53
atgaaataca cgtctcactt cccgctgggg atcgtcattc ctctgctcgc ctgtagcgtg     60
ccgctgcagg cggcagagaa catgaccgaa caatcgacgc ctgacgagag cgccgccact    120
gccgaaaatc acgaggagac gatggtcata accgccgcca ggcagaacct gcaggcgccg    180
ggcgtgtcga ccatcaccgc agaagagatc cgcaaacatc cccccgcccg cgatgtgtcg    240
gagttaattc gtacgcagcc cggggtaaac ctgaccggca actccaccag cgggcagcgc    300
ggcaacaacc ggcaaattga tatccgtggc atggggcccg agaatacgct ggtgctggtc    360
gatggtaaac cggtgaccag ccgtaactcg gtgcggtatg gctggcgcgg cgatcgtgac    420
tcccgcggcg ataccagttg ggtgccagcg gagatgatcg atcatatcga tgtgatccgc    480
ggcccggcgg cggcgcgcta tggtaatggc gcgatgggcg gggtcgtcaa catcgtgacc    540
aaaccgacca cgcgagaatg gcacgggtcg tggaatacct atatgaatgc tccgcagcac    600
cgtaaagaag gggcgacgaa acgtactaac tttagcctca atggtccgct gtcggacagt    660
gtcagcttca atctctgggg taatctgagt aaaacccagg ccgatgcaca ggatattaac    720
gccgggcatg aagcggaacg taccggttcc tacgccggtt cttatcccgc cggacgtgaa    780
ggggtggtga acaaagatat tcacagtaag ctgcgctggg agtttgcccc gatgcaggcc    840
ctggagtttg aggccggtta cagccgccag ggtaatctct atgccggcga cacacaaaac    900
accaatacca gtacgctggt gaagagtatg tacgggaaag agaccaaccg tctctaccgg    960
caaacttacg gcgtaacatg gaccggcggc tgggataatg gcgtgaccag caacagctat   1020
gcccagtacg aacacacccg taactcgcga atggatgaag gctggcgggg cggtacggaa   1080
```

```
gggatcttct ccagtagcga gttttcagat atcgatctgg ccgatgtcct gctacatagt      1140
gaagtgaata ttccgtttac gctggggtc gatcagaatc tgacgctggg ggcagaatgg       1200
aatcagcagc ggatgaaaga tggcgtatcg acaacccagg cgctctctta tggcactatc     1260
gatggcgtat cggctaccgg tcgtagcccg tactccagtg ccgagatctt ctcgctgttt     1320
accgaagata atatggcgct aacggacagc accatgctga cacccgctct gcgcttcgat    1380
caccacagca tcgtcggcaa taactggagc ccctcactga acctgtctca ggagctgacg     1440
gacgactgga cgctgaagct gggcattgcc cgtgcttaca aggcgcctaa cctctaccag      1500
ttgaacccga actatattct ctacagcaac ggtcaaggct gttacgccag tagttccgcc      1560
tgctatctga tggggaatag cgatctgaaa gcggagacca gcgttaataa agagattggt      1620
cttgagtaca gcatgatgg ctatcaggcg ggatcacct ggttccgtaa cgactatcac        1680
aataagattg agtcagggta tgcggcggtg ggtaccgcca gcaacggcac caccaatatc     1740
tatcagtggg aaaacgtacc aaaggcgtta gtggaaggcc tggaaggaac gctgaatctg     1800
ccggtggggg aggcggttaa ctggagcaat aacctgacct ggatgctgca gagcaagaat      1860
aagacgaccg cgaccggct gtcagtgatc ccgcagttta ccctgaactc gactttgagc      1920
tggcaggttc gtgaagatct ctccctgcag agcacctta cctggtatgg ccgacagaaa      1980
ccaaaacgct tcaattataa gggcgaggcg gtcagcggca gcgaactaaa cgaagtcagc     2040
ccatacagca ttgtcggcct cagtgcgacc tgggatgtga caaaaatct gagcttcacc      2100 agcgggatag ataacctgtt tgatattcgc cactaccggg cagggaatgc gcaaacgacc     2160
ggcaacgcga cgacgggagc ttatctgtat ggcgcgggtg ccgagaccta taacgaatcg     2220
gggcggacct tctttatgag cgttaatact catttctga                                2259

<210> SEQ ID NO 54
<211> LENGTH: 2286
<212> TYPE: DNA
<213> ORGANISM: Klebsiella pneumoniae

<400> SEQUENCE: 54
atggaaaaaa acgcttctct gccttttcggc agtttcaact cattggcatt gtttacaggt       60
ctgtgtctgg gagcctcgcc ggcagcaggc atcgcagcgg aaaattcggt caaaaatagt       120
gaagagacgc tggtagtgga agccgctccg ccttcactct actccccggg cgcttccgcc       180
gatcccaagt tcaataaacc gctggtcgat accacccgca ccatcaccgt gatcccggaa      240
caggtgatta agatcagggg cgtcaccaac ctgactgacg ccctcaaaaa cgttcccggc     300
gtcggggcgt tttatgccgg ggagaatggc agctcaacca ccggggatgc catctttatg      360
cgcggcgtgg ataccctaa cagcatctat gtggacggca ttcgcgacat cggtagcgtg       420
acgcgcgata ccttcaatac ccagcaggtg gaagtcatca aagggcccgc cggcacggac     480
tatgccgcca gcgcgccctc cggctcgatc aatatgatca gcaagcagcc cgcgccttgac     540 tccgggatcg acgctcggc cagcatcggc agcgcctggt cgcgccgggg cactctcgac      600
ctgaaccagg cgtttagcga caacgctgcg ttccgtctga acctgatggg ggaaaaaacg     660
catgacgctg tcgggaccg cattgaaaac gaacgctatg catcgcaccc gtcgctggcc      720
ttcggccttg ataccccaac tcgtctgtat ctgaactatc tgcacgtccg gcagaacaac    780
accccggatg gcgggatccc taccgtcggc ctgccgggct attcggcgcc ttcgccgaag     840
tatgccgcac tcaactccgc cgggaaggtc gataccagca atttctatgg caccgactcc     900
gattacgata aatctactac cgacagcggt accctgcgct tcgaacacga tctgacggag     960
```

```
aataccaccg tgcgcaatac cacccgctgg tcgcgagtga acaggagta tcttttgacc    1020 gcggtgatgg gcggcgcgaa caatatcacc gcccccgata tcaatgacgt caacacctgg   1080
agctggtcgc gtctggttaa taccaaagat gtcagcaacc gtattctgac caaccagacc   1140
aatatcacct cgactttcaa tactggctcg ataggccatg acgtcagcgc cggcgtggag   1200
tttacccggg aaaaccagac caactatggc gttaacgcca ggaccgcgcc ggcggtgaat   1260
ctctaccatc cggtgagcaa cctgtcgatt ggcgggctgg acagaaacgg ggcgaacgcc   1320
aacggccaga ccgatacctt cgggatttat gcctttgata cgctgacgct gaccgagcgg   1380
attgagatca acgcgggct gcgtctcgac aattaccata ccaaatatga cagcgccacc    1440
gcctgcggcg gcagcggacg cggggctatc gcctgcccgc ccggacagtc gaccggcagc   1500
ccggtcacca ctgtcgatac cgctaaatcc ggcaatctgg ttaactggaa agccggggcg   1560
ctgtaccgct taaccgagca gggcaatgtc tacgtcaact acgccatctc acagcagccg   1620
ccgggaggca gcagcttcgc cctggccgcc agcggcagcg gcaacagcgc taaccggacc   1680
gactttaagc cacagaaggc gaaatccagc gagctgggca ccaagtggca aatcttcgac   1740
aaccgtctgc tgctcagcgc ggcgttattc cgcaccgata ttgaaaacga agtggccgcc   1800
aacgatgacg gaacctggtc gcagtacggc aaaaagcgcg tggagggta tgaactctcc    1860 gcgaccggaa acctgacccc ggactggacg attatcgccg gctacactca gcagcatgcg   1920
acagtgacgg agggacagaa cgttgcacag gatggatctt ccgccctggc ctacaccccg   1980
aaacatgcct ttacgctgtg gacgcagtat caggccacca gcgatctgtc cgtcggcggc   2040
ggtgtgcgct atgtcggaag cctgcgccgg ggcagcgatg gtgcagtcgg tacccccggat  2100 cacaccgagg gctactgggt tgccgacgcc aaactgggct atcgggtcaa cagcaacctc   2160
gatctgcagc tcaatatgta taacctgttt gataccgatt acgtggcctc catcaacaag   2220
agcggctatc gctatcatcc gggcgaaccc cggaccttta tgctgacggc gaacgtccat   2280
ttctga                                                              2286
```

<210> SEQ ID NO 55
<211> LENGTH: 2373
<212> TYPE: DNA
<213> ORGANISM: Klebsiella pneumoniae

<400> SEQUENCE: 55

```
atggcgacta tgtacaaatc gactccgtca gcagcatggt gtaaaaaacg cctgctggtg     60
acctctttgt ttgcagcaat ttatcagact tctgccatcg cagcagatac ttccgccgtt    120
agcggcgagg cggtggatga cacctcggaa caaatgaccg tcaccgcccc cgcgccggtg    180
cagaaagccg gtagcgaaca cagcatcagc gcccgggagc tggagaataa aggcgctaac    240
gatttcggct caatcatgcg ctatgagccg ctcatcagcg ccaccggggc cagcggcggc    300
tccggcaacg gcaaaagcgg cttcgaccgc ggaggttaca ccggctacaa cattcgcggt    360
atggagagca accgcgtagg catcgacgtg gacggtatcg cgcaacccaa cgccaccggc    420
cgcggctacg tcggccgcgc cgggctcaac accttcggca tcggccgcga ttatatcgac    480
ccgtatatgt acgcagcgt tgatatccag tccggcgcca cctcgacgga aacgccaac     540 agcgctatcg gggggaatgt ctccttccgc ccgaaatcag cggatgatta cctgcgcccg    600
ggcaagacca cgcgccttcgg ctaccgcagc ggttacgact ctgcgggatcg cagctggcac   660 aacgggtgta ccgtcgccgg cggcgatgag ttcctgcgcg ggattttggt ctatagccgc   720
```

```
cgtgacggcc aggaaactga aaacaacagc ggcaccgtcg acgcctaccc ggcgaactgg      780
cactccgatg cttttctggc ctccgggatc tggcagccta acgatgagca caagctgacc      840
agcaccttcg actattacca taaaaccaac cacacccact acgatacctg ggactccagc      900
ggcaacagca ccatcggcac cgccaaccag accagccaga cccggcgctg gggcctgagc      960
ctgaaggatg actggacgcc gatgaacgac tacctcgaca gcgtctccac aaaaatctac     1020
taccagcata ccgaagccca tgactggact tatatgccgg acagcgtcac cgcaaaatg      1080 cagacggtga actctaacta cgataccgac acctggggcc tgcagaccgc gctggcgaaa     1140
accctgggcc gccacgatct gagcgccggt ttcaacgcca gcaccagcaa acccagcgg      1200 ccgttcagcc agtcgccgat ccccagcgtt tacagcgaga tcatgcagcc ggaggcagac     1260
agccgcagct acaccctcgg cggctttgtc caggataaga tcaacttcga tctcgacagc     1320
cacaacttcg ccgttattcc cggcgtgcgc gtggtgcatc aatcgactaa gccggaaaat     1380
ctgtccgatc tcgccgccaa cagcagcgtg ctgagcgaat cgtcggtggc gaatctgtac     1440
ggcaaaaaca gcgataccca ggttctgccg tcgttgacct tccagtacga cctcaccccg     1500
cgcctgatga cctacctgca gtaccagcgc ggggcgcagt tccccaacgc cagccagctg     1560
tatggctcct ggaacctcgg ctccagctac gccggcagcc agcagtatgc cctgatcggc     1620
aataccgatc tgaagacgga aaccagcgat aatctcgagt ggggggctga aggggaagtt     1680
accgaaggca tcccctgcg cacggcgctg ttctacaaca gctataagaa ctttatcgcc      1740
tatacccgct atacccgcgc caacaatccg ggccagttca cgaatgtgcc gtcgaacatc     1800
tacaccattt atcaggcgga aaaccgcgat aaagcctata tctacggcgg tgagattagc     1860
accaaattta actttggcac ctggtttgag caggtggacg gcctgagcgc caccctcgcc     1920
ctcggctata gcgaagggaa atcgaaatcc agctacagcg gcgataaata cgtcgacctc     1980
gacagcgtgg cgccaatgaa agccatcgtc ggcgtggcgt gggacgatcc ggcgaaacgc     2040
tacggcaccg ccctgacggc gacctttgtc aaagggaaac aggcgaccgc caccaaccgc     2100
gaaagctaca gcaacagcgg atccgccatc accgatgcca gcagcgacta tgcgcgtg      2160 ccgggctacg gcatgctgga ctggaccgcg tactggcagg tggcgaaaaa cgtgcgcctc     2220
aatggcgggg tctacaacct caccgatcgt aaatactggg attacctgag cagccgcaat     2280
atcgagaccg gcaccaacca ggacgccaac gataaagcgc tggcggtgat gccgggccgc     2340
acctggcagc tgggcgtcaa cgtcgacttc tga                                  2373

<210> SEQ ID NO 56
<211> LENGTH: 2430
<212> TYPE: DNA
<213> ORGANISM: Klebsiella pneumoniae

<400> SEQUENCE: 56
atggcgatga aaaagttgct catagcgtcg ctgctgttta gcagcgcgac tgtatacggt       60
gctgaagggt tcgtggtgaa ggacattcat ttcgaaggct gcagcgtgt cgctgttggt      120 gcggccctcc tcagtatgcc agtgcgtcct ggcgatacgg tgaccgacga tgatatcagt      180
aacactattc gcgcgctgtt tgccactggc aacttcgagg acgtccgcgt cctgcgcgat      240
ggtgataccc tgctggttca ggtgaaagag cgtccgacga tcgccagcat cactttctcc      300
ggcaacaagt cggtgaaaga tgacatgctc aagcagaacc ttgaggcctc aggcgttcgg      360
gtgggcgagt cgcttgaccg cacgaccatc gcggatatcg agaagggtct tgaagacttc      420
tactacagcg tcggtaaaata cagcgccagc gtcaaagcag tcgttacgcc gctgccgcgt      480
```

```
aaccgtgtcg atttgaagct ggtcttccag gaaggcgtct ccgcaaaaat tcaacagatc      540
aacatcgtcg gcaaccatgc gttttcgacc gatgagctga tctcccactt ccagctgcgc      600
gatgaggtgc cgtggtggaa cgtggtcggc gaccgtaaat accagaagca gaagctagcg      660
ggcgaccttg aaaccctgcg cagctactac ctggatcgcg gctatgcccg tttcaacatc      720
gattctaccc aggtcagcct gacgccggat aagaaaggga tctacatcac cgtcaacatc      780
accgaaggcg atcagtacaa gttttccgga gtgcaggtga cgggcaacct cgctggccat      840
tccgcggaaa tcgaagcgct gactaaagtt gagccaggcg aactgtacaa cggcgcgaaa      900
gtgaccaaga tggaaaacga catcaagaaa ctgttgggtc gttatggtta cgcctatccg      960
cgcgtgcagt cgcagccgga gatcaacgac agcgataaaa ccgttaagct gcacgttaac     1020
gtcgacgcag gcaaccgtta ttacgtgcgt aaaattcgct tcgaaggcaa cgacacctct     1080
aaagatgccg tactgcgccg cgaaatgcgc cagatggaag gcgcatggct gggcagcgac     1140
ctcgtcgatc agggtaaaga ccgtctcaat cgtttaggtt tctttgaaac ggtggatact     1200 gataccccagc gcgtgccggg cagcccggac caggtcgacg ttgtctacaa ggtgaaagag     1260
cgtaacaccg gtagcttcaa cttcggtatc ggctacggca ccgagagcgg cgtcagcttc     1320
caggcgggcg ttcagcagga taactggtta ggtactggct atgctgtcgg gatcaacggt     1380
accaaaaacg actaccagac ctataccgag ctgtcggtga ccaaccccgta cttcaccgta     1440 gacggtgtaa gcctcggcgg tcgtgtcttc tataatgact ttgatgcgaa cgatgcggat     1500
ctgtctgact ataccaacaa aagctatggt acagacatta cgctgggctt cccggtcaac     1560
gaatacaaca cgctgcgcgc cggcgtcggt tatgtgcata actccctgtc caatatgcag     1620
ccgcaggtgg caatgtggcg ttaccttaac tcgatgggcc agtatccgga caacaccaac     1680
gaccggaact cgttcagtgc gaatgacttc accttcaact acggttggac ctataacaag     1740
cttgaccgcg gcttcttccc aacggaaggt tcgcgcgtca acctgaacgg taaggtgacc     1800
attccgggct cagacaacga gtactacaaa gcgacgctgg ataccgcgac ctacgtgccg     1860
atcgacaacg atcatcagtg ggtagtactg ggtcgtacgc gctttggtta tggcgatggt     1920
atcggcggca aagagatgcc gttctatgag aacttctatg ccggtggttc cagcaccgtg     1980
cgtggcttcc agtcgaacac cattggtccg aaggcggtgt acttcccggc aagcagtcgt     2040
catgatgatg acgatagtta cgataatgaa tgtaagagca ccgaatccgc accgtgtaaa     2100
tccgatgatg cggtgggcgg taacgcgatg gcggtggcca gccttgagct gattaccccg     2160
acgccgttta ttagtgacaa atatgcgaac tcggtccgta cttccgtctt ctgggatatg     2220
ggtaccgtat gggatactca ctgggattcg agcgcgtacg ctggttatcc ggattacagc     2280
gatccgagca catccgtat gtctgcgggt attgccgtgc agtggatgtc gccgttgggg     2340
ccgttggtct tctcctacgc ccaaccgttc aaaaagtacg atggagacaa agccgaacag     2400
ttccagttta acattggtaa aacctggtaa                                      2430

<210> SEQ ID NO 57
<211> LENGTH: 2691
<212> TYPE: DNA
<213> ORGANISM: Klebsiella pneumoniae

<400> SEQUENCE: 57
atgacagatg tgactattaa agcgctggcc tcagagattc agacctctgt ggatcgcctg       60
atacagcaat ttgctgacgc aggcatccgc aaatcggctg atgattctgt gacctcgcaa      120
```

```
gagaaacaaa ctttgttgac gcacctgaac cgtgaacacg gctcggcgcc agacaagctg      180
acgttacagc gtaagacgcg cagtacgtta aatattccag gtaccggtgg aaagagtaaa      240
tcggtacaaa tcgaagtccg caagaaacgc acctttgtga acgcgatcc gcaagaggct       300 gaacgcctgg ccgcggaaga gcaggcgcag cgtgaagcgg aagagcaggc ccgtcgtgaa      360
gctgaagaag cagcgaaacg cgaggcgcaa ttaaaagctg aacgtgaggc cgcagaacaa      420
gctaaacgtg aagtcgctga taaagcgaaa cgtgaagctg cggaaaaaga caaagtgagc      480
aatcaacata ccgacgaaat gaccaaaacc gcccaggctg aaaagatccg tcgcgagaac      540
gaagccgcgg aattgaagcg caaatcggaa gaagaagcac gccgcaaact gaagaagaa       600 gcgcgccgtg tagcggaaga agcacgccgt atggctgaag aaaacgaaaa aaattggtct      660
gaaacctcag acagcccgga agatagcagc gactatcacg tcaccacatc acagcatgct      720
cgtcaggctg aagatgataa cgatcgtgaa gtcgaaggcg gtcgcggccg tagccgtagc      780
agcaaagcgg ctcgtccggc gaagaaaggc aacaaacacg ctgaatcgaa agctgatcgt      840
gaagaagccc gcgcggccgt gcgcggcggt aaaggcggta agcaccgtaa aggttccgct      900
ctgcagcagg gcttccagaa gccagcgcag gccgttaacc gtgacgtcgt aatcggcgaa      960
accatcaccg ttggcgaact ggctaacaag atggcggtga aaggttctca ggtcatcaaa     1020
gcgatgatga agctgggcgc catggcgacc atcaaccagg tcatcgacca ggaaaccgca     1080
cagctggttg ccgaagagat gggccacaaa gttatcctgc gtcgtgaaaa cgaactggaa     1140
gaagccgtaa tgagcgaccg tgacaccggc gcggcggctg aaccgcgcgc accggtcgtg     1200
accattatgg gtcacgttga ccacggtaaa acctcgctgc tggactacat tcgttctacc     1260
aaggttgcct ccggcgaagc gggtggtatt acccagcaca tcggtgctta ccacgtcgaa     1320
accgacaacg gcatgatcac cttcctggat accccgggcc acgccgcgtt tacctccatg     1380
cgtgctcgtg gcgcgcaggc gacggatatc gtggttctgg tggtggcggc agacgacggc     1440
gtgatgccgc agactatcga agctatccag cacgctaaag cggcgcaggt accggtggta     1500
gtggcggtga acaagatcga taagccagaa gccgatccgg atcgcgtgaa gaacgaactg     1560
tcccagtacg gcatcctgcc ggaagagtgg ggcggcgaga gccagttcgt ccacgtttcc     1620
gcgaaagcgg gtaccggcat cgacgacctg ctggacgcga tcctgctgca ggctgaagtt     1680
cttgagctga agcggtccg caacggtatg gcgagcggcg cggtcatcga atccttcctt     1740
gataaaggtc gtggtccggt agctaccgtt ctggttcgcg aaggtactct gcacaagggc     1800
gacattgttc tgtgcggctt cgaatatggc cgtgtgcgcg cgatgcgtga cgaactgggt     1860
cgcgaagtgc tggaagcggg tccgtccatt ccggtggaaa tcctcggcct gtccggtgtg     1920
ccggctgccg gtgatgaagt gaccgtagtg cgtgacgaga aaaagcgcg tgaagtggcg      1980 ctgtatcgtc agggcaaatt ccgtgaagtt aagctggcgc gtcagcagaa atctaaactg     2040
gaaaacatgt cgctaacat gaccgaaggc gaagttcacg aagtgaacat cgtactgaaa      2100
gcggacgtac agggttctgt cgaagcgatt tccgattcct tactgaaact gtctaccgac     2160
gaagtgaaag tgaagatcat cggttccggc gtaggtggta tcaccgaaac cgacgctacc     2220
ctggcagcag catccaacgc gattctgtt ggcttcaacg ttcgtgccga tgcctctgcg      2280
cgtaaagtta tcgaagcgga aagcctggat ctgcgttact actccgtcat ctataacctg     2340
atcgacgaag tgaaagcggc gatgagcggc atgctgtctc cggaactgaa acagcagatc     2400
atcggtctgg ctgaagtgcg tgatgtcttc aaatcgccga aattcggcgc catcgcgggc     2460
tgtatggtta ccgaagggac gatcaaacgt cacaacccaa tccgcgttct gcgtgacaac     2520
```

```
gtggttatct atgaaggcga gctggaatcc ctgcgccgct tcaaagatga cgttaacgaa    2580
gtccgtaacg gcatggaatg tggtatcggc gtgaagaact acaacgacgt tcgcgttggc    2640
gatatgatcg aagtgttcga aatcatcgaa atccagcgta gcatcgatta a             2691
```

<210> SEQ ID NO 58
<211> LENGTH: 3234
<212> TYPE: DNA
<213> ORGANISM: Klebsiella pneumoniae

<400> SEQUENCE: 58

```
atgaaaagaa tgttaatcaa cgcaactcag caggaagagt tgcgcgtcgc ccttgttgat      60
gggcagcgcc tgtacgacct ggatatcgaa agccccgggc acgaacagaa aaaagcgaac    120
atctacaaag gcaaaatcac ccgcattgaa cccagccttg aagccgcgtt tgttgattac    180
ggcgccgagc gtcatggttt cctccccctc aaagaaatcg cccgcgaata cttccccgcc    240
aactacaatg cgcatggtcg tcctaatatc aaagacgtac tgcgggaagg tcaggaagtt    300
atcgtgcaga ttgataaaga agaacgcggc aacaaaggcg ctgcgctcac caccttatc    360 agcctcgcgg gcagctatct ggtactgatg ccgaacaacc cgcgcgccgg ggaatttcc    420 cgccgtatcg agggcgacga ccgtaccgaa ctgaaagaag cgctggcgag cctggagctt    480
ccggacggca tgggcctgat cgttcgcacc gctggcgtcg gcaaatccgc cgaagccctg    540
cagtgggacc tgagcttccg cctgaagcac tgggaagcga ttcagaaagc cgcggaaagc    600
cgtccggcgc cgttcctgat ccaccaggaa agcaacgtca ttgtccgcgc cttccgtgac    660
tacctgcgcc aggacatcgg cgaaatcctg atcgataacc cgaaagtgct tgagctggcg    720
cgccagcata tcgccgcgct gggtcgtccg gatttcagca gcaaaataaa actgtacacc    780
ggtgaaatcc cgctgttcag ccattatcag atcgaatcgc aaattgagtc cgccttccag    840
cgcgaagtgc gcctgccttc cggcgggtct atcgttatcg atagcaccga agcgctgacc    900
gcgatcgata tcaactccgc ccgcgccacc cgcggcggcg atatcgaaga gacagccttc    960
aataccaacc tcgaagcggc tgacgaaatt gcccgccagc tgcgtctgcg cgacctcggc   1020
ggcctgatcg ttatcgactt catcgatatg accccggttc gccaccagcg cgccgtggag   1080
aatcgtctgc gcgaagccgt ccgtcaggac cgtgcgcgca ttcagatcag ccatatttcg   1140
cgcttcggcc tgctggagat gtcccgtcag cgcctgagcc gtcgctggg cgagtccagc   1200 caccacgtct gcccgcgctg ctccggcacc ggcaccgtgc gtgataacga atcgctgtcg   1260
ctctctattc tgcgtctgat cgaagaagaa gcgctgaaag agaataccaa agaagtccac   1320
gccattgttc cggtaccgat cgcctcctat ctgctgaacg aaaaacgtgc cgcagtgagc   1380
gctatcgaat cccgtcaggg cgatgtgcgc gttattatcg tgccaaacga cgaaatgcaa   1440
acgccgcact actccgtcct gcgcgtgcgc aaaggtgaag aaacctcaac gctgagctat   1500
ctgctgccga agctgcatga agaagaaatg gcgctgccag cgacgatga gccggcggag   1560 cggaaacgtc cggaacagcc ggccctggcc gcttttgtca tgccagatgc gccgccagcc   1620
ccgatgctcg aagagcctgc cgccgcgcct gtcgccgcag cggcaccggt cgcggccgcc   1680
gcaccggcgc agcctggcct gctctcacgc ttcttcagcg cgctgaagaa tatcttctct   1740
ggcgccgaag aggccaaacc ggctgaagtt caggtcgaga gaaagcgga agaaaaaccg   1800 gagcgtcagc aggagcgtcg taaaccgcgc gccaacaacc gccgcgaccg caacgaccgc   1860
cgtgataacc gcgacaatcg tgacaaccgc gataaccgtg acaatcgcga cacccgtgcg   1920
```

```
gacaatgccg agggccgtga accgcgcgaa tcgcgtgaag agaaccgtcg caaccgtcgc    1980
gagaagccgt cgcagaacgt ggaagcccgt gatgttcgcc aaacctcagg cgacgacgcg    2040
gagaaagcga atcccgtgac gagcagcag ccgcgccgcg aacgcacccg ccgccgcagt     2100
gacgacaaac gtcaggcgca gcaggaagcc aaagcgcaga ctcgcgaaga gccggttgtg    2160
caggagacgg agcaggaaga gcgtgtacaa actctgccgc gtcgtaaacc cgccagctg    2220 gcacagaaag tgcgcgttga gtccgctgtc gtcgagccag ttgccgagat cgtgccagaa    2280
gccgtagtgg ctgaagttat cgctccgcac agcgagccgg tgaaagccga gctgccggca    2340
ggggtggaga gcgtggcgga ccaggacgaa aatggcgaat cccgtgaagc gaacggtatg    2400
ccgcgtcgct cacgtcgctc cccgcgtcac ctgcgcgtca gcggtcagcg tcgtcgtcgc    2460
tatcgtgacg aacgctatcc gacccagtcg cctatgccgc tgaccgtagc ctgcgcatcg    2520
ccggagatgg cttccggtaa agtctggatc cgctacccgg tggttcgtcc gcaggatcag    2580
cagccggaag aggttcaggt tcaggacgcc agcgtcgcga aaactgtcga ggccgtagcg    2640
gccccggtcg ccgtcgttga aaccgttacc gctgcgccgg tcaccgtcga gccggctacc    2700
atggaaccag taaccgctga ccggtagtc gtcgagccgg tagcggccgc cgagccgctg    2760
gtcgttgatg ctgcggaagt tgtcgcgcca gcagccgtcg agccagcgcc tcaggagccg    2820
gtcaccgaag caccggctgt cgaagcgcct caggctatcg cgccagtgac gctcgacgcc    2880
gagccggtgg tggtagaacc tgaagcggtg gaaacgacgc tgtcgttgc agcgccagtg    2940 gaaactatcg ccccggtcgc agaaaccgtg gagcaagcgc cagtgaccga agcggcccct    3000
gccgaaccgg tcaaagccga gccccggtg agcaagccgg tcgtagtggc gggtcatcgc    3060
catgccaccg cgccaatgac ccgtgcgcca gctccggact atgtcccgga agcaccgcgt    3120
catagcacct gggtgcgccc gccgttcgcc tttgaaggta aaggcgccgc cggtggtcat    3180
agcgcgaccc ataaagccac cgctgaaccg actcgcccac agcccgtcga gtaa        3234
```

<210> SEQ ID NO 59
<211> LENGTH: 3480
<212> TYPE: DNA
<213> ORGANISM: Klebsiella pneumoniae

<400> SEQUENCE: 59

```
atgcgcaagc tctcactaag tttactcacg ctgtccctcg gcgttgcgct gctgccgtta     60
gcgcaggcgg cgacgacgcc tgcccaggag catctgctgg agcaggtccg cctcggcgag    120
gccagcaatc gtgaagacct ggtgcgccag tcgctgtacc gtctggagct gattgatccc    180
aacaacccgg agctgattgc cgcgcggatg cgctatctgc tgcgtcaggg ggatgccgcc    240
ggggcgcaaa aagagctgga acgactgacg aagcaggcgc cggactcccc ggagctgaag    300
gcgtcgcgca atgagatgaa aagcaacacc ggcgagggcc gccaggcgct gcagcaggcg    360
cgactgctgg gcgtggccgg gaaggtcgat gaagccatcg ccgcctatga aaaactgtac    420
ggcggggtgc cggatgacgt tgacgtcgcc attgagtact ggacgctggt ggcgcgcctg    480
ccggcccgcc atagcgaagg cgtcagccag ttgaaaaaac tgaacgccag cgcgccgggc    540
aacgtcagcc tgctgacttc gctggcgaag cagatgttcg ccgataacaa accgcaggag    600
gggttcgcct atctggcgga gatggcccga tcggcctcgg acgcggtat cgccgccgat    660 atgtggttca gtgaggtgaa aagcatgccg gtgagtaagg ccagcgtgca ggcgttgcag    720
caatttcttc tgcagtttcc caccggctcg gtggcggcga acgcccgcgt tctgctcgac    780
caacagcagg cgcagctgca ggatccgact ttccgcgccc gctcggaagg gctggcggcg    840
```

```
gtcaagtccg ggaataccac gcaggcggtc gcggatctgc agaaagccgt tcaggccgac      900
agccgcgaca gcgacgcggt gggcgctctc ggccaggcct attcccagcg cggcgaccgc      960
gcgcgggcag tggcgcagct cagtaaagcg attgctatgg accctgacag cccgaaccgc     1020
ggcaagtggg acagcctgct gcaaactaac cgctactggc tgctgataaa gcaggggggat    1080 aacgccctga agccggcca gctttcgcag gcgcagaact attatgccca ggcgcagcgg     1140
gtcgatcgca ccgacagcta tgccgtgctg gggctggggg acgtcgcggc ggcgcgcaaa     1200
gaggcggcgg cggcggagcg ctattaccag caggcgttgc gcctggatcg cggcaataac     1260
ctggcggtgc gcgcctggc caacctctat cgcgccgaat cgccggagaa agccagcgcc     1320
tggatcgccg gcctccctcc cgctcagcgg cggagcatcg atgatattga gcgcagcctg     1380
actaacgacc ggctggagaa acaggcgcag gctctggaga gccagggcaa ctgggcgcag     1440
gcggcggaag ttcagcgtcg gcgcctggcg ctggatccgg acagcgtctg gataacctac     1500
cgtctggcgc gggatctggt cagcgccggc gaacgccagg aggccgacgc gctgatgcgg     1560
acgatggtca accgccagcc gcaggacgcc gaacgggtct acgcctcggg actctacctg     1620
tcggggaacg accaggacga tctggctctg gcgcaaatcg ccgctctgcc gcgcagcgcg     1680
tggacggata acattcgtga gctcgaagcg cgtttgcaaa gcgaccgggt gctgcgccag     1740
gccaaccagc tgcgcgacag cggtaacgaa gcgcaggcga tcgcccttat ccgacagcag     1800
cccgcctcgg tgcgctatga cctgacgctc gccgactggg cgcagcagcg cggcgacagc     1860
cagacggcga ttgccaacta tcagcgggtg ctgcgccagg aggccgacaa cggcgatgcg     1920
cgcctcggcc ttgcggaagt ctacctggcc gagggcgata accggccgc ccgggcgcag     1980 gtcatgcagc tgaaaggcgc agagaccgaa tccatgaaca tgcagcggcg ggtggcgctg     2040
gcgcgagctg gccttggcga taccgctgac gcgcaacgga ttttttaatca gattgtgccg     2100 caggcgaagg cgcagccgcc ctcgatgag agcgcgctgg tgctgcgcga tgccgcgcgc     2160
tttgccaccc agagcggggc gccgcagcag gcgctgacgc actaccggga agctatggtg     2220
gcctccggca ttaccccgc gcagccgcag gataacgata cttttacgcg gctgacgcgc     2280
aacgacagcc atgatgactg gctgaagcgc gggatccgca gcgatgccgc cgaccttat     2340 cgtcagcagg atctgaacgt caccctggaa catgacttct ggggttccag cggcaccggc     2400
ggctattccg acctgaaggc gcataccacc atgctgcaga tggatgctcc gctggcggat     2460
ggccggatgt tcttccgcac cgacctggtc aatatggatg ccggcagctt ttccacccac     2520
agcgacggga gctactcgcc cagctggggc acctgcgggg agatcgcctg taccagcggc     2580
agtaaaaatc agaccgacag cggggccagc gtggcggtcg gctggaagaa tgacacctgg     2640 agcgggata tcgcaccac gccgatgggc ttcaatgtcg tcgatgtggt gggggggctg     2700
agctacagca gcgacgtcgg gccggtgggg tacacggtca acgtccaccg gcggcctatc     2760
tccagctcgc tgctctcctt tggcgggcag aaggacagca gcagccatac cggcgccacc     2820
tggggcggcg tccgcgccga cggcggcggc ctgagcctga gctacgatcg cggggaggct     2880
cacggcatct ggtcctcgct gggcgccgac tcgctgaccg gtaaaaacgt ggcggataac     2940
tggcgcgtgc gctggatgac cgggtactac tacaaggtca tcaacgagaa taatcgtcgc     3000
gtcaccgtcg gcctcaacaa tatgatctgg cactacgaca aagatctcag cggctacacc     3060
ctcgccaggg cggctatta cagcccacag gagtatctct cgttcgccgt gccggtgacc     3120
tggcgtcagc gcaccgagaa ctggtcctgg gagctcggcg ggtcggtgtc atggtcccat     3180
```

```
tcgcgcaccc agacgcaagc ccgctatccg ctgctgaacc tgatcccgtc cgactaccgg   3240
cagcgcgcca gcgagctgac ggaggagggg agcagcagcc atggattcgg ttacaccgcc   3300
agagcgctgg tggagcggcg ggtgaccagc aactggttcg tcggcgccgc ggtcgatatt   3360
cagcaggcga aggattacac cccgagccat gcgctgcttt acgtccgcta ctcggcggcc   3420
ggctggcagg gggatctgga tatgccgccc cagccgctgg tgccctacgc cgactggtag   3480
```

<210> SEQ ID NO 60
<211> LENGTH: 4236
<212> TYPE: DNA
<213> ORGANISM: Klebsiella pneumoniae

<400> SEQUENCE: 60

```
atgagccagg aatacaccga agacaaagaa gtcaaactaa ccaaactcag cagcgggcgc     60
cgactccttg aggcgatgct catcctttgc tccctcttcg ccatctggct gatggcggca    120
ctactgagct ttaaccccte ggaccccagc tggtcgcaaa cggcatggca tgagcctatt    180
cataatttag gcggcgcccc cggcgcgtgg cttgccgata ccctcttttt cattttggc    240 gtcatggcct acaccatccc ggtgatcatc atcggcggat gctggtttgc ctggcggcat    300
caggaaaacg acgaatacat tgattatttt gccgtttccc ttcgcctcat cggtgcgtta    360
gccctgatcc tgacctcctg tggtctggcg gcgattaacg ccgatgatat ctggtacttc    420
gcctccggcg gggtgatcgg cagcctgctg agcaccacgc tgcaaccct gctgcacagc    480 agcggcggca ccatcgccct gttgtgtatc tgggcggccg ggctgacgct gttcaccggc    540
tggtcgtggg tcagcattgc ggaaaagctg gcggcggca cctgtccgt tctcaccttt    600 gccagcaacc gtacccgtcg ggatgatacc tgggtcgatg aaggcgaata tgaagacgac    660
gaggaagagt acgacgacga agaggcggcc aggccgcagg aatcgcgtcg cgcccgtatc    720
ttacgcagcg cgctggcgcg gcgtaagcgt ctggccgaga agtttaccaa ccctatgggg    780
cgtaaaaccg acgctgcgct tttctccggc aaacggatgg atgacggcga agaggtggtg    840
caatacagcg ccagcggggc gcctgttgcc gccgacgatg tactgttttc cggcgccagc    900
gccgcgcgtc ccgcagagga tgatgtgctg ttctccggcg ccagcgccgt gcgcccgggc    960
gatttcgacc cttacgatcc gttgttgaat ggccacagta tcgctgagcc ggtaagcgca   1020
gcggcggcgg ctacagccgc gccgcaggcg tgggcagaat caccggtggg ccatcacggc   1080
gctgcgccag cttatcagcc ggaagccagc tatccgccgc agcaggccta tcagcctgaa   1140
cccgctccgt tccagcaggc ctatcagcct gaacccgctc cgttccagca ggctgcttat   1200
cagccgccag cggggcaaac cgcaccgcag gcgtatcagc ctgagccagc gccgtatcaa   1260
cagccggttt acgatccgcg tgccggtcaa cctgcgccgc aggcctatca gcctgagcca   1320
gcgccgtatc agcagccggc ttacgatccg tatgccggtc aacctgcgcc gcaggcctat   1380
cagcctgaac ctgcgccgta tcagcagccg gcttacgatc cgcatgccgg tcaacctgca   1440
ccgcaggcct atcagcctga ccagcgccg tatcagcagc cggcttacga tcctatgcc   1500 ggtcaacctg cgccgcaggc ctatcagccg gagccagcgc gtatcagca gccaacttac   1560 gatccctatg ccggtcagcc tgcgcctcag acctatcagc agccggctta cgatccgaat   1620
gccggtcagc ccgcgccgca gccgtatcag ccggagccag cggcgtatca gccgcaaagc   1680
gcgccagttc ccccaccgga gccagagccc gaggtcgtgc aggaggaagt gaaacgtccg   1740
ccgctctatt atttcgagga agtggaagag aagcgggcgc gcgaacgcga gctgttggcc   1800
tcctggtatc agccaattcc tgagccggaa agtccgattg ccactaaacc gctgacgccg   1860
```

```
ccgaccactg cgtccaaacc gccagtggag acaaccgtag tctctgcggt agcggctggg   1920
gtgcatcagg ctaccgccgc cagcggcggc gcggcggcag caacctcgtc cactgccgca   1980
tccgctgcgg ctacgccatt gttcagcccg gcgtccagcg gcccaagggt tcaggtgaaa   2040
gagggcatcg gtccaaaact accgcggccc aatcgcgtgc gtgttcctac gcgtcgggaa   2100
ctggcctcct acggcatcaa gctaccgtcg cagcgggagg cggaacagcg cgcgcggcag   2160
gcggagcgcg atccgcatta tgatgatgag ctgctctcgg atgaggaagc ggatgctatg   2220
gagcaggatg aactggctcg ccagttcgcc gccacccagc agcagcgcta cggtcatcgc   2280
tgggaagacg ataacgcgac tgatgacgat gaggccgacg ccgcggcgga gcggagctg    2340
gcgcgtcagt ttgccgctac ccagcagcag cggtacgcta ccgagcagcc gccgggcgcc   2400
aacccgttct cgccggcaga ttatgaattc tcgccgatga aaacgttggt caatgacggc   2460
ccgagcgaac cgctgtttac gccgacgccg gaagtccagc cgcagcagcc ggcccagcgc   2520
tatcaacaac cggcggccgc tccgcagcag ggttatcaac ctgcgcagca tcagccgata   2580
caccatcagc ctgtgccgcc acagccgcag tcctatccga ctgcgtcgca gcccgtacag   2640
ccgcaacaac cggttgcccc gcaggggcat cagcctgccg cccctgcgcc gcaggagagc   2700
ctgatccacc cgctgctgat gcgcaatggc gatagtcgac cgctgcaaaa gccgaccacg   2760
ccactgccgt cgctggatct gcttaccccg ccgccgagtg aagtcgagcc ggtggatacc   2820
tttgctctcg agcagatggc acgcctggtg gaagcgcgac tcgctgattt ccgcattaaa   2880
gcggatgtgg tgaactactc accggggccg gtgatcaccc gcttcgaact gaatctggcg   2940
cctggcgtta aggccgcacg gatctctaac ctgtcacggg acctggcgcg atcgctgtca   3000
acggtcgccg tgcgcgtggt ggaggtgatc ccgggcaaac cgtatgtcgg gcttgagctg   3060
ccgaataaaa aacgccagac cgtctacctg cgtgaagtgc tcgacaacgc caagttccgt   3120
gataacccat ctccgctcac cgtggtgttg ggtaaagaca tcgctggcga tccggtagta   3180
gccgatctgg cgaaaatgcc gcatctgctg gtggccggta ccaccggttc cggtaagtct   3240
gttggcgtca acgccatgat cctcagcatg ctctacaagg cgcagccgga agatgtgcgt   3300
ttcattatga tcgacccgaa aatgctcgag ctgtcggtct acgaaggaat tccgcacctg   3360
ctgacggaag tggtcaccga catgaaagac gccgccaatg cgctgcgctg gagcgtcaat   3420
gagatggagc gccgctacaa gctgatgtcg gcgctgggcg tgcgtaacct cgcgggctac   3480
aacgagaaga tcgccgaagc cgcgcgcatg ggacgtccga tcccggatcc gtactggaag   3540
cctggcgaca gcatggacgc cgtacatccg gtgctggaaa aactgccgta catcgtggtg   3600
ctggtggatg aattcgccga tctgatgatg accgtcggca aaaggtgga agagctgatc   3660
gctcgcctgg cgcagaaagc gcgcgcgcg gggatccacc tggtgctggc gacacagcgt   3720
ccgtcggtag atgttattac cggcctgatt aaggccaaca tcccgacgcg catcgccttt   3780
accgtgtcga gtaaaattga ctcacgtacc attctcgatc agggcggcgc ggaatcgctg   3840
ctgggtatgg gggatatgct ttactccggg ccgaactcta ccacgccggt gcgtgtccac   3900
ggggcgtttg tgcgcgacca ggaagtccac gccgtggttc aggactggaa agcccgcggt   3960
cgcccgcaat atgtggatgg cattacctcc gacagcgaaa gcgaaggcgg cggtggcggc   4020
ttcgacggcg gggaagagtt ggatccgttg ttcgatcagg cagtcaactt tgtgaccgag   4080
aagcgcaaag cgtcgatttc cggggttcag cgtcagttcc gcatcggcta taaccgtgcc   4140
gcgcgtatta tcgaacagat ggaagcgcag ggtatcgtca gcgagcaggg ccataacggt   4200
```

```
aaccgcgaag tgctggcgcc gccgcccttt gaatga              4236
```

<210> SEQ ID NO 61
<211> LENGTH: 285
<212> TYPE: RNA
<213> ORGANISM: Klebsiella pneumoniae

<400> SEQUENCE: 61

```
augaagaagu uagcuuuacu cuccgccgua augacgcuug gaaugucguc augggcuuuu    60
gcugccgaca acccgccgcc gccgccggaa aaaggcgcgc agcaucaggg uaaaccgccg   120
gugaaaaacg gccaacacga agguaagcaa gcgcaauaca acagaaaaca gccacaacga   180
gacggcaaac agccgcagca cgacgguaaa cagccgcagc acaacggcaa gcagccgcca   240
aaagggagcg agcacagcgg gaaaccgcug ccgccgaaag cguaa                   285
```

<210> SEQ ID NO 62
<211> LENGTH: 354
<212> TYPE: RNA
<213> ORGANISM: Klebsiella pneumoniae

<400> SEQUENCE: 62

```
augaaacguu acgcaaccgc acugcucuuu ugcacucugu cgcugaccag ccuggccgcu    60
cgcgccgaua uuaucgauga cgcgaucggc aauauucagc aagccauuaa cgacgccuau   120
aaccccggca gcagucgcuc cgaugacgac gacagauacg augacgaugg ccgguaugau   180
gacgggcgcu aucaggggag ccgucagcag agccgugaca gucagcgcca guaugacgag   240
cggcaacgcc agcuggacga gcgccgccgc cagcuggaug aacgccagcg ucagcucgac   300
cgcgaucguc gucaguuaga aagcgaccag cgucgucugg augauagcua cuga         354
```

<210> SEQ ID NO 63
<211> LENGTH: 360
<212> TYPE: RNA
<213> ORGANISM: Klebsiella pneumoniae

<400> SEQUENCE: 63

```
auguucaggu cacugauucu ggcagcagua cugcuggccg cagggccacu ggucgcuaac    60
gcuggugaaa ucacccugcu gccaucggua aaauuacaaa uaggcgaucg ugacaauuac   120
gguaacuacu gggacggugg cagcuggcgc gaccgugauu acuggcgucg ucacuaugaa   180
uggcgugaua accguuggca ucgucaugac aacggcuggc acaaaggcug guacaaaggc   240
agagauaaag ccugggagcg cggcuaucgu gcuggcugga acgaccgcga ugaccaccgc   300
ggcggcuggg gucgcggccc gggcgggcgc ggucacgguc auggacaugg ccaucacuaa   360
```

<210> SEQ ID NO 64
<211> LENGTH: 363
<212> TYPE: RNA
<213> ORGANISM: Klebsiella pneumoniae

<400> SEQUENCE: 64

```
augaaggaaa ucggcuuacc guuauugcua cugaccgcgc uggccagucc ggcuuuugcu    60
gcagacuguc agccaaacgg cauuggcggc ucguuuugca uuaacgauga cgguacgacu   120
accgacacgg ugccuaacga agucaacggc auggauacgu acucgaauaa uggcggcuau   180
accaguuccc ugcccgaucg gucagggcg gaugaagcac uggaagguuc aucgcugucg   240
acgcagcaag gcgucggcag cggacagagc gacagugcgc uggcgggucg cgacuggcau   300
ucgcccgcca aucugaauga uggcgccgcc accuccagua ugagccugcu ggauaaaccc   360
``` uga                                                                          363

<210> SEQ ID NO 65
<211> LENGTH: 366
<212> TYPE: RNA
<213> ORGANISM: Klebsiella pneumoniae

<400> SEQUENCE: 65
augaauauga aaaacugac gacccuuuug cucaccgcca ccuuaggucu ugccagcggc      60
gcggcccugg cggcagacac cggcgcccag uccaauaaug gccaggccaa ucuuccgcg     120 gaugccgguc aggugggcgcc ggaugcccgu gagaacgugg cgccgaacaa cguggacaau   180
agucagauca acucuggcuc uggggggcacc acgggcucga cgaugaccca ggauaauaug   240
ucgagcaaug agguacauaa aaacucgaug uguaaagacg gccgcugucc ggacaccggu    300
aaaaaacugg acaacggugg caauacgacc caagacaaca gcaaaaccga cggcaccacc    360
caguaa                                                              366

<210> SEQ ID NO 66
<211> LENGTH: 369
<212> TYPE: RNA
<213> ORGANISM: Klebsiella pneumoniae

<400> SEQUENCE: 66
augaaacacc gcaucgcucu gcuucugguc cugacuucac uuagcgccag cgcccuagcc     60
gccucucccu gccaggaaaa agagcaggau auucaacgag agaucagcua cgccgaaaag    120
caucauaauc aaagucgcau ugaugggcua aauaccgcgc uacgucaggu ucgggaaaac    180
uguagcgaca guaaacucaa agccgaucau cagcaaaaaa uugccaaaca gcggaagag    240 aucgcugaac gucagcgcga ucugcaggaa gcccggaaga aaggcgaugc ggacaaaauu    300
aacaaacgcc agcauaaacu caaugaagcg caacaggagu uaaaaacgcu ggagucucgg   360
gauuacuaa                                                           369

<210> SEQ ID NO 67
<211> LENGTH: 426
<212> TYPE: RNA
<213> ORGANISM: Klebsiella pneumoniae

<400> SEQUENCE: 67
augcgacuca uaacacgaca cgugagagag gauauuauga aaaagcaau gauugcguua      60 ucggcuauuc ugguugcggc uccgguuuuu gcugcgacaa cacaugcaac agaugauacc    120
gucgcggcgg cgaaugccaa cgccaacacc gcuaaagaga agcugcauca ggcccagcac    180
gagggcgaag agcagcagcu gaaggcgaaa cacgccgccg aaggcaagca ggacagcguc    240
ggcagccagg ugagcgaagg cgcgcagaaa accuggaaca agaccaaaga aggcaccgag    300 aaggggugggg auaagaccaa agaggucagu gaaaaaggcu ggaacgccac caaauccggu    360
gcggaaaagg gcugggauaa aaccaaaacc ggcgccgaag aguuaaaaaa uaaagugacu    420
gaauaa                                                              426

<210> SEQ ID NO 68
<211> LENGTH: 456
<212> TYPE: RNA
<213> ORGANISM: Klebsiella pneumoniae

<400> SEQUENCE: 68

```
augaaaaaga ugauuucucu ggcaguaauu uuauccugug ugcugagcgu cccggccuuu    60
gccgauggcc cgaacgacgg ccaucgcccg gagcagccca cggugugggca gaacggguccg   120 gaccaugacg ggcaugcacc gcagggcgga ccugacgcgc aucaucaggg cgaccaugac   180 cagcgguggcc cggaucgcga cggccaugac aaacgcgauc uggcacguca ugagcaggac   240
cauuucgccu ggcgcgggaa cgauuuccgc aaaggccacc cggcuccggc gccguuccgu   300
ggcgaugaau aucgcguccg cgacuggagc gaccgcggcc ugccgccccc gccggaaggc   360
caucacuggu ccuauaucga cgguaacuau gugcugaucg ccgcggcgac cgggaucauc   420
accucgauuc uggugagcgg cgcccucggc cacuaa                             456

<210> SEQ ID NO 69
<211> LENGTH: 507
<212> TYPE: RNA
<213> ORGANISM: Klebsiella pneumoniae

<400> SEQUENCE: 69
augaaaaaac cgacauccgc cacccgugggc aaauccggcc gcaagucgcg ugaagaguua    60
aaucaggaag cucgcgaucg caaacggcag aagaaacauc gugggccacgc ggcaggcagu   120 cgcgcgaacg gcgcgaugc ggcuucagcg gguaaaaaac agcgucaggc gcaagauccg   180
cgcgugggua gcaaaaaacc gaucccgcug ggcgugagcg aaagcagcgu ccagcucccc   240
aagcagcaua aaccaaagag cgagaaaccu augcuuucac cgcaggcuga gcuggaguug   300
cuggagaaug augagcgccu ggacgcgcug cuggaacguc uggaagagggg cggcacccug   360 aaugcugaag agcagagcug gguggacgcc aaacuggauc gcauugauga gcugaugcag   420
cagcucggcc ucucuuacga ugaugaagau gaagaagagg aagagcguca ggaagauaug   480
augcgucugc ugaagggugg aaacuaa                                        507

<210> SEQ ID NO 70
<211> LENGTH: 690
<212> TYPE: RNA
<213> ORGANISM: Klebsiella pneumoniae

<400> SEQUENCE: 70
auggcgagua aguuucagaa ccguuuaguc gggacaaucg ugcugguggc gcuggggggug    60 auuauccugc cagggcugcu ggacgggcag aaaaagcauu accaggauga guuugccgcg   120 auccccgcugg uaccgaaaacc aggcgaucgc gaugaaccgg auauguugcc ggcggcaacc   180
caggcguugc cuucgcaacc gccggaaggg gcggcggaag aggugcgggc gggcgaugcc   240
gccgcgccau cguuagaucc aucgcguauu ccggugaaca gcaacagcuu cgaugacguu   300
caggagccgg ugguggccgc gaaaccgcag cccaagccgc agccgaaacc gcagccgcaa   360
cagcaggccu cgacgccaac gccgccgccg gcuaagccac agcagcaaca gccaccgcag   420
cagcaggcgg cccugccggc gccgaccggc aaagccuaug ugguucagcu gggcgcguug   480
aagaacgccg auaaggugaa ugagauugcu gguaaacugc gggccucggg uuucaaaguc   540
uauacgucgc cuucgacgcc gguacaggggu aaaauuaccc gcauccucgu cggcccggau   600
gcgucaaaag acaagcugaa aggccagcug ggcgaucugc agcagaucuc cgggcuuagc   660
ggggugguga uggcuucac cccgaacuga                                      690

<210> SEQ ID NO 71
<211> LENGTH: 969
<212> TYPE: RNA
<213> ORGANISM: Klebsiella pneumoniae
```

<400> SEQUENCE: 71
auggcacaac gagauuaugu acgccgcagc caaccggcuu cuucgcggcg caaaaagagc 60
acgacccgaa gcucaaggaa uaagcaaagc agccuuccgg cgauuucacc ggcgauggug 120
gcgaucgcgg cggcugugcu gguggccuuu aucgguggcc ucuauuucau uacgcaucau 180
aagaaagaag aagcggaagc gaugcaaaau cgccaggccg ccggcaacgg cuugccgccc 240
aaaccggaag agcgcuggcg cuauauuaaa gagcuggaaa gccgccagcc uggcguccgc 300
gcgccgaccg aaccgaccgc cgguggcgaa gucaugaaac cggaacagcu gaccgacgag 360
cagcgccagc ugcucgccca gaugcaggcc gauaugcgcc agcagccgac ccagcugacc 420
gaagugccgu ggaacgaaca aacgccggcg cagcgccagc agacgcuuca gcgucagcgu 480
uuagcgcagc aacagcagca ggcgcagcag caacaguggg cgcagacuca ggcgcagacc 540
guccaacagc agccgccgcg cguucagcag ccgaagccgg uucagcagca acagccgaag 600
cagaccgcgu caaaccagca gccguaccag gaucugcugc agacgccagc gcauaccaau 660
accacgcagc cgcguaccca ggccgcggcg ccgguaacuc ggguggaaga agcgccgaaa 720
accaccgccg agaagaaaga cgaucguagc uggaugaucc agugcggcuc uuuuaaaggc 780
gccgagcagg ccgaaaccgu ccgcgcucag cuggcuuucg aaggguuugc uucgcacauu 840
accacuaaca acggcuggaa ccgcgugguu auuggcccgu ugaaaggcaa agaaagcgcc 900
aacgagauga ucacccgccu gaagauggcu ggacacgcga acugcauucg ucucgccgcc 960
agggguuga 969

<210> SEQ ID NO 72
<211> LENGTH: 1131
<212> TYPE: RNA
<213> ORGANISM: Klebsiella pneumoniae

<400> SEQUENCE: 72
augagcgcgg gaagcaccaa auuuaccguc agccguauug cggcucuuuc acugguuuca 60
cucuggcugg ccggguguac caacaccaau aauccgccug cgccgguuag cucugccggc 120
ggcgccgccu cuuccagcac caacuccggc augcugauua cgccgccacc cuccggcguc 180
aaguccgcuc cucaggcgca gccgauucag ccgaugcaga cccagaccau ucagccggcg 240
ccgguggcgc aggagccggu acagacggua aauggccgga ucguuuacaa ccgcaaauau 300
ggcgauauuc cgaaagguag cuauaccggc ggcaguaccu auacgguaaa acgcggcgac 360
acgcuauucu auaucgccug ggucaccggc aacgauuucc gcgaccuggc gcaacguaac 420
aauaucccgg ccccguacgc gcugaacgug gggcagguac ugcaggucgg uaacgccuca 480
ggccagccga ucaccggcga aaacgccguu ucucaggcca gcgcaagagc gagcggcggu 540
gcgacgacca gcacaacuuc ugcacaaaaa ucgaccgcgg ugguugcuuc acaaccgacu 600
auuacguauu cugaaucuuc aggugaacag agugcuacca agauguugcc uaauaauaaa 660
ccagcgacca caaccacaac gguugucgcg ccggugacgg caccaacaac ggugagcaca 720
acccagccga cugcaagcag uacgucaacc aguucgccga ucucagcaug gcgcuggccg 780
acugauggca agguuaucga gaacuuuagc ggcgcggaag gcggcaauaa aggcaucgau 840
auugcaggca guaagggaca ggcuauuguc gcgaccgccg augggcgcgu cgucuaugcc 900
gguaacgcac ugcgcggcua cgguaaucuu auuaucauca aacacaacga ugauuaccug 960
agugccuacg cucauaacga uaccaugcug guucgggagc aacaggaagu caaagcgggg 1020

| | |
|---|---:|
| cagaaaaucg cuaccaugggg uagcaccgga accagcucaa caagauuaca uuuugaaauu | 1080 |
| cguuacaagg ggaaauccgu caacccgcug caguacuuac cgcagcgaua a | 1131 |

<210> SEQ ID NO 73
<211> LENGTH: 1149
<212> TYPE: RNA
<213> ORGANISM: Klebsiella pneumoniae

<400> SEQUENCE: 73

| | |
|---|---:|
| augcguaagc aauggcuggg gaucugcaua gcagcggggc ugcuggcggc auguucgagu | 60 |
| gaugacgugc aacaaaaaac ggucaguacu ccacagccgg ccgucuguaa uggcccgacg | 120 |
| guugagauca gcggcgccga uccgcaguau gaaacgccga acgccacggc gaaucaggau | 180 |
| uaugagcgcg acguaaaag cuacaaaauc guucaggauc cggccaacuu uacucaggcc | 240 |
| gguuucgcgg cgaucuauga cgcagaaccc aacagcaacc ugaccgccag cggcgaagcc | 300 |
| uucgauccga cucaguugac cgcagcgcac ccgacgcugc cgaucccgag cuacgcgcgg | 360 |
| aucacuaacc uugccaacgg acggaugauc gucgugcgga uuaacgaucg cggucccuau | 420 |
| ggcaacgauc gggucaucuc gcuuucccgc gcauccgcug accgccugaa caccuccaac | 480 |
| aacaccaaag ugcgcaucga ccccaucauc gucgcgccua acguucgcu uccggcccg | 540 |
| gggauggccu guaccaccgu cgccaaacag acuuacgccc ugcccgcccg uccgaaucug | 600 |
| gacgugggg acgccgcugg caugagccag cccgcgccca cugacguucg cccgaucagc | 660 |
| aacagcacgc ugacgccggc agacagcgug ggcgcgccgg ugaacagcgg cgguuuccuc | 720 |
| ggcgcgccga cgccccugaa caacggcgug cuggagagua gcgaaccagc ggcagccgcc | 780 |
| gcgacggcuc cugccgccgg cgccacgcca acagcgccag ugaccgcgcc uggcuccauu | 840 |
| cagggguaaug uggugcccgc ucgcgccacc gccgcagccg cuggcgccgu ggcggccucg | 900 |
| uccuccgcga ccuccagcgc cagcggcuaau uuuguugucc agguggggcgc aguaagcgac | 960 |
| cagacgcggg cgcagcagua ucagcagcgc cugagccagc aguuucugu gccaggccgg | 1020 |
| gucaugcaaa acggcgcggu cuggcguauu cagcuggguc ccuuugcuga uaaagcacag | 1080 |
| gccagcgccg ugcagcagcg ccugcaaagc gaagcgcagc ugcagccuu uauuacucgc | 1140 |
| gccaacuaa | 1149 |

<210> SEQ ID NO 74
<211> LENGTH: 1287
<212> TYPE: RNA
<213> ORGANISM: Klebsiella pneumoniae

<400> SEQUENCE: 74

| | |
|---|---:|
| auggaugauu ucaaaccaga agacgauaug aaagccgauc gcaacgaucg ucgugcuggu | 60 |
| cguucccguc agucuuccga gcgugaugcc gauccgcaga ucaauuuuga cgauguugau | 120 |
| cuugaugccg augaaggccg uccgacgcgc gcugguaagg cccgucgcga gcugaagag | 180 |
| gaagaguucg aagaagaacu ggaugcgcaa gacgaggaga ugcucgaaga gcagccugua | 240 |
| gagcgucguc cgcgcaagcg uaaaaaagcg ccggccaaac cggccucccg ccaguacauc | 300 |
| augaugggug uggggauucu ggugcugcug cuguugaucg uggguaucgg uuccgcacug | 360 |
| aaaucgccau caucuuccag ccagcagacc gcuuccggcg agaagagcau uaaucugucu | 420 |
| gacgaccagu ccgccagcau gccugcgccc ggccaggacc agacugccgc cgcuaacagc | 480 |
| accucacagc aggacguaac gguaccgccu auugccgcga acccgacgca gggccaggca | 540 |
| gcgguugcgc cgcagggcca gcagcguauc gaaguucagg gcgaucugaa caaugccuug | 600 |

```
acccagcagc agggccaacu ggacggcgcc guggcuaacu cgacgcugcc gacugaaccg      660
gcuaccgucg cgccaauccg gaauggcgcc aauggcaccg cggcgccgcg ccaggcgacc      720
gagcgucaga cagcagcgac cccgcguccg gcugaacgua agcauaccgu uaucgaagcg      780
aagccgcagu cgaagccaca ggccguggcg aaaacgccgg uagaaucgaa gccgguccag      840
ccgaagcaug uugaaagcac ggcgaccacc gcuccggcga aaacguccgu cagcgaaagc      900
aaaccggugg ccaccgcuca gagcaaaccg accacgacga ccgcagcgcc agcggcaacg      960
gcagcugcgg cagcgccggc agcgaagacc gggaagacgg caggugacgu cagcucaaug     1020
aaaacugcgc cgucggguca cuauacucug cagcucagca gcuccucuaa cuacgacaac     1080
cucaacaacu gggcgaagaa agagaagcug auaaauaug uugucuauga acgucgcgu      1140 aacggccaac caugguacgu gcuggugagc gguaucuaug caucgaaaga ugaagcgaaa     1200
cgugcuguca ccucgcugcc ggcggacgug caggcgaaaa uccaugggc aaaaccgcug      1260 caucagguuc aggcugaccu gaaauaa                                         1287

<210> SEQ ID NO 75
<211> LENGTH: 1326
<212> TYPE: RNA
<213> ORGANISM: Klebsiella pneumoniae

<400> SEQUENCE: 75
augucaaagg caaccgaaca aaacgacaag cuuaaacgag cgaucaucau uucagucgcg       60
cugcacauca uucugaucgc gcugcugauc uggaguucgu uugacgagca ucuggaugcc      120
ucugccggcg gcggcggcgg aucgucgauu gaugccguca uggucgaucc ggggggcggug     180 guaaauaacu auaaccgguca gcaacagcag caggccagcg cacgucgcgc cgcugaacag     240
cgugaaaaac aggcgcagca gcaggcggaa gaguuacgug agaaacaggc ggcggaacag      300
gaacggcuga aacagcucga acaggagcgg cugcaggcgc aggaagcggc gaaagaagcg      360
aaggagcagc agaagcaggc ugaagaagcg gcugccaagg ccgccgcggc ggcaaaagcc      420
aaagcggacg cacaggcaaa agaagcgcag gaagccgcug ccaaagcggc cgccgaggcg      480
aaagcgaagg cggaugccca ggcgaaagcg gcagaacagg cggcggccaa ggcggcugcu      540
gacgcgaaaa agcaggccga agccgcugca gcgaaagccg cugccgaggc gaagaaacag      600
gcggaagcug aagcggcgaa agcugcggcc gaggcgcaga gaaagcgga agcggcggcu      660 gcgaagaaag cgcaacagga agcggagaaa aaagcccagc aggaagcggc uaagcaggcg      720
gcagcugaaa aagcggcugc cgaaaaagcc gcugagaaag ccgccgcgca aaagcggcc      780 gcugagaagg ccgccgccga aaagccgca gccgcugaaa aagcggcggc agcgaaagcg      840
gcugcagcag agaaggcugc agcugauaaa gcggccaaag cggcagcagc aaaagccgcg      900
gcggcgaaga agcggcggc ugcgaaagaa gcggacggcg uugacaaccu gcucggcgau      960
cugaguucug guaagaaugc gccuaaaaca ggcgguggg ccaaaggaaa caugccucc      1020 gcugccggga gugguaauac uaaaaacagu gccucagggg cugauaucaa caacuaugcc     1080
ggacagauaa aaucggcgau ugaaaguaag uuuuaugacg caucguccua ugcgggcaaa     1140
acauguaccu ugcguaucaa acuugcuccu gacggccugu uguuaaauau acaguccgaa     1200
gguggugauc cugcucugug ccaggccgcu cuugccgcag cccgacaggc uaaguuuccg      1260
aaaccaccua gccaggcagu auaugaaguc uucaaaaaug cgccacugga cuucaaaccu      1320
caguga                                                                1326
```

<210> SEQ ID NO 76
<211> LENGTH: 1455
<212> TYPE: RNA
<213> ORGANISM: Klebsiella pneumoniae

<400> SEQUENCE: 76

| | | | | | |
|---|---|---|---|---|---|
| auguuuuuuu | uaaguauuuu | uuacauggag | augacaaaag | ugaaauuaag | cgcucuguuu | 60 |
| auugcccuga | uuccucuacu | gggcucgccg | guuauucaug | cagaaacuac | ugcugcgccg | 120 |
| guucuggaaa | aucgcgcugc | gcagggagau | aucaccacuc | cuggcggcgc | gcgucguuua | 180 |
| acaggcgauc | aaaccgaagc | gcugcgcgcc | ucguuaauca | auaagccagc | uaaaaacguu | 240 |
| auuuugcuga | uuggcgaugg | cauggugau | ucggaaauua | ccgcugcgcg | aaacuaugcc | 300 |
| gaggggggcgg | gcgguuucuu | uaaaggaauu | gaugcucugc | cguuaaccgg | gcaguacacg | 360 |
| cauuauucgc | uggauaaaaa | aaccgggaaa | ccggacuacg | ugaccgacuc | ggcggccucc | 420 |
| gccaccgccu | ggaccaccgg | cgugaagacu | uauaacggcg | cgcugggcgu | cgauauucau | 480 |
| gagaaugcgc | aucagaccau | ccucgagcug | gcgaaagcgg | cggggcuggc | caccggcaac | 540 |
| guuuccaccg | ccgagcugca | ggacgccacc | cccgcggcgu | ugguagcgca | ugugacaucg | 600 |
| cguaaaugcu | acgcccgac | ggucaccagc | gaaaaaugcc | ccagcaaugc | gcuggaaaaa | 660 |
| gggggcaaag | gcuccauuac | cgaacagcug | cugaacgccc | gaccggaugu | caccuugggc | 720 |
| ggcggcgcga | agaccuuuac | cgaaacgcg | acggcgggcg | aguggcaggg | caaaacccug | 780 |
| cgcgagcagg | cgcaagcgcg | cggcuaccag | auugugaccg | acgcggcuuc | ucuugccgcc | 840 |
| gcgacggaag | ccagucagga | uaaaccgcug | cuggacucu | uugccgaugg | caauaugccc | 900 |
| guacgcuggg | aagggccgaa | ggcgucuuau | cacgguaaua | ucgauaagcc | gccggugacc | 960 |
| uguacgccaa | acccgaagcg | ugacgccucg | gugccgacgc | uggcgcagau | gacgagaaaa | 1020 |
| gcgauugacc | ugcucagucg | caacgagaaa | gguucuucc | ugcaagucga | aggcgcuucc | 1080 |
| aucgauaagc | aggaccaugc | ggcgaauccg | ugcggccaga | ucggcgaaac | gguugaucuu | 1140 |
| gacgaagcgg | ugcagaaggc | gcuggaauuc | gcgcgaaaag | acgguaauac | ccuggugauc | 1200 |
| gucaccgccg | accaugcgca | ugccagccag | aucauccccgg | cggauagcaa | agccccgggg | 1260 |
| cugacccagg | cucugaacac | gcacgauggc | gcggugaugg | ugaugagcua | cggcaacucu | 1320 |
| gaggaagagu | cgauggagca | caccggcacc | caacugcgca | uugcggccua | cgguccgcau | 1380 |
| gcggcuaacg | ucguaggccu | gaccgaucag | accgaccugu | ucacgaccau | gaaagcugcc | 1440 |
| cugagucuca | aauaa | | | | | 1455 |

<210> SEQ ID NO 77
<211> LENGTH: 1608
<212> TYPE: RNA
<213> ORGANISM: Klebsiella pneumoniae

<400> SEQUENCE: 77

| | | | | | |
|---|---|---|---|---|---|
| augucacugc | cguucaaacc | ccauauuauc | gcccugcucu | uagcgcuugg | cuuacucgcg | 60 |
| gcggcaggaa | cacucuaugu | gcaaagccga | accccagcga | cgaucgcuga | accgccugcg | 120 |
| cagcaagcgc | cagcgcccgc | agcgucgacg | acacagccgg | uggccgccac | uuacacccag | 180 |
| gcgcaaauug | aucaguggu | cgccccuauc | gcgcucuacc | cggacagccu | gcugucgcag | 240 |
| guguugaugg | ccuccacuua | ucccgacaac | guccugcagg | cggucccagug | gucccaggau | 300 |
| aaccccgcga | ugaaagggga | ugcggccgug | caggcgguug | ccagccagcc | gugggacccu | 360 |
| agcgucaaau | cucuugucgc | uuucccugcc | cugcuggcga | ugaugggcga | gaauccgccc | 420 |

| | | | | |
|---|---|---|---|---|
| ugggugaaaa | aucuuggcaa | ugcguuuuug | gcccagccgc | augaugugau ggauucagug | 480 |
| cagcgccugc | gcgccauugc | ccaacaaacc | gggacgcuga | aauccacacc gcagcagaaa | 540 |
| gugauuguca | ccccugccgc | accguuuuca | gccagcagca | gcacggcagc aaccgcaacc | 600 |
| gcccacacag | cggcgccugc | gcccacgcag | gucauuaaaa | uagagccgac caauccacag | 660 |
| guggucuaug | ucccagcua | uaccccucc | accgucuaug | guaccuggcc gaacagcgcc | 720 |
| uauccgccgg | ucuaucugcc | gccccucccc | ggggagcagu | uuaccgauag cuucgucaaa | 780 |
| ggcuucgggu | acagccucgg | cguggccacc | accugggcgc | uguucagcag uaucgacugg | 840 |
| gaugaugaug | accaucacca | ucacgaugac | gacuaccacc | acggcgauua ucgcauaau | 900 |
| ggcgauaaca | ucaauauuaa | uguaaauaau | uucaaucaua | uaacaggaga aaaccugccg | 960 |
| ggaaaccacg | uuaacuggca | gcacaauccu | gccuaucgcg | gacacacacc guaucccgau | 1020 |
| aauacgguag | cucagcgcuu | ccaucagacc | aacguuuccg | gcggacugag cgcgacccaa | 1080 |
| caugcgccag | ucgaucgcga | agcgcagcgc | caggcagcga | ugaccagcu gcagcauaac | 1140 |
| guaccgacgg | ccacagcggg | caaccuggcg | gcaaacaacg | ccucacgcga cgcccagcgu | 1200 |
| caggcggccu | cggcgcagcu | gaagcaagcc | acccaacgca | guaauuaccg cgguuacgac | 1260 |
| aguacgccga | cccaacagca | gcgucgcgag | gcggcaaaaa | cgcagcugaa aaaccccacg | 1320 |
| ccgcagcaac | agcagcgucg | agaagccgcc | aggagccacg | agcagaaccg cacaccucag | 1380 |
| cagcagcagc | gccggcagca | guccaguccc | gccacgccag | cccagcguca gcagacgcuc | 1440 |
| agccaucugc | gcgccaacgc | ccuuagcggc | aacgaaagcc | gcgccccuc cuggcaagcg | 1500 |
| cagcaggaac | gaggacugca | gagccgccag | uuuuccggcg | uaaaccgcga guuacgcgau | 1560 |
| ggcaccagag | aacgucuuuc | cgaacaccau | gaacugcguc | gccgcuaa | 1608 |

<210> SEQ ID NO 78
<211> LENGTH: 1794
<212> TYPE: RNA
<213> ORGANISM: Klebsiella pneumoniae

<400> SEQUENCE: 78

| | | | | |
|---|---|---|---|---|
| auguuaagu | uuaaggcuuc | uuaugucgca | cuggcggcag | uauuaaccuc gucgguaguu | 60 |
| uaugccgacc | ccacaagcua | uacgcacucu | uccggcgcca | cgguuaucga uauugaaaag | 120 |
| ccgaacgccg | ccgugucuc | ccauaaccug | uaccgcgacu | ucaacgucgg cgccaauggc | 180 |
| accauccuca | auaacagcgg | cgaugaugc | agccacagca | cauuuggcaa uaucgcccgc | 240 |
| aacaauaaauc | ugaccgccgg | cagcgcuucg | cgugauuuuga | acgaggugac cuccaaaaac | 300 |
| gccaguagcc | ugaagggcuu | uaucgaaguc | aacggucaga | aagcggaugu gguaaucgcc | 360 |
| aacccgaacg | gcaucaccug | uuccggcugu | agcuuuguua | uaccaacaa ggcuauccug | 420 |
| accaccggca | agguuaauau | gaccgacgau | ggcgcuaucg | gcagcuauac cguaacgggc | 480 |
| ggcacccuca | ccaucggcga | aaauggcaug | aacgccgcca | acggcuaugc gguucugcuc | 540 |
| gccgacgcga | ucaauaucaa | cgguaaagug | caggccaaca | acgcccuggu cagcgcgggc | 600 |
| aacuucacca | uggauaacag | cucuggcucg | gugaccuccg | cugguaaaaa ggccaccccug | 660 |
| auccagauga | cgguuaaccc | gcaguacagc | aucgacguca | gcagccuugg cggcauugag | 720 |
| gccaacagca | ucagcauggu | cggcaauaac | aucggcuuug | gcguacguaa uaaaggcucu | 780 |
| aucgucgcga | auaguccgcu | gcagcucacc | agcaacggua | aucgcugaa caaaggcacg | 840 |
| aucaaaagca | acggucugcu | gagucaagguc | gccaccgccu | cgggcaucac caaugacggu | 900 |

| | |
|---|---:|
| agcaucgccg gcgccuauua uuuaaugcuc uccaguggcg auuauaucgu uaacaccggu | 960 |
| ucucucuccg gcggccagcu gauugccacc gcuaacggca acaucaccaa cggcgacuca | 1020 |
| ggcacgauga ccggcaccag uggauuaagc cugaccagcg gcgggaaaau ccgcaacgaa | 1080 |
| gaaaaagccu cccugcuguc aaauaaccag auugccgcca cggcaaucgg ugauuccuc | 1140 |
| aaugaaggca aaaucagcgc caaacacacc agccugacgu uugucggcga cagcuuuaaa | 1200 |
| aacacuggca auauuaacuc uacuggccaa accaccauuc agucgcuuaa acaggacggc | 1260 |
| agcgccaaua cgggcgagau cuauaaccuc ggcaauauca ccggcgaaaa uaucaaucug | 1320 |
| cagaccaaug gcacgcuggc gcaaagcagc aguggucgua ugaggcaac caacgccauu | 1380 |
| accgcccaca gcuacuggcu gaaccaaaau gguuauauga augccgcga uaucaccacc | 1440 |
| gaucacggcg uagugaauaa uuauggcaau auuacugcca aaauauuuc aaucacgacc | 1500 |
| uacucagaua ucaccaacga agggcagauc agcagcaccg gcgaccugac cuuaaauacc | 1560 |
| aaaaauaaag gcgcgaucua caauuauuca acccucagcg cgggcggcaa caugacguua | 1620 |
| accgccacca aaguggucaa uggugguaaa aguugcggca uacugggccu ggcgaaaugc | 1680 |
| ggcgucggga cguuaacugc ugacaagcug guacugaacu caucgcagaa auauguuagc | 1740 |
| gacaugggug gaaaacagua uuucaagagc accgaaguca cacggugaa auaa | 1794 |

<210> SEQ ID NO 79
<211> LENGTH: 1875
<212> TYPE: RNA
<213> ORGANISM: Klebsiella pneumoniae

<400> SEQUENCE: 79

| | |
|---|---:|
| augauggaca accuacgcac ggccgccaac agcgucgugc ucaagauuau uuucgguauc | 60 |
| auuaucgucu cguucauuuu gaccgggguG aguggUuacc ugauuggcgg uggcaaaaac | 120 |
| uaugccgcaa aagugaaugg ccaggagauu ggccgugggc aguugaaaa cgccgucgcc | 180 |
| agcgaacgua accguaugca gcagcagcuu ggcgaucaau ucccgagcu ggcggcgaac | 240 |
| gaaaacuaca ugaaaaccau cgccagcag gugcugaacc gccugaucga ugagucgcuu | 300 |
| cuggaucagu augcccgcga gcugggccuc agcaucagcg augagcaggu gaagcaggcg | 360 |
| aucuuccaga cccaggcguu ccagacgaac gguaaguucg acaaccagcg uuucaguggu | 420 |
| auugucgccc gauggggau gaccaccgau caguacgccc aggcgcugcg uaaccagcug | 480 |
| accacgcagc agcugauuaa cgccauugcg gguaccgacu ucaugcugcc gggcgaguicc | 540 |
| gaucagcugg cggcgcuggu aucucaacag cggguggucc gcgaagcgac caucaacgua | 600 |
| aaugcccugg cggcaaaaca gaccgccagc gaugaggaaa ucaacgccuu cuggcagcag | 660 |
| aaucaggccc guuuuauggc gccggagcag uuccgcguca gcuacaucaa auggaugcc | 720 |
| gccagcaugc aggagagcgc cucugacgaa gagauucagu cauggauacga ccagcacaag | 780 |
| gaucaguuca cucagccgca gcgcaaccgc uacagcguga uucagaccaa acugaagcc | 840 |
| gaugcgaaag cgguacuggc cgagcugcaa aaaggagcgg acuucgccac gcuggcgaaa | 900 |
| gaaaaaucga ccgauauuau cucugcccgc aacgguggcg auaugggGug gauggaagau | 960 |
| gccucuaccg ugccugagcu gaaagaugcc gggcugaaag agaaaggcca gcugucuggc | 1020 |
| gugaucaaau cccucguugg cuuccuggua gcucgucugg acgacguucca gccggcgcag | 1080 |
| gugaagccgc uggcugacgu gcguaaugac auucgcgcga agugaagca ggaaaaagcg | 1140 |
| uuggaugcuu acuacgcgcu gcagcagaag gugagcgaug cggccagcaa cgauaaugaa | 1200 |
| ucgcuggcga gcgcagcgca ggucgccggg cugaagguch uagaaaccgg cugguuggc | 1260 |

```
cgcgauaacc ugccggagga gcugaacuuu aaaccggucg cugacgcuau uuucaacggc    1320
ggucuggugg gugagaacgg cgcgccgggc agcaacuccg auaucauuac cguugacggc    1380
gaucgcgcuu uuguucugcg cauuagcgaa cacaaagccg aggcggugaa gccgcuggcc    1440
gaagugaagg cacagguuag cgauaucguu agcacaauaa aagcggaaca gcaggcgaaa    1500
cuggaggccg acaagcugcu ggcggcgcug aaagacggca aggcgauga  agcgaugaag    1560 gcggcuggcc ugagcuuugg cgcgccgcag acgcuuucuc guaccggcca ggauccgcug    1620
agccagcugg cauuuacccu gccgcugccg cagcagggua accggucua cggcguggc     1680 agcaauaugc aaggcgaugu ggugcuggua cgcuggaug  aggugaaagc cggcagcaug    1740
ccggaagagc agaagaaggc cauguucag  gggaucaccc agaacaaugc ccaaaucgcu    1800
uucgaagcgc ugaugagcaa ccugcgcaag gcggcgaaaa uuaagcucgg cgacagcauc    1860
gaccagcagc aguaa                                                    1875

<210> SEQ ID NO 80
<211> LENGTH: 1974
<212> TYPE: RNA
<213> ORGANISM: Klebsiella pneumoniae

<400> SEQUENCE: 80
auguucaggu uaaacccuuu uauccgggcg ggauugucug cguccgucgu aucguuggcg      60
uuuccggcuc uggccgaugu gaaugaagaa acgcuggugg ugaccgccuc ggccacugaa     120
cagaauguca aagacgcgcc ggcgagcauc agcgucauca cccaacagga uuuacaacgc     180
aagccuguuc agaaccugaa agacgugcug cgcgaugugc cuggggucca gcucaccaac     240 gaagggggaua accgcaaggg cguuagcauc cgcggucuga gcagcagcua uacccugauc     300
cuggucgacg gcaagcgcgu uaacucgcgg aacgccgucu ccgccacaa ugacuucgac      360 cuuaacugga ucccgguggga ugcuauuag cguaucgaag uggugcgcgg cccgaugucc     420
ucccucuacg gcuccgaugc gcucgguggg gugguucaaca uuauuaccaa aaaaaucggc     480
cagaaaugga ccgggacgcu gagugcugau accacuauuc aggagcaccg cgaucgcggg     540
gauaccugga acggccaguu cuucaccagc ggcccgcuga ucgacggcgu acuuggaaug     600
aaggccuacg gcagccuggc aaaacgcgcc aaggacgauc cgcagucauc caguaaugcc     660
accggcgaga cgccgcgcau cgagggcuuc accagccgcg auggcaaugu gaauucgcc     720 uggacgccga acgaaaacca cgauuuuacc gcaggcuacg gcuuugaccg ucaggaucgc     780
gauuccgauu cccuugaccg caaccgccuu gagcgggaga acuacucucu gagccauaac     840
ggccgcuggg auaucggcaa uagcgagcuc aaguucuacg gcgaaaaggu ggauaacaaa     900
aauccagggc agagcgggac uauuaccucg gaaagcaaug ccaucgacgg caaguauguc     960
cugccgcugg gcaugauuaa ccagcuggug accuucggcg gcgaauggcg ccacgacaaa    1020
cuuaaagauc cggucaaccu gagcagcggc ggccagucaa cgucggccag ccaguacgcc    1080
cuguuuaucg aagacgaaug gcgcaucauc gagccgcugg cgcugaccac cggcauucgu    1140
auggacgacc aucagaccua uggcgaucac uggagcccgc gcgccuaucu gguguauaac    1200
gccaccgaua ccgucaccgu caaaggcggc ugggcgacgg cguuuaaagc cccgucgcug    1260
cugcagcuua accccgacug gaccaccaac uccugccgcg gcucgugcag caucgucggu    1320
aacccggauc ugaaaccgga aaccagcgaa agcuucgagc ucggucucua cuaccgcggg    1380
gaagagggcu ggcuugaaaa ugucgaaggc agcaucacca ccuuccagaa uaaugucgac    1440
```

| | |
|---|---|
| gacaugaucg acguucugcg caccuccagc gccagcgaag cgccgggcua cccgaacuuu | 1500 |
| gucggcugga aaacugucaa cggcaagcgc gugccgaucu uccgcuauuu caacgucaac | 1560 |
| aaagcccgca ucaaaggggu ggagacggag gugaagaucc cguuuggcga ugaguggaag | 1620 |
| cugacgguga acuacaccua caacgauggu cgcgaucuga gcaauggcgg cgacaaaccg | 1680 |
| cugcagacgc ugccguucca uaccgccaac ggcacgcucg acuggaaacc gcuggacgac | 1740 |
| ugguccuucu acgugacggc caacuauacc ggccagcagc gcgcggugag cgccaccggc | 1800 |
| aaaacgccgg gcggcuacac ccuguuugac guuggcgcgg cauggcaggu gaccaaaaac | 1860 |
| gugaaacugc gcuccggggu gcagaacgug ggugauaaag aucugagccg ggacgacuac | 1920 |
| agcuauaccg aagaaggccg ucgcuacuuu auggcggugg auuaucgcuu cuga | 1974 |

<210> SEQ ID NO 81
<211> LENGTH: 2028
<212> TYPE: RNA
<213> ORGANISM: Klebsiella pneumoniae

<400> SEQUENCE: 81

| | |
|---|---|
| augaacagag ccgccacgcu gacccucaac gcgccccugc ugaugcucgu cgcugcgcug | 60 |
| gcgcuuucaa ccccuuucac cgccggcgcc gcgccggccu uccuugauua cgcccaacag | 120 |
| caaacccagc aaucucaggc gcaagaaaaa aacgaugccg caagcgcaaa acaaacacaa | 180 |
| gaaagccgcc agagcgcaga uaauaaaaaa accgguacca gcaccucaca auuacaaaaa | 240 |
| agaaucacca gccagcaggc ggcgauugca caaaaagaua agcuuauaca gcauuaaaa | 300 |
| aaacagcuug ccgcuacgcc gcaaacggau acugccggag cgaaugagca agcggcguug | 360 |
| aauaagagaa uuaaugaauu acaggucgcc uuaagcgccg cuacugcaga aaagaggca | 420 |
| uuaauaaaaa aagcaggcgu ugugcagaau aauaaucuac agcaaagcca ggccgcggcg | 480 |
| cgucagcaga uccagcaauu aacgacgcag auucagcaag ccgaagcuga aaauaaacgc | 540 |
| cucagcgcca gcuuuaccac gcuuaauaaa gauaaaacg cgcuaaugac ccaacuggcc | 600 |
| gcaacggaaa aagagaaaca ggccgcucuu gagcagguca aagcgcuuaa cgcugacaaa | 660 |
| cagccgcuga cgacccggcu ggccgccgcg gaaaaagaga acaggccgu ccucgagcag | 720 |
| guuaaggccc uuaacgccga uaaacagucg cugacuauuc gccucgccgc ugcggagaaa | 780 |
| gcgcagcagg ccgcguuuga ccaggcuaaa gcgcuuaacg cugacaaaca gccgcuggcu | 840 |
| acccgacugg ccgccgcgga aaaagagaaa caggccgucc ucgagcaggu uaaggcccuu | 900 |
| agcgccgaua agcagucgcu gacuauucgc cucgccgcug cggagaaggc gcagcaggcc | 960 |
| gcucuugacc aggcuaaagc gcuuaacgcu gacaaacagc cgcuggcgac ccggcuggcc | 1020 |
| gccgcggaaa aagagaaaca ggccguccuc gagcagguua agcccuuaa cgccgauaag | 1080 |
| cagucgcuga cuauucgccu cgccgcugcg aaaagacgc agcaggcugc ccucgaucag | 1140 |
| gucaaagccc uuaacgccga uaaacaaucg cuguccaccc ggcuggccgc cgcggauaaa | 1200 |
| gcgccgcaug gccccgcuaa cgacgccgcu gcgcaaaaaa augagccacc agagauggcg | 1260 |
| gccauagugg cagccuaucg ccugcaggcg gauaagacac acgcccagcu acggaugaaa | 1320 |
| gaagaugaaa ucgaacugcu gagaacgcag cuuucguac aguccaaaac gcgcagcggc | 1380 |
| gagagcgccg ccgccaaacu cagcgcaucg ggagaacagc aggcuuaugc gaucggcgcc | 1440 |
| ucgaugggaa gcgaggcgcu caacguccuu accacccguc guacucaggg aguuaccguc | 1500 |
| gacgcaggcc ugguscugca gggcaucgaa gaugccuuuc gcggccagcu ucgcucgga | 1560 |
| gagcaggaac guaacaaggc gcuguuugau gugucgcagc agguuuuuca gaaccugaau | 1620 |

-continued

| | |
|---|---|
| aaaauagagc agaaaaacau cagugccggc aagaaauauc agcaggcguu ugcgcgcaaa | 1680 |
| aaagaugugg ucuuuaaaga gggcgucuac agccgcgucg auuaccuggg uaaaggaaaa | 1740 |
| auaagcggua augaccuggu uaccguggug aucaaagaga ugcugacgga cgggacggug | 1800 |
| aucaacgaua uggaagcgaa agaucaggcg cuuacgcaaa agcuggaugc cuaucccccg | 1860 |
| guguuucgcg aaccgcugaa gcgucuacag aaccacggcu ccgugacgcu cgucgucccg | 1920 |
| ccugaaaagg ccuauggcag uaaaggauua ccgccaaaaa ucccgccagg cgccaccaug | 1980 |
| guuuauuccg ugcggauagu agauagccaa cccgagccgg caaaauag | 2028 |

<210> SEQ ID NO 82
<211> LENGTH: 2106
<212> TYPE: RNA
<213> ORGANISM: Klebsiella pneumoniae

<400> SEQUENCE: 82

| | |
|---|---|
| augaaaaucc uguccgugcg ucacgccgcc cuccccggccc ugcucuugcc gcucauugcg | 60 |
| gcagcccagg ccgcugauga acaaaccaug guggugaccg ccgccaac cacgguuucu | 120 |
| gaacuggaua cccccgccgc cgucagcgug gugaauggg augagaugcg ccaggccgcg | 180 |
| ccgcgcguca aucucucuga aucgcugggc gccgugccgg ccugcaggu gcagaaccgg | 240 |
| caaaacuaug cccaggaucu gcagcugucg auucgcggcu uggcucgcg cucaaccuau | 300 |
| ggcgugcgcg gacugcgcau cuauguggau ggcauuccgg ccaccaugcc cgacggccag | 360 |
| gggcagaccu caaauauuga uaucggcagc guugacacca uugaggugcu cgcggcccc | 420 |
| uucucugccc uguacgguaa cucguccggc ggggugauca acgucaccag ccagaccggc | 480 |
| acccagccgc ccaccgugga agccagcagc uacuauggca gcuucggcac cuggcacuac | 540 |
| gggaugaaag ccacuggcgc cguuggcgac ggcagccacg caggcgaugu ggauuacacg | 600 |
| gucucaaacca aucgcuucac cacccauggc uaucgauc acagcggcgc gcgcaaaaau | 660 |
| cuggcgaacg cccggcugg ggugcgcauc aacgacguca guaagcugac ucugcugcug | 720 |
| aauagcgugg auaucaaagc caugacgcc gguggccuga ccgccgauga auggcgcgau | 780 |
| aacccgcgcc agucgccgcg cggcgaccag uauaauaccc gcaagaauac ccgacagacc | 840 |
| caggccggcc ugcgcuauga gcgccagcuc agugcccagg acgaucucag cguuaugaug | 900 |
| uacgcuggag aacgugaaac cacucaguuc cagucgaucc cgcgcgcgcc gcagcugaag | 960 |
| ccgagccaug ccggcggggu gaucgaccuu acccgucacu accaggggau cgauacccgg | 1020 |
| cugacccauc gcggagagcu gcuggugccc gucacgcuca ccgccggucu cgacuacgaa | 1080 |
| aacaugagcg agcggcgcaa agggaugaa acuuuguga uggucaacgg cgcgccgcag | 1140 |
| uauggcgaac agggcgcgcu gcgccguaac gaacgcaacc ugauguggaa cgucgacccc | 1200 |
| uaccugcaga cccaguggca gcucacugac aaacucucgc ucgaugccgg gguucgcuac | 1260 |
| agcucgguau gguucgacuc gaacgacuac uacaucaccc caggcaaugg cgaugacagc | 1320 |
| ggugaugcca gcuaucacaa auggcugccc gcgggcucgc ugaaauaugc ccugaccgac | 1380 |
| gcguggaacg ucuaucuuuc cgccggccgc ggcuucgaga cgccaaccau uaacgaacuc | 1440 |
| uccuaccgcu ccgauaacca gagcggccuc aacuucggcc ugaaacccuc caccaacgac | 1500 |
| acgguggaga ucggcagcaa gacgcggauc ggcaaugggc uguucaccgc cgcccuguuc | 1560 |
| cagaccaaua ccgauaauga gauuguggu cacagcagca gcgccgggcg caccaguuau | 1620 |
| aaaaacgccg gcaagacccg ccgucagggg auggagcugg ggcuggauca gcaguuuggc | 1680 |

| | |
|---|---|
| gagagcuggc gucugaaggc ggccuggacc uggcuggacg cgaccuaucg cacuaacguc | 1740 |
| ugcgacgacg ccagcugcaa uggcaaucgc auuccgggga ucgcgcgcaa uaugggcuac | 1800 |
| gccuccuuug gcuaucagcc ggagcaaggu ugguacgccg ggagcgauau ucgcuauaug | 1860 |
| agcgauauca uggccaauga cgaaaacacc gccaaagcgc ccuccuggac ggugguuggc | 1920 |
| cugacgacug gcuauaaaug gagcuacggc aggauggaua uggaucuguu cggucgcauc | 1980 |
| gacaaccugu cgaccgggga guacgucggg ucugucaucg uuaacgaguc uaacggacgu | 2040 |
| uacuacgagc cugccccggg acguaacuac ggcaucggcc ugaaccucgc cuggcgcuuc | 2100 |
| gaauaa | 2106 |

<210> SEQ ID NO 83
<211> LENGTH: 2259
<212> TYPE: RNA
<213> ORGANISM: Klebsiella pneumoniae

<400> SEQUENCE: 83

| | |
|---|---|
| augaaauaca cgucucacuu cccgcugggg aucgucauuc cucugcucgc cuguagcgug | 60 |
| ccgcugcagg cggcagagaa caugaccgaa caaucgacgc cugacgagag cgccgccacu | 120 |
| gccgaaaauc acgaggagac gauggucaua accgccgcca gcagaaccu gcaggcgccg | 180 |
| ggcgugucga ccaucaccgc agaagagauc cgcaaacauc cccccgcccg cgaugugucg | 240 |
| gaguuaauuc uacgcagcc cggggbuaaac cugaccggca acuccaccag cgggcagcgc | 300 |
| ggcaacaacc ggcaaauuga uauccgugge augggggcccg agaauacgcu ggugcugguc | 360 |
| gaugguaaac cggugaccag ccguaacucg gugcgguaug cuggcgcgg cgaucgugac | 420 |
| ucccgcggcg auaccaguug ggugccagcg gagaugaucg aucauaucga ugugauccgc | 480 |
| ggcccggcgg cggcgcgcua ugguaauggc gcgauggggcg gggucgucaa caucgugacc | 540 |
| aaaccgacca cgcgagaaug gcacgggucg uggaauaccu auaugaaugc uccgcagcac | 600 |
| cguaaagaag gggcgacgaa acguacuaac uuuagcccuca augguccgcu ucgagacagu | 660 |
| gucagcuuca aucucugggg uaaucugagu aaaaacccagg ccgaugcaca ggauauuaac | 720 |
| gccgggcaug aagcggaacg uaccgguucc uacgccgguu cuuaucccgc cggacgugaa | 780 |
| ggggugguga acaaagauau ucacaguaag cugcgcuggg aguugccccc gaugcaggcc | 840 |
| cuggaguuug aggccgguua cagccgccag gguaaucucu augccggcga cacacaaaac | 900 |
| accaauacca guacgcuggu gaagaguaug uacgggaaag agaccaaccg ucucuaccgg | 960 |
| caaacuuacg gcguaacaug gaccggcggc ugggauaaug gcugaccag caacagcuau | 1020 |
| gcccaguacg aacacacccg uaacucgcga auggaugaag ggcuggcggg cgguacggaa | 1080 |
| gggaucuucu ccaguagcga guuuucagau aucgaucugg ccgauguccu gcuacauagu | 1140 |
| gaagugaaua uuccguuuac gcuggggguc gaucagaauc ugacgcuggg ggcagaaugg | 1200 |
| aaucagcagc ggaugaaaga uggcguaucg acaacccagg cgcucucuua uggcacuauc | 1260 |
| gauggcguau cggcuaccgg ucuagcccg uaccccagug ccgagaucuu ucgcuguuu | 1320 |
| accgaagaua uauggcgcu aacggacagc accaugcuga cacccgcucu gcgcuucgau | 1380 |
| caccacagca ucgucggcaa uaacuggagc cccucacuga accugcuca ggagcugacg | 1440 |
| gacgacugga cgcugaagcu gggcauugcc cgugcuuaca aggcgccuaa ccucuaccag | 1500 |
| uugaacccga acuauauucu cuacagcaac ggucaaggcu guuacgccag uaguccgcc | 1560 |
| ugcuaucuga uggggaauag cgaucugaaa gcggagacca gcguuaauaa agagauuggu | 1620 |
| cuugaguaca agcaugaugg cuaucaggcg gggaucaccu gguuccguaa cgacuaucac | 1680 |

-continued

```
aauaagauug agucagggua ugcggcggug gguaccgcca gcaacggcac caccaauauc    1740
uaucagaggg aaaacguacc aaaggcguua guggaaggcc uggaaggaac gcugaaucug    1800 ccggugggggg aggcgguuaa cuggagcaau aaccugaccu ggaugcugca gagcaagaau    1860
aagacgaccg cgaccggcu gucagugauc ccgcaguuua cccugaacuc gacuuugagc    1920
uggcagguuc gugaagaucu cucccugcag agcaccuuua ccugguaugg ccgacagaaa    1980
ccaaaacgcu ucaauuauaa gggcgaggcg gucagcggca gcgaacuaaa cgaagucagc    2040 ccaucagca uugucggccu cagugcgacc ugggaugugu acaaaaaucu gagcuucacc    2100
agcgggauag auaaccuguu ugauauucgc cacuaccggg cagggaaugc gcaaacgacc    2160
ggcaacgcga cgacgggagc uuaucuguau ggcgcgggug ccgagaccua uaacgaaucg    2220
gggcggaccu ucuuuaugag cguuaauacu cauuucuga                          2259
```

<210> SEQ ID NO 84
<211> LENGTH: 2286
<212> TYPE: RNA
<213> ORGANISM: Klebsiella pneumoniae
<400> SEQUENCE: 84

```
auggaaaaaa acgcuucucu gccuuucggc aguuucaacu cauuggcauu guuuacaggu      60
cugugucugg gagccucgcc ggcagcaggc aucgcagcgg aaaauucggu caaaaauagu    120
gaagagacgc uguagugga agccgcuccg ccuucacucu acucccccgg cgcuuccgcc    180
gaucccaagu ucaauaaacc gcuggucgau accaccccgca ccaucaccgu gaucccggaa    240
caggugauua agaucaggg cgucaccaac cugacugacg cccucaaaaa cguucccggc    300
gucggggcgu uuaugccgg ggagaauggc agcucaacca ccggggaugc caucuuuaug    360
cgcggcgugg auaccucuaa cagcaucuau guggacggca uucgcgacau cgguagcgug    420
acgcgcgaua ccuucaauac ccagcaggug aagucauca aagggccgc cggcacggac    480 uauggccgca gcgcgcccuc cggcucgauc aauuaugauca gcaagcagcc gcgccuugac    540
uccgggaucg acggcucggc cagcaucggc agcgccuggu cgcgccgggg cacucucgac    600
cugaaccagg cguuuagcga caacgcugcg uuccgucuga accugaugg ggaaaaaacg    660 caugacgcug gucgggaccg cauugaaaac gaacgcuaug gcaucgcacc gucgcuggcc    720
uucggccuug uaccccaac ucgucuguau cugaacuauc ugcacguccg gcagaacaac    780
accccggaug gcgggaucc uaccgucggc cugccgggcu auucggcgcc uucgccgaag    840
uaugccgcac ucaacuccgc cgggaagguc gauaccagca uuucuaugg caccgacucc    900 gauuacgaua aaucuacuac cgacagcggu acccugcgcu ucgaacacga ucugacggag    960
aauaccaccg ugcgcaauac caccgcugg ucgcgagaga acaggagua ucuuuugacc   1020 gcggugaugg gcggcgcgaa caauaucacc gcccccgaua ucaugacgcu caacaccugg   1080
agcuggucgc gucugguuaa uaccaaagau gucagcaacc guauucgac caaccagacc   1140 aauaucaccu cgacuuucaa uacuggcucg auaggccaug acgucagcgc cggcguggag   1200
uuuacccggg aaaaccagac caacuauggc guuaacgcca ggaccgcgcc ggcggugaau   1260
cucuaccauc cgguucagcaa ccugucgauu ggcgggcugg acagaaacgg ggcgaacgcc   1320
aacggccaga ccgauaccuu cgggauuuau gccuuugaua cgcugacgcu gaccgagcgg   1380
auugagauca acggcgggcu gcgucucgac aauuaccaua ccaaauauga cagccccacc   1440
gccugcggcg gcagcggacg cggggcuauc gccugcccgc ccggacaguc gaccggcagc   1500
```

| | |
|---|---|
| ccggucacca cugucgauac cgcuaaaucc ggcaaucugg uuaacuggaa agccggggcg | 1560 |
| cguuaccgcu uaaccgagca gggcaauguc uacgucaacu acgccaucuc acagcagccg | 1620 |
| ccgggaggca gcagcuucgc ccuggccgcc agcggcagcg gcaacagcgc uaaccggacc | 1680 |
| gacuuuaagc cacagaaggc gaaauccagc gagcugggca ccaaguggca aaucuucgac | 1740 |
| aaccgucugc ugcucagcgc ggcguuauuc cgcaccgaua uugaaaacga aguggccgcc | 1800 |
| aacgaugacg gaaccugguc gcaguacggc aaaaagcgcg uggaggggua ugaacucucc | 1860 |
| gcgaccggaa accugacccc ggacuggacg auuaucgccg gcuacacuca gcagcaugcg | 1920 |
| acagugacgg agggacagaa cguugcacag gauggaucuu ccgcccuggc cuacaccccg | 1980 |
| aaacaugccu uuacgcugug gacgcaguau caggccacca gcgaucuguc cgucggcggc | 2040 |
| ggugugcgcu augucggaag ccugcgccgg ggcagcgaug gugcagucgg uaccccggau | 2100 |
| cacaccgagg gcuacugggu ugccgacgcc aaacugggcu aucgggucaa cagcaaccuc | 2160 |
| gaucugcagc ucaauaugua uaaccuguuu gauaccgauu acguggccuc caucaacaag | 2220 |
| agcggcuauc gcuaucaucc gggcgaaccc cggaccuuua gcugacggc gaacguccau | 2280 |
| uucuga | 2286 |

<210> SEQ ID NO 85
<211> LENGTH: 2373
<212> TYPE: RNA
<213> ORGANISM: Klebsiella pneumoniae

<400> SEQUENCE: 85

| | |
|---|---|
| auggcgacua uguacaaauc gacuccguca gcagcauggu guaaaaaacg ccugcuggug | 60 |
| accucuuugu uugcagcaau uuaucagacu cugccaucg cagcagauac uuccgccguu | 120 |
| agcggcgagg cgguggauga caccucgaa caaaugaccg ucaccgcccc cgcgccggug | 180 |
| cagaaagccg guagcgaaca cagcaucagc gcccgggagc uggagaauaa aggcgcuaac | 240 |
| gauuucggcu caaucaugcg cuaugagccg cucaucagcg ccaccggggc cagcggcggc | 300 |
| uccggcaacg gcaaaagcgg cuucgaccgc ggagguuaca ccggcuacaa cauucgcggu | 360 |
| auggagagca accgcguagg caucgacgug gacggguaucg cgcaacccaa cgccaccggc | 420 |
| cgcggcuacg ucggccgcgc cgggcucaac accuucggca ucggccgcga uuauaucgac | 480 |
| ccguauaugu acggcagcgu ugauauccag uccggcgcca ccucgacgga aacgccaac | 540 |
| agcgcuaucg ggggaaugu cucccuuccgc ccgaaaucag cggaugauua ccugcgcccg | 600 |
| ggcaagacca cgccuucgg cuaccgcagc gguacgacu cugcggaucg cagcuggcac | 660 |
| aacgggguga ccgucgccgg cggcgaugag uuccugcgcg ggauuuuggu cuauagccgc | 720 |
| cgugacggcc aggaaacuga aaacaacagc ggcaccgucg acgccuaccc ggcgaacugg | 780 |
| cacuccgaug cuuuucuggc cucccgggauc uggcagccua acgaugagca caagcugacc | 840 |
| agcaccuucg acuauuacca uaaaaccaac cacacccacu acgauaccug gacuccagc | 900 |
| ggcaacagca ccaucggcac cgccaaccag accagccaga cccggcgcug ggccugagc | 960 |
| cugaaggaug acuggacgcc gaugaacgac uaccucgaca gcgucuccac aaaaaucuac | 1020 |
| uaccagcaua ccgaagccca ugacuggacu uauaugccgg acagcgucac ccgcaaaaug | 1080 |
| cagacgguga acucuaacua cgauaccgac accuggggcc ugcagaccgc gcuggcgaaa | 1140 |
| acccugggcc gccacgaucu gagcgccggu ucaacgccca gcaccagcaa acccagcgg | 1200 |
| ccguucagcc agucgccgau ccccagcguu uacagcgaga ucaugcagcc ggaggcagac | 1260 |
| agccgcagcu acacccucgg cggcuuuguc caggauaaga ucaacuucga ucucgacagc | 1320 |

| | | | | |
|---|---|---|---|---|
| cacaacuucg | ccguuauucc | cggcgugcgc | guggugcauc | aaucgacuaa gccggaaaau | 1380 |
| cguccgauc | ucgccgccaa | cagcagcgug | cugagcgaau | cgucgguggc gaaucuguac | 1440 |
| ggcaaaaaca | gcgauaccca | gguucugccg | ucguugaccu | uccaguacga ccucaccccg | 1500 |
| cgccugauga | ccuaccugca | guaccagcgc | ggggcgcagu | uccccaacgc cagccagcug | 1560 |
| uauggcuccu | ggaaccucgg | cuccagcuac | gccggcagcc | agcaguaugc ccugaucggc | 1620 |
| aauaccgauc | ugaagacgga | aaccagcgau | aaucucgagu | gggggcugaa aggggaaguu | 1680 |
| accgaaggca | ucacccugcg | cacggcgcug | uucuacaaca | gcuauaagaa cuuuaucgcc | 1740 |
| uauaccgcu | auaccgcgc | caacaauccg | ggccaguuca | cgaaugugcc gucgaacauc | 1800 |
| uacaccauuu | aucaggcgga | aaaccgcgau | aaagccuaua | cuacggcgg ugagauuagc | 1860 |
| accaaauuua | acuuuggcac | cugguuugag | cagguggacg | gccugagcgc cacccucgcc | 1920 |
| cucggcuaua | gcgaagggaa | aucgaaaucc | agcuacagcg | gcgauaaaua cgucgaccuc | 1980 |
| gacagcgugg | cgccaaugaa | agccaucguc | ggcguggcgu | gggacgaucc ggcgaaacgc | 2040 |
| uacggcaccg | cccugacggc | gaccuuuguc | aaagggaaac | aggcgaccgc caccaaccgc | 2100 |
| gaaagcuaca | gcaacagcgg | auccgccauc | accgaugcca | gcagcgacua uaugcgcgug | 2160 |
| ccgggcuacg | gcaugcugga | cuggaccgcg | uacuggcagg | uggcgaaaaa cgucgccuc | 2220 |
| aauggcgggg | ucuacaaccu | caccgaucgu | aaauacuggg | auuaccugag cagccgcaau | 2280 |
| aucgagaccg | gcaccaacca | ggacgccaac | gauaaagcgc | uggcggugau gccgggccgc | 2340 |
| accuggcagc | ugggcgucaa | cgucgacuuc | uga | | 2373 |

<210> SEQ ID NO 86
<211> LENGTH: 2430
<212> TYPE: RNA
<213> ORGANISM: Klebsiella pneumoniae

<400> SEQUENCE: 86

| | | | | |
|---|---|---|---|---|
| auggcgauga | aaaaguugcu | cauagcgucg | cugcuguuua | gcagcgcgac uguauacggu | 60 |
| gcugaagggu | ucguggugaa | ggacauucau | uucgaaggcu | ugcagcgugu cgcuguuggu | 120 |
| gcggcccucc | ucaguaugcc | agugcgucc | ggcgauacgg | ugaccgacga ugauaucagu | 180 |
| aacacuauuc | gcgcgcuguu | ugccacuggc | aacuucgagg | acguccgcgu ccugcgcgau | 240 |
| ggugauaccc | ugcugguuca | ggugaaagag | cguccgacga | ucgccagcau cacuuucucc | 300 |
| ggcaacaagu | cggugaaaga | ugacaugcuc | aagcagaacc | uugaggccuc aggcguucgg | 360 |
| gugggcgagu | cgcuugaccg | cacgaccauc | gcggauaucg | agaagggucu ugaagacuuc | 420 |
| uacuacagcg | ucgguaaaua | cagcgccagc | gucaaagcag | ucguuacgcc gcugccgcgu | 480 |
| aaccgugucg | auuugaagcu | ggucuuccag | gaaggcgucu | ccgcaaaaau ucaacagauc | 540 |
| aacaucgucg | gcaaccaugc | guuuucgacc | gaugagcuga | ucucccacuu ccagcugcgc | 600 |
| gaugaggugc | cguggguggaa | cguggucggc | gaccguaaau | accagaagca gaagcuagcg | 660 |
| ggcgaccuug | aaacccugcg | cagcuacuac | cuggaucgcg | gcuaugcccg uuucaacauc | 720 |
| gauucuaccc | aggucagccu | gacgccgau | aagaaaggga | cuacaucac cgucaacauc | 780 |
| accgaaggcg | aucaguacaa | guuuccggga | gucagguga | cgggcaaccu cgcuggccau | 840 |
| uccgcggaaa | ucgaagcgcu | gacuaaaguu | gagccaggcg | aacuguacaa cggcgcgaaa | 900 |
| gugaccaaga | uggaaaacga | caucaagaaa | cuguugggc | guuaugguua cgccuauccg | 960 |
| cgcgugcagu | cgcagccgga | gaucaacgac | agcgauaaaa | ccguuaagcu gcacguuaac | 1020 |

| | |
|---|---|
| gucgacgcag gcaaccguua uuacgugcgu aaaauucgcu cgaaggcaa cgacaccucu | 1080 |
| aaagaugccg uacugcgccg cgaaaugcgc cagauggaag gcgcauggcu gggcagcgac | 1140 |
| cucgucgauc aggguaaaga ccgucucaau cguuuagguu ucuuugaaac gguggauacu | 1200 |
| gauacccagc gcgugccggg cagcccggac caggucgacg uugucuacaa ggugaaagag | 1260 |
| cguaacaccg guagcuucaa cuucgguauc ggcuacggca ccgagagcgg cgucagcuuc | 1320 |
| caggcgggcg uucagcagga uaacggguua ggguacuggcu augcugucgg gaucaacggu | 1380 |
| accaaaaacg acuaccagac cuauaccgag cugucggguga ccaacccgua cuucaccgua | 1440 |
| gacgguguaa gccucggcgg ucgugucuuc uauaaugacu uugaugcgaa cgaugcggau | 1500 |
| cugucugacu auaccaacaa aagcuauggu acagacauua cgcugggcuu cccggucaac | 1560 |
| gaauacaaca cgcugcgcgc cggcgucggu uaugugcaua acucccuguc caauaugcag | 1620 |
| ccgcaggugg caauguggcg uuaccuuaac ucgaugggcc aguauccgga caacaccaac | 1680 |
| gaccggaacu cguucagugc gaaugacuuc accuucaacu acgguuggac cuauaacaag | 1740 |
| cuugaccgcg gcuucuuccc aacggaaggu ucgcgcguca accugaacgg uaaggugacc | 1800 |
| auccgggcu cagacaacga guacuacaaa gcgacgcugg uaccgcgac cuacgugccg | 1860 |
| aucgacaacg aucaucagug gguaguacug ggucguacgc gcuuugguua uggcgauggu | 1920 |
| aucggcggca aagagaugcc guucuauag aacuucuaug ccggugguuc cagcaccgug | 1980 |
| cguggcuucc agcgaacac cauuggguccg aaggcggugu acuucccggc aagcagucgu | 2040 |
| caugaugaug acgauaguua cgauaaugaa uguaagagca ccgaauccgc accguguaaa | 2100 |
| uccgaugaug cggugggcgg uaacgcgaug gcgguggcca gccuugagcu gauuaccccg | 2160 |
| acgccguuua uuagugacaa auaugcgaac ucguccgua cuccgucuu cugggauaug | 2220 |
| ggauaccguau gggauacuca cugggauucg agcgcguacg cugguuaucc ggauuacagc | 2280 |
| gauccgagca acauccguau gucugcgggu auugccgugc aguggaugue ccgguugggg | 2340 |
| ccguuggucu ucuccuacgc ccaaccguuc aaaaaguacg auggagacaa agccgaacag | 2400 |
| uuccaguuua acauugguaa aaccugguaa | 2430 |

<210> SEQ ID NO 87
<211> LENGTH: 2691
<212> TYPE: RNA
<213> ORGANISM: Klebsiella pneumoniae

<400> SEQUENCE: 87

| | |
|---|---|
| augacagaug ugacuauuaa agcgcuggcc ucagagauuc agaccucugu ggaucgccug | 60 |
| auacagcaau uugcugacgc aggcauccgc aaaucggcug augauucugu gaccucgcaa | 120 |
| gagaaacaaa cuuuguugac gcaccugaac cgugaacacg gcucggcgcc agacaagcug | 180 |
| acguuacagc guaagacgcg caguacguua aauauuccag guaccggugg aaagaguaaa | 240 |
| ucgguacaaa ucgaagucgg caagaaacgc accuuuguga acgcgauccg caagagggcu | 300 |
| gaacgccugg ccgcggaaga gcaggcgcag cgugaagcgg aagagcaggc ccgucgugaa | 360 |
| gcugaagaag cagcgaaacg cgaggcgcaa uuaaagcug aacgugaggc cgcagaacaa | 420 |
| gcuaaacgug aagucgcuga uaaagcgaaa cgugaagcug cggaaaaaga caaagugagc | 480 |
| aaucaacaua ccgacgaaau gaccaaaacc gcccaggcug aaaagauccg ucgcgagaac | 540 |
| gaagccgcgg aauugaagcg caaaucggaa gaagaagcac gccgcaaacu gaagaagaa | 600 |
| gcgcgccgug uagcggaaga agcacgccgu augcugaag aaaacgaaaa aaauuggucu | 660 |
| gaaaccucag acagcccgga agauagcagc gacuaucacg ucaccacauc acagcaugcu | 720 |

```
cgucaggcug aagaugauaa cgaucgugaa gucgaaggcg gucgcggccg uagccguagc      780
agcaaagcgg cucguccggc gaagaaaggc aacaaacacg cugaaucgaa agcugaucgu      840
gaagaagccc gcgcggccgu gcgcggcggu aaaggcggua agcaccguaa agguccgcu       900 cugcagcagg gcuuccagaa gccagcgcag gccguuaacc gugacgucgu aaucggcgaa      960
accaucaccg uuggcgaacu ggcuaacaag auggcggugu aagguucuca ggucaucaaa     1020
gcgaugauga agcugggcgc cauggcgacc aucaaccagg ucaucgacca ggaaaccgca     1080
cagcugguug ccgaagagau gggccacaaa guuauccugc gucgugaaaa cgaacuggaa     1140
gaagccguaa ugagcgaccg ugacccggcc gcggcggcug aaccgcgcgc accgguccgug    1200 accauuaugg gucacguuga ccacgguaaa accucgcugc uggacuacau ucguucuacc     1260
aagguugccu ccggcgaagc ggugguauu acccagcaca ucggugcuua ccacgucgaa      1320
accgacaacg gcaugaucac cuuccuggau accccgggcc acgccgcguu uaccuccaug     1380
cgugcucgug gcgcgcaggc gacggauauc guggucuggg ugguggcggc agacgacggc     1440
gugaugccgc agacuaucga agcuauccag cacgcuaaag cggcgcaggu accgguggua     1500
guggcgguga caagaucga uaagccagaa gccgauccgg aucgcgugaa gaacgaacug      1560
ucccaguacg gcauccugcc ggaagagugg ggcggcgaga gccaguucgu ccacguuucc     1620
gcgaaagcgg guaccggcau cgacgaccug cuggacgcga uccugcugca ggcugaaguu     1680
cuugagcuga aagcggcccg caacggcuaug gcgagcggcg cggucaucga auccuuccuu    1740 gauaaaagguc guggccggu agcuaccguu cugguucgcg aagguacucu gcacaagggc     1800
gacauuguuc ugugcggcuu cgaauauggc cgugugcgcg cgaugcguga cgaacugggu    1860
cgcgaagugc uggaagcggg uccguccauu ccgguggaaa uccucggccu guccggugug     1920
ccggcugccg gugaugaagu gaccguagug cgugacgaga aaaagcgcg ugaaguggcg     1980 cuguaucguc agggcaaauu ccgugaaguu aagcuggcgc gucagcagaa aucuaaacug    2040
gaaaacaugu ucgcuaacau gaccgaaggc gaaguucacg aagugaacau cguacugaaa     2100
gcggacguac agggucuguu cgaagcgauu uccgauuccu uacugaaacu gcuaccgac      2160 gaagugaaag ugaagaucau cgguuccggc guaggugugua ucaccgaaac cgacgcuacc    2220
cuggcagcag caucaacgc gauucugguu ggcuucaacg uucgugccga ugccucugcg     2280
cguaaaguua ucgaagcgga aagccuggau cugcguuacu acuccgucau cuauaaccug    2340
aucgacgaag ugaaagcggc gaugagcggc augcugcuc cggaacugaa acagcagauc     2400
aucgucuggg cugaagugcg ugaugucuuc aaaucgccga aauucggcgc caucgcgggc   2460 uguauggcuua ccgaagggac gaucaaacgu cacaacccaa uccgcguucu gcgugacaac    2520 ugguuaucu augaaggcga gcuggaaucc cugcgccgcu ucaaagauga cguuaacgaa    2580
guccguaacg gcauggaaug uggaucggc gugaagaacu acaacgacgu ucgcguuggc     2640
gauaugaucg aaguguucga aaucaucgaa auccagcgua gcaucgauua a              2691

<210> SEQ ID NO 88
<211> LENGTH: 3234
<212> TYPE: RNA
<213> ORGANISM: Klebsiella pneumoniae

<400> SEQUENCE: 88
augaaaagaa uguuaaucaa cgcaacucag caggaagagu ugcgcgucgc ccuuguugau       60
gggcagcgcc uguacgaccu ggauaucgaa agccccgggc acgaacagaa aaaagcgaac      120
```

| | |
|---|---|
| aucuacaaag gcaaaaucac ccgcauugaa cccagccuug aagccgcguu uguugauuac | 180 |
| ggcgccgagc gucauggusu ccuccccccuc aaagaaaucg cccgcgaaua cuucccccgcc | 240 |
| aacuacaaug cgcauggucg uccuaauauc aaagacguac ugcgggaagg ucaggaaguu | 300 |
| aucgugcaga uugauaaaga agaacgcggc aacaaaggcg cugcgcucac caccuuuauc | 360 |
| agccucgcgg gcagcuaucu gguacugaug ccgaacaacc cgcgcgccgg gggaauuucc | 420 |
| cgccguaucg agggcgacga ccguaccgaa cugaaagaag cgcuggcgag ccuggagcuu | 480 |
| ccggacggca ugggccugau cguucgcacc gcuggcgucg gcaaauccgc cgaagcccug | 540 |
| cagugggacc ugagcuuccg ccugaagcac ugggaagcga uucagaaagc gcggaaagc | 600 |
| cguccggcgc cguccugau ccaccaggaa agcaacguca uuguccgcgc cuuccgugac | 660 |
| uaccugcgcc aggacaucgg cgaaauccug aucgauaacc cgaaagugcu ugagcuggcg | 720 |
| cgccagcaua ucgccgcgcu gggucguccg gauuucagca gcaaaauaaa acuguacacc | 780 |
| ggugaaaucc cgcuguucag ccauuауcag aucgaaucgc aaauugaguc cgccuuccag | 840 |
| cgcgaagugc gccugccuuc cggcgggucu aucguuaucg auagcaccga agcgcugacc | 900 |
| gcgaucgaua ucaaccuccgc ccgcgccacc cgcggcggcg auaucgaaga dacagccuuc | 960 |
| aauaccaacc ucgaagcggc ugacgaaauu gcccgccagc ugcgucugcg cgaccucggc | 1020 |
| ggccugaucg uuaucgacuu caucgauaug accccgguuc gccaccagcg cgccguggag | 1080 |
| aaucgucugc gcgaagccgu ccgucaggac cgugcgcgca uucagaucag ccauauuucg | 1140 |
| cgcuucggcc ugcuggagau gucccgucag cgccugagcc cgucgcuggg cgaguccagc | 1200 |
| caccacgucu gcccgcgcug cuccggcacc ggcaccgugc gugauaacga aucgcugucg | 1260 |
| cucucuauuc ugcgucugau cgaagaagaa gcgcugaaag agaauaccaa agaagueсac | 1320 |
| gccauuguuc cgguaccgau cgcccuccuau cugcugaacg aaaaacgugc cgcagugagc | 1380 |
| gcuaucgaau cccgucaggg cgaugugcgc guuauuaucg ugccaaacga cgaaaugcaa | 1440 |
| acgccgcacu acuccguccu gcgcgugcgc aaaggugaag aaaccucaac gcugagcuau | 1500 |
| cugcugccga agcugcauga agaagaaaug gcgcugccag gcgacgauga ccggcggag | 1560 |
| cggaaacguc cggaacagcc ggcccuggcc gcuuuuguca ugccagaugc gccgccagcc | 1620 |
| ccgaugcucg aagagccugc cgccgcgccu gucgccgcag cggcaccggu cgcggccgcc | 1680 |
| gcaccggcgc agccuggccu gcucucacgc uucuucagcg cgcugaagaa uaucuucucu | 1740 |
| ggcgccgaag aggccaaacc ggcugaaguu caggucgaga agaaagcgga agaaaaaccg | 1800 |
| gagcgucagc aggagcgucg uaaaccgcgc gccaacaacc gccgcgaccg caacgaccgc | 1860 |
| cgugauaacc gcgacaaucg ugacaaccgc gauaaccgug acaaucgcga cacccgugcg | 1920 |
| gacaaugccg agggccguga accgcgcgaa ucgcgugaag agaaccgucg caaccgucgc | 1980 |
| gagaagccgu cgcagaacgu ggaagcccgu gauguucgcc aaaccucagg cgacgacgcg | 2040 |
| gagaaagcga aaucccguga cgagcagcag ccgcgccgcg aacgcacccg ccgccgcagu | 2100 |
| gacgacaaac gucaggcgca gcaggaagcc aaagcgcaga cucgcgaaga gccgguugug | 2160 |
| caggagacgg agcaggaaga gcgguacaa acucugccgc gucguaaacc gcgccagcug | 2220 |
| gcacagaaag ugcgcguuga guccgcuguc gucgagccag uugccgagau cgugccagaa | 2280 |
| gccguagugg cugaaguuau cgcucgcac agcgagccgg ugaaagccga gcugccggca | 2340 |
| ggguggaga gcguggcgga ccaggacgaa aauggcgaau cccgugaagc gaacgguaug | 2400 |
| ccgcgucgcu cacgucgcuc cccgcgucac cugcgcguca gcggucagcg ucgucgcgc | 2460 |
| uaucgugacg aacgcuaucc gacccagucg ccuaugccgc ugaccguagc cugcgcaucg | 2520 |

| | |
|---|---|
| ccggagaugg cuuccgguaa agucuggauc cgcuacccgg ugguucgucc gcaggaucag | 2580 |
| cagccggaag agguucaggu ucaggacgcc agcgucgcga aaacugucga ggccguagcg | 2640 |
| gccccggucg ccgucguuga aaccguuacc gcugcgccgg ucaccgucga gccggcuacc | 2700 |
| auggaaccag uaaccgcuga gccgguaguc gucgagccgu agcggccgc cgagccgcug | 2760 |
| gucguugaug cugcggaagu gucgcgcca gcagccgucg agccagcgcc ucaggagccg | 2820 |
| gucaccgaag caccggcugu cgaagcgccu caggcuaucg cgccagugac gcucgacgcc | 2880 |
| gagccggugg ugguagaacc ugaagcggug gaaacgacgc cugucguugc agcgccagug | 2940 |
| gaaacuaucg ccccggucgc agaaccgugu gagcaagcgc cagugaccga agcggccccu | 3000 |
| gccgaaccgg ucaaagccga gccccggug agcaagccgg ucguaguggc gggucaucgc | 3060 |
| caugccaccg cgccaaugac ccgucgcca gcuccggacu augucccgga agcaccgcgu | 3120 |
| cauagcaccu gggugcgccc gccguucgcc uuugaaggua aaggcgccgc cgguggucau | 3180 |
| agcgcgaccc auaaagccac cgcugaaccg acucgcccac agcccgucga guaa | 3234 |

<210> SEQ ID NO 89
<211> LENGTH: 3480
<212> TYPE: RNA
<213> ORGANISM: Klebsiella pneumoniae

<400> SEQUENCE: 89

| | |
|---|---|
| augcgcaagc ucucacuaag uuuacucacg cugucccucg gcguugcgcu gcugccguua | 60 |
| gcgcaggcgg cgacgacgcc ugcccaggag caucugcugg agcagguccg ccucggcgag | 120 |
| gccagcaauc gugaagaccu ggugcgccag ucgcuguacc gucuggagcu gauugauccc | 180 |
| aacaacccgg agcugauugc cgcgcggau cgcuaucgc ugcgucaggg ggaugccgcc | 240 |
| ggggcgcaaa aagagcugga acgacugacg aagcaggcgc cggacucccc ggagcugaag | 300 |
| gcgucgcgca augagaugaa aagcaacacc ggcgagggcc gccaggcgcu gcagcaggcg | 360 |
| cgacugcugg gcguggccgg aaggucgau gaagccaucg ccgccauga aaaacuguac | 420 |
| ggcggggugc cggaugacgu ugacgucgcc auugaguacu ggacgcuggu ggcgcgccug | 480 |
| ccggcccgcc auagcgaagg cgucagccag uugaaaaaac ugaacgccag cgcgccgggc | 540 |
| aacgucagcc ugcugacuuc gcuggcgaag cagauguucg ccgauaacaa accgcaggag | 600 |
| ggguucgccu aucggcgga ugggcccga ucggccucgg gacgcgguau cgccgccgau | 660 |
| augugguuca gugaggugaa aagcaugccg gugaguaagg ccagcgugca ggcguugcag | 720 |
| caauuucuuc ugcaguuucc caccggcucg guggcggcga acgcccgcgu ucugcucgac | 780 |
| caacagcagg cgcagcugca ggauccgacu uccgcgccc gcucggaagg gcuggcggcg | 840 |
| gucaaguccg ggaauaccac gcaggcgguc gcggaucugc agaaagccgu ucaggccgac | 900 |
| agccgcgaca gcgacgcggu gggcgcucuc ggccaggccu auucccagcg cggcgaccgc | 960 |
| gcgcgggcag uggcgcagcu caguaaagcg auugcuaugg acccgacag cccgaaccgc | 1020 |
| ggcaagugg acagccugcu gcaaacuaac cgcuacuggc ugcugauaaa gcaggggau | 1080 |
| aacgcccuga agccggcca gcuuucgcag gcgcagaacu auuaugccca ggcgcagcgg | 1140 |
| gucgaucgca ccgacagcua ugccgugcug ggcggggga cgucgcggc ggcgcgcaaa | 1200 |
| gaggcggcgg cggcggagcg cuauuaccag caggcguugc gccuggaucg cggcaauaac | 1260 |
| cuggcggugc gcgcccuggc caaccucuau cgcgccgaau cgccgagaa agccagcgcc | 1320 |
| uggaucgccg gccuccccucc cgcucagcgg cggagcaucg augauauuga gcgcagccug | 1380 |

| | |
|---|---|
| acuaacgacc ggcuggagaa acaggcgcag gcucuggaga gccagggcaa cugggcgcag | 1440 |
| gcggcggaag uucagcgucg gcgccuggcg cuggauccgg acagcgucug gauaaccuac | 1500 |
| cgucuggcgc gggaucuggu cagcgccggc gaacgccagg aggccgacgc gcugaugcgg | 1560 |
| acgaugguca accgccagcc gcaggacgcc gaacggguCu acgccucggg acucuaccug | 1620 |
| ucggggaacg accaggacga ucuggcucug gcgcaaaucg ccgcucugcc gcgcagcgcg | 1680 |
| uggacggaua acauucguga gcucgaagcg cguuugcaaa gcgaccgggu gcugcgccag | 1740 |
| gccaaccagc ugcgcgacag cgguaacgaa gcgcaggcga ucgcccuuau ccgacagcag | 1800 |
| cccgccucgg ugcgcauauga ccugacgcuc gccgacuggg cgcagcagcg cggcgacagc | 1860 |
| cagacggcga uugccaacua ucagcggguG cugcgccagg aggccgacaa cggcgaugcg | 1920 |
| cgccucggcc uugcgaaagu cuaccuggcc gagggcgaua aaccggccgc ccgggcgcag | 1980 |
| gucaugcagc ugaaaggcgc agagaccgaa uccaugaaca ugcagcggcg gguggcgcug | 2040 |
| gcgcgagcug gccuuggcga uaccgcugac gcgcaacgga uuuuaauca gauugugccg | 2100 |
| caggcgaagg cgcagccgcc cucgauggag agcgcgcugg ugcugcgcga ugccgcgcgc | 2160 |
| uuugccaccc agagcggggc gccgcagcag gcgcugacgc acuaccggga agcuauggug | 2220 |
| gccuccggca uuaccccgc gcagccgcag gauaacgaua cuuuuacgcg gcugacgcgc | 2280 |
| aacgacagcc augaugacug gcugaagcgc gggauccgca gcgaugccgc cgaccuuuau | 2340 |
| cgucagcagg aucugaacgu caccuggaa caugacuucu ggggguccag cggcaccggc | 2400 |
| ggcuauuccg accugaaggc gcauaccacc augcugcaga uggaugcucc gcuggcggau | 2460 |
| ggccggaugu ucuuccgcac cgaccugguc aauauggaug ccggcagcuu uuccacccac | 2520 |
| agcgacggga gcuacucgcc cagcuggggc accgcgggg agaucgccug uaccagcggc | 2580 |
| aguaaaaauc agaccgacag cggggccagc guggcggucg gcuggaagaa ugacaccugg | 2640 |
| agcggggaua ucggcaccac gccgaugggc uucaaugucg ucgauguggu gggggggcug | 2700 |
| agcuacagca gcgacgucgg gccggugggg uacacgguca acguccaccg gcggccuauc | 2760 |
| uccagcucgc ugcucuccuu uggcgggcag aaggacagca gcagccauac cggcgccacc | 2820 |
| uggggcggcg uccgcgccga cggcggcggc cugagccuga gcuacgaucg cggggaggcu | 2880 |
| cacggcaucu gguccucgcu gggcgccgac ucgcugaccg guaaaaacgu ggcggauaac | 2940 |
| uggcgcgugc gcuggaugac cggguacuac uacaaggucA ucaacgagaa uaaucgucgc | 3000 |
| gucaccgucg gccucaacaa uaugaucugg cacuacgaca aagaucucag cggcuacacc | 3060 |
| cucgccagg gcggcuauua cagcccacag gaguaucucu cguucgccgu gccggugacc | 3120 |
| uggcgucagc gcaccgagaa cugguccugg gagcucggcg ggucggVguc augguccaU | 3180 |
| ucgcgcaccc agacgcaagc ccgcuauccg cugcugaacc ugaucccguc cgacuaccgg | 3240 |
| cagcgcgcca gcgagcugac ggaggagggg agcagcagcc auggauucgg uuacaccgcc | 3300 |
| agagcgcugg uggagcggcg ggugaccagc aacugguucg ucggcgccgc ggucgauauu | 3360 |
| cagcaggcga aggauuacac cccgagccau gcgcugcuuu acguccgcua ucggcgcc | 3420 |
| ggcuggcagg gggaucugga uaugccgccc cagccgcugg ugcccuacgc cgacugguag | 3480 |

<210> SEQ ID NO 90
<211> LENGTH: 4236
<212> TYPE: RNA
<213> ORGANISM: Klebsiella pneumoniae

<400> SEQUENCE: 90

| | |
|---|---|
| augagccagg aauacaccga agacaaagaa gucaaacuaa ccaaacucag cagcgggcgc | 60 |

-continued

```
cgacuccuug aggcgaugcu cauccuuugc ucccucuucg ccaucuggcu gauggcggca    120
cuacugagcu uuaaccccuc ggaccccagc uggucgcaaa cggcauggca ugagccuauu    180
cauaauuuag gcggcgcccc cggcgcgugg cuugccgaua cccucuuuuu cauuuuggc     240 gucauggccu acaccaucuc ggugaucauc aucggcggau gcugguuugc cuggcggcau    300
caggaaaacg acgaauacau ugauuauuuu gccguuuccc uucgccucau cggugcguua    360
gcccugaucc ugaccuccug ggucuggcg gcgauuaacg ccgaugauau cugguacuuc     420
gccuccggcg gggugaucgg cagccugcug agcaccacgc ugcaacccccu gcugcacagc   480 agcggcggca ccaucgcccu guugguguauc ugggcggccg ggcugacgcu guucaccggc   540
uggucguggg ucagcauugc ggaaaagcug ggcggcggca uccugucccgu ucucaccuuu   600 gccagcaacc guacccgucg ggaugauacc ugggucgaug aaggcgaaua ugaagacgac    660
gaggaagagu acgacgacga agaggcggcc aggccgcagg aaucgcgucg cgcccguauc    720
uuacgcagcg cgcuggcgcg gcguaagcgu cuggccgaga aguuuaccaa cccuaugggg    780
cguaaaaccg acgcugcgcu uuucuccggc aaacggaugg augacggcga agagguggug    840
caauacagcg ccagcggggc gccuguugcc ccgacgaugu acuguuuuc cggcgccagc     900 gccgcgcguc ccgcagagga ugaugugcug uucuccggcg ccagcgccgu gcgcccgggc    960
gauuucgacc cuuacgaucc guuguugaau ggccacagua ucgcugagcc gguaagcgca   1020
gcggcggcgg cuacagccgc gccgcaggcg ugggcagaau caccgguggg ccaucacggc   1080
gcugcgccag cuuaucagcc ggaagccagc uauccgccgc agcaggccua ucagccugaa   1140
cccgcuccgu uccagcaggc cuaucagccu gaacccgcuc cguccagca ggcugcuuau    1200 cagccgccag cggggcaaac cgcaccgcag gcguaucagc cugagccagc gccguaucaa   1260
cagccgguuu acgauccgcg ugccggucaa ccugcgccgc aggccuauca gccugagcca   1320
gcgccguauc agcagccggc uuacgauccg uaugccgguc aaccgcgccc gcaggccuau   1380
cagccugaac cugcgccgua ucagcagccg gcuuacgauc gcaugccgg ucaaccugca    1440 ccgcaggccu aucagccuga ccagcgccg uaucagcagc cggcuuacga ucccuaugcc    1500
ggucaaccug cgccgcaggc cuaucagccg gagccagcgc cguaucagca gccaacuuac   1560
gaucccuaug ccggucagcc ugcgccucag accaucagc agccggcuua cgauccgaau   1620
gccggucagc ccgcgccgca gccguaucag ccggagccag cggcguauca gccgcaaagc   1680
gcgccaguuc ccccaccgga gccagagcc gaggucgugc aggaggaagu gaaacguccg   1740
ccgcucuauu auuucgagga aguggaagag aagcgggcgc gcgaacgcga gcuguuggcc   1800
uccugguauc agccaauucc ugagccggaa aguccgauug ccacuaaaacc gcugacgccg   1860 ccgaccacug cguccaaacc gccagugag acaaccgug ucucugcggu agcggcuggg     1920
gugcaucagg cuaccgccgc cagcggcggc gcggcggcag caaccucguc cacugccgca   1980
uccgcugcgc cuacgccauu guucagcccg gcguccagcg gcccaagggu ucaggugaaa   2040
gagggcaucg guccaaaacu accgcggccc aaucgcgugc guguuccuac gcgucgggaa   2100
cuggccuccu acggcaucaa gcuaccgucg cagcggagg cggaacagcg cgcgcggcag    2160
gcggagcgcg auccgcauua ugaugaugag cugcucucgg augaggaagc ggaugcuaug   2220
gagcaggaug aacuggcucg ccaguucgcc gccacccagc agcagcgcua cggucaucgc   2280
ugggaagacg auaacgcgac ugaugacgau gaggccgacg ccgcggcgga agcggagcug   2340
gcgcgucagu uugccgcuac ccagcagcag cgguacgcua ccgagcagcc gccgggcgcc   2400
```

-continued

| | |
|---|---|
| aacccguucu cgccggcaga uuaugaauuc ucgccgauga aaacguuggu caaugacggc | 2460 |
| ccgagcgaac cgcuguuuac gccgacgccg aaguccagc cgcagcagcc ggcccagcgc | 2520 |
| uaucaacaac cggcggccgc uccgcagcag gguuaucaac cugcgcagca ucagccgaua | 2580 |
| caccaucagc cugugccgcc acagccgcag uccuauccga cugcgucgca gcccguacag | 2640 |
| ccgcaacaac cgguugcccc gcaggggcau cagccugccg ccccugcgcc gcaggagagc | 2700 |
| cugauccacc cgcugcugau gcgcaauggc gauagucgac cgcugcaaaa gccgaccacg | 2760 |
| ccacugccgu cgcuggaucu gcuuaccccg ccgccgagug aagucgagcc gguggauacc | 2820 |
| uuugcucucg agcagauggc acgccuggug gaagcgcgac ucgcugauuu ccgcauuaaa | 2880 |
| gcggaugugg ugaacuacuc accggggccg gugaucaccc gcuucgaacu gaaucuggcg | 2940 |
| ccuggcguua aggccgcacg gaucucuaac cugucacggg accuggcgcg aucgcuguca | 3000 |
| acggucgccg ugcgcguggu ggaggugauc ccgggcaaac cguaugucgg gcuugagcug | 3060 |
| ccgaauaaaa aacgccagac cgucuaccug cgugaagugc ucgacaacgc caaguuccgu | 3120 |
| gauaacccau cuccgcucac cguggugung ggunaagaca ucgcuggcga uccgguagua | 3180 |
| gccgaucugg cgaaaaugcc gcaucugcug guggccggua ccaccggnuc cgguaagucu | 3240 |
| guuggcguca acgccaugau ccucagcaug cucuacaagg cgcagccgga agaugugcgu | 3300 |
| uucauuauga ucgaccccgaa aaugcucgag cugucgguucu acgaaggaau uccgcaccug | 3360 |
| cugacggaag uggucaccga caugaaagac gccgccaaug cgcugcgcug gagcgucaau | 3420 |
| gagauggagc gccgcuacaa gcugaugucg gcgcugggcg ugcguaaccu cgcgggcuac | 3480 |
| aacgagaaga ucgccgaagc cgcgcgcaug ggacguccga ucccggaucc guacuggaag | 3540 |
| ccuggcgaca gcauggacgc cguacauccg gugcuggaaa aacugccgua caucguggug | 3600 |
| cugguggaug aauucgccga ucugaugaug accgucggca aaaaggugga agagcugauc | 3660 |
| gcucgccugg cgcagaaagc gcgcgcggcg gggauccacc uggugcuggc gacacagcgu | 3720 |
| ccgucgguag auguuauuac cggcugauu aaggccaaca ucccgacgcg caucgccuuu | 3780 |
| accgugucga guaaaauuga cucacguacc auucucgauc agggcggcgc ggaaucgcug | 3840 |
| cugggauaugg gggauaugcu uuacuccggg ccgaacucua ccacgccggu gcguguccac | 3900 |
| ggggcguuug ugcgcgacca ggaaguccac gccguggunc aggacuggaa agcccgcggu | 3960 |
| cgcccgcaau augguggaugg cauuaccucc gacagcgaaa gcgaaggcgg cgguggcggc | 4020 |
| uucgacggcg gggaagaguu ggauccguug uucgaucagg cagucaacuu ugugaccgag | 4080 |
| aagcgcaaag cgucgauuuc cggggunucag cgucaguucc gcaucggcua uaaccgugcc | 4140 |
| gcgcguauua ucgaacagau ggaagcgcag gguaucguca gcgagcaggg ccauaacggu | 4200 |
| aaccgcgaag ugcuggcgcc gccgcccuuu gaauga | 4236 |

<210> SEQ ID NO 91
<211> LENGTH: 742
<212> TYPE: PRT
<213> ORGANISM: Klebsiella pneumoniae

<400> SEQUENCE: 91

Met Asn Asn Arg Ile Lys Ser Leu Ala Leu Leu Val Asn Leu Gly Ile
1               5                   10                  15

Tyr Gly Val Ala Phe Pro Leu Ser Ala Ala Glu Thr Ala Thr Asp Asp
                20                  25                  30

Lys Asn Ser Ala Ala Glu Glu Thr Met Val Val Thr Ala Ala Glu Gln
        35                  40                  45

-continued

```
Asn Leu Gln Ala Pro Gly Val Ser Thr Ile Thr Ala Asp Glu Ile Arg
 50                  55                  60
Lys Arg Pro Pro Ala Arg Asp Val Ser Glu Ile Ile Arg Thr Met Pro
 65                  70                  75                  80
Gly Val Asn Leu Thr Gly Asn Ser Thr Ser Gly Gln Arg Gly Asn Asn
                     85                  90                  95
Arg Gln Ile Asp Ile Arg Gly Met Gly Pro Glu Asn Thr Leu Ile Leu
                    100                 105                 110
Ile Asp Gly Lys Pro Val Thr Ser Arg Asn Ser Val Arg Leu Gly Trp
                115                 120                 125
Arg Gly Glu Arg Asp Thr Arg Gly Asp Thr Ser Trp Val Pro Pro Glu
130                 135                 140
Met Ile Glu Arg Ile Glu Val Ile Arg Gly Pro Ala Ala Arg Tyr
145                 150                 155                 160
Gly Asn Gly Ala Ala Gly Gly Val Val Asn Ile Ile Thr Lys Lys Thr
                165                 170                 175
Gly Asp Glu Trp His Gly Ser Trp Asn Thr Tyr Met Asn Ala Pro Glu
                180                 185                 190
His Lys Asp Glu Gly Ser Thr Lys Arg Thr Asn Phe Ser Leu Ser Gly
                195                 200                 205
Pro Leu Gly Gly Asp Phe Ser Phe Arg Leu Phe Gly Asn Leu Asp Lys
210                 215                 220
Thr Gln Ala Asp Ala Trp Asp Ile Asn Gln Gly His Gln Ser Glu Arg
225                 230                 235                 240
Thr Gly Ile Tyr Ala Asp Thr Leu Pro Ala Gly Arg Glu Gly Val Lys
                245                 250                 255
Asn Lys Asn Ile Asp Gly Leu Val Arg Trp Glu Phe Ala Pro Met Gln
                260                 265                 270
Ser Leu Glu Phe Glu Ala Gly Tyr Ser Arg Gln Gly Asn Leu Tyr Ala
                275                 280                 285
Gly Asp Thr Gln Asn Thr Asn Ser Asn Asp Leu Val Lys Glu Asn Tyr
                290                 295                 300
Gly Lys Glu Thr Asn Arg Leu Tyr Arg Asn Thr Tyr Ser Val Thr Trp
305                 310                 315                 320
Asn Gly Ala Trp Asp Asn Gly Val Thr Thr Ser Asn Trp Ala Gln Tyr
                325                 330                 335
Glu Arg Thr Arg Asn Ser Arg Lys Gly Gly Leu Ala Gly Gly Thr
                340                 345                 350
Glu Gly Ile Phe Asn Ser Asn Gln Phe Thr Asp Ile Asp Leu Ala Asp
                355                 360                 365
Val Met Leu His Ser Glu Val Ser Ile Pro Phe Asp Tyr Leu Val Asn
                370                 375                 380
Gln Asn Leu Thr Leu Gly Ser Glu Trp Asn Gln Gln Arg Met Lys Asp
385                 390                 395                 400
Asn Ala Ser Asn Thr Gln Ala Leu Ser Gly Gly Ser Ile Pro Gly Tyr
                405                 410                 415
Asp Ser Thr Gly Arg Ser Pro Tyr Ser Gln Ala Glu Ile Phe Ser Leu
                420                 425                 430
Phe Ala Glu Asn Asn Met Glu Leu Thr Asp Thr Met Leu Thr Pro
                435                 440                 445
Ala Leu Arg Phe Asp His His Ser Ile Val Gly Asn Asn Trp Ser Pro
450                 455                 460
Ser Leu Asn Leu Ser Gln Gly Leu Trp Asp Asp Phe Thr Leu Lys Met
```

```
                465                 470                 475                 480
Gly Ile Arg Ala Tyr Lys Ala Pro Ser Leu Tyr Gln Thr Asn Pro
                    485                 490                 495

Asn Tyr Ile Leu Tyr Ser Lys Gly Gln Gly Cys Tyr Ala Ser Lys Asp
                500                 505                 510

Gly Cys Tyr Leu Gln Gly Asn Asp Asp Leu Lys Ala Glu Thr Ser Ile
                515                 520                 525

Asn Lys Glu Ile Gly Leu Glu Phe Lys Arg Asp Gly Trp Leu Ala Gly
                530                 535                 540

Val Thr Trp Phe Arg Asn Asp Tyr Arg Asn Lys Ile Glu Ala Gly Tyr
545                 550                 555                 560

Ala Pro Val Tyr Gln Asn Asn Lys Gly Thr Asp Leu Tyr Gln Trp Glu
                565                 570                 575

Asn Val Pro Lys Ala Val Val Glu Gly Leu Glu Gly Thr Leu Asn Val
                580                 585                 590

Pro Val Ser Glu Thr Val Asn Trp Thr Asn Asn Ile Thr Tyr Met Leu
                595                 600                 605

Gln Ser Lys Asn Lys Lys Thr Gly Asp Arg Leu Ser Ile Ile Pro Glu
                610                 615                 620

Tyr Thr Leu Asn Ser Thr Leu Ser Trp Gln Val Arg Asp Asp Val Ser
625                 630                 635                 640

Leu Gln Ser Thr Phe Thr Trp Tyr Gly Lys Gln Glu Pro Lys Lys Tyr
                645                 650                 655

Asn Tyr Lys Gly Gln Pro Val Thr Gly Ser Glu Lys Asn Glu Val Ser
                660                 665                 670

Pro Tyr Ser Ile Leu Gly Leu Ser Ala Thr Trp Asp Val Thr Lys Tyr
                675                 680                 685

Val Ser Leu Thr Gly Gly Val Asp Asn Val Phe Asp Lys Arg His Trp
                690                 695                 700

Arg Ala Gly Asn Ala Gln Thr Thr Gly Gly Ala Thr Gly Thr Met Tyr
705                 710                 715                 720

Gly Ala Gly Ala Glu Thr Tyr Asn Glu Ser Gly Arg Thr Trp Tyr Leu
                725                 730                 735

Ser Val Asn Thr His Phe
                740

<210> SEQ ID NO 92
<211> LENGTH: 356
<212> TYPE: PRT
<213> ORGANISM: Klebsiella pneumoniae

<400> SEQUENCE: 92

Met Lys Lys Thr Ala Ile Ala Ile Ala Val Ala Leu Ala Gly Phe Ala
1               5                   10                  15

Thr Val Ala Gln Ala Ala Pro Lys Asp Asn Thr Trp Tyr Ala Gly Gly
                20                  25                  30

Lys Leu Gly Trp Ser Gln Tyr His Asp Thr Gly Phe Tyr Gly Asn Gly
                35                  40                  45

Phe Gln Asn Asn Asn Gly Pro Thr Arg Asn Asp Gln Leu Gly Ala Gly
                50                  55                  60

Ala Phe Gly Gly Tyr Gln Val Asn Pro Tyr Leu Gly Phe Glu Met Gly
65              70                  75                  80

Tyr Asp Trp Leu Gly Arg Met Ala Tyr Lys Gly Ser Val Asp Asn Gly
                85                  90                  95
```

Ala Phe Lys Ala Gln Gly Val Gln Leu Thr Ala Lys Leu Gly Tyr Pro
                100                 105                 110

Ile Thr Asp Asp Leu Asp Ile Tyr Thr Arg Leu Gly Met Val Trp
            115                 120                 125

Arg Ala Asp Ser Lys Gly Asn Tyr Ala Ser Thr Gly Val Ser Arg Ser
        130                 135                 140

Glu His Asp Thr Gly Val Ser Pro Val Phe Ala Gly Gly Val Glu Trp
145                 150                 155                 160

Ala Val Thr Arg Asp Ile Ala Thr Arg Leu Glu Tyr Gln Trp Val Asn
                165                 170                 175

Asn Ile Gly Asp Ala Gly Thr Val Gly Thr Arg Pro Asp Asn Gly Met
            180                 185                 190

Leu Ser Leu Gly Val Ser Tyr Arg Phe Gly Gln Glu Asp Ala Ala Pro
        195                 200                 205

Val Val Ala Pro Ala Pro Ala Pro Glu Val Ala Thr Lys His
210                 215                 220

Phe Thr Leu Lys Ser Asp Val Leu Phe Asn Phe Asn Lys Ala Thr Leu
225                 230                 235                 240

Lys Pro Glu Gly Gln Gln Ala Leu Asp Gln Leu Tyr Thr Gln Leu Ser
                245                 250                 255

Asn Met Asp Pro Lys Asp Gly Ser Ala Val Val Leu Gly Tyr Thr Asp
            260                 265                 270

Arg Ile Gly Ser Glu Ala Tyr Asn Gln Gln Leu Ser Glu Lys Arg Ala
        275                 280                 285

Gln Ser Val Val Asp Tyr Leu Val Ala Lys Gly Ile Pro Ala Gly Lys
290                 295                 300

Ile Ser Ala Arg Gly Met Gly Glu Ser Asn Pro Val Thr Gly Asn Thr
305                 310                 315                 320

Cys Asp Asn Val Lys Ala Arg Ala Leu Ile Asp Cys Leu Ala Pro
                325                 330                 335

Asp Arg Arg Val Glu Ile Glu Val Lys Gly Tyr Lys Glu Val Val Thr
            340                 345                 350

Gln Pro Ala Ala
        355

<210> SEQ ID NO 93
<211> LENGTH: 245
<212> TYPE: PRT
<213> ORGANISM: Klebsiella pneumoniae

<400> SEQUENCE: 93

Met Asp Gly Trp Gln Arg Ala Phe Val Leu His Ser Arg Pro Trp Ser
1                   5                   10                  15

Glu Thr Ser Leu Met Leu Asp Val Phe Thr Glu Ser Gly Arg Val
                20                  25                  30

Arg Leu Val Ala Lys Gly Ala Arg Ser Lys Arg Ser Asn Leu Lys Gly
            35                  40                  45

Ala Leu Gln Pro Phe Thr Pro Leu Leu Val Arg Phe Gly Gly Arg Gly
        50                  55                  60

Glu Val Lys Thr Leu Arg Ser Ala Glu Ala Val Ser Leu Ala Leu Pro
65                  70                  75                  80

Leu Ser Gly Ile Thr Leu Tyr Ser Gly Leu Tyr Val Asn Glu Leu Ile
                85                  90                  95

Ser Arg Val Leu Glu His Glu Thr Arg Phe Ser Glu Leu Phe Phe Asp
            100                 105                 110

```
Tyr Leu His Cys Ile Gln Ala Leu Ala Gly Ala Ser Gly Ser Pro Glu
        115                 120                 125

Pro Ala Leu Arg Arg Phe Glu Leu Ala Leu Leu Gly His Leu Gly Tyr
130                 135                 140

Gly Val Asp Phe Leu His Cys Ala Gly Ser Gly Glu Pro Val Asp Asp
145                 150                 155                 160

Thr Met Thr Tyr Arg Tyr Arg Glu Glu Lys Gly Phe Ile Ala Ser Leu
                165                 170                 175

Val Ile Asp Asn Asn Thr Phe Thr Gly His His Leu Lys Ala Leu Ala
                180                 185                 190

Ser Arg Glu Phe Pro Asp Val Asp Thr Leu Arg Ala Ala Lys Arg Phe
            195                 200                 205

Thr Arg Ile Ala Leu Lys Pro Tyr Leu Gly Gly Lys Pro Leu Lys Ser
        210                 215                 220

Arg Glu Leu Phe Arg Gln Phe Met Pro Ala Arg Lys Ala Arg Ala Asp
225                 230                 235                 240

Asn Thr Asn Asn Asp
            245

<210> SEQ ID NO 94
<211> LENGTH: 1649
<212> TYPE: PRT
<213> ORGANISM: Klebsiella pneumoniae

<400> SEQUENCE: 94

Met Lys Pro Phe Arg Leu Ala Ala Leu Ser Leu Ala Leu Leu Thr Ala
1               5                   10                  15

Phe Ser Leu Thr Gly Cys Asp Asp Ser Gly Thr Pro Gln Ala Ser Ala
            20                  25                  30

Pro Ala Pro Ala Ala Asp Ser Asn Pro Gly Ala Thr Ala Lys Pro Asp
        35                  40                  45

Arg Ala Gln Leu Ala Ala Leu Glu Lys Ser Gln Gly Lys Ala Leu
    50                  55                  60

Thr Leu Leu Asp Ala Ser Glu Val Gln Leu Asp Gly Ala Ala Thr Leu
65                  70                  75                  80

Val Leu Thr Phe Ser Val Pro Leu Gln Pro Asp Gln Asp Phe Ser Arg
                85                  90                  95

Ser Val His Leu Val Asp Lys Lys Ser Gly Lys Val Asp Gly Ala Trp
            100                 105                 110

Glu Leu Ala Pro Asn Leu Lys Glu Leu Arg Leu Arg His Leu Glu Pro
        115                 120                 125

Lys Arg Glu Leu Ile Val Ser Val Asp Pro Thr Leu Thr Ala Leu Asn
    130                 135                 140

Lys Ala Thr Leu Asp Lys Pro Phe Glu Lys Thr Leu Thr Thr Arg Asp
145                 150                 155                 160

Ile Ala Pro Ser Val Gly Phe Ala Ser Arg Gly Ser Leu Leu Pro Gly
                165                 170                 175

Asn Val Val Ala Gly Leu Pro Val Met Ala Leu Asn Val Asp Asn Val
            180                 185                 190

Asp Val Asn Phe Phe Arg Ile Lys Pro Glu Ser Leu Ser Ala Phe Val
        195                 200                 205

Ser Gln Trp Glu Tyr Arg Asn Ser Leu Ser Asn Trp Glu Ser Asp Glu
    210                 215                 220

Leu Leu Lys Met Ala Asp Leu Val Tyr Ser Gly Arg Phe Asp Leu Asn
```

```
            225                 230                 235                 240
        Pro Ala Arg Asn Thr Arg Glu Lys Leu Leu Pro Leu Ser Asp Ile
                        245                 250                 255
        Lys Pro Leu Gln Gln Pro Gly Val Tyr Val Ala Val Met Asn Pro Ala
                        260                 265                 270
        Gly Arg Tyr Ser Tyr Ser Asn Ala Ala Thr Leu Phe Thr Leu Ser Asp
                        275                 280                 285
        Ile Gly Val Ser Ala His Arg Tyr His Asn Arg Leu Asp Val Phe Thr
                290                 295                 300
        Gln Ser Leu Glu Asn Gly Ala Ala Gln Ser Gly Ile Glu Val Gln Leu
        305                 310                 315                 320
        Leu Asn Ala Lys Gly Gln Thr Leu Ala Glu Ala Lys Ser Asp Ser Gln
                        325                 330                 335
        Gly His Val Thr Leu Gln Thr Asp Lys Glu Ala Ala Leu Leu Leu Ala
                        340                 345                 350
        Arg Lys Glu Gly Gln Thr Thr Leu Leu Asp Leu Lys Leu Pro Ala Leu
                        355                 360                 365
        Asp Leu Ala Glu Phe Ser Ile Ala Gly Ala Pro Gly Phe Ser Lys Gln
                        370                 375                 380
        Phe Phe Met Phe Gly Pro Arg Asp Leu Tyr Arg Pro Gly Glu Thr Val
        385                 390                 395                 400
        Ile Leu Asn Ala Leu Leu Arg Asp Ser Asp Gly Lys Pro Leu Ala Glu
                        405                 410                 415
        Gln Pro Val Lys Leu Glu Val Val Gln Pro Asp Gly Gln Val Ile Arg
                        420                 425                 430
        Ser Val Met Ser Lys Pro Val Asn Gly Leu Tyr Gln Phe Thr Tyr Pro
                        435                 440                 445
        Leu Asp Ser Gly Ala Ala Thr Gly Met Trp His Ile Arg Ala Ser Ala
                        450                 455                 460
        Gly Asp Asn Gln Pro Arg Glu Trp Asp Phe His Val Glu Asp Phe Met
        465                 470                 475                 480
        Pro Glu Arg Met Ala Leu Asn Leu Thr Pro Gln Ala Ala Pro Val Ala
                        485                 490                 495
        Pro Asp Ala Asp Val Thr Phe Gly Val Ser Gly Ala Tyr Leu Tyr Gly
                        500                 505                 510
        Ala Pro Ala Ser Gly Asn Gln Leu Gln Gly Lys Leu Phe Leu Arg Pro
                        515                 520                 525
        Leu Arg Asp Ala Val Ala Ala Leu Pro Gly Phe Gln Phe Gly Asp Ile
                        530                 535                 540
        Ala Glu Glu Asn Leu Ser Arg Ser Leu Asp Glu Val Gln Leu Thr Leu
        545                 550                 555                 560
        Asp Glu Lys Gly His Gly Glu Val Thr Thr Ser Ser Gln Trp Gln Asp
                        565                 570                 575
        Ser His Ser Pro Leu Gln Val Val Leu Gln Ala Ser Leu Leu Glu Ser
                        580                 585                 590
        Gly Gly Arg Pro Val Thr Arg Thr Val Lys Gln Pro Ile Trp Pro Ala
                        595                 600                 605
        Glu Ala Leu Pro Gly Ile Arg Pro Gln Phe Thr Leu Lys Asp Val Tyr
                        610                 615                 620
        Asp Tyr Arg Thr Asp Thr Thr Val Lys Gln Pro Val Val Asp Glu Asn
        625                 630                 635                 640
        Ser Asn Ala Ala Phe Asp Ile Val Tyr Ala Asp Val Lys Gly Glu Lys
                        645                 650                 655
```

```
Lys Ala Ile Ser Gly Leu Gln Val Arg Leu Ile Arg Glu Arg Arg Asp
                660                 665                 670

Tyr Tyr Trp Asn Trp Ser Asp Ser Glu Gly Trp Gln Ser Gln Phe Asp
            675                 680                 685

Gln Lys Asp Leu Gln Glu Gly Glu Ser Leu Asp Leu Gln Ala Gly
        690                 695                 700

Gln Ile Gly Lys Val Ser Phe Pro Val Glu Trp Gly Ser Tyr Arg Leu
705                 710                 715                 720

Glu Val Lys Gly Pro Asp Val Val Ser Val Arg Phe Trp Ala
                725                 730                 735

Gly Tyr Ser Trp Gln Asp Asn Ser Glu Gly Ala Gly Ala Ala Arg Pro
            740                 745                 750

Asp Arg Val Thr Met Lys Leu Asp Lys Pro Ser Tyr Lys Pro Gly Asp
            755                 760                 765

Thr Ile Arg Leu His Ile Ala Ala Pro Ala Ala Gly Lys Gly Tyr Ala
        770                 775                 780

Met Val Glu Ser Ser Glu Gly Pro Leu Trp Trp Gln Glu Ile Asp Val
785                 790                 795                 800

Pro Ala Glu Gly Met Asp Leu Ser Ile Pro Val Asp Lys Thr Trp Asn
                805                 810                 815

Arg His Asp Leu Tyr Leu Ser Thr Leu Val Val Arg Pro Gly Asp Lys
            820                 825                 830

Ser Arg Ser Ala Thr Pro Lys Arg Ala Val Gly Leu Leu His Leu Pro
        835                 840                 845

Leu Gly Asp Glu Asn Arg Arg Leu Thr Leu Ala Leu Glu Ala Pro Asp
        850                 855                 860

Lys Met Arg Pro Asn Gln Pro Leu Thr Val Lys Val Lys Ala Ser Val
865                 870                 875                 880

Lys Glu Gly Glu Ala Pro Lys Gln Val Asn Val Leu Ser Ala Val
                885                 890                 895

Asp Ser Gly Val Leu Asn Ile Thr Asp Tyr Ala Thr Pro Asp Pro Trp
            900                 905                 910

Asn Ala Phe Phe Gly Gln Lys Arg Tyr Gly Ala Asp Ile Tyr Asp Ile
        915                 920                 925

Tyr Gly Gln Val Ile Glu Gly Gln Gly Arg Val Ala Ser Leu Arg Phe
    930                 935                 940

Gly Gly Asp Gly Asp Glu Leu Lys Arg Gly Gly Lys Pro Pro Val Asn
945                 950                 955                 960

His Val Thr Ile Val Ala Gln Gln Ala Gln Pro Val Val Leu Asn Asp
                965                 970                 975

Gln Gly Glu Gly Thr Val Thr Leu Pro Ile Gly Asp Phe Asn Gly Glu
            980                 985                 990

Leu Arg Val Met Ala Gln Ala Trp Thr Ala Asp Asp Phe Gly Ser Ser
        995                 1000                1005

Glu Asp Lys Val Val Val Ala Ala Pro Val Ile Ala Glu Leu Asn
    1010                1015                1020

Thr Pro Arg Phe Leu Ala Ser Gly Asp Thr Thr Arg Leu Ala Leu
    1025                1030                1035

Asp Leu Ser Asn Leu Thr Asp Lys Pro Gln Thr Leu Gln Val His
    1040                1045                1050

Leu Thr Ala Ser Gly Leu Val Thr Leu Ser Glu Gly Gln Leu Pro
    1055                1060                1065
```

-continued

Pro Val Gln Leu Ala Pro Gly Ala Arg Ser Thr Leu Phe Ile Pro
    1070                1075                1080

Val Ser Ala Leu Ala Gly Phe Gly Asp Gly Gln Val Asn Ala Thr
    1085                1090                1095

Ile Ser Gly Leu Ser Leu Pro Gly Glu Thr Phe Ala Pro Leu Gln
    1100                1105                1110

Lys Gln Trp Lys Ile Gly Val Arg Pro Ala Tyr Pro Ala Gln Thr
    1115                1120                1125

Val Asn Ser Gly Ala Val Leu Gln Pro Gly Glu Ser Trp Gln Pro
    1130                1135                1140

Pro Ala Ala Gln Ser Gln Gly Phe Ala Pro Gln Thr Leu Gln Gly
    1145                1150                1155

Gln Leu Leu Leu Ser Gly Lys Pro Pro Leu Asn Leu Ala Arg Tyr
    1160                1165                1170

Ile Arg Glu Leu Lys Ala Tyr Pro Tyr Gly Cys Leu Glu Gln Thr
    1175                1180                1185

Ala Ser Gly Leu Phe Pro Ser Leu Tyr Thr Ser Ala Ala Gln Leu
    1190                1195                1200

Lys Ala Leu Gly Ile Ser Gly Asp Ser Asp Glu Lys Arg Arg Ala
    1205                1210                1215

Ala Ile Asp Val Gly Ile Ser Arg Leu Leu Gln Met Gln Leu Glu
    1220                1225                1230

Asn Gly Gly Phe Ala Leu Trp Asp Arg Glu Gly Pro Glu Glu Tyr
    1235                1240                1245

Trp Leu Thr Ala Tyr Ala Met Asp Phe Leu Val Arg Ala Ser Glu
    1250                1255                1260

Gln Gly Tyr Ser Val Pro Val Asn Ala Ile Asn Lys Gly Asn Glu
    1265                1270                1275

Arg Leu Leu Arg Tyr Leu Gln Glu Pro Gly Leu Met Thr Val Arg
    1280                1285                1290

Tyr Ser Asp Asp Ala Gln Ala Ser Arg Phe Ala Ala Gln Ala Tyr
    1295                1300                1305

Ala Ala Leu Val Leu Ala Arg Gln Gln Lys Ala Pro Leu Gly Ala
    1310                1315                1320

Leu Arg Glu Ile Trp Ser Arg His Asp Gln Ala Arg Ser Gly Leu
    1325                1330                1335

Pro Leu Leu Gln Leu Gly Ile Ala Leu Lys Thr Met Gly Asp Ala
    1340                1345                1350

Pro Arg Gly Asp Ala Ala Leu Lys Leu Ala Val Ala Thr Pro Arg
    1355                1360                1365

Gln Asp Glu Asn Arg Trp Leu Gly Asp Tyr Gly Ser Pro Leu Arg
    1370                1375                1380

Asp Asn Ala Leu Lys Leu Ala Leu Leu Glu Glu Asn Lys Leu Leu
    1385                1390                1395

Pro Glu Val Gln Thr Gln Leu Leu Ser Thr Leu Ser Glu Glu Ala
    1400                1405                1410

Tyr Gly Gln Arg Trp Leu Ser Thr Gln Glu Thr Asn Ala Leu Phe
    1415                1420                1425

Leu Ala Gly Arg Thr Leu Ala Asp Leu Pro Gly Ser Trp Gln Ala
    1430                1435                1440

Gln Thr Ser Leu Gln Ala Glu Pro Leu Ala Gly Asp Lys Ala Gln
    1445                1450                1455

Thr Arg Asn Leu Asp Gly Asp Arg Leu Ala Ala Leu Gln Val Ser

|  | 1460 |  | 1465 |  |  | 1470 |  |  |  |  |
|---|---|---|---|---|---|---|---|---|---|---|
| Asn | Thr | Gly | Ser | Gln | Pro | Leu | Trp | Leu | Arg | Leu | Asp | Ser | Ser | Gly |
|  | 1475 |  |  |  | 1480 |  |  |  | 1485 |  |

| Tyr | Pro | Gln | Ser | Ala | Pro | Gln | Pro | Gly | Gly | Asn | Val | Leu | Gly | Ile |
|---|---|---|---|---|---|---|---|---|---|---|---|---|---|---|
|  | 1490 |  |  |  | 1495 |  |  |  | 1500 |  |

| Glu | Arg | Thr | Ile | Phe | Asp | Thr | Gln | Gly | Gln | Gln | Lys | Ser | Leu | Ser |
|---|---|---|---|---|---|---|---|---|---|---|---|---|---|---|
|  | 1505 |  |  |  | 1510 |  |  |  | 1515 |  |

| Ser | Leu | Arg | Ser | Gly | Glu | Leu | Val | Leu | Val | Lys | Leu | Glu | Val | Thr |
|---|---|---|---|---|---|---|---|---|---|---|---|---|---|---|
|  | 1520 |  |  |  | 1525 |  |  |  | 1530 |  |

| Ala | Lys | Arg | Asn | Val | Pro | Asp | Ala | Leu | Val | Val | Asp | Leu | Leu | Pro |
|---|---|---|---|---|---|---|---|---|---|---|---|---|---|---|
|  | 1535 |  |  |  | 1540 |  |  |  | 1545 |  |

| Ala | Gly | Leu | Glu | Leu | Glu | Asn | Gln | Asn | Leu | Ala | Asn | Ser | Ser | Ala |
|---|---|---|---|---|---|---|---|---|---|---|---|---|---|---|
|  | 1550 |  |  |  | 1555 |  |  |  | 1560 |  |

| Ser | Leu | Gln | Glu | Asn | Gly | Asp | Ala | Val | Gln | Asn | Leu | Leu | Asn | Gln |
|---|---|---|---|---|---|---|---|---|---|---|---|---|---|---|
|  | 1565 |  |  |  | 1570 |  |  |  | 1575 |  |

| Met | Gln | Gln | Ala | Asp | Ile | Gln | His | Ile | Glu | Phe | Arg | Asp | Asp | Arg |
|---|---|---|---|---|---|---|---|---|---|---|---|---|---|---|
|  | 1580 |  |  |  | 1585 |  |  |  | 1590 |  |

| Phe | Val | Ala | Ala | Val | Ala | Val | Asn | Glu | Gly | Gln | Pro | Val | Thr | Leu |
|---|---|---|---|---|---|---|---|---|---|---|---|---|---|---|
|  | 1595 |  |  |  | 1600 |  |  |  | 1605 |  |

| Val | Tyr | Leu | Ala | Arg | Ala | Val | Thr | Pro | Gly | Thr | Tyr | Gln | Val | Pro |
|---|---|---|---|---|---|---|---|---|---|---|---|---|---|---|
|  | 1610 |  |  |  | 1615 |  |  |  | 1620 |  |

| Gln | Pro | Gln | Val | Glu | Ser | Met | Tyr | Ala | Pro | Gln | Trp | Arg | Ala | Thr |
|---|---|---|---|---|---|---|---|---|---|---|---|---|---|---|
|  | 1625 |  |  |  | 1630 |  |  |  | 1635 |  |

| Gly | Ala | Ala | Ser | Gly | Pro | Leu | Thr | Val | Thr | Pro |
|---|---|---|---|---|---|---|---|---|---|---|
|  | 1640 |  |  |  | 1645 |  |

<210> SEQ ID NO 95
<211> LENGTH: 2229
<212> TYPE: DNA
<213> ORGANISM: Klebsiella pneumoniae

<400> SEQUENCE: 95

```
atgaataaca ggatcaaatc cctggccttg ctggtcaatc tgggaattta cggggttgct      60
tttccgttaa gcgcagcgga aaccgccacc gacgataaaa acagcgccgc tgaagagacc     120
atggtggtca ccgccgccga gcagaacctg caggcgccgg gcgtctccac catcaccgcc     180
gatgagatcc gcaaacgccc cccggcgcgc gacgtctcgg agatcattcg caccatgccg     240
ggggtcaacc tgaccggcaa ctccaccagc ggccagcgcg caacaaccg  ccagattgat     300
atccgcggca tgggcccgga aaatacccctg atcctgatcg acggcaagcc ggtcaccagc     360
cgcaactccg tgcgccttgg ctggcgcggc gagcgcgaca cccgcggcga taccagctgg     420
gtgccgccgg agatgatcga acgtatcgaa gtgattcgcg cccggccgc  cgcccgctac     480
ggcaacggcg ccgccggcgg cgtggtgaat atcatcacca aaaaaaccgg cgatgagtgg     540
cacggctcat ggaacaccta tatgaacgcc ccggagcaca aggatgaagg ctccaccaaa     600
cgcactaact tcagcctcag cggcccgctg ggcggcgatt ttagcttccg cctgttcggt     660
aacctcgaca aaacgcaggc tgacgcctgg gatatcaacc agggccatca gtccgagcgt     720
accgggatct atgccgatac tctgccggcc gggcgcgaag gggtgaaaaa caaaaacatc     780
gatggtctgg tgcgctggga attcgctccg atgcagtcgc tggagtttga ggccggctac     840
agccgccagg gcaacctcta cgccggcgat acccagaaca ccaactccaa cgacctggta     900
aaagagaact acgcaaaga  gaccaaccgt ctgtatcgca cacctactc  ggttacctgg     960
aacggcgcct gggacaacgg ggtgaccacc agcaactggg cgcagtacga acgcaccgc    1020
```

```
aactcgcgca aaggcgaagg cctggccggc ggcaccgagg ggatctttaa cagcaaccag    1080
ttcacggata tcgatctggc ggatgtgatg ctgcacagcg aagtcagcat tcccttcgac    1140
tatctggtta atcagaacct gacgctgggc agcgagtgga accagcagcg gatgaaggat    1200
aacgcctcca atacccaggc gctgtcgggc ggcagcatcc cgggctacga cagcaccggc    1260
cgcagcccgt actcgcaggc ggaaatcttc tcgctgttcg ctgagaacaa catggagctg    1320
accgacacca ccatgctgac cccggcgctg cgtttcgatc atcacagcat cgtgggcaat    1380
aactggagcc cgtccctcaa cctgtcgcag ggcctgtggg atgacttcac gctgaagatg    1440
ggcatcgccc gcgcctataa agcgccgagc ctgtatcaga ccaacccgaa ctacattctc    1500
tacagtaaag gccagggctg ctatgccagt aaagacggct gctatctgca gggtaacgac    1560
gacttaaaag ccgagaccag catcaacaaa gagattggcc tcgagtttaa acgcgacggc    1620
tggctggctg gcgtcaccct gttccgcaac gactaccgca acaagattga agcgggctat    1680
gccccggtct atcaaaacaa taaaggtacc gatctctacc agtgggaaaa cgtgccgaaa    1740
gcggtggtgg aaggtctgga ggggacgttg aacgttccgg tgagcgagac cgtcaactgg    1800
accaacaaca tcacctatat gctgcagagt aagaacaaaa agaccggcga tcgtctgtcg    1860
attatcccgg aatacacgct gaactccacc ctgagctggc aggttcgcga tgacgtttcg    1920
ctgcagtcga ccttcacctg gtacggcaag caggagccga agaagtacaa ctacaagggt    1980
caaccggtca ccggcagcga agaacgag gttagcccct acagcatcct cggcctgagc    2040
gcgacctggg acgtcaccaa atacgtcagt ctgaccggcg cgtggataa cgtcttcgat    2100 aagcgccact ggcgcgcggg caacgcccag accaccgggg gcgccaccgg cacgatgtac    2160
ggcgccggcg ccgagaccta caatgaatcg ggccgcacct ggtacctgag cgtcaacacc    2220
cacttctga                                                             2229

<210> SEQ ID NO 96
<211> LENGTH: 1071
<212> TYPE: DNA
<213> ORGANISM: Klebsiella pneumoniae

<400> SEQUENCE: 96
atgaaaaaga cagctatcgc gattgcagtg gcactggctg gcttcgctac cgtagcgcag      60
gccgctccga aagataacac ctggtatgca ggtggtaaac tgggttggtc ccagtatcac     120
gacaccggtt tctacggtaa cggttttccag aacaacaacg gtccgacccg taacgatcag    180
cttggtgctg tgcgttcgg tggttaccag gttaacccgt acctcggttt cgaaatgggt     240
tatgactggc tgggccgtat ggcatataaa ggcagcgttg acaacggtgc tttcaaagct     300
cagggcgttc agctgaccgc taaactgggt tacccgatca ctgacgatct ggacatctac     360
acccgtctgg gcggcatggt ttggcgcgct gactccaaag caactacgc ttctaccggc     420 gtttcccgta gcgaacacga cactggcgtt tccccagtat ttgctggcgg cgtagagtgg     480
gctgttactc gtgacatcgc taccgtctg gaataccagt gggttaacaa catcggcgac     540
gcgggcactg tgggtacccg tcctgataac ggcatgctga gcctgggcgt ttcctaccgc     600
ttcggtcagg aagatgctgc accggttgtt gctccggctc cggctccggc tccggaagtg     660
gctaccaagc acttcacccct gaagtctgac gttctgttca acttcaacaa agctaccctg     720
aaaccggaag gtcagcaggc tctggatcag ctgtacactc agctgagcaa catggatccg     780
aaagacggtt ccgctgttgt tctgggctac accgaccgca tcggttccga agcttacaac    840
```

| | |
|---|---|
| cagcagctgt ctgagaaacg tgctcagtcc gttgttgact acctggttgc taaaggcatc | 900 |
| ccggctggca aaatctccgc tcgcggcatg ggtgaatcca acccggttac tggcaacacc | 960 |
| tgcgacaacg tgaaagctcg cgctgccctg atcgattgcc tggctccgga tcgtcgtgta | 1020 |
| gagatcgaag ttaaaggcta caaagaagtt gtaactcagc cggcggctta a | 1071 |

<210> SEQ ID NO 97
<211> LENGTH: 738
<212> TYPE: DNA
<213> ORGANISM: Klebsiella pneumoniae

<400> SEQUENCE: 97

| | |
|---|---|
| gtggatggat ggcagcgcgc ctttgtcctg catagccgtc cgtggagcga aaccagcctg | 60 |
| atgctggacg tcttcacgga gaatccggt cgcgtgcgcc tggttgccaa gggcgcacgc | 120 |
| tccaaacgct ctaatctcaa aggcgcttta cagcccttta cccccttgtt ggttcgcttc | 180 |
| ggcgggcgcg gcgaagtcaa aaccctgcgc agcgcggaag ccgtttcgct ggcgctgccg | 240 |
| ctcagcggca tcaccctcta cagcggtctc tacgttaacg agcttatctc ccgcgtgctg | 300 |
| gagcacgaaa cacgcttctc cgaactcttt ttcgactacc tgcactgcat tcaggcgctc | 360 |
| gccggggcca gcggctcgcc ggagcccgcg ctgcggcgtt ttgagctggc gctgctcggg | 420 |
| cacctgggct atggcgtgga ttttctccac tgcgccggga gcggcgagcc ggtagacgac | 480 |
| accatgacct accgctatcg tgaagaaaaa ggctttattg ccagcctggt gattgataac | 540 |
| aacacgttta ccgggcacca tttgaaagca ttggcgagtc gcgagtttcc tgatgttgat | 600 |
| acgctgcgcg ccgcgaagcg ctttacccgt atcgccctga agcccatctc cggcggcaaa | 660 |
| ccgctcaaga gccgggagtt gtttcgccag tttatgcccg cgcgaaaggc gcgagccgat | 720 |
| aatacgaata atgattaa | 738 |

<210> SEQ ID NO 98
<211> LENGTH: 4950
<212> TYPE: DNA
<213> ORGANISM: Klebsiella pneumoniae

<400> SEQUENCE: 98

| | |
|---|---|
| atgaaaccat ttcgtttagc ggcgctatca ctggcgctcc ttaccgcatt ttcattaacc | 60 |
| gggtgtgatg acagcggtac accgcaggcc tcggccccgg cgccagccgc ggatagcaac | 120 |
| ccaggcgcga cggcaaaacc ggaccgcgcc cagctggcgg cgctggcgga aaaaagccag | 180 |
| ggtaaagcgc tgacgctcct cgacgcctcg gaggtgcaac tggatggcgc cgcgaccctg | 240 |
| gtgctgacgt tttccgtccc gctgcagccg gaccaggatt tctcccgcag cgtgcatctg | 300 |
| gtcgacaaga aaagcggtaa ggtggacggt gcctgggagc tggcgccgaa tctgaaagag | 360 |
| ctgcgtctgc gtcaccttga gccaaagcgc gagctgattg tctcggtcga cccgacgttg | 420 |
| accgccctga caaggcgac gctcgacaaa ccgtttgaga agaccctgac cacccgcgat | 480 |
| atcgcaccga gcgttgggtt tgccagccgc ggctcgctgc tgccgggcaa tgtggtcgcc | 540 |
| gggctgccgg tgatggcgct taacgtcgat aatgtcgacg ttaatttctt ccgcattaag | 600 |
| ccggaatcgc tctccgcctt tgtcagtcag tgggaatacc gtaactcgtt aagcaactgg | 660 |
| gaatctgatg aactgctgaa gatggcggat ctggtctaca gcggccgctt cgatctcaac | 720 |
| ccggcgcgta atactcgcga aaagctgctg ctgccgctga gcgacatcaa gccgctccag | 780 |
| cagcctggcg tctacgtggc ggtcatgaac ccggcgggcc gttatagcta cagcaacgcg | 840 |
| gcgacgctgt ttaccctcag cgatatcggc gtctcggcgc atcgctacca taaccggctg | 900 |

-continued

```
gacgttttta cccagagtct ggaaaacggc gccgcccagt cgggtattga ggtgcagttg    960
ctcaatgcca aagggcagac cctggcggaa gcgaaaagcg acagccaggg ccacgtcacc   1020
ctgcaaaccg ataaagaagc cgcgctgctg ctggcgcgca agaggggca gaccacgctc    1080
ctcgacctca agctgccggc gctggatctg gcggaattct ctatcgcagg cgcgcccggc   1140
tttagcaaac agttctttat gtttggcccg cgcgatctct atcgtcccgg cgaaacggtg   1200
atccttaatg cgctgttgcg cgatagcgac ggcaagccgc tggcggagca gccggtgaaa   1260
ctggaggtgg ttcagccgga cggccaggtg atccgctcgg tgatgagtaa accagtgaat   1320
ggcctgtacc agtttactta tccgctcgac agcggcgcgg ctaccggcat gtggcacatt   1380
cgcgccagcg ccggcgacaa ccagccgcgc gaatgggatt ccacgttga agactttatg    1440
ccggaacgca tggccctgaa cctgacgccg caggccgcgc cagtcgcgcc ggatgccgac   1500
gtcacctttg gcgttagcgg cgcttatctc tacggcgcgc cggccagcgg caaccagctg   1560
cagggcaagc tgttcctgcg cccgctgcgc gacgccgtcg ctgcgctgcc gggcttccag   1620
ttcggcgata ttgcggaaga aaacctctcc cgtagtctgg atgaagtcca gctgacgctg   1680
gacgaaaaag gccatggcga agtgaccacc tcaagccagt ggcaggatag ccattcgccg   1740
ctgcaggtgg tgctgcaggc cagcctgctg gaatccggcg gtcgcccggt gacccgtacg   1800
gttaagcagc cgatctggcc cgccgaggcg ctgccgggga tccgcccgca atttacgctg   1860
aaggacgttt acgattaccg caccgatacc accgtgaaac agccggtggt ggatgaaaac   1920
agtaacgccg cgtttgatat cgtctatgcc gacgtcaaag gcgagaaaaa agcgatctcc   1980
ggtctccagg tgcggctgat ccgcgagagg cgcgactact actggaactg gtccgacagc   2040
gaaggctggc agtcgcagtt cgatcaaaaa gatctgcagg agggcgagga gtcgctggac   2100
ctgcaggccg gccagatcgg caaagtgagc ttccggtgg agtggggatc ctatcgcctg    2160
gaggtgaaag gaccggacga cgtggtcagc agcgtgcgct tctgggcggg ctacagctgg   2220
caggataaca gcgaaggcgc cggcgcggcg cgtcctgacc gggtcaccat gaagctggat   2280
aaaccgagct ataaaccggg cgacaccatc aggctgcaca tcgccgcccc ggcggcgggt   2340
aaaggctacg caatggtgga atccagcgaa gggccgctgt ggtggcagga aattgacgtc   2400
ccggcggagg ggatggacct gtcgatcccg gtggataaaa cctggaatcg ccacgacctc   2460
tacctcagca cgctggtggt tcgtcccggc gataaatcgc gctcggcaac gccgaaacgc   2520
gcggtgggcc tgctgcatct gccgctgggc gatgaaaacc gtcgcctgac gctggcgctg   2580
gaggccccgg acaaaatgcg ccccaaccag ccgctgacgt tgaaagtgaa agccagcgtc   2640
aaagagggcg aggcgccgaa acaggtcaat gtcctgctct cggcggtgga tagcggggta   2700
ctgaatatca ccgattacgc taccccggat ccgtggaacg ccttctttgg ccagaagcgt   2760
tacggcgcag atatctatga catctacggc caggtgatcg aagggcaggg acgtgtggcc   2820
agcctgcgct tcggcggcga tggcgacgag ttaaaacgcg gcggcaaacc gccggttaac   2880
cacgtgacga tcgtcgccca gcaggcgcag ccggtggtat tgaacgatca gggcgaaggc   2940
acggtgacgt tacccattgg cgattttaac ggcgagctgc gggtgatggc ccaggcgtgg   3000
acggcggatg acttcggcag cagcgaagat aaagtggtgg tggccgcccc ggtcatcgcc   3060
gagctgaaca ctccgcgctt cctcgccagc ggcgatacta cgcgtctggc gctggatctc   3120
agcaatctga ccgataaacc gcaaaccctg caggttcacc ttaccgccag cgggctggta   3180
acgttgagcg agggtcaact gccgccggta cagctggcgc cggggggcgcg cagcacgctg   3240
```

```
tttataccag tgagcgcgct ggcgggcttc ggcgatggtc aggttaatgc caccatcagc      3300
ggcctgagcc tgccgggcga aaccttcgcc ccgctgcaaa acagtggaa atcggcgtg       3360 cgtccggcgt acccggcaca gaccgtcaac agcggcgcag tgctgcagcc aggtgaaagc      3420
tggcagccgc cggcggcgca gagccagggc tttgccccgc aaacgctgca gggccaactg      3480
ctgctcagcg gtaaaccacc gttgaatctc gcccgctata ccgcgagct gaaagcctat      3540 ccttacggct gccttgagca gaccgccagc ggcctgttcc cgtccctgta taccagcgcg      3600
gcgcagctaa aggcgctggg cattagcggg gacagcgacg aaaaacgccg cgcggccatc      3660
gatgtcggta tttcacgcct gctgcagatg cagctgaaaa acggcggctt tgcgctatgg      3720
gatagagagg ggccggaaga gtactggctg accgcctacg ccatggactt cctcgtgcgc      3780
gccagcgagc agggctatag cgtaccggtc aacgccatta ataaaggcaa cgagcgcctg      3840
ctgcgctatc tgcaggagcc gggcctgatg accgtgcgct acagcgacga cgcccaggct      3900
agccgctttg ccgcccaggc atacgccgcg ctggtgctgg cgcgtcagca aaaagcgccg      3960
ctcggcgcct tgcgtgaaat ctggagccgt cacgaccagg cgccgatccgg cttgccgctg      4020 ctgcagctcg gcattgcgct gaaaactatg gcgatgcgc cgcgcggcga cgccgccctg      4080
aagctggcgg ttgccacccc cgccaggat gagaatcgtt ggctgggcga ttacggtagc      4140
ccgctgcgcg ataacgccct gaagctggcg ctgctggaag agaataagct gctgccggag      4200
gtgcaaactc agctgttgag cacgctgtcg gaagaggcct atggccagcg ctggctgtcg      4260
acccaggaaa ccaacgcctt gttccttgcc ggacgtacgc tggcggacct gccgggcagc      4320
tggcaggcgc aaacctcgct gcaggcggag ccgctggccg cgacaaagc gcaaacccgc      4380 aacctcgacg gcgatcggct ggcggcgctg caggtgagta ataccggcag tcagccgctg      4440
tggctgcgtc tcgacagcag cggctatccg caaagcgcgc cgcagccggg cggtaacgtc      4500
ctggggattg aacgcactat tttcgatacc caggggcagc agaaatcgct gtcttcactg      4560
cgcagcggcg aactggtgct cgtcaagctg gaggtgaccg ccaaacgcaa cgtgcctgac      4620
gcgctggtgg ttgatctgtt gccagccggt ctggagctgg aaaaccagaa tctggccaac      4680
agcagcgcca gcctgcagga gaatggcgac gcggtgcaaa acctgcttaa ccagatgcag      4740
caggcggata ttcagcatat cgagttccgc gatgaccgtt tcgtcgccgc cgtcgctgtc      4800
aatgaaggcc agccggtgac gctggtctat ctggcgcggg cggtgacgcc gggcactttat     4860 caggtcccgc agccgcaggt ggaatcgatg tatgcgccgc agtggcgggc gacaggagcg      4920
gccagcggtc cgctcaccgt gacgccgtaa                                       4950
```

<210> SEQ ID NO 99
<211> LENGTH: 2229
<212> TYPE: RNA
<213> ORGANISM: Klebsiella pneumoniae

<400> SEQUENCE: 99

```
augaauaaca ggaucaaauc ccuggccuug cuggucaauc ugggaauuua cggggguugcu      60 uuuccguuaa gcgcagcgga aaccgccacc gacgauaaaa acagcgccgc ugaagagacc     120
augguggucg ccgccgccga gcagaaccug caggcgccgg cgucuccac caucaccgcc     180 gaugagaucc gcaaacgccc cccggcgcgc gacgucucgg agaucauucg caccaugccg     240 gggucaacc ugaccggcaa cuccaccagc ggccagcgcg gcaacaaccg ccagauugau     300
auccgcggca ugggcccgga aaauacccug auccugaucg acggcaagcc ggucaccagc     360
cgcaacuccg ugcgccuugg cuggcgcggc gagcgcgaca cccgcggcga uaccagcugg     420
```

| | |
|---|---|
| gugccgccgg agaugaucga acguaucgaa gugauucgcg gcccggccgc cgccgcuac | 480 |
| ggcaacggcg ccgccggcgg cguggugaau aucaucacca aaaaaaccgg cgaugagugg | 540 |
| cacggcucau ggaacaccua uaugaacgcc ccggagcaca aggaugaagg cuccaccaaa | 600 |
| cgcacuaacu ucagccucag cggcccgcug ggcggcgauu uuagcuuccg ccuguucggu | 660 |
| aaccucgaca aaacgcaggc ugacgccugg gauaucaacc agggccauca guccgagcgu | 720 |
| accgggaucu augccgauac ucugccgccc gggcgcgaag ggugaaaaa caaaaacauc | 780 |
| gauggucugg ugcgcuggga auucgcuccg augcagucgc uggaguuuga ggccggcuac | 840 |
| agccgccagg gcaaccucua cgccggcgau acccagaaca ccaacuccaa cgaccugguc | 900 |
| aaagagaacu acggcaaaga gaccaaccgu cuguaucgca acaccuacuc gguuaccugg | 960 |
| aacgcgccu gggacaacgg ggugaccacc agcaacuggg cgcaguacga acgcacccgc | 1020 |
| aacucgcgca aggcgaagg ccuggccggc ggcaccgagg ggaucuuuaa cagcaaccag | 1080 |
| uucacggaua ucgaucuggc ggaugugaug cugcacagca aagucagcau ucccuucgac | 1140 |
| uaucugguua aucagaaccu gacgcugggc agcgagugga accagcagcg gaugaaggau | 1200 |
| aacgccucca uacccaggc gcugucgggc ggcagcaucc cgggcuacga cagcaccggc | 1260 |
| cgcagcccgu acucgcaggc ggaaaucuuc ucgcuguucg cugagaacaa cauggagcug | 1320 |
| accgacacca ccaugcugac cccggcgcug cguuucgauc aucacagcau cgugggcaau | 1380 |
| aacuggagcc cgucccucaa ccugucgcag ggccugggg augacuucac gcugaagaug | 1440 |
| ggcaucgccc gcgccuauaa agcgccgagc cuguaucaga ccaacccgaa cuacauucuc | 1500 |
| uacaguaaag gccagggcug cuaugccagu aaagacggcu gcuaucugca ggguaacgac | 1560 |
| gacuuaaaag ccgagaccag caucaacaaa gagauuggcc ucgaguuuaa acgcgacggc | 1620 |
| uggcuggcug gcgucaccug guccgcaac gacuaccgca caagauuga gcgggcuau | 1680 |
| gccccggucu aucaaaacaa uaaaggguacc gaucucuacc aguggaaaa cgugccgaaa | 1740 |
| gcgguggugg aaggucugga ggggacguug aacguuccgg ugagcgagac cgucaacugg | 1800 |
| accaacaaca ucaccuauau gcugcagagu aagaacaaaa agaccggcga ucgucgucg | 1860 |
| auuaucccgg aauacacgcu gaacuccacc cugagcuggc agguucgcga ugacguuucg | 1920 |
| cugcagucga ccuucaccug gucaggcaag caggagccga agaaguacaa cuacaagggu | 1980 |
| caaccgguca ccggcagcga gaagaacgag guuagcccu acagcauccu cggccugagc | 2040 |
| gcgaccuggg acgucaccaa auacgucagu cugaccggcg gcguggauaa cgucuucgau | 2100 |
| aagcgccacu ggcgcgcggg caacgcccag accaccgggg gcgccaccgg cacgauguac | 2160 |
| ggcgccggcg ccgagaccua caaugaaucg ggccgcaccu gguaccugag cgucaacacc | 2220 |
| cacuucuga | 2229 |

<210> SEQ ID NO 100
<211> LENGTH: 1071
<212> TYPE: RNA
<213> ORGANISM: Klebsiella pneumoniae

<400> SEQUENCE: 100

| | |
|---|---|
| augaaaaaga cagcuaucgc gauugcagug gcacuggcug gcuucgcuac cguagcgcag | 60 |
| gccgcuccga agauaacac cugguaugca gguguaaac ugggcuuggu ccaguaucac | 120 |
| gacaccgguu ucuacgguaa cgguuuccag aacaacaacg guccgacccg uaacgaucag | 180 |
| cuuggugcug gugcguucgg ugguuaccag gguaacccgu accucgguuu cgaaaugggu | 240 |

| | |
|---|---|
| uaugacuggc ugggccguau ggcauauaaa ggcagcguug acaacggugc uuucaaagcu | 300 |
| cagggcguuc agcugaccgc uaaacugggu uacccgauca cugacgaucu ggacaucuac | 360 |
| acccgucugg gcggcauggu uggcgcgcu gacuccaaag caacuacgc uucuaccggc | 420 |
| guuucccgua gcgaacacga cacuggcguu uccccaguau ugcuggcgg cguagagugg | 480 |
| gcuguuacuc gugacaucgc uacccgucug gaauaccagu ggguuaacaa caucggcgac | 540 |
| gcgggcacug ugggacccg uccugauaac ggcaugcuga gccugggcgu uccuaccgc | 600 |
| uucggucagg aagaugcugc accgguuguu gcuccggcuc cggcuccggc uccggaagug | 660 |
| gcuaccaagc acuucacccu gaagucgac guucuguuca acuucaacaa agcuaccccug | 720 |
| aaaccggaag gucagcaggc ucuggaucag cuguacacuc agcugagcaa cauggauccg | 780 |
| aaagacgguu ccgcuguugu ucugggcuac accgaccgca ucgguuccga agcuuacaac | 840 |
| cagcagcugu cugagaaacg ugcucagucc guuguugacu accgguuugc uaaaggcauc | 900 |
| ccggcuggca aaaucccgc ucgcggcaug ggugaaucca acccgguuac uggcaacacc | 960 |
| ugcgacaacg ugaaagcucg cgcugcccug aucgauugcc uggcuccgga ucgucgugua | 1020 |
| gagaucgaag uuaaaggcua caaagaaguu guaacucagc cggcggcuua a | 1071 |

<210> SEQ ID NO 101
<211> LENGTH: 738
<212> TYPE: RNA
<213> ORGANISM: Klebsiella pneumoniae

<400> SEQUENCE: 101

| | |
|---|---|
| guggauggau ggcagcgcgc cuuugcccug cauagccguc cguggagcga aaccagccug | 60 |
| augcuggacg ucuucacgga agaauccggu cgcgugcgcc ugguugccaa gggcgcacgc | 120 |
| uccaaacgcu cuaaucucaa aggcgcuuua cagcccuuua cccccuuguu gguucgcuuc | 180 |
| ggcgggcgcg gcgaagucaa aacccugcgc agcgcggaag ccguuucgcu ggcgcugccg | 240 |
| cucagcggca ucacccucua cagcggucuc uacguuaacg agcuuaucuc ccgcgugcug | 300 |
| gagcacgaaa cacgcuucuc cgaacucuuu uucgacuacc ugcacugcau ucaggcgcuc | 360 |
| gccggggcca gcggcucgcc ggagcccgcg cugcggcguu uugagcuggc gcugcucggg | 420 |
| caccugggcu auggcgugga uuuucuccac ugcgccggga gcggcgagcc gguagacgac | 480 |
| accaugaccu accgcuaucg ugaagaaaaa ggcuuuauug ccagccuggu gauugauaac | 540 |
| aacacguuua ccgggcacca uuugaaagca uggcgagcuc gcgaguuucc ugauguugau | 600 |
| acgcugcgcg ccgcgaagcg cuuuaccgu aucgcccuga gcccuaucu cggcggcaaa | 660 |
| ccgcucaaga gccgggaguu guuucgccag uuuaugcccg cgcgaaaggc gcgagccgau | 720 |
| aauacgaaua augauuaa | 738 |

<210> SEQ ID NO 102
<211> LENGTH: 4950
<212> TYPE: RNA
<213> ORGANISM: Klebsiella pneumoniae

<400> SEQUENCE: 102

| | |
|---|---|
| augaaaccau uucguuuagc ggcgcuauca cuggcgcucc uuaccgcauu ucauuaacc | 60 |
| ggguguguaug acagcgguac accgcaggcc ucggccccgg cgccagccgc ggauagcaac | 120 |
| ccaggcgcga cggcaaaaacc ggaccgcgcc cagcuggcgg cgcuggcgga aaaaagccag | 180 |
| gguaaagcgc ugacgcuccu cgacgcccucg gaggugcaac uggauggcgc cgcgacccug | 240 |
| gugcugacgu uuccguccc gcugcagccg gaccaggauu ucucccgcag cgugcaucug | 300 |

```
gucgacaaga aaagcgguaa ggug gacggu gccugg gagc uggcgccgaa ucugaaagag    360
cugcgucugc gucaccuuga gccaaagcgc gagcugauug ucucggucga cccgacguug    420
accgcccuga acaaggcgac gcucgacaaa ccguuugaga agaccc ugac cacccgcgau    480
aucgcaccga gcguugggu u ugccagccgc ggcucgcugc ugccgggcaa uggg ucgcc    540
gggcugccgg ugauggcgcu uaacgucgau aaugucgacg uuaauucuu ccgcauuaag    600
ccggaaucgc ucuccgccuu ugucagcag ugggaauacc guaacucguu aagcaacugg    660
gaaucugaug aacugcugaa gauggcggau cugg ucuaca gcggccgcuu cgaucucaac    720
ccggcgcgua auacucgcga aaagcugcug cugccgcuga gcgacaucaa gccgcuccag    780
cagccuggcg ucuacguggc ggucaugaac ccggcgggcc guuauagcua cagcaacgcg    840
gcgacgcugu uuacccucag cgauaucggc gucucggcgc aucgcuacca uaaccggcug    900
gacguuuuua cccagagucu ggaaaacggc gccgcccagu cggguauuga ggugcaguug    960
cucaaugcca aagggcagac ccuggcgaaa gcgaaaagcg acagccaggg ccacgucacc    1020
cugcaaaccg auaagaagc cgcgcugcug cuggcgcgca aaagagggga gaccacgcuc    1080
cucgaccuca agcugccggc gcuggaucug gcggaauucu cuaucgcagg cgcgcccggc    1140
uuuagcaaac aguucuuuau guuuggcccg cgcgaucucu aucgucccgg cgaaacggug    1200
auccuuaaug cgcuguugcg cgauagcgac ggcaagccgc uggcggagca gccggugaaa    1260
cuggaggugg uucagccgga cggccaggug auccgcucgg ugaugaguaa accagugaau    1320
ggccuguacc aguuuacuua uccgcucgac agcggcgcgg cuaccggcau gggcacauu    1380
cgcgccagcg ccggcgacaa ccagccgcgc gaaugggauu uccacguuga agacuuuaug    1440
ccggaacgca uggcccugaa ccugacgccg caggccgcgc cagucgcgcc ggaugccgac    1500
gucaccuuug gcguuagcgg cgcuuaucuc uacggcgcgc cggccagcgg caaccagcug    1560
cagggcaagc uguccugcg cccgcugcgc gacgccgucg cugcgcugcc gggcuuccag    1620
uucggcgaua uugcggaaga aaaccucucc cguagucugg augaaguccca gcugacgcug    1680
gacgaaaaag gccauggcga agugaccacc ucaagccagu ggcaggauag ccauucgccg    1740
cugcagguggu ugcugcaggc cagccugcug gaauccggcg gucgcccggu gacccguacg    1800
guuaagcagc cgaucuggcc cgccgaggcg cugccgggga uccgcccgca auuuacgcug    1860
aaggacguuu acgauuaccg caccgauacc accgugaaac agccggguggu ggaugaaaac    1920
aguaacgccg cguuugauau cgucauaugcc gacgucaaag gcgagaaaaa agcgaucucc    1980
ggucccagg ugcggcugau ccgcgagagg cgcgacuacu acuggaacug guccgacagc    2040
gaaggcuggc agucgcaguu cgaucaaaaa gaucugcagg agggcgagga gucgcuggac    2100
cugcaggccg ccagaucgg caaagugagc uucccggugg aguggggauc cuaucgccug    2160
gaggugaaag gaccggacga cguggucagc agcgugcgcu ucugggcggg cuacagcugg    2220
caggauaaca gcgaaggcgc cggcgcggcg cguccugacc gggucaccau gaagcuggau    2280
aaaccgagcu auaaaccggg cgacaccauc aggcugcaca ucgccgcccc ggcggcgggu    2340
aaagcuacg caaugguggaa auccagcgaa gggccgcugu ggguggcagga aauugacguc    2400
ccggcggagg ggauggaccu gucgaucccg guggauaaaa ccuggaaucg ccacgaccuc    2460
uaccucagca cgcuggugu ucguccggc gauaaaucgc gcucggcaac gccgaaacgc    2520
gcggugggcc ugcugcaucu gccgcugggc gaugaaaacc gucgccugac gcuggcgcug    2580
gaggccccgg acaaaaugcg ccccaaccag ccgcugacgg ugaaagugaa agccagcguc    2640
```

-continued

```
aaagagggcg aggcgccgaa acaggucaau guccugcucu cggcggugga uagcggggua    2700
cugaauauca ccgauuacgc uaccccggau ccguggaacg ccuucuuugg ccagaagcgu    2760
uacggcgcag auaucuauga caucuacggc caggugaucg aagggcaggg acguguggcc    2820
agccugcgcu ucggcggcga uggcgacgag uuaaaacgcg gcggcaaacc gccgguuaac    2880
cacgugacga ucgucgccca gcaggcgcag ccggugguau ugaacgauca gggcgaaggc    2940
acggugacgu uacccauugg cgauuuuaac ggcgagcugc gggugauggc ccaggcgugg    3000
acggcggaug acuucggcag cagcgaagau aaaguggugg uggccgcccc ggucaucgcc    3060
gagcugaaca cuccgcgcuu ccucgccagc ggcgauacua cgcgucuggc gcuggaucuc    3120
agcaaucuga ccgauaaacc gcaaacccug cagguucacc uuaccgccag cgggcuggua    3180
acguugagcg agggucaacu gccgccggua cagcuggcgc cggggggcgcg cagcacgcug    3240 uuuauaccag ugagcgcgcu ggcgggcuuc ggcgaugguc agguuaaugc caccaucagc    3300
ggccugagcc ugccgggcga aaccuucgcc ccgcugcaaa acaguggaa aucggcgug    3360 cguccggcgu acccggcaca gaccgucaac agcggcgcag ugcugcagcc aggugaaagc    3420
uggcagccgc cggcggcgca gagccagggc uuugccccgc aaacgcugca gggccaacug    3480
cugcucagcg guaaaccacc guugaaucuc gcccgcuaua uccgcgagcu gaaagccuau    3540
ccuuacggcu gccuugagca gaccgccagc ggccuguucc cguccugua uaccagcgcg    3600 gcgcagcuaa aggcgcuggg cauuagcggg gacagcgacg aaaaacgccg cgcggccauc    3660
gaugucggua uuucacgccu gcugcagaug cagcuggaaa acggcggcuu ugcgcuaugg    3720
gauagagagg ggcggaaga guacuggcug accgccuacg ccauggacuu ccucgugcgc    3780
gccagcgagc agggcuauag cguaccgguc aacgccauua auaaaggcaa cgagcgccug    3840
cugcgcuauc ugcaggagcc gggccugaug accgugcgcu acagcgacga cgcccaggcu    3900
agccgcuuug ccgccaggc auacgccgcg cugguguggg cgcgucagca aaaagcgccg    3960
cucggcgccu ugcgugaaau cuggagccgu cacgaccagg cgcgauccgg cuugccgcug    4020
cugcagcucg gcauugcgcu gaaaacuaug ggcgaugcgc cgcgcggcga cgccgcccug    4080
aagcuggcgg uugccacccc cgccaggau gagaaucguu ggcugggcga uuacgguagc    4140
ccgcugcgcg auaacgcccu gaagcuggcg cugcuggaag agaauaagcu gcugccggag    4200
gugcaaacuc agcuguugag cacgcugucg gaagaggccu auggccagcg cuggcugucg    4260
acccaggaaa ccaacgccuu guccuugcc ggacguacgc uggcggaccu gccgggcagc    4320
uggcaggcgc aaaccucgcu gcaggcggag ccgcuggccg gcgacaaagc gcaaacccgc    4380
aaccucgacg gcgaucggcu ggcggcgcug caggugagua auaccggcag ucagccgcug    4440
uggcugcguc ucgacagcag cggcuauccg caaagcgcgc cgcagccggg cgguaacguc    4500
cuggggauug aacgcacuau uuucgauacc caggggcagc agaaaucgcu gucuucacug    4560
cgcagcggcg aacuggugcu cgucaagcug gaggugaccc caaacgcaa cgugccugac    4620 gcgcuggugg uugaucuguu gccagccggu cuggagcugg aaaccagaa ucuggccaac    4680 agcagcgcca gccugcagga gaauggcgac gcggugcaaa accugcuuaa ccagaugcag    4740
caggcggaua uucagcauau cgaguccgc gaugaccguu ucgucgccgc cgucgcuguc    4800
aaugaaggcc agccggugac gcuggucuau cuggcgcggg cggugacgcc gggcacuuau    4860 cagguccccgc agccgcaggu ggaaucgaug uaucgccgc aguggcgggc gacaggagcg    4920
gccagcgguc cgcucaccgu gacgccguaa                                     4950
```

PROTEINS AND NUCLEIC ACIDS USEFUL IN VACCINES TARGETING *KLEBSIELLA PNEUMONIAE*

CROSS REFERENCE TO RELATED APPLICATIONS

This is a national stage filing in accordance with 35 U.S.C. § 371 of PCT/EP2016/050468, filed Jan. 12, 2016, which claims the benefit of the priority of European Patent Application No. 15150819.9, filed Jan. 12, 2015, the contents of each are incorporated herein by reference.

FIELD OF THE INVENTION

The present invention relates to the field of antimicrobial prophylaxis and therapy. In particular the present invention relates to novel proteins and polynucleotides derived from *Klebsiella pneumoniae*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is *Klebsiella pneumoniae*.

The genus *Klebsiella* belongs to the family Enterobacteriaceae and is divided into at least 4 species. They are gram-negative, capsulated, oxidase-negative, non-motile, straight rods. They are facultative anaerobes, having both a respiratory and fermentative metabolism. Most strains can use citrate and glucose as their sole carbon source. Some strains can fix nitrogen. They are commonly found in the intestines, clinical samples, soil, water and grains. The species *Klebsiella pneumoniae* can be divided into 3 subspecies; *pneumoniae*, *ozaenae* and *rhinoscleromatis* (Orskov, I. 1984. Genus V. *Klebsiella* Trevisan 1885, 105. Krieg and Holt (editors) In Bergey's Manual of Systematic Bacteriology, 1:461-465). *Klebsiella pneumoniae* is the most common gram-negative pathogen causing community acquired pneumonia (Carpenter, J., et al, 1990. Rev Infect. Dis. 12:672-682). *Klebsiella* is also responsible for an estimated 8% of all nosocomial infections (Sahly, H. and Podschun, R., 1997. Clin. Diagn. Lab. Immunol. 4:393-399).

*K. pneumoniae* is an opportunistic pathogen that is associated with pneumonia, septicemia, meningitis, endocarditis, ventriculitis, and infections of urinary tract and wounds. These diseases are both nosocomial and community acquired. *K. pneumoniae* also plays a large role in two major nonrheumatoid arthritic diseases, Ankylosing Spondylitis and Reiter's Syndrome (Schwimmbeck, P. and Oldstone, M., 1989. Current Topics in Microbiology and Immunology. 145:45-56.). Despite available antibiotics, observed mortality rates for pneumonia are approximately 50%, but when bacteremic *K. pneumoniae* occurs in alcoholics, the mortality rises to almost 100% (Sahly, H. and Podschun, R., 1997. Clin. Diagn. Lab. Immunol. 4:393-399). The overall mortality rate for *Klebsiella* bacteremia in one study was 37% and has ranged in others from 25% to 55% (Watanakunakron, C. and Jura, J., 1991. Scand. J. Infect. Dis. 23:399-405).

Incidence of *K. pneumoniae* meningitis is on the rise. A study of 3377 cases of Bacterial meningitis in 1948, found only 7 were *K. pneumoniae*. In 1957, *K. pneumonia* accounted for 1.5% of all cases of meningitis. In an eleven-year study, from 1981 to 1991, 13% of culture proven bacterial meningitis cases were *K. pneumoniae*. There was an increase occurrence of *K. pneumoniae* meningitis within this study with 7% occurrence in the first 6 years, and 16% occurrence in the last 5 years (Tang, L-M and Chen, S-T., 1994. Scand. J. Infect. Dis. 26:95-102).

In recent years, *Klebsiella* strains have become multi-resistant to many antibiotics. In the 1970's, the resistance was mainly to aminoglycoside antibiotics. Since 1982, some *Klebsiella* strains have become resistant to the extended-spectrum cephalosporins (Sahly, H. and Podschun, R., 1997. Clin. Diagn. Lab. Immunol. 4:393-399). Resistance to the extended-spectrum cephalosporins among clinical isolates of *Klebsiella* in France and England has been reported at 14 to 16% (Sirot, D. 1995 J. Antimicrob. Chemother. 36:19-34). Since *Klebsiella* is a good recipient for R factors, resistance has been gained to β-lactams, tetracycline, chloramphenicols, ceftazidime, sulfonamides and trimethoprim. Today, almost all strains of *Klebsiella* are resistant to ampicillin. (Orskov, I. 1984. Genus V. *Klebsiella* Trevisan 1885, 105. Krieg and Holt (editors) In Bergey's Manual of Systematic Bacteriology, 1:461-465).

Microbial fermentation is an important way to convert renewable resources to products of biological and industrial importance. *K. pneumoniae* has been used to convert simple sugars to the commodity chemicals 1,3-propanediol and 1,2-propanediol. These products have been made by fed-batch fermentation of glycerol by *K. pneumoniae*. (Cameron, D. et al, 1998. Biotechnol. Prog. 14:116-125). Genes from the 1,3-propanediol pathway of *K. pneumoniae* have recently been cloned and expressed into both *E. coli* and *S. cerevisiae*. Metabolic engineering of these genes can significantly improve the product yield and productivity (Cameron, D. et al, 1998. Biotechnol. Prog. 14:116-125).

With *K. pneumoniae* playing the lead role, the *Klebsiella* genus is becoming an increasingly important pathogen. Over the past 10 years, discovery of multi-drug resistant strains has emphasized the importance of this genus. Furthermore, *Klebsiella* is considered to be a model for systemic infections caused by capsulated bacteria.

Vaccination is considered to be a very effective method of preventing infectious diseases in human and veterinary health care. Vaccination is the administration of immungenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *K. pneumoniae* derived antigenic polypeptides that may serve as constituents in vaccines against *K. pneumoniae* infections and in diagnosis of *K. pneumoniae* infections. It is also an object to provide nucleic acids, vectors, transformed cells, vaccine compositions, and other useful means for molecular cloning as well as for therapy and diagnosis with relevance for *K. pneumoniae*.

SUMMARY OF THE INVENTION

It has been found by the present inventor(s) that *K. pneumoniae*, in particular drug resistant *K. pneumoniae*, expresses a number of hitherto unknown putatively surface exposed proteins which are candidates as vaccine targets as well as candidates as immunizing agents for preparation of antibodies that target *K. pneumoniae*.

So, in a first aspect the present invention relates to a polypeptide comprising
a) an amino acid sequence selected from the group consisting of any one of SEQ ID NOs: 1-30, 93, and 94, or
b) an amino acid sequence consisting of at least or exactly or at most 5 contiguous amino acid residues from any one of SEQ ID NOs: 1-30, 93, and 94, or
c) an amino acid sequence having a sequence identity of at least 60% with the amino acid sequence of a),
d) an amino acid sequence having a sequence identity of at least 60% with the amino acid sequence of b), or
e) an assembly of amino acids derived from any one of SEQ ID NOs: 1-30, 93, and 94, which has essentially the same 3D conformation as in the protein from which said assembly is derived so as to constitute a B-cell epitope, said polypeptide being antigenic in a mammal.

In a second aspect, the invention relates to an isolated nucleic acid fragment, which comprises
i) a nucleotide sequence encoding a polypeptide of the invention, or
ii) a nucleotide sequence consisting of any one of SEQ ID NOs: 31-90 and 95-102,
iii) a nucleotide sequence consisting of at least or exactly or at most 10 consecutive nucleotides in any one of SEQ ID NOs: 31-90 and 95-102,
iv) a nucleotide sequence having a sequence identity of at least 60% with the nucleotide sequence in i) or ii),
v) a nucleotide sequence having a sequence identity of at least 60% with the nucleotide sequence in iii),
vi) a nucleotide sequence complementary to the nucleotide sequence in i)-v), or
vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immungenically effective amount of a polypeptide of the invention, a nucleic acid fragment of the invention, a vector of the invention, a transformed cell of the invention, or a pharmaceutical composition of the fifth aspect of the invention so as to induce adaptive immunity against *K. pneumoniae* in the animal.

In a seventh and eighth aspect, the invention relates to 1) a polyclonal antibody in which the antibodies specifically bind to at least one polypeptide of the invention, and which is essentially free from antibodies binding specifically to other *K. pneumoniae* polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with *K. pneumoniae*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *K. pneumoniae*, in particular the presence of *K. pneumoniae*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *K. pneumoniae*, in particular the presence of antibodies specific for *K. pneumoniae*, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *K. pneumoniae*, in particular the presence of a nucleic acid characteristic of *K. pneumoniae*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a 15$^{th}$ aspect, the invention relates to a method for determining whether a substance, such as an antibody, is potentially useful for treating infection with K. pneumoniae, the method comprising contacting the polypeptide of the invention with the substance and subsequently establishing whether the substance has at least one of the following characteristics:
1) the ability to bind specifically to said polypeptide,
2) the ability to compete with said polypeptide for specific binding to a ligand/receptor, and
3) the ability to specifically inactivate said polypeptide.

Finally, in a 16$^{th}$ aspect, the invention relates to a method for determining whether a substance, such as a nucleic acid, is potentially useful for treating infection with K. pneumoniae, the method comprising contacting the substance with the nucleic acid fragment of claim of the invention and subsequently establishing whether the substance has either the ability to
1) bind specifically to the nucleic acid fragment, or
2) bind specifically to a nucleic acid that hybridizes specifically with the nucleic acid fragment.

LEGENDS TO THE FIGURE

FIGS. 1-6 show Kaplan-Meier survival plots in groups of mice subjected to challenge infection with K. pneumoniae, i.e. survival plot corresponding to the data in tables 1-6 herein.

Figure 2:
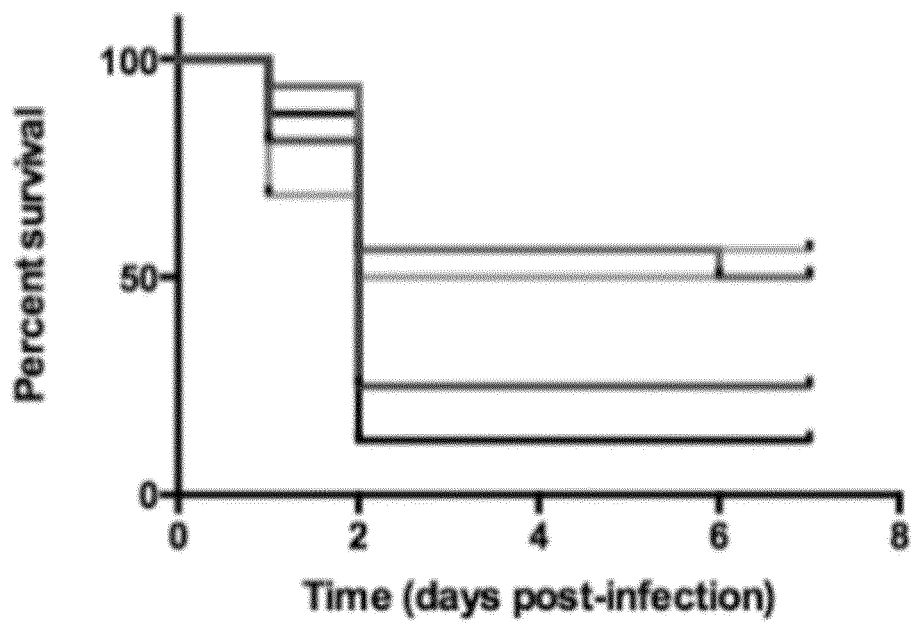
Figure 3:
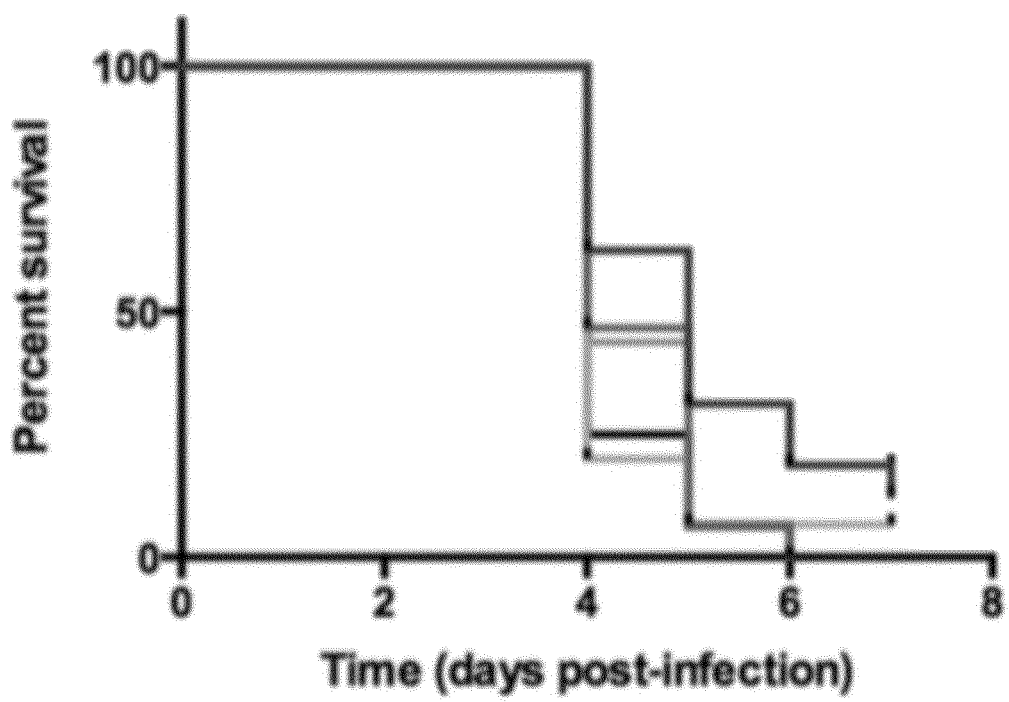
Figure 4:
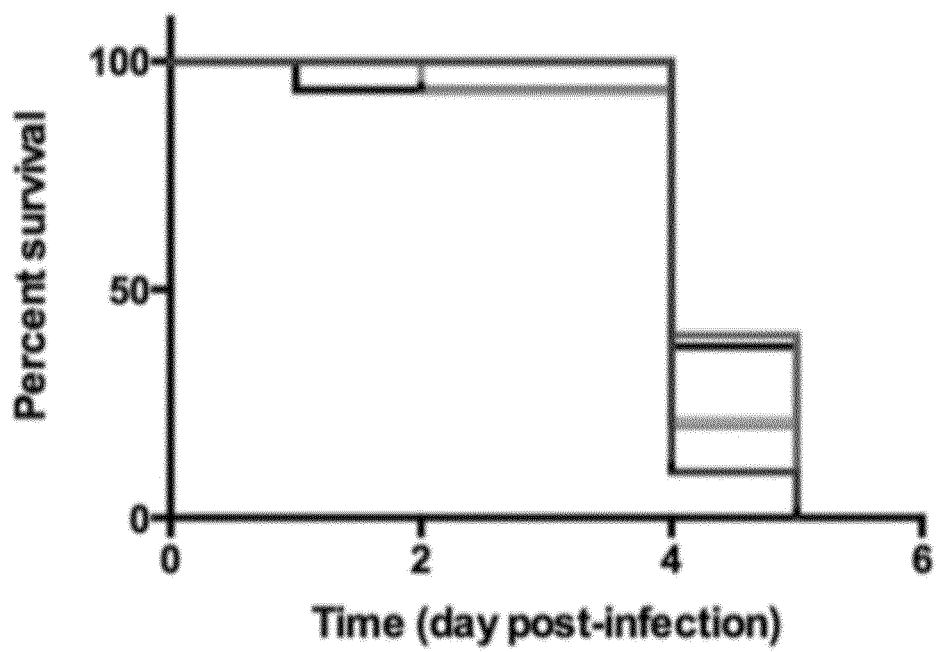
Figure 5:
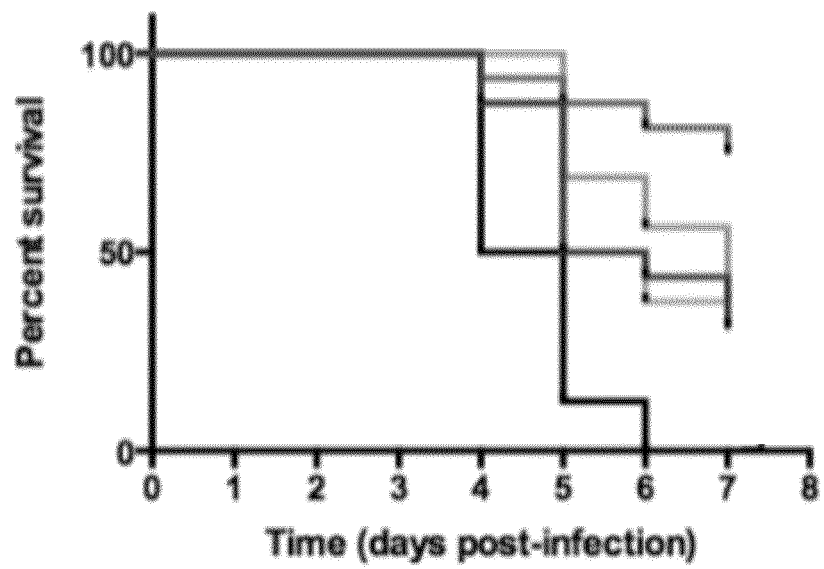
Figure 6:
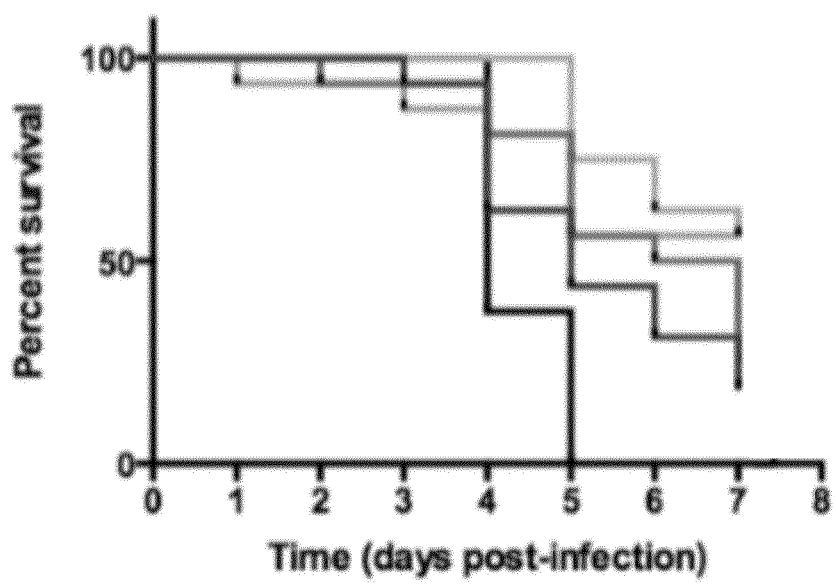

FIGS. 1 and 3-6 show the survival plots from experiments 1 and 3-6, respectively, where mice received the infectious challenge via the intranasal route, whereas FIG. 2 shows the survival plots for mice challenged via the intraperitoneal route.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Furthermore, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" s the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref}-N_{dif}) \cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAACC-3' and 5'-ATACGGGACC-3' will provide the sequence identity 80% ($N_{ref}$=10 and $N_{dif}$=2).

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immungon by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule press An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence The term "expression vector" refers to a vector containing a nucleic acid sequence coding for at least part of a gene product capable of being transcribed. In some cases, when the transcription product is an mRNA molecule, this is in trun translated into a protein, polypeptide, or peptide.

Specific Embodiments of the Invention

The Polypeptides of the Invention

In some embodiments the at least or exactly 5 contiguous amino acids referred to in option b) in the definition of the first aspect of the invention constitute at least or exactly 5, at least or exactly or at most 6, at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, and at least or exactly or at most 93 contiguous amino acid residues.

The number of contiguous amino acids can be higher, for all of SEQ ID NOs: 2-30. Another way to phrase this is that for each of SEQ ID NOs: 1-30, 93, and 94, the number of the contiguous amino acid residues is at least or exactly or at most N-n, where N is the length of the sequence ID in question and n is any integer between N−5 and 0; that is, the at least 5 contiguous amino acids can be at least any number between 5 and the length of the reference sequence minus one, in increments of one. Consequently:

Insofar as embodiment b relates to SEQ ID NO: 2-30, 93, and 94, the at least 5 contiguous amino acids referred to in option b) in the definition of the first aspect of the invention may also constitute at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, and at least or exactly or at most 116 contiguous amino acid residues.

Insofar as embodiment b relates to SEQ ID NO: 3-30, 93, and 94, the at least 5 contiguous amino acids referred to in option b) in the definition of the first aspect of the invention may also constitute at least or exactly or at most 117, or at least or exactly or at most 118 contiguous amino acid residues.

Insofar as embodiment b relates to SEQ ID NO: 4-30, 93, and 94, the at least 5 contiguous amino acids referred to in option b) in the definition of the first aspect of the invention may also constitute at least or exactly or at most 119 contiguous amino acid residues.

Insofar as embodiment b relates to SEQ ID NO: 5-30, 93, and 94, the at least 5 contiguous amino acids referred to in option b) in the definition of the first aspect of the invention may also constitute at least or exactly or at most 120 contiguous amino acid residues.

Insofar as embodiment b relates to SEQ ID NO: 6-30, 93, and 94, the at least 5 contiguous amino acids referred to in option b) in the definition of the first aspect of the invention may also constitute at least or exactly or at most 121 contiguous amino acid residues.

Insofar as embodiment b relates to SEQ ID NO: 7-30, 93, and 94, the at least 5 contiguous amino acids referred to in option b) in the definition of the first aspect of the invention may also constitute at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, or at least or exactly or at most 140 contiguous amino acid residues.

Insofar as embodiment b relates to SEQ ID NO: 8-30, 93, and 94, the at least 5 contiguous amino acids referred to in option b) in the definition of the first aspect of the invention may also constitute at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, or at least or exactly or at most 150 contiguous amino acid residues.

Insofar as embodiment b relates to SEQ ID NO: 9-30, 93, and 94, the at least 5 contiguous amino acids referred to in option b) in the definition of the first aspect of the invention may also constitute at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, or at least or exactly or at most 167 contiguous amino acid residues.

Insofar as embodiment b relates to SEQ ID NO: 10-30, 93, and 94, the at least 5 contiguous amino acids referred to in option b) in the definition of the first aspect of the invention may also constitute at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, or at least or exactly or at most 192 at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, or at least or exactly or at most 208 at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, or at least or exactly or at most 228 contiguous amino acid residues.

Insofar as embodiment b relates to SEQ ID NO: 11-30, 93, and 94, the at least 5 contiguous amino acids referred to in option b) in the definition of the first aspect of the invention may also constitute at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, or at least or exactly or at most 241, at least or exactly or at most 242, at least or exactly or at most 243, at least or exactly or at most 244, or at least or exactly or at most 245 contiguous amino acid residues.

Insofar as embodiment b relates to SEQ ID NO: 11-30 and 94, the at least 5 contiguous amino acids referred to in option b) in the definition of the first aspect of the invention may also constitute at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, or at least or exactly or at most 321 contiguous amino acid residues.

Insofar as embodiment b relates to SEQ ID NO: 12-30 and 94, the at least 5 contiguous amino acids referred to in option b) in the definition of the first aspect of the invention may also constitute at least or exactly or at most 322, at least or exactly or at most 323, at least or exactly or at most 324, at least or exactly or at most 325, or at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356 at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, or at least or exactly or at most 375 contiguous amino acid residues.

Insofar as embodiment b relates to SEQ ID NO: 13-30 and 94, the at least 5 contiguous amino acids referred to in option b) in the definition of the first aspect of the invention may also constitute at least or exactly or at most 376, at least or exactly or at most 377, at least or exactly or at most 378, at least or exactly or at most 379, at least or exactly or at most 380, or at least or exactly or at most 381 contiguous amino acid residues.

Insofar as embodiment b relates to SEQ ID NO: 14-30 and 94, the at least 5 contiguous amino acids referred to in option b) in the definition of the first aspect of the invention may also constitute at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, or at least or exactly or at most 427 contiguous amino acid residues.

Insofar as embodiment b relates to SEQ ID NO: 15-30 and 94, the at least 5 contiguous amino acids referred to in option b) in the definition of the first aspect of the invention may also constitute at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, or at least or exactly or at most 440 contiguous amino acid residues.

Insofar as embodiment b relates to SEQ ID NO: 16-30 and 94, the at least 5 contiguous amino acids referred to in option b) in the definition of the first aspect of the invention may also constitute at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, or at least or exactly or at most 483 contiguous amino acid residues.

Insofar as embodiment b relates to SEQ ID NO: 17-30 and 94, the at least 5 contiguous amino acids referred to in option b) in the definition of the first aspect of the invention may also constitute at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, or at least or exactly or at most 494 at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508 at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, or at least or exactly or at most 534 contiguous amino acid residues.

Insofar as embodiment b relates to SEQ ID NO: 18-30 and 94, the at least 5 contiguous amino acids referred to in option b) in the definition of the first aspect of the invention may also constitute at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, or at least or exactly or at most 563, 427 at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, or at least or exactly or at most 596 contiguous amino acid residues.

Insofar as embodiment b relates to SEQ ID NO: 19-30 and 94, the at least 5 contiguous amino acids referred to in option b) in the definition of the first aspect of the invention may also constitute at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, or at least or exactly or at most 623 contiguous amino acid residues.

Insofar as embodiment b relates to SEQ ID NO: 20-30 and 94, the at least 5 contiguous amino acids referred to in option b) in the definition of the first aspect of the invention may also constitute at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, or at least or exactly or at most 656 contiguous amino acid residues.

Insofar as embodiment b relates to SEQ ID NO: 21-30 and 94, the at least 5 contiguous amino acids referred to in option b) in the definition of the first aspect of the invention may also constitute at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, or at least or exactly or at most 674 contiguous amino acid residues.

Insofar as embodiment b relates to SEQ ID NO: 22-30 and 94, the at least 5 contiguous amino acids referred to in option b) in the definition of the first aspect of the invention may also constitute at least or exactly or at most 675, at least or exactly or at most 676, at least or exactly or at most 677, at least or exactly or at most 678, at least or exactly or at most 679, at least or exactly or at most 680, at least or exactly or at most 681, at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, or at least or exactly or at most 700 contiguous amino acid residues.

Insofar as embodiment b relates to SEQ ID NO: 23-30 and 94, the at least 5 contiguous amino acids referred to in option b) in the definition of the first aspect of the invention may also constitute at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, or at least or exactly or at most 751 contiguous amino acid residues.

Insofar as embodiment b relates to SEQ ID NO: 24-30 and 94, the at least 5 contiguous amino acids referred to in option b) in the definition of the first aspect of the invention may also constitute at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, or at least or exactly or at most 760 contiguous amino acid residues.

Insofar as embodiment b relates to SEQ ID NO: 25-30 and 94, the at least 5 contiguous amino acids referred to in option b) in the definition of the first aspect of the invention may also constitute at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, or at least or exactly or at most 789 contiguous amino acid residues.

Insofar as embodiment b relates to SEQ ID NO: 26-30 and 94, the at least 5 contiguous amino acids referred to in option b) in the definition of the first aspect of the invention may also constitute at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, or at least or exactly or at most 808 contiguous amino acid residues.

Insofar as embodiment b relates to SEQ ID NO: 27-30 and 94, the at least 5 contiguous amino acids referred to in option b) in the definition of the first aspect of the invention may also constitute at least or exactly or at most 809, at least or exactly or at most 810, at least or exactly or at most 811, at least or exactly or at most 812, at least or exactly or at most 813, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 811, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, or at least or exactly or at most 895 contiguous amino acid residues.

Insofar as embodiment b relates to SEQ ID NO: 28-30 and 94, the at least 5 contiguous amino acids referred to in option b) in the definition of the first aspect of the invention may also constitute at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, or at least or exactly or at most 1076 contiguous amino acid residues.

Insofar as embodiment b relates to SEQ ID NO: 29-30 and 94, the at least 5 contiguous amino acids referred to in option b) in the definition of the first aspect of the invention may also constitute at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110, at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, or at least or exactly or at most 1158 contiguous amino acid residues.

Insofar as embodiment b relates to SEQ ID NO: 30 and 94, the at least 5 contiguous amino acids referred to in option b) in the definition of the first aspect of the invention may also constitute at least or exactly or at most 1159, at least or exactly or at most 1160, at least or exactly or at most 1161, at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228, at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284, at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, or at least or exactly or at most 1411 contiguous amino acid residues.

Insofar as embodiment b relates to SEQ ID NO: 94, the at least 5 contiguous amino acids referred to in option b) in the definition of the first aspect of the invention may also constitute at least or exactly or at most 1412, at least or exactly or at most 1413, at least or exactly or at most 1414, at least or exactly or at most 1415, at least or exactly or at most 1416, at least or exactly or at most 1417, at least or exactly or at most 1418, at least or exactly or at most 1419, at least or exactly or at most 1420, at least or exactly or at most 1421, at least or exactly or at most 1422, at least or exactly or at most 1423, at least or exactly or at most 1424, at least or exactly or at most 1425, at least or exactly or at most 1426, at least or exactly or at most 1427, at least or exactly or at most 1428, at least or exactly or at most 1429, at least or exactly or at most 1430, at least or exactly or at most 1431, at least or exactly or at most 1432, at least or exactly or at most 1433, at least or exactly or at most 1434, at least or exactly or at most 1435, at least or exactly or at most 1436, at least or exactly or at most 1437, at least or exactly or at most 1438, at least or exactly or at most 1439, at least or exactly or at most 1440, at least or exactly or at most 1441, at least or exactly or at most 1442, at least or exactly or at most 1443, at least or exactly or at most 1444, at least or exactly or at most 1445, at least or exactly or at most 1446, at least or exactly or at most 1447, at least or exactly or at most 1448, at least or exactly or at most 1449, at least or exactly or at most 1450, at least or exactly or at most 1451, at least or exactly or at most 1452, at least or exactly or at most 1453, at least or exactly or at most 1454, at least or exactly or at most 1455, at least or exactly or at most 1456, at least or exactly or at most 1457, at least or exactly or at most 1458, at least or exactly or at most 1459, at least or exactly or at most 1460, at least or exactly or at most 1461, at least or exactly or at most 1462, at least or exactly or at most 1463, at least or exactly or at most 1464, at least or exactly or at most 1465, at least or exactly or at most 1466, at least or exactly or at most 1467, at least or exactly or at most 1468, at least or exactly or at most 1469, at least or exactly or at most 1470, at least or exactly or at most 1471, at least or exactly or at most 1472, at least or exactly or at most 1473, at least or exactly or at most 1474, at least or exactly or at most 1475, at least or exactly or at most 1476, at least or exactly or at most 1477, at least or exactly or at most 1478, at least or exactly or at most 1479, at least or exactly or at most 1480, at least or exactly or at most 1481, at least or exactly or at most 1482, at least or exactly or at most 1483, at least or exactly or at most 1484, at least or exactly or at most 1485, at least or exactly or at most 1486, at least or exactly or at most 1487, at least or exactly or at most 1488, at least or exactly or at most 1489, at least or exactly or at most 1490, at least or exactly or at most 1491, at least or exactly or at most 1492, at least or exactly or at most 1493, at least or exactly or at most 1494, at least or exactly or at most 1495, at least or exactly or at most 1496, at least or exactly or at most 1497, at least or exactly or at most 1498, at least or exactly or at most 1499, at least or exactly or at most 1500, at least or exactly or at most 1501, at least or exactly or at most 1502, at least or exactly or at most 1503, at least or exactly or at most 1504, at least or exactly or at most 1505, at least or exactly or at most 1506, at least or exactly or at most 1507, at least or exactly or at most 1508, at least or exactly or at most 1509, at least or exactly or at most 1510, at least or exactly or at most 1511, at least or exactly or at most 1512, at least or exactly or at most 1513, at least or exactly or at most 1514, at least or exactly or at most 1515, at least or exactly or at most 1516, at least or exactly or at most 1517, at least or exactly or at most 1518, at least or exactly or at most 1519, at least or exactly or at most 1520, at least or exactly or at most 1521, at least or exactly or at most 1522, at least or exactly or at most 1523, at least or exactly or at most 1524, at least or exactly or at most 1525, at least or exactly or at most 1526, at least or exactly or at most 1527, at least or exactly or at most 1528, at least or exactly or at most 1529, at least or exactly or at most 1530, at least or exactly or at most 1531, at least or exactly or at most 1532, at least or exactly or at most 1533, at least or exactly or at most 1534, at least or exactly or at most 1535, at least or exactly or at most 1536, at least or exactly or at most 1537, at least or exactly or at most 1538, at least or exactly or at most 1539, at least or exactly or at most 1540, at least or exactly or at most 1541, at least or exactly or at most 1542, at least or exactly or at most 1543, at least or exactly or at most 1544, at least or exactly or at most 1545, at least or exactly or at most 1546, at least or exactly or at most 1547, at least or exactly or at most 1548, at least or exactly or at most 1549, at least or exactly or at most 1550, at least or exactly or at most 1551, at least or exactly or at most 1552, at least or exactly or at most 1553, at least or exactly or at most 1554, at least or exactly or at most 1555, at least or exactly or at most 1556, at least or exactly or at most 1557, at least or exactly or at most 1558, at least or exactly or at most 1559, at least or exactly or at most 1560, at least or exactly or at most 1561, at least or exactly or at most 1562, at least or exactly or at most 1563, at least or exactly or at most 1564, at least or exactly or at most 1565, at least or exactly or at most 1566, at least or exactly or at most 1567, at least or exactly or at most 1568, at least or exactly or at most 1569, at least or exactly or at most 1570, at least or exactly or at most 1571, at least or exactly or at most 1572, at least or exactly or at most 1573, at least or exactly or at most 1574, at least or exactly or at most 1575, at least or exactly or at most 1576, at least or exactly or at most 1577, at least or exactly or at most 1578, at least or exactly or at most 1579, at least or exactly or at most 1580, at least or exactly or at most 1581, at least or exactly or at most 1582, at least or exactly or at most 1583, at least or exactly or at most 1584, at least or exactly or at most 1585, at least or exactly or at most 1586, at least or exactly or at most 1587, at least or exactly or at most 1588, at least or exactly or at most 1589, at least or exactly or at most 1590, at least or exactly or at most 1591, at least or exactly or at most 1592, at least or exactly or at most 1593, at least or exactly or at most 1594, at least or exactly or at most 1595, at least or exactly or at most 1596, at least or exactly or at most 1597, at least or exactly or at most 1598, at least or exactly or at most 1599, at least or exactly or at most 1600, at least or exactly or at most 1601, at least or exactly or at most 1602, at least or exactly or at most 1603, at least or exactly or at most 1604, at least or exactly or at most 1605, at least or exactly or at most 1606, at least or exactly or at most 1607, at least or exactly or at most 1608, at least or exactly or at most 1609, at least or exactly or at most 1610, at least or exactly or at most 1611, at least or exactly or at most 1612, at least or exactly or at most 1613, at least or exactly or at most 1614, at least or exactly or at most 1615, at least or exactly or at most 1616, at least or exactly or at most 1617, at least or exactly or at most 1618, at least or exactly or at most 1619, at least or exactly or at most 1620, at least or exactly or at most 1621, at least or exactly or at most 1622, at least or exactly or at most 1623, at least or exactly or at most 1624, at least or exactly or at most 1625, at least or exactly or at most 1626, at least or exactly or at most 1627, at least or exactly or at most 1628, at least or exactly or at most 1629, at least or exactly or at most 1630, at least or exactly or at most 1631, at least or exactly or at most 1632, at least or exactly or at most 1633, at least or exactly or at most 1634, at least or exactly or at most 1635, at least or exactly or at most 1636, at least or exactly or at most 1637, at least or exactly or at most 1638, at least or exactly or at most 1639, at least or exactly or at most 1640, at least or exactly or at most 1641, at least or exactly or at most 1642, at least or exactly or at most 1643, at least or exactly or at most 1644, at least or exactly or at most 1645, at least or exactly or at most 1646, at least or exactly or at most 1647, at least or exactly or at most 1648, at least or exactly or at most 1649 amino acid residues.

In some embodiments the invention relates to a polypeptide comprising an amino acid sequence consisting of at most 5 contiguous amino acid residues from any one of SEQ ID NOs 1-30. In these embodiment, the at most 5 contiguous amino acids can, for example, constitute 2, 3, 4 contiguous amino acid residues; preferably 4 contiguous amino acids.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 63, 64, 65, 66, 67, 68, 69, 70, 71, 72, 73, 74, 75, 76, 77, 78, 79, 80, 81, 82, 83, 84, 85, 86, 87, 88, 89, and 90 in any one of SEQ ID NOs: 1-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 91, 92, 93, 94, 95, 96, 97, 98, 99, 100, 101, 102, 103, 104, 105, 106, 107, 108, 109, 110, 111, 112, and 113 in any on of SEQ ID NOs: 2-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 114 and 115 in any one of SEQ ID NOs: 3-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to amino acid residue 116 in any one of SEQ ID NOs: 4-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any amino acid residue 117 in any one of SEQ ID NOs: 5-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to amino acid residue 118 in any one of SEQ ID NOs: 6-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 119, 120, 121, 122, 123, 124, 125, 126, 127, 128, 129, 130, 131, 132, 133, 134, 135, 136, and 137 in any one of SEQ ID NOs: 7-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 138, 139, 140, 141, 142, 143, 144, 145, 146, and 147 in any one of SEQ ID NOs: 8-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 148, 149, 150, 151, 152, 153, 154, 155, 156, 157, 158, 159, 160, 161, 162, 163, and 164 in any one of SEQ ID NOs: 9-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 165, 166, 167, 168, 169, 170, 171, 172, 173, 174, 175, 176, 177, 178, 179, 180, 181, 182, 183, 184, 185, 186, 187, 188, 189, 190, 191, or 192 193, 194, 195, 196, 197, 198, 199, 200, 201, 202, 203, 204, 205, 206, 207, or 208 209, 210, 211, 212, 213, 214, 215, 216, 217, 218, 219, 220, 221, 222, 223, 224, and 225 in any one of SEQ ID NOs: 10-30, 93, and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 226, 227, 228, 229, 230, 231, 232, 233, 234, 235, 236, 237, 238, 239, 240, and 241 and 318 in any one of SEQ ID NOs: 11-30, 93 and 94 if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, and 318 in any one of SEQ ID NOs: 11-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, or 356 357, 358, 359, 360, 361, 362, 363, 364, 365, 366, 367, 368, 369, 370, 371, and 372 in any one of SEQ ID NOs: 12-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 373, 374, 375, 376, 377, and 378 in any one of SEQ ID NOs: 13-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, and 424 in any one of SEQ ID NOs: 14-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 425, 426, 427, 428, 429, 430, 431, 432, 433, 434, 435, 436, and 437 in any one of SEQ ID NOs: 15-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, and 480 in any one of SEQ ID NOs: 16-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 481, 482, 483, 484, 485, 486, 487, 488, 489, 490, 491, 492, 493, 494, 495, 496, 497, 498, 499, 500, 501, 502, 503, 504, 505, 506, 507, 508 509, 510, 511, 512, 513, 514, 515, 516, 517, 518, 519, 520, 521, 522, 523, 524, 525, 526, 527, 528, 529, 530, and 531 in any one of SEQ ID NOs: 17-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, or 563, 427564, 565, 566, 567, 568, 569, 570, 571, 572, 573, 574, 575, 576, 577, 578, 579, 580, 581, 582, 583, 584, 585, 586, 587, 588, 589, 590, 591, 592, and 593 in any one of SEQ ID NOs: 18-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 594, 595, 596, 597, 598, 599, 600, 601, 602, 603, 604, 605, 606, 607, 608, 609, 610, 611, 612, 613, 614, 615, 616, 617, 618, 619, and 620 in any one of SEQ ID NOs: 19-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, and 653 in any one of SEQ ID NOs: 20-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 654, 655, 656, 657, 658, 659, 660, 661, 662, 663, 664, 665, 666, 667, 668, 669, 670, and 671 in any one of SEQ ID NOs: 21-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 672, 673, 674, 675, 676, 677, 678, 679, 680, 681, 682, 683, 684, 685, 686, 687, 688, 689, 690, 691, 692, 693, 694, 695, 696, and 697 in any one of SEQ ID NOs: 22-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, and 748 in any one of SEQ ID NOs: 23-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 749, 750, 751, 752, 753, 754, 755, 756 and 757 in any one of SEQ ID NOs: 24-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 758, 759, 760, 761, 762, 763, 764, 765, 766, 767, 768, 769, 770, 771, 772, 773, 774, 775, 776, 777, 778, 779, 780, 781, 782, 783, 784, 785 and 786 in any one of SEQ ID NOs: 25-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 787, 788, 789, 790, 791, 792, 793, 794, 795, 796, 797, 798, 799, 800, 801, 802, 803, 804 and 805 in any one of SEQ ID NOs: 26-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 806, 807, 808, 809, 810, 811, 812, 813, 815, 816, 817, 818, 819, 820, 821, 811, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891 and 892 in any one of SEQ ID NOs: 27-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072 and 1073 in any one of SEQ ID NOs: 28-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154 and 1155 in any one of SEQ ID NOs: 29-30 and 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409 and 1410 in SEQ ID NO: 30 or 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least or exactly or at most 5 contiguous amino acid residues defined for option b) above and also has its N-terminal amino acid residue corresponding to any one of amino acid residues 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, and 1645 in SEQ ID NO: 94, if the length of the at least or exactly or at most 5 amino acid residues so permits—the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs: 1-30. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, diphtheria toxoid or a fragment thereof. Other suitable carrier molecules are discussed infra. One further fusion partner which is preferably incorporated is a "His tag", i.e. a stretch of amino acids, which is rich in or only consists of histidinyl residues so as to facilitate protein purification.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *K. pneumoniae*. The polypeptide may in these cases induce a humeral and/or a cellular immune response.

A particularly preferred polypeptide of the invention is derived from SEQ ID NO: 6 and is otherwise as defined above.

Epitopes

SEQ ID NOs: 1-30 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised against *K. pneumoniae* or *K. pneumoniae* derived proteins disclosed herein are tested for binding to overlapping oligomeric peptides derived from any one of SEQ ID NO: 1-30. Thereby, the regions of the *K. pneumoniae* polypeptide which are responsible for or contribute to binding to the antibodies can be identified.

Alternatively, or additionally, one can produce mutated versions of the polypeptides of the invention, e.g. version where each single non-alanine residue in any one of SEQ ID NOs: 1-30 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (of a sequence such as SEQ ID NOs: 31-60 and 95-98) or an RNA fragment (of a sequence such as SEQ ID NOs 61-90 and 99-102).

In some embodiments the at least or exactly 10 consecutive nucleotides referred to in option iii) in the definition of the second aspect consists of at least or exactly 10, such as at least or exactly or at most 11, such as at least or exactly or at most 12, at least or exactly or at most 13, at least or exactly or at most 14, at least or exactly or at most 15, at least or exactly or at most 16, at least or exactly or at most 17 at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27, at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, and at least or exactly or at most 285 consecutive nucleotides in any one of SEQ ID NOs:31-60. Longer fragments are contemplated, i.e. fragments having at least 200, at least 300 at least 400, at least 500, at least 600, at least 700, at least 800, at least 900, at least 1000, at least 1500, at least 2000, at least 2500, at least 3000, at least 3500, and at least 4000 consecutive nucleotides from those of SEQ ID NOs: 31-90 and 95-102 that encompass fragments of such lengths.

In some embodiments the at most 10 consecutive nucleotides referred to in option iii) in the definition of the second aspect of the invention constitute 6, 7, 8, 9 or 10 nucleotides.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention described above comprises in certain embodiments at least or exactly or at most X distinct nucleic acid sequences each encoding a polypeptide of the invention, where each of said X distinct nucleic acid sequences encodes at least or exactly or at most one immunogenic amino acid sequence present in or derived from any one of SEQ ID NOs: 1-30 and wherein said X distinct nucleic acid sequences together encode immunogenic amino acid sequences present in or derived from at least or exactly or at most X of SEQ ID NOs: 1-30, 93 or 94, wherein X is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, and 32. In other words, such a nucleic acid fragment encodes several polypeptides of the invention. In some embodiments, the X nucleic acid sequences are expressed as separate encoded proteins and in other embodiments as "pearls on a string", i.e. fused proteins. In some embodiments, immunogenic amino acid sequences from any one of SEQ ID NOs: 1-30, 93 and 94 are only present in one of said X nucleic acid sequences.

It will be understood that the nucleic acid fragments of the invention may be used for both production, carrier and vaccine purposes—the latter will require that the sequences are included in expression vectors that may lead to production of immunogenic proteins in the host animal receiving the vector.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in E. coli. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

Particularly interesting vectors are viral vectors (in particular those useful as vaccine agents). These may be selected from the group consisting of a retrovirus vector, such as a lentivirus vector, an adenovirus vector, an adeno-associated virus vector, and a pox virus vector. Certain pox virus vectors are preferred, in particular vaccinia virus vectors. A particularly preferred vaccinia virus vector is a modified vaccinia Ankara (MVA) vector.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain (Banerji et al, 1983; Gilles et al, 1983; Grosschedl et al, 1985; Atchinson et al, 1986, 1987; toiler et al, 1987; Weinberger et al, 1984; Kiledjian et al, 1988; Porton et al; 1990), Immunoglobulin Light Chain (Queen et al, 1983; Picard et al, 1984), T Cell Receptor (Luria et al, 1987; Winoto et al, 1989; Redondo et al; 1990), HLA DQα and/or DQβ (Sullivan et al, 1987), β-Interferon (Goodbourn et al, 1986; Fujita et al, 1987; Goodbourn et al, 1988), Interleukin-2 (Greene et al, 1989), Interleukin-2 Receptor (Greene et al, 1989; Lin et al, 1990), MHC Class II 5 (Koch et al, 1989), MHC Class II HLA-DRα (Sherman et al, 1989), β-Actin (Kawamoto et al, 1988; Ng et al; 1989), Muscle Creatine Kinase (MCK) (Jaynes et al, 1988; Horlick et al, 1989; Johnson et al, 1989), Prealbumin (Transthyretin) (Costa et al, 1988), Elastase I (Omitz et al, 1987), Metallothionein (MTII) (Karin et al, 1987; Culotta et al, 1989), Collagenase (Pinkert et al, 1987; Angel et al, 1987), Albumin (Pinkert et al, 1987; Tranche et al, 1989, 1990), α-Fetoprotein (Godbout et al, 1988; Campere et al, 1989), γ-Globin (Bodine et al, 1987; Perez-Stable et al, 1990), β-Globin (Trudel et al, 1987), c-fos (Cohen et al, 1987), c-HA-ras (Triesman, 1986; Deschamps et al, 1985), Insulin (Edlund et al, 1985), Neural Cell Adhesion Molecule (NCAM) (Hirsh et al, 1990), αl-Antitrypain (Larimer et al, 1990), H2B (TH2B) Histone (Hwang et al, 1990), Mouse and/or Type I Collagen (Ripe et al, 1989), Glucose-Regulated Proteins (GRP94 and GRP78) (Chang et al, 1989), Rat Growth Hormone (Larsen et al, 1986), Human Serum Amyloid A (SAA) (Edbrooke et al, 1989), Troponin I (TN I) (Yutzey et al, 1989), Platelet-Derived Growth Factor (PDGF) (Pech et al, 1989), Duchenne Muscular Dystrophy (Klamut et al, 1990), SV40 (Banerji et al, 1981; Moreau et al, 1981; Sleigh et al, 1985; Firak et al, 1986; Herr et al, 1986; Imbra et al, 1986; Kadesch et al, 1986; Wang et al, 1986; Ondek et al, 1987; Kuhl et al, 1987; Schaffner et al, 1988), Polyoma (Swartzendruber et al, 1975; Vasseur et al, 1980; Katinka et al, 1980, 1981; Tyndell et al, 1981; Dandolo et al, 1983; de Villiers et al, 1984; Hen et al, 1986; Satake et al, 1988; Campbell et al, 1988), Retroviruses (Kriegler et al, 1982, 1983; Levinson et al, 1982; Kriegler et al, 1983, 1984a, b, 1988; Bosze et al, 1986; Miksicek et al, 1986; Celander et al, 1987; Thiesen et al, 1988; Celander et al, 1988; Choi et al, 1988; Reisman et al, 1989), Papilloma Virus (Campo et al, 1983; Lusky et al, 1983; Spandidos and Wilkie, 1983; Spalholz et al, 1985; Lusky et al, 1986; Cripe et al, 1987; Gloss et al, 1987; Hirochika et al, 1987; Stephens et al, 1987), Hepatitis B Virus (Bulla et al, 1986; Jameel et al, 1986; Shaul et al, 1987; Spandau et al, 1988; Vannice et al, 1988), Human Immunodeficiency Virus (Muesing et al, 1987; Hauber et al, 1988; Jakobovits et al, 1988; Feng et al, 1988; Takebe et al, 1988; Rosen et al, 1988; Berkhout et al, 1989; Laspia et al, 1989; Sharp et al, 1989; Braddock et al, 1989), Cytomegalovirus (CMV) IE (Weber et al, 1984; Boshart et al, 1985; Foecking et al, 1986), Gibbon Ape Leukemia Virus (Holbrook et al, 1987; Quinn et al, 1989).

Inducible Elements include, but are not limited to MT II—Phorbol Ester (TFA)/Heavy metals (Palmiter et al, 1982; Haslinger et al, 1985; Searle et al, 1985; Stuart et al, 1985; Imagawa et al, 1987, Karin et al, 1987; Angel et al, 1987b; McNeall et al, 1989); MMTV (mouse mammary tumor virus)—Glucocorticoids (Huang et al, 1981; Lee et al, 1981; Majors et al, 1983; Chandler et al, 1983; Lee et al, 1984; Ponta et al, 1985; Sakai et al, 1988); β-Interferon—poly(rl)x/poly(rc) (Tavernier et al, 1983); Adenovirus 5 E2-EIA (Imperiale et al, 1984); Collagenase—Phorbol Ester (TPA) (Angel et al, 1987a); Stromelysin—Phorbol Ester (TPA) (Angel et al, 1987b); SV40-Phorbol Ester (TPA) (Angel et al, 1987b); Murine MX Gene—Interferon, Newcastle Disease Virus (Hug et al, 1988); GRP78 Gene—A23187 (Resendez et al, 1988); α-2-Macroglobulin—IL-6 (Kunz et al, 1989); Vimentin—Serum (Rittling et al, 1989); MHC Class I Gene H-2κb—Interferon (Blanar et al, 1989); HSP70-E1A/SV40 Large T Antigen (Taylor et al, 1989, 1990a, 1990b); Proliferin—Phorbol Ester/TPA (Mordacq et al, 1989); Tumor Necrosis Factor—PMA (Hensel et al, 1989); and Thyroid Stimulating Hormonea Gene—Thyroid Hormone (Chatterjee et al, 1989).

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells.

Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli*), *Bacillus* (e.g. *Bacillus subtilis*), *Salmonella*, and *Mycobacterium* (preferably non-pathogenic, e.g. *M. bovis* BCG).

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5a, JMI 09, and KC8, as well as a number of commercially available bacterial hosts such as SURE® Competent Cells and SOLOPACK™ Gold Cells (STRATAGENE®, La Jolla, Calif.). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al, 1993; U.S. Pat. Nos. 4,684,611 and 4,952,500, each incorporated herein by reference); by desiccation/inhibition mediated DNA uptake (Potrykus et al, 1985). Through the application of techniques such as these, organelle(s), cell(s), tissue(s) or organism(s) may be stably or transiently transformed.

The Antibodies of the Invention—and their Production/Isolation

Antibodies directed against the proteins of the invention are useful for affinity chromatography, immunoassays, and for distinguishing/identifying *Klebsiella* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4 C for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 125I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 115I may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 125I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an F(ab')$_2$, an scFV; cf. also the definition of the term "antibody" presented above.

Compositions of the Invention; Vaccines

Pharmaceutical compositions, in particular vaccines, according to the invention may either be prophylactic (ie. to prevent infection) or therapeutic (ie, to treat disease after infection).

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition.

In some embodiments of the invention, the pharmaceutical compositions such as vaccines include merely one single antigen, immunogen, polypeptide, protein, nucleic acid or vector of the invention, but in other embodiments, the pharmaceutical compositions comprise "cocktails" of the antigens or of the immunogens or of the polypeptides or of the protein or of the nucleic acids or of the vectors of the invention.

In particularly interesting embodiments, the pharmaceutical composition is an MVA vector mentioned herein, which encodes and can effect expression of at least 2 nucleic acid fragments of the invention.

Another interesting embodiment of a pharmaceutical composition comprises RNA as the active principle, i.e. at least one mRNA encoding a polypeptide of the invention.

An embodiment of a pharmaceutical composition of the invention comprises Y or at least Y or at most Y distinct polypeptides of the invention described above, where each of said Y or at least Y or at most Y distinct polypeptides comprises an immunogenic amino acid sequence present in or derived from any one of SEQ ID NOs: 1-30 and wherein said Y or at least Y or at most Y distinct polypeptides together comprise immunogenic amino acid sequences present in or derived from Y or at least Y or at most Y of SEQ ID NOs: 1-30, 93 or 94, wherein Y is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, and 32.

Another embodiment of the pharmaceutical composition of the invention comprises Z or at least Z or at most Z distinct nucleic acid molecules (such as DNA and RNA) each encoding a polypeptide of the invention, where each of said Z or at least Z or at most Z distinct nucleic acid molecules encodes an immunogenic amino acid sequence present in or derived from any one of SEQ ID NOs: 1-30, 93, or 94 and wherein said at Z or least Z distinct nucleic acid molecules together encode immunogenic amino acid sequences present in or derived from Z or at least Z or at most Z of SEQ ID NOs: 1-30, 93, or 94, wherein Z is an integer selected from 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, and 32.

Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+ CWS (Detox™); (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuma primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 µg and 500 mg (however, often not higher than 5,000 µg), and very often in the range between 10 and 200 µg.

The immunogenic compositions are conventionally administered parenterally, eg, by injection, either subcutaneously, intramuscularly, or transdermally/transcutaneously (eg. WO98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Immunol 9: 271-283; Donnelly et al. (1997) Avnu Rev Innnunol 15: 617-648; later herein].

A further aspect of the invention is as mentioned above the recognition that combination vaccines can be provided, wherein 2 or more antigens disclosed herein are combined to enhance the immune response by the vaccinated animal, including to optimize initial immune response and duration of immunity. For the purposes of this aspect of the invention, multiple antigenic fragments derived from the same, longer protein can also be used, such as the use of a combination of different lengths of polypeptide sequence fragments from one protein.

Thus, embodiments of the invention relate to a composition (or the use as a vaccine thereof) comprising 2 distinct (i.e. non-identical) proteinaceaous immunogens disclosed herein wherein the first of said immunogens is SEQ ID NO: 1 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceaous immunogens disclosed herein wherein the first of said immunogens is SEQ ID NO: 2 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceaous immunogens disclosed herein wherein the first of said immunogens is SEQ ID NO: 3 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceaous immunogens disclosed herein wherein the first of said immunogens is SEQ ID NO: 4 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceaous immunogens disclosed herein wherein the first of said immunogens is SEQ ID NO: 5 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceaous immunogens disclosed herein wherein the first of said immunogens is SEQ ID NO:

6 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 7 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 8 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 9 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 10 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 11 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, and 16 or in combination with a variant or fragment disclosed herein of any one of SEQ ID NOs: 1, 2, 3, 4, 5, 6, 7, 8, 9, 10, 11, 12, 13, 14, 15, and 16.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 12 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 13 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 14 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 3, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 15 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 3, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 16 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 17 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 18 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 19 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 20 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 21 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 22 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 23 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 24 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 25 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 26 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 27 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 28 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 29 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 30 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 93 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Also, embodiments of the invention relate to a composition (or the use as a vaccine thereof) comprising 2 distinct (i.e. non-identical) proteinaceous immunogens disclosed herein wherein the first of said immunogens is SEQ ID NO: 94 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94 or in combination with a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 93, and 94.

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 µg of the polypeptide of the invention per administration.

In preferred embodiments of the sixth aspect, the immunization scheme includes that the animal (e.g. the human) receives a priming administration and one or more booster administrations.

Preferred embodiments of the $6^{th}$ aspect of the invention comprise that the administration is for the purpose of inducing protective immunity against *K. pneumoniae*. In this embodiment it is particularly preferred that the protective immunity is effective in reducing the risk of attracting infection with *K. pneumoniae* or is effective in treating or ameliorating infection with *K. pneumoniae*.

As mentioned herein, the preferred vaccines of the invention induce humoral immunity, so it is preferred that the administration is for the purpose of inducing antibodies specific for *K. pneumoniae* and wherein said antibodies or B-lymphocytes producing said antibodies are subsequently recovered from the animal.

But, as also mentioned the method of the $6^{th}$ aspect may also be useful in antibody production, so in other embodiments the administration is for the purpose of inducing antibodies specific for *K. pneumoniae* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claims, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with K. pneumoniae;

the nucleic acid fragment of the invention or the vector of the invention is for use as a pharmaceutical, in particular for use as a pharmaceutical in the treatment, prophylaxis or amelioration of infection with K. pneumoniae;

the transformed cell of the invention is for use as a pharmaceutical, in particular for use as a pharmaceutical in the treatment, prophylaxis or amelioration of infection with K. pneumoniae.

the antibody, antibody fragment or antibody analogue of the invention is for use as a pharmaceutical, in particular for use as a pharmaceutical in the treatment, prophylaxis or amelioration of infection with K. pneumoniae.

SEQUENCE INFORMATION

The sequence listing included sets forth the sequences of polypeptides and nucleic acids of the present invention. For easy reference, the sequences are presented in the following:

The polypeptides of the invention have or derive from the following amino acid sequences:

```
                                                                     SEQ ID NO: 1
MKKLALLSAVMTLGMSSWAFAADNPPPPPEKGAQHQGKPPVKNGQHEGKQAQYNRKQPQRDGKQPQH

DGKQPQHNGKQPPKGSEHSGKPLPPKA

SEQ ID NO: 2
MKRYATALLFCTLSLTSLAARADIIDDAIGNIQQAINDAYNPGSSRSDDDDRYDDDGRYDDGRYQGSRQ

QSRDSQRQYDERQRQLDERRRQLDERQRQLDRDRRQLESDQRRLDDSY

SEQ ID NO: 3
MFRSLILAAVLLAAGPLVANAGEITLLPSVKLQIGDRDNYGNYWDGGSWRDRDYWRRHYEWRDNRWHR

HDNGWHKGWYKGRDKAWERGYRAGWNDRDDHRGGWGRGPGGRGHGHGHGHH

SEQ ID NO: 4
MKEIGLPLLLLTALASPAFAADCQPNGIGGSFCINDDGTTTDTVPNEVNGMDTYSNNGGYTSSLPDRSGA

DEALEGSSLSTQQGVGSGQSDSALAGRDWHSPANLNDGAATSSMSLLDKP

SEQ ID NO: 5
MNMKKLTTLLLTATLGLASGAALAADTGAQSNNGQANSSADAGQVAPDARENVAPNNVDNSQINSGSG

GTTGSTMTQDNMSSNEVHKNSMCKDGRCPDTGKKLDNGGNTTQDNSKTDGTTQ

SEQ ID NO: 6
MKHRIALLLVLTSLSASALAASPCQEKEQDIQREISYAEKHHNQSRIDGLNTALRQVRENCSDSKLKADH

QQKIAKQREEIAERQRDLQEARKKGDADKINKRQHKLNEAQQELKTLESRDY

SEQ ID NO: 7
MRLITRHVREDIMKKAMIALSAILVAAPVFAATTHATDDTVAAANANANTAKEKLHQAQHEGEEQQLKAK

HAAEGKQDSVGSQVSEGAQKTWNKTKEGTEKGWDKTKEVSEKGWNATKSGAEKGWDKTKTGAEELK

NKVTE

SEQ ID NO: 8
MKKMISLAVILSCVLSVPAFADGPNDGHRPEQPTVWQNGPDHDGHAPQGGPDAHHQGDHDQRGPDRD

GHDKRDLARHEQDHFAWRGNDFRKGHPAPAPFRGDEYRVRDWSDRGLPPPPEGHHWSYIDGNYVLIAA

ATGIITSILVSGALGH

SEQ ID NO: 9
MKKPTSATRGKSGRKSREELNQEARDRKRQKKHRGHAAGSRANGGDAASAGKKQRQAQDPRVGSKKP

IPLGVSESSVPAPKQHKPKSEKPMLSPQAELELLENDERLDALLERLEEGGTLNAEEQSWVDAKLDRIDEL

MQQLGLSYDDEDEEEERQEDMMRLLKGGN

SEQ ID NO: 10
MASKFQNRLVGTIVLVALGVIILPGLLDGQKKHYQDEFAAIPLVPKPGDRDEPDMLPAATQALPSQPPEGA

AEEVRAGDAAAPSLDPSRIPVNSNSFDDVQEPVVAAKPQPKPQPKPQPQQQASTPTPPPAKPQQQQPPQ

QQAALPAPTGKAYVVQLGALKNADKVNEIVGKLRASGFKVYTSPSTPVQGKITRILVGPDASKDKLKGQL
```

GDLQQISGLSGVVMGFTPN

SEQ ID NO: 11
MAQRDYVRRSQPASSRRKKSTTRSSRNKQSSLPAISPAMVAIAAAVLVAFIGGLYFITHHKKEEAEAMQN

RQAAGNGLPPKPEERWRYIKELESRQPGVRAPTEPTAGGEVMKPEQLTDEQRQLLAQMQADMRQQPTQL

TEVPWNEQTPAQRQQTLQRQRLAQQQQQAQQQQWAQTQAQTVQQQPPRVQQPKPVQQQQPKQTAS

NQQPYQDLLQTPAHTNTTQPRTQAAAPVTRVEEAPKTTAEKKDDRSWMIQCGSFKGAEQAETVRAQLAF

EGFASHITTNNGWNRVVIGPLKGKESANEMITRLKMAGHANCIRLAARG

SEQ ID NO: 12
MSAGSTKFTVSRIAALSLVSLWLAGCTNTNNPPAPVSSAGGAASSSTNSGMLITPPPSGVKSAPQAQPIQ

PMQTQTIQPAPVAQEPVQTVNGRIVYNRKYGDIPKGSYTGGSTYTVKRGDTLFYIAWVTGNDFRDLAQRN

NIPAPYALNVGQVLQVGNASGQPITGENAVSQASARASGGATTSTTSAQKSTAVVASQPTITYSESSGEQ

SATKMLPNNKPATTTTVVAPVTAPTTVSTTQPTASSTSTSSPISAWRWPTDGKVIENFSGAEGGNKGIDI

AGSKGQAIVATADGRVVYAGNALRGYGNLIIIKHNDDYLSAYAHNDTMLVREQQEVKAGQKIATMGSTG

TSSSTRLHFEIRYKGKSVNPLQYLPQR

SEQ ID NO: 13
MRKQWLGICIAAGLLAACSSDDVQQKTVSTPQPAVCNGPTVEISGADPQYETPNATANQDYERDGKSYK

IVQDPANFTQAGFAAIYDAEPNSNLTASGEAFDPTQLTAAHPTLPIPSYARITNLANGRMIVVRINDRGPYG

NDRVISLSRASADRLNTSNNTKVRIDPIIVAPDGSLSGPGMACTTVAKQTYALPARPNLDGGDAAGMSQP

APTDVRPISNSTLTPADSVGAPVNSGGFLGAPTPLNNGVLESSEPAAAAATAPAAGATPTAPVTAPGSIQG

NVVPAAATAAAAGAVAASSSATSSASGNFVVQVGAVSDQTRAQQYQQRLSQQFSVPGRVMQNGAVWR

IQLGPFADKAQASAVQQRLQSEAQLQSFITRAN

SEQ ID NO: 14
MDDFKPEDDMKADRNDRRAGRSRQSSERDADPQINFDDVDLDADEGRPTRAGKARREREEEEFEEELD

AQDEEMLEEQPVERRPRKRKKAPAKPASRQYIMMGVGILVLLLLIVGIGSALKSPSSSSQQTASGEKSINL

SDDQSASMPAAGQDQTAAANSTSQQDVTVPPIAANPTGQAAVAPQGQQRIEVQGDLNNALTQQQGQ

LDGAVANSTLPTEPATVAPIRNGANGTAAPRQATERQTAATPRPAERKHTVIEAKPQSKPQAVAKTPVESK

PVQPKHVESTATTAPAKTSVSESKPVATAQSKPTTTTAAPAATAAAAPAAKTGKTAGDVSSMKTAPSGH

YTLQLSSSSNYDNLNNWAKKEKLDKYVVYETSRNGQPWYVLVSGIYASKDEAKRAVTSLPADVQAKNPW

AKPLHQVQADLK

SEQ ID NO: 15
MSKATEQNDKLKRAIIISVALHIILIALLIWSSFDEHLDASAGGGGGSSIDAVMVDPGAVVNNYNRQQQQ

QASARRAAEQREKQAQQQAEELREKQAAEQERLKQLEQERLQAQEEAAKEAKEQQKQAEEEAAAKAAAAA

KAKADAQAKEAQEAAAKAAAEAKAKADAQAKAAEQAAAKAAADAKKQAEAAAAKAAAEAKKQAEAEAA

KAAAEAQKKAEAAAAKKAQQEAEKKAQQEAAKQAAAEKAAAEKAAAEKAAAQKAAAEKAAAEKAAAAEK

AAAAKAAAAEKAAADKAAKAAAAKAAAAKKAAAAKEADGVDNLLGDLSSGKNAPKTGGGAKGNNASAA

GSGNTKNSASGADINNYAGQIKSAIESKFYDASSYAGKTCTLRIKLAPDGLLLNIQSEGGDPALCQAALAA

ARQAKFPKPPSQAVYEVFKNAPLDFKPQ

SEQ ID NO: 16
MFFLSIFYMEMTKVKLSALFIALIPLLGSPVIHAETTAAPVLENRAAQGDITTPGGARRLTGDQTEALRASLI

NKPAKNVILLIGDGMGDSEITAARNYAEGAGGFFKGIDALPLTGQYTHYSLDKKTGKPDYVTDSAASATA

WTTGVKTYNGALGVDIHENAHQTILELAKAAGLATGNVSTAELQDATPAALVAHVTSRKCYGPTVTSEKC

PSNALEKGGKGSITEQLLNARPDVTLGGGAKTFTETATAGEWQGKTLREQAQARGYQIVTDAASLAAATE

ASQDKPLLGLFADGNMPVRWEGPKASYHGNIDKPPVTCTPNPKRDASVPTLAQMTEKAIDLLSRNEKGFF

-continued

LQVEGASIDKQDHAANPCGQIGETVDLDEAVQKALEFARKDGNTLVIVTADHAHASQIIPADSKAPGLTQ

ALNTHDGAVMVMSYGNSEEESMEHTGTQLRIAAYGPHAANVVGLTDQTDLFTTMKAALSLK

SEQ ID NO: 17
MSLPFKPHIIALLCSAGLLAAAGTLYVQSRTPATIAEPPAQQAPAPAASTTQPVAATYTQAQIDQWVAPIAL

YPDSLLSQVLMASTYPDNVLQAVQWSQDNPAMKGDAAVQAVASQPWDPSVKSLVAFPALLAMMGENPP

WVENLGNAFLAQPHDVMDSVQRLRAIAQQTGTLKSTPQQKVIVTPAAPVSASSSTAATATAHTAAPAPTQ

VIKIEPTNPQVVYVPSYNPSTVYGTWPNSAYPPVYLPPPPGEQFTDSFVKGFGYSLGVATTWALFSSIDWD

DDDHHHHDDDYHHGDYSHNGDNININVNNFNHITGENLPGNHVNWQHNPAYRGHTPYPDNTVAQRFH

QTNVSGGLSATQHAPVDREAQRQAAMTQLQHNVPTATAGNLAANNASRDAQRQAASAQLKQATQRSN

YRGYDSTPTQQQRREAAKTQLKNPTPQQQQRREAARSHEQNRTPQQQQRRQQFQSATPAQRQQTLSHL

RANALSGNESRAPSWQAQQERGLQSRQFSGVNRELRDGTRERLSEHHELRRR

SEQ ID NO: 18
MFKFKASYVALAAVLTSSVVYADPTSYTHSSGATVIDIEKPNAAGVSHNLYRDFNVGANGTILNNSGDDV

SHSTFGNIARNNNLTAGSASVILNEVTSKNASSLKGFIEVNGQKADVVIANPNGITCSGCSFVNTNKAILT

TGKVNMTDDGAIGSYTVTGGTLTIGENGMNAANGYAVLLADAININGKVQANNALVSAGNFTMDNSSG

SVTSAGKKATLIQMTVNPQYSIDVSSLGGIEANSISMVGNNIGFGVRNKGSIVANSSLQLTSNGNLLNKG

TIKSNGLLSQVATASGITNDGSIAGAYYLMLSSGDYIVNTGSLSGGQLIATANGNITNGDSGTMTGTSGL

SLTSGGKIRNEEKASLLSNNQIAATAIGDFLNEGKISAKHTSLTFVGDSFKNTGNINSTGQTTIQSLKQDG

SANTGEIYNLGNITGENINLQTNGTLAQSSSGRIEATNAITAHSYWLNQNGYMNAADITTDHGVVNNYG

NITAKNISITTYSDITNEGQISSTGDLTLNTKNKGAIYNYSTLSAGGNMTLTATKVVNGGKSCGILGLAKC

GVGTLTADKLVLNSSQKYVSDMGGKQYFKSTEVNTVK

SEQ ID NO: 19
MMDNLRTAANSVVLKIIFGIIIVSFILTGVSGYLIGGGKNYAAKVNGQEIGRGQFENAVASERNRMQQQL

GDQFSELAANENYMKTMRQQVLNRLIDESLLDQYARELGLSISDEQVKQAIFQTQAFQTNGKFDNQRFS

GIVAQMGMTTDQYAQALRNQLTTQQLINAIAGTDFMLPGESDQLAALVSQQRVVREATINVNALAAKQT

ASDEEINAFWQQNQARFMAPEQFRVSYIKMDAASMQESASDEEIQSWYDQHKDQFTQPQRNRYSVIQT

KTEADAKAVLAELQKGADFATLAKEKSTDIISARNGGDMGWMEDASTVPELKDAGLKEKGQLSGVIKSS

VGFLVARLDDVQPAQVKPLADVRNDIAAKVKQEKALDAYYALQQKVSDAASNDNESLASAAQVAGLKVV

ETGWFGRDNLPEELNFKPVADAIFNGGLVGENGAPGSNSDIITVDGDRAFVLRISEHKAEAVKPLAEVKA

QVSDIVKHNKAEQQAKLEADKLLAALKDGKGDEAMKAAGLSFGAPQTLSRTGQDPLSQLAFTLPLPQQG

KPVYGVGSNMQGDVVLVALDEVKAGSMPEEQKKAMVQGITQNNAQIAFEALMSNLRKAAKIKLGDSIDQ

QQ

SEQ ID NO: 20
MFRLNPFIRAGLSASVVSLAFPALADVNEETLVVTASATEQNVKDAPASISVITQQDLQRKPVQNLKDVLR

DVPGVQLTNEGDNRKGVSIRGLSSSYTLILVDGKRVNSRNAVFRHNDFDLNWIPVDAIERIEVVRGPMSS

LYGSDALGGVVNIITKKIGQKWTGTLSADTTIQEHRDRGDTWNGQFFTSGPLIDGVLGMKAYGSLAKRA

KDDPQSSSNATGETPRIEGFTSRDGNVEFAWTPNENHDFTAGYGFDRQDRDSDSLDRNRLERENYSLSH

NGRWDIGNSELKFYGEKVDNKNPGQSGTITSESNAIDGKYVLPLGMINQLVTFGGEWRHDKLKDPVNLS

SGGGQSTSASQYALFIEDEWRIIEPLALTTGIRMDDHQTYGDHWSPRAYLVYNATDTVTVKGGWATAFKA

PSLLQLNPDWTTNSCRGSCSIVGNPDLKPETSESFELGLYYRGEEGWLENVEGSITTFQNNVDDMIDVLR

TSSASEAPGYPNFVGWKTVNGKRVPIFRYFNVNKARIKGVETEVKIPFGDEWKLTVNYTYNDGRDLSNGG

DKPLQTLPFHTANGTLDWKPLDDWSFYVTANYTGQQRAVSATGKTPGGYTLFDVGAAWQVTKNVKLRS

GVQNVGDKDLSRDDYSYTEEGRRYFMAVDYRF

SEQ ID NO: 21

MNRAATLTLNAPLLMLVAALALSTPFTAGAAPAFLDYAQQQTQQSQAQEKNDAASAKQTQESRQSADNK

KTGTSTSQLQKRITSQQAAIAQKDKLIQQLKKQLAATPQTDTAGANEQAALNKRINELQVALSAATAEKE

ALIKKAGVVQNNNLQQSQAAARQQIQQLTTQIQQAEAENKRLSASFTTLNKDKHALMTQLAATEKEKQA

ALEQVKALNADKQPLTTRLAAAEKEKQAVLEQVKALNADKQSLTIRLAAAEKAQQAAVDQAKALNADKQP

LATRLAAAEKEKQAVLEQVKALSADKQSLTIRLAAAEKAQQAALDQAKALNADKQPLATRLAAAEKEKQA

VLEQVKALNADKQSLTIRLAAAEKTQQAALDQVKALNADKQSLSTRLAAADKAPHGPANDAAAPKNEPPE

MAAIVAAYRLQADKDNAQLRMKEDEIELLRTQLSVQSKTRSGESAAAKLSASGEQQAYAIGASMGSEAL

NVLTTRRTQGVTVDAGLVLQGIEDAFRGQLRLGEQERNKALFDVSQQVFQNLNKIEQKNISAGKKYQQA

FARKKDVVFKEGVYSRVDYLGKGKISGNDLVTVVIKEMLTDGTVINDMEAKDQALTQKLDAYPPVFREPL

KRLQNHGSVTLVVPPEKAYGSKGLPPKIPPGATMVYSVRIVDSQPEPAK

SEQ ID NO: 22

MKILSVRHAALPALLLPLIAAAQAADEQTMVVTAAPTTVSELDTPAAVSVVNGDEMRQAAPRVNLSESLGA

VPGLQVQNRQNYAQDLQLSIRGFGSRSTYGVRGLRIYVDGIPATMPDGQGQTSNIDIGSVDTIEVLRGPF

SALYGNSSGGVINVTSQTGTQPPTVEASSYYGSFGTWHYGMKATGAVGDGSHAGDVDYTVSTNRFTTH

GYRDHSGARKNLANARLGVRINDVSKLTLLLNSVDIKANDAGGLTADEWRDNPRQSPRGDQYNTRKNT

RQTQAGLRYERQLSAQDDLSVMMYAGERETTQFQSIPRAPQLKPSHAGGVIDLTRHYQGIDTRLTHRGEL

LVPVTLTAGLDYENMSERRKGYENFVMVNGAPQYGEQGALRRNERNLMWNVDPYLQTQWQLTDKLSLD

AGVRYSSVWFDSNDYYITPGNGDDSGDASYHKWLPAGSLKYALTDAWNVYLSAGRGFETPTINELSYRS

DNQSGLNFGLKPSTNDTVEIGSKTRIGNGLFTAALFQTNTDNEIVVDSSSGGRTSYKNAGKTRRQGMEL

GLDQQFGESWRLKAAWTWLDATYRTNVCDDASCNGNRIPGIARNMGYASFGYQPEQGWYAGSDIRYM

SDIMANDENTAKAPSWTVVGLTTGYKWSYGRMDMDLFGRIDNLFDREYVGSVIVNESNGRYYEPAPGRN

YGIGLNLAWRFE

SEQ ID NO: 23

MKYTSHFPLGIVIPLLACSVPLQAAENMTEQSTPDESAATAENHEETMVITAARQNLQAPGVSTITAEEIRK

HPPARDVSELIRTQPGVNLTGNSTSGQRGNNRQIDIRGMGPENTLVLVDGKPVTSRNSVRYGWRGDRD

SRGDTSWVPAEMIDHIDVIRGPAAARYGNGAMGGVVNIVTKPTTREWHGSWNTYMNAPQHRKEGATK

RTNFSLNGPLSDSVSFNLWGNLSKTQADAQDINAGHEAERTGSYAGSYPAGREGVVNKDIHSKLRWEFA

PMQALEFEAGYSRQGNLYAGDTQNTNTSTLVKSMYGKETNRLYRQTYGVTWTGGWDNGVTSNSYAQYE

HTRNSRMDEGLAGGTEGIFSSSEFSDIDLADVLLHSEVNIPFTLGVDQNLTLGAEWNQQRMKDGVSTTQ

ALSYGTIDGVSATGRSPYSSAEIFSLFTEDNMALTDSTMLTPALRFDHHSIVGNNWSPSLNLSQELTDDW

TLKLGIARAYKAPNLYQLNPNYILYSNGQGCYASSSACYLMGNSDLKAETSVNKEIGLEYKHDGYQAGIT

WFRNDYHNKIESGYAAVGTASNGTTNIYQWENVPKALVEGLEGTLNLPVGEAVNWSNNLTWMLQSKNK

TTGDRLSVIPQFTLNSTLSWQVREDLSLQSTFTWYGRQKPKRFNYKGEAVSGSELNEVSPYSIVGLSATW

DVNKNLSFTSGIDNLFDIRHYRAGNAQTTGNATTGAYLYGAGAETYNESGRTFFMSVNTHF

SEQ ID NO: 24

MEKNASLPFGSFNSLALFTGLCLGASPAAGIAAENSVKNSEETLVVEAAPPSLYSPGASADPKFNKPLVDT

TRTITVIPEQVIKDQGVTNLTDALKNVPGVGAFYAGENGSSTTGDAIFMRGVDTSNSIYVDGIRDIGSVTR

DTFNTQQVEVIKGPAGTDYGRSAPSGSINMISKQPRLDSGIDGSASIGSAWSRRGTLDLNQAFSDNAAF

RLNLMGEKTHDAGRDRIENERYGIAPSLAFGLDTPTRLYLNYLHVRQNNTPDGGIPTVGLPGYSAPSPKYA

ALNSAGKVDTSNFYGTDSDYDKSTTDSGTLRFEHDLTENTTVRNTTRWSRVKQEYLLTAVMGGANNITA

PDINDVNTWSWSRLVNTKDVSNRILTNQTNITSTFNTGSIGHDVSAGVEFTRENQTNYGVNARTAPAVN

-continued

LYHPVSNLSIGGLDRNGANANGQTDTFGIYAFDTLTLTERIEINGGLRLDNYHTKYDSATACGGSGRGAIA

CPPGQSTGSPVTTVDTAKSGNLVNWKAGALYRLTEQGNVYVNYAISQQPPGGSSFALAASGSGNSANRT

DFKPQKAKSSELGTKWQIFDNRLLLSAALFRTDIENEVAANDDGTWSQYGKKRVEGYELSATGNLTPDW

TIIAGYTQQHATVTEGQNVAQDGSSALAYTPKHAFTLWTQYQATSDLSVGGGVRYVGSLRRGSDGAVGT

PDHTEGYWVADAKLGYRVNSNLDLQLNMYNLFDTDYVASINKSGYRYHPGEPRTFMLTANVHF

SEQ ID NO: 25

MATMYKSTPSAAWCKKRLLVTSLFAAIYQTSAIAADTSAVSGEAVDDTSEQMTVTAPAPVQKAGSEHSIS

ARELENKGANDFGSIMRYEPLISATGASGGSGNGKSGFDRGGYTGYNIRGMESNRVGIDVDGIAQPNAT

GRGYVGRAGLNTFGIGRDYIDPYMYGSVDIQSGATSTETANSAIGGNVSFRPKSADDYLRPGKTSAFGYR

SGYDSADRSWHNGVTVAGGDEFLRGILVYSRRDGQETENNSGTVDAYPANWHSDAFLASGIWQPNDE

HKLTSTFDYYHKTNHTHYDTWDSSGNSTIGTANQTSQTRRWGLSLKDDWTPMNDYLDSVSTKIYYQHT

EAHDWTYMPDSVTRKMQTVNSNYDTDTWGLQTALAKTLGRHDLSAGFNASTSKTQRPFSQSPIPSVYSE

IMQPEADSRSYTLGGFVQDKINFDLDSHNFAVIPGVRVVHQSTKPENLSDLAANSSVLSESSVANLYGKN

SDTQVLPSLTFQYDLTPRLMTYLQYQRGAQFPNASQLYGSWNLGSSYAGSQQYALIGNTDLKTETSDNLE

WGLKGEVTEGITLRTALFYNSYKNFIAYTRYTRANNPGQFTNVPSNIYTIYQAENRDKAYIYGGEISTKFNF

GTWFEQVDGLSATLALGYSEGKSKSSYSGDKYVDLDSVAPMKAIVGVAWDDPAKRYGTALTATFVKGK

QATATNRESYSNSGSAITDASSDYMRVPGYGMLDWTAYWQVAKNVRLNGGVYNLTDRKYWDYLSSRNI

ETGTNQDANDKALAVMPGRTWQLGVNVDF

SEQ ID NO: 26

MAMKKLLIASLLFSSATVYGAEGFVVKDIHFEGLQRVAVGAALLSMPVRPGDTVTDDDISNTIRALFATGN

FEDVRVLRDGDTLLVQVKERPTIASITFSGNKSVKDDMLKQNLEASGVRVGESLDRTTIADIEKGLEDFYY

SVGKYSASVKAVVTPLPRNRVDLKLVFQEGVSAKIQQINIVGNHAFSTDELISHFQLRDEVPWWNVVGD

RKYQKQKLAGDLETLRSYYLDRGYARFNIDSTQVSLTPDKKGIYITVNITEGDQYKFSGVQVTGNLAGHS

AEIEALTKVEPGELYNGAKVTKMENDIKKLLGRYGYAYPRVQSQPEINDSDKTVKLHVNVDAGNRYYVRKI

RFEGNDTSKDAVLRREMRQMEGAWLGSDLVDQGKDRLNRLGFFETVDTDTQRVPGSPDQVDVVYKVKE

RNTGSFNFGIGYGTESGVSFQAGVQQDNWLGTGYAVGINGTKNDYQTYTELSVTNPYFTVDGVSLGGRV

FYNDFDANDADLSDYTNKSYGTDITLGFPVNEYNTLRAGVGYVHNSLSNMQPQVAMWRYLNSMGQYPD

NTNDRNSFSANDFTFNYGWTYNKLDRGFFPTEGSRVNLNGKVTIPGSDNEYYKATLDTATYVPIDNDHQ

WVVLGRTRFGYGDGIGGKEMPFYENFYAGGSSTVRGFQSNTIGPKAVYFPASSRHDDDDSYDNECKSTE

SAPCKSDDAVGGNAMAVASLELITPTPFISDKYANSVRTSVFWDMGTVWDTHWDSSAYAGYPDYSDPS

NIRMSAGIAVQWMSPLGPLVFSYAQPFKKYDGDKAEQFQFNIGKTW

SEQ ID NO: 27

MTDVTIKALASEIQTSVDRLIQQFADAGIRKSADDSVTSQEKQTLLTHLNREHGSAPDKLTLQRKTRSTLN

IPGTGGKSKSVQIEVRKKRTFVKRDPQEAERLAAEEQAQREAEEQARREAEEEAAKREAQLKAEREAAEQA

KREVADKAKREAAEKDKVSNQHTDEMTKTAQAEKIRRENEAAELKRKSEEEARRKLEEEARRVAEEARR

MAEENEKNWSETSDSPEDSSDYHVTTSQHARQAEDDNDREVEGGRGRSRSSKAARPAKKGNKHAESK

ADREEARAAVRGGKGGKHRKGSALQQGFQKPAQAVNRDVVIGETITVGELANKMAVKGSQVIKAMMKL

GAMATINQVIDQETAQLVAEEMGHKVILRRENELEEAVMSDRDTGAAAEPRAPVVTIMGHVDHGKTSLL

DYIRSTKVASGEAGGITQHIGAYHVETDNGMITFLDTPGHAAFTSMRARGAQATDIVVLVVAADDGVMP

QTIEAIQHAKAAQVPVVVAVNKIDKPEADPDRVKNELSQYGILPEEWGGESQFVHVSAKAGTIDDLLDA

ILLQAEVLELKAVRNGMASGAVIESFLDKGRGPVATVLVREGTLHKGDIVLCGFEYGRVRAMRDELGREVL

EAGPSIPVEILGLSGVPAAGDEVTVVRDEKKAREVALYRQGKFREVKLARQQKSKLENMFANMTEGEVHE

-continued

VNIVLKADVQGSVEAISDSLLKLSTDEVKVKIIGSGVGGITETDATLAAASNAILVGFNVRADASARKVIEA
ESLDLRYYSVIYNLIDEVKAAMSGMLSPELKQQIIGLAEVRDVFKSPKFGAIAGCMVTEGTIKRHNPIRVLR
DNVVIYEGELESLRRFKDDVNEVRNGMECGIGVKNYNDVRVGDMIEVFEIIEIQRSID

SEQ ID NO: 28

MKRMLINATQQEELRVALVDGQRLYDLDIESPGHEQKKANIYKGKITRIEPSLEAAFVDYGAERHGFLPLK
EIAREYFPANYNAHGRPNIKDVLREGQEVIVQIDKEERGNKGAALTTFISLAGSYLVLMPNNPRAGGISRRI
EGDDRTELKEALASLELPDGMGLIVRTAGVGKSAEALQWDLSFRLKHWEAIQKAAESRPAPFLIHQESNV
IVRAFRDYLRQDIGEILIDNPKVLELARQHIAALGRPDFSSKIKLYTGEIPLFSHYQIESQIESAFQREVRLPS
GGSIVIDSTEALTAIDINSARATRGGDIEETAFNTNLEAADEIARQLRLRDLGGLIVIDFIDMTPVRHQRAV
ENRLREAVRQDRARIQISHISRFGLLEMSRQRLSPSLGESSHHVCPRCSGTGTVRDNESLSLSILRLIEEE
ALKENTKEVHAIVPVPIASYLLNEKRAAVSAIESRQGDVRVIIVPNDEMQTPHYSVLRVRKGEETSTLSYLL
PKLHEEEMALPGDDEPAERKRPEQPALAAFVMPDAPPAPMLEEPAAAPVAAAAPVAAAAPAQPGLLSRFFS
ALKNIFSGAEEAKPAEVQVEKKAEEEKPERQQERRKPRANNRRDRNDRRDNRDNRDNRDNRDTRAD
NAEGREPRESREENRRNRREKPSQNVEARDVRQTSGDDAEKAKSRDEQQPRRERTRRRSDDKRQAQQ
EAKAQTREEPVVQETEQEERVQTLPRRKPRQLAQKVRVESAVVEPVAEIVPEAVVAEVIAPHSEPVKAELP
AGVESVADQDENGESREANGMPRRSRRSPRHLRVSGQRRRRYRDERYPTQSPMPLTVACASPEMASGK
VWIRYPVVRPQDQQPEEVQVQDASVAKTVEAVAAPVAVVETVTAAPVTVEPATMEPVTAEPVVVEPVAAA
EPLVVDAAEVVAPAAVEPAPQEPVTEAPAVEAPQAIAPVTLDAEPVVVEPEAVETTPVVAAPVETIAPVAETV
EQAPVTEAAPAEPVKAEPPVSKPVVVAGHRHATAPMTRAPAPDYVPEAPRHSTWVRPPFAFEGKGAAGGH
SATHKATAEPTRPQPVE

SEQ ID NO: 29

MRKLSLSLLTLSLGVALLPLAQAATTPAQEHLLEQVRLGEASNREDLVRQSLYRLELIDPNNPELIAARMRY
LLRQGDAAGAQKELERLTKQAPDSPELKASRNEMKSNTGEGRQALQQARLLGVAGKVDEAIAAYEKLYG
GVPDDVDVAIEYWTLVARLPARHSEGVSQLKKLNASAPGNVSLLTSLAKQMFADNKPQEGFAYLAEMAR
SASGRGIAADMWFSEVKSMPVSKASVQALQQFLLQFPTGSVAANARVLLDQQQAQLQDPTFRARSEGLA
AVKSGNTTQAVADLQKAVQADSRDSDAVGALGQAYSQRGDRARAVAQLSKAIAMDPDSPNRGKWDSL
LQTNRYWLLIKQGDNALKAGQLSQAQNYYAQAQRVDRTDSYAVLGLGDVAAARKEAAAAERYYQQALRL
DRGNNLAVRGLANLYRAESPEKASAWIAGLPPAQRRSIDDIERSLTNDRLEKQAQALESQGNWAQAAEV
QRRRLALDPDSVWITYRLARDLVSAGERQEADALMRTMVNRQPQDAERVYASGLYLSGNDQDDLALAQI
AALPRSAWTDNIRELEARLQSDRVLRQANQLRDSGNEAQAIALIRQQPASVRYDLTLADWAQQRGDSQT
AIANYQRVLRQEADNGDARLGLAEVYLAEGDKPAARAQVMQLKGAETESMNMQRRVALARAGLGDTAD
AQRIFNQIVPQAKAQPPSMESALVLRDAARFATQSGAPQQALTHYREAMVASGITPAQPQDNDTFTRLTR
NDSHDDWLKRGIRSDAADLYRQQDLNVTLEHDFWGSSGTGGYSDLKAHTTMLQMDAPLADGRMFFRT
DLVNMDAGSFSTHSDGSYSPSWGTCGEIACTSGSKNQTDSGASVAVGWKNDTWSGDIGTTPMGFNVV
DVVGGLSYSSDVGPVGYTVNVHRRPISSSLLSFGGQKDSSSHTGATWGGVRADGGGLSLSYDRGEAHG
IWSSLGADSLTGKNVADNWRVRWMTGYYYKVINENNRRVTVGLNNMIWHYDKDLSGYTLGQGGYYSP
QEYLSFAVPVTWRQRTENWSWELGGSVSWSHSRTQTQARYPLLNLIPSDYRQRASELTEEGSSSHGFGY
TARALVERRVTSNWFVGAAVDIQQAKDYTPSHALLYVRYSAAGWQGDLDMPPQPLVPYADW

SEQ ID NO: 30

MSQEYTEDKEVKLTKLSSGRRLLEAMLILCSLFAIWLMAALLSFNPSDPSWSQTAWHEPIHNLGGAPGAW
LADTLFFIFGVMAYTIPVIIIGGCWFAWRHQENDEYIDYFAVSLRLIGALALILTSCGLAAINADDIWYFASG
GVIGSLLSTTLQPLLHSSGGTIALLCIWAAGLTLFTGWSWVSIAEKLGGGILSVLTFASNRTRRDDTWVDE

-continued

```
GEYEDDEEEYDDEEAARPQESRRARILRSALARRKRLAEKFTNPMGRKTDAALFSGKRMDDGEEVVQYS

ASGAPVAADDVLFSGASAARPAEDDVLFSGASAVRPGDFDPYDPLLNGHSIAEPVSAAAAATAAPQAWA

ESPVGHHGAAPAYQPEASYPPQQAYQPEPAPFQQAYQPEPAPFQQAAYQPPAGQTAPQAYQPEPAPYQQP

VYDPRAGQPAPQAYQPEPAPYQQPAYDPYAGQPAPQAYQPEPAPYQQPAYDPHAGQPAPQAYQPEPAPY

QQPAYDPYAGQPAPQAYQPEPAPYQQPTYDPYAGQPAPQTYQQPAYDPNAGQPAPQPYQPEPAAYQPQS

APVPPPEPEPEVVQEEVKRPPLYYFEEVEEKRARERELLASWYQPIPEPESPIATKPLTPPTTASKPPVETTVV

SAVAAGVHQATAASGGAAAATSSTAASAAATPLFSPASSGPRVQVKEGIGPKLPRPNRVRVPTRRELASY

GIKLPSQREAEQRARQAERDPHYDDELLSDEEADAMEQDELARQFAATQQQRYGHRWEDDNATDDDEA

DAAAEAELARQFAATQQQRYATEQPPGANPFSPADYEFSPMKTLVNDGPSEPLFTPTPEVQPQQPAQRYQ

QPAAAPQQGYQPAQHQPIHHQPVPPQPQSYPTASQPVQPQQPVAPQGHQPAAPAPQESLIHPLLMRNGD

SRPLQKPTTPLPSLDLLTPPPSEVEPVDTFALEQMARLVEARLADFRIKADVVNYSPGPVITRFELNLAPGVK

AARISNLSRDLARSLSTVAVRVVEVIPGKPYVGLELPNKKRQTVYLREVLDNAKFRDNPSPLTVVLGKDIA

GDPVVADLAKMPHLLVAGTTGSGKSVGVNAMILSMLYKAQPEDVRFIMIDPKMLELSVYEGIPHLLTEVVT

DMKDAANALRWSVNEMERRYKLMSALGVRNLAGYNEKIAEAARMGRPIPDPYWKPGDSMDAVHPVLEK

LPYIVVLVDEFADLMMTVGKKVEELIARLAQKARAAGIHLVLATQRPSVDVITGLIKANIPTRIAFTVSSKID

SRTILDQGGAESLLGMGDMLYSGPNSTTPVRVHGAFVRDQEVHAVVQDWKARGRPQYVDGITSDSESE

GGGGGFDGGEELDPLFDQAVNFVTEKRKASISGVQRQFRIGYNRAARIIEQMEAQGIVSEQGHNGNREV

LAPPPF
```

The nucleic acid fragments of the present invention have or derive from the following sequences:

```
                                                          SEQ ID NO: 31
ATGAAGAAGTTAGCTTTACTCTCCGCCGTAATGACGCTTGGAATGTCGTCATGGGCTTTTGCTGCCGA

CAACCCGCCGCCGCCGCCGGAAAAAGGCGCGCAGCATCAGGGTAAACCGCCGGTGAAAAACGGCCA

ACACGAAGGTAAGCAAGCGCAATACAACAGAAAACAGCCACAACGAGACGGCAAACAGCCGCAGCAC

GACGGTAAACAGCCGCAGCACAACGGCAAGCAGCCGCCAAAAGGGAGCGAGCACAGCGGGAAACCG

CTGCCGCCGAAAGCGTAA

SEQ ID NO: 32
ATGAAACGTTACGCAACCGCACTGCTCTTTTGCACTCTGTCGCTGACCAGCCTGGCCGCTCGCGCCGA

TATTATCGATGACGCGATCGGCAATATTCAGCAAGCCATTAACGACGCCTATAACCCCGGCAGCAGTC

GCTCCGATGACGACGACAGATACGATGACGATGGCCGGTATGATGACGGGCGCTATCAGGGGAGCC

GTCAGCAGAGCCGTGACAGTCAGCGCCAGTATGACGAGCGGCAACGCCAGCTGGACGAGCGCCGCC

GCCAGCTGGATGAACGCCAGCGTCAGCTCGACCGCGATCGTCGTCAGTTAGAAAGCGACCAGCGTCG

TCTGGATGATAGCTACTGA

SEQ ID NO: 33
ATGTTCAGGTCACTGATTCTGGCAGCAGTACTGCTGGCCGCAGGGCCACTGGTCGCTAACGCTGGTG

AAATCACCCTGCTGCCATCGGTAAAATTACAAATAGGCGATCGTGACAATTACGGTAACTACTGGGAC

GGTGGCAGCTGGCGCGACCGTGATTACTGGCGTCGTCACTATGAATGGCGTGATAACCGTTGGCATC

GTCATGACAACGGCTGGCACAAAGGCTGGTACAAAGGCAGAGATAAAGCCTGGGAGCGCGGCTATC

GTGCTGGCTGGAACGACCGCGATGACCACCGCGGCGGCTGGGGTCGCGGCCCGGGCGGGCGCGGT

CACGGTCATGGACATGGCCATCACTAA

SEQ ID NO: 34
ATGAAGGAAATCGGCTTACCGTTATTGCTACTGACCGCGCTGGCCAGTCCGGCTTTTGCTGCAGACTG
```

```
TCAGCCAAACGGCATTGGCGGCTCGTTTTGCATTAACGATGACGGTACGACTACCGACACGGTGCCTA

ACGAAGTCAACGGCATGGATACGTACTCGAATAATGGCGGCTATACCAGTTCCCTGCCCGATCGGTCA

GGGGCGGATGAAGCACTGGAAGGTTCATCGCTGTCGACGCAGCAAGGCGTCGGCAGCGGACAGAGC

GACAGTGCGCTGGCGGGTCGCGACTGGCATTCGCCCGCCAATCTGAATGATGGCGCCGCCACCTCCA

GTATGAGCCTGCTGGATAAACCCTGA

SEQ ID NO: 35
ATGAATATGAAAAAACTGACGACCCTTTTGCTCACCGCCACCTTAGGTCTTGCCAGCGGCGCGGCCCT

GGCGGCAGACACCGGCGCCCAGTCCAATAATGGCCAGGCCAACTCTTCCGCGGATGCCGGTCAGGT

GGCGCCGGATGCCCGTGAGAACGTGGCGCCGAACAACGTGGACAATAGTCAGATCAACTCTGGCTCT

GGGGGCACCACGGGCTCGACGATGACCCAGGATAATATGTCGAGCAATGAGGTACATAAAAACTCGA

TGTGTAAAGACGGCCGCTGTCCGGACACCGGTAAAAAACTGGACAACGGTGGCAATACGACCCAAGA

CAACAGCAAAACCGACGGCACCACCCAGTAA

SEQ ID NO: 36
ATGAAACACCGCATCGCTCTGCTTCTGGTCCTGACTTCACTTAGCGCCAGCGCCCTAGCCGCCTCTCC

CTGCCAGGAAAAGAGCAGGATATTCAACGAGAGATCAGCTACGCCGAAAAGCATCATAATCAAAGTC

GCATTGATGGGCTAAATACCGCGCTACGTCAGGTTCGGGAAAACTGTAGCGACAGTAAACTCAAAGC

CGATCATCAGCAAAAAATTGCCAAACAGCGGGAAGAGATCGCTGAACGTCAGCGCGATCTGCAGGAA

GCCCGGAAGAAAGGCGATGCGGACAAAATTAACAAACGCCAGCATAAACTCAATGAAGCGCAACAGG

AGTTAAAAACGCTGGAGTCTCGGGATTACTAA

SEQ ID NO: 37
ATGCGACTCATAACACGACACGTGAGAGAGGATATTATGAAAAAAGCAATGATTGCGTTATCGGCTAT

TCTGGTTGCGGCTCCGGTTTTTGCTGCGACAACACATGCAACAGATGATACCGTCGCGGCGGCGAAT

GCCAACGCCAACACCGCTAAAGAGAAGCTGCATCAGGCCCAGCACGAGGGCGAAGAGCAGCAGCTG

AAGGCGAAACACGCCGCCGAAGGCAAGCAGGACAGCGTCGGCAGCCAGGTGAGCGAAGGCGCGCA

GAAAACCTGGAACAAGACCAAAGAAGGCACCGAGAAGGGGTGGGATAAGACCAAAGAGGTCAGTGA

AAAAGGCTGGAACGCCACCAAATCCGGTGCGAAAAGGGCTGGGATAAAACCAAAACCGGCGCCGA

AGAGTTAAAAAATAAAGTGACTGAATAA

SEQ ID NO: 38
ATGAAAAAGATGATTTCTCTGGCAGTAATTTTATCCTGTGTGCTGAGCGTCCCGGCCTTTGCCGATGG

CCCGAACGACGGCCATCGCCCGGAGCAGCCCACGGTGTGGCAGAACGGTCCGGACCATGACGGGCA

TGCACCGCAGGGCGGACCTGACGCGCATCATCAGGGCGACCATGACCAGCGTGGCCCGGATCGCGA

CGGCCATGACAAACGCGATCTGGCACGTCATGAGCAGGACCATTTCGCCTGGCGCGGGAACGATTTC

CGCAAAGGCCACCCGGCTCCGGCGCCGTTCCGTGGCGATGAATATCGCGTCCGCGACTGGAGCGAC

CGCGGCCTGCCGCCCCCGCCGGAAGGCCATCACTGGTCCTATATCGACGGTAACTATGTGCTGATCG

CCGCGGCGACCGGGATCATCACCTCGATTCTGGTGAGCGGCGCCCTCGGCCACTAA

SEQ ID NO: 39
ATGAAAAAACCGACATCCGCCACCCGTGGCAAATCCGGCCGCAAGTCGCGTGAAGAGTTAAATCAGG

AAGCTCGCGATCGCAAACGGCAGAAGAAACATCGTGGCCACGCGGCAGGCAGTCGCGCGAACGGCG

GCGATGCGGCTTCAGCGGGTAAAAAACAGCGTCAGGCGCAAGATCCGCGCGTGGGTAGCAAAAAAC

CGATCCCGCTGGGCGTGAGCGAAAGCAGCGTTCCAGCTCCCAAGCAGCATAAACCAAAGAGCGAGAA

ACCTATGCTTTCACCGCAGGCTGAGCTGGAGTTGCTGGAGAATGATGAGCGCCTGGACGCGCTGCTG

GAACGTCTGGAAGAGGGCGGCACCCTGAATGCTGAAGAGCAGAGCTGGGTGGACGCCAAACTGGAT

CGCATTGATGAGCTGATGCAGCAGCTCGGCCTCTCTTACGATGATGAAGATGAAGAAGAGGAAGAGC
```

GTCAGGAAGATATGATGCGTCTGCTGAAGGGTGGAAACTAA

SEQ ID NO: 40
ATGGCGAGTAAGTTTCAGAACCGTTTAGTCGGGACAATCGTGCTGGTGGCGCTGGGGGTGATTATCC

TGCCAGGGCTGCTGGACGGGCAGAAAAAGCATTACCAGGATGAGTTTGCCGCGATCCCGCTGGTACC

GAAACCAGGCGATCGCGATGAACCGGATATGTTGCCGGCGGCAACCCAGGCGTTGCCTTCGCAACCG

CCGGAAGGGGCGGCGGAAGAGGTGCGGGCGGGCGATGCCGCCGCGCCATCGTTAGATCCATCGCG

TATTCCGGTGAACAGCAACAGCTTCGATGACGTTCAGGAGCCGGTGGTGGCCGCGAAACCGCAGCCC

AAGCCGCAGCCGAAACCGCAGCCGCAACAGCAGGCCTCGACGCCAACGCCGCCGCCGGCTAAGCCA

CAGCAGCAACAGCCACCGCAGCAGCAGGCGGCCCTGCCGGCGCCGACCGGCAAAGCCTATGTGGTT

CAGCTGGGCGCGTTGAAGAACGCCGATAAGGTGAATGAGATTGTCGGTAAACTGCGGGCCTCGGGTT

TCAAAGTCTATACGTCGCCTTCGACGCCGGTACAGGGTAAAATTACCCGCATCCTCGTCGGCCCGGAT

GCGTCAAAAGACAAGCTGAAAGGCCAGCTGGGCGATCTGCAGCAGATCTCCGGGCTTAGCGGGGTG

GTGATGGGCTTCACCCCGAACTGA

SEQ ID NO: 41
ATGGCACAACGAGATTATGTACGCCGCAGCCAACCGGCTTCTTCGCGGCGCAAAAAGAGCACGACCC

GAAGCTCAAGGAATAAGCAAAGCAGCCTTCCGGCGATTTCACCGGCGATGGTGGCGATCGCGGCGG

CTGTGCTGGTGGCCTTTATCGGTGGCCTCTATTTCATTACGCATCATAAGAAAGAAGAAGCGGAAGCG

ATGCAAAATCGCCAGGCCGCCGGCAACGGCTTGCCGCCCAAACCGGAAGAGCGCTGGCGCTATATTA

AAGAGCTGGAAAGCCGCCAGCCTGGCGTCCGCGCCGACCGAACCGACCGCCGGTGGCGAAGTCA

TGAAACCGGAACAGCTGACCGACGAGCAGCGCCAGCTGCTCGCCCAGATGCAGGCCGATATGCGCC

AGCAGCCGACCCAGCTGACCGAAGTGCCGTGGAACGAACAAACGCCGGCGCAGCGCCAGCAGACGC

TTCAGCGTCAGCGTTTAGCGCAGCAACAGCAGCAGGCGCAGCAGCAACAGTGGGCGCAGACTCAGG

CGCAGACCGTCCAACAGCAGCCGCCGCGCGTTCAGCAGCCGAAGCCGGTTCAGCAGCAACAGCCGA

AGCAGACCGCGTCAAACCAGCAGCCGTACCAGGATCTGCTGCAGACGCCAGCGCATACCAATACCAC

GCAGCCGCGTACCCAGGCCGCGGCGCCGGTAACTCGGGTGGAAGAAGCGCCGAAAACCACCGCCGA

GAAGAAAGACGATCGTAGCTGGATGATCCAGTGCGGCTCTTTTAAAGGCGCCGAGCAGGCCGAAACC

GTCCGCGCTCAGCTGGCTTTCGAAGGGTTTGCTTCGCACATTACCACTAACAACGGCTGGAACCGCGT

GGTTATTGGCCCGTTGAAAGGCAAAGAAAGCGCCAACGAGATGATCACCCGCCTGAAGATGGCTGGA

CACGCGAACTGCATTCGTCTCGCCGCCAGGGGTTGA

SEQ ID NO: 42
ATGAGCGCGGGAAGCACCAAATTTACCGTCAGCCGTATTGCGGCTCTTTCACTGGTTTCACTCTGGCT

GGCCGGGTGTACCAACACCAATAATCGCCTGCGCCGGTTAGCTCTGCCGGCGGCGCCGCCTCTTCC

AGCACCAACTCCGGCATGCTGATTACGCCGCCACCCTCCGGCGTCAAGTCCGCTCCTCAGGCGCAGC

CGATTCAGCCGATGCAGACCCAGACCATTCAGCCGGCGCCGGTGGCGCAGGAGCCGGTACAGACGG

TAAATGGCCGGATCGTTTACAACCGCAAATATGGCGATATTCCGAAAGGTAGCTATACCGGCGGCAGT

ACCTATACGGTAAAACGCGGCGACACGCTATTCTATATCGCCTGGGTCACCGGCAACGATTTCCGCGA

CCTGGCGCAACGTAACAATATCCCGGCCCCGTACGCGCTGAACGTGGGGCAGGTACTGCAGGTCGGT

AACGCCTCAGGCCAGCCGATCACCGGCGAAAACGCCGTTTCTCAGGCCAGCGCAAGAGCGAGCGGC

GGTGCGACGACCAGCACAACTTCTGCACAAAAATCGACCGCGGTGGTTGCTTCACAACCGACTATTAC

GTATTCTGAATCTTCAGGTGAACAGAGTGCTACCAAGATGTTGCCTAATAATAAACCAGCGACCACAA

CCACAACGGTTGTCGCGCCGGTGACGGCACCAACAACGGTGAGCACAACCCAGCCGACTGCAAGCA

GTACGTCAACCAGTTCGCCGATCTCAGCATGGCGCTGGCCGACTGATGGCAAGGTTATCGAGAACTTT

```
AGCGGCGCGGAAGGCGGCAATAAAGGCATCGATATTGCAGGCAGTAAGGGACAGGCTATTGTCGCG

ACCGCCGATGGGCGCGTCGTCTATGCCGGTAACGCACTGCGCGGCTACGGTAATCTTATTATCATCAA

ACACAACGATGATTACCTGAGTGCCTACGCTCATAACGATACCATGCTGGTTCGGGAGCAACAGGAAG

TCAAAGCGGGGCAGAAAATCGCTACCATGGGTAGCACCGGAACCAGCTCAACAAGATTACATTTTGAA

ATTCGTTACAAGGGGAAATCCGTCAACCCGCTGCAGTACTTACCGCAGCGATAA

SEQ ID NO: 43
ATGCGTAAGCAATGGCTGGGGATCTGCATAGCAGCGGGGCTGCTGGCGGCATGTTCGAGTGATGAC

GTGCAACAAAAAACGGTCAGTACTCCACAGCCGGCCGTCTGTAATGGCCCGACGGTTGAGATCAGCG

GCGCCGATCCGCAGTATGAAACGCCGAACGCCACGGCGAATCAGGATTATGAGCGCGACGGTAAAA

GCTACAAAATCGTTCAGGATCCGGCCAACTTTACTCAGGCCGGTTTCGCGGCGATCTATGACGCAGAA

CCCAACAGCAACCTGACCGCCAGCGGCGAAGCCTTCGATCCGACTCAGTTGACCGCAGCGCACCCGA

CGCTGCCGATCCCGAGCTACGCGGGATCACTAACCTTGCCAACGGACGGATGATCGTCGTGCGGAT

TAACGATCGCGGTCCCTATGGCAACGATCGGGTCATCTCGCTTTCCCGCGCATCCGCTGACCGCCTGA

ACACCTCCAACAACACCAAAGTGCGCATCGACCCCATCATCGTCGCGCCTGACGGTTCGCTTTCCGGC

CCGGGGATGGCCTGTACCACCGTCGCCAAACAGACTTACGCCCTGCCCGCCCGTCCGAATCTGGACG

GTGGGGACGCCGCTGGCATGAGCCAGCCCGCGCCCACTGACGTTCGCCCGATCAGCAACAGCACGC

TGACGCCGGCAGACAGCGTGGGCGCGCCGGTGAACAGCGGCGGTTTCCTCGGCGCGCCGACGCCCC

TGAACAACGGCGTGCTGGAGAGTAGCGAACCAGCGGCAGCCGCCGCGACGGCTCCTGCCGCCGGCG

CCACGCCAACAGCGCCAGTGACCGCGCCTGGCTCCATTCAGGGTAATGTGGTGCCCGCTGCGGCCAC

CGCCGCAGCCGCTGGCGCCGTGGCGGCCTCGTCCTCCGCGACCTCCAGCGCCAGCGGTAATTTTGTT

GTCCAGGTGGGCGCAGTAAGCGACCAGACGCGGGCGCAGCAGTATCAGCAGCGCCTGAGCCAGCAG

TTTTCTGTGCCAGGCCGGGTCATGCAAAACGGCGCGGTCTGGCGTATTCAGCTGGGTCCCTTTGCTG

ATAAAGCACAGGCCAGCGCCGTGCAGCAGCGCCTGCAAAGCGAAGCGCAGCTGCAGTCCTTTATTAC

TCGCGCCAACTAA

SEQ ID NO: 44
ATGGATGATTTCAAACCAGAAGACGATATGAAAGCCGATCGCAACGATCGTCGTGCTGGTCGTTCCCG

TCAGTCTTCCGAGCGTGATGCCGATCCGCAGATCAATTTTGACGATGTTGATCTTGATGCCGATGAAG

GCCGTCCGACGCGCGCTGGTAAGGCCCGTCGCGAGCGTGAAGAGGAAGAGTTCGAAGAAGAACTGG

ATGCGCAAGACGAGGAGATGCTCGAAGAGCAGCCTGTAGAGCGTCGTCCGCGCAAGCGTAAAAAAG

CGCCGGCCAAACCGGCCTCCCGCCAGTACATCATGATGGGTGTGGGGATTCTGGTGCTGCTGCTGTT

GATCGTGGGTATCGGTTCCGCACTGAAATCGCCATCATCTTCCAGCCAGCAGACCGCTTCCGGCGAG

AAGAGCATTAATCTGTCTGACGACCAGTCCGCCAGCATGCCTGCTGCCGGCCAGGACCAGACTGCCG

CCGCTAACAGCACCTCACAGCAGGACGTAACGGTACCGCCTATTGCCGCGAACCCGACGCAGGGCCA

GGCAGCGGTTGCGCCGCAGGGCCAGCAGCGTATCGAAGTTCAGGGCGATCTGAACAATGCCTTGAC

CCAGCAGCAGGGCCAACTGGACGGCGCCGTGGCTAACTCGACGCTGCCGACTGAACCGGCTACCGT

CGCGCCAATCCGGAATGGCGCCAATGGCACCGCGGCGCCGCGCCAGGCGACCGAGCGTCAGACAGC

AGCGACCCCGCGTCCGGCTGAACGTAAGCATACCGTTATCGAAGCGAAGCCGCAGTCGAAGCCACAG

GCCGTGGCGAAAACGCCGGTAGAATCGAAGCCGGTCCAGCCGAAGCATGTTGAAAGCACGGCGACC

ACCGCTCCGGCGAAAACGTCCGTCAGCGAAAGCAAACCGGTGGCCACCGCTCAGAGCAAACCGACCA

CGACGACCGCAGCGCCAGCGGCAACGGCAGCTGCGGCAGCGCCGGCAGCGAAGACCGGGAAGACG

GCAGGTGACGTCAGCTCAATGAAAAACTGCGCCGTCGGGTCACTATACTCTGCAGCTCAGCAGCTCCTC
```

-continued

TAACTACGACAACCTCAACAACTGGGCGAAGAAAGAGAAGCTGGATAAATATGTTGTCTATGAAACGT
CGCGTAACGGCCAACCATGGTACGTGCTGGTGAGCGGTATCTATGCATCGAAAGATGAAGCGAAACG
TGCTGTCACCTCGCTGCCGGCGGACGTGCAGGCGAAAAATCCATGGGCAAAACCGCTGCATCAGGTT
CAGGCTGACCTGAAATAA

SEQ ID NO: 45

ATGTCAAAGGCAACCGAACAAAACGACAAGCTTAAACGAGCGATCATCATTTCAGTCGCGCTGCACAT
CATTCTGATCGCGCTGCTGATCTGGAGTTCGTTTGACGAGCATCTGGATGCCTCTGCCGGCGGCGGC
GGCGGATCGTCGATTGATGCCGTCATGGTCGATCCGGGGCGGTGGTAAATAACTATAACCGTCAGC
AACAGCAGCAGGCCAGCGCACGTCGCGCCGCTGAACAGCGTGAAAAACAGGCGCAGCAGCAGGCGG
AAGAGTTACGTGAGAAACAGGCGGCGGAACAGGAACGGCTGAAACAGCTCGAACAGGAGCGGCTGC
AGGCGCAGGAAGCGGCGAAAGAAGCGAAGGAGCAGCAGAAGCAGGCTGAAGAAGCGGCTGCCAAG
GCCGCCGCGGCGGCAAAAGCCAAAGCGGACGCACAGGCAAAAGAAGCGCAGGAAGCCGCTGCCAAA
GCGGCCGCCGAGGCGAAAGCGAAGGCGGATGCCCAGGCGAAAGCGGCAGAACAGGCGGCGGCCAA
GGCGGCTGCTGACGCGAAAAAGCAGGCCGAAGCCGCTGCAGCGAAAGCCGCTGCCGAGGCGAAGAA
ACAGGCGGAAGCTGAAGCGGCGAAAGCTGCGCCGAGGCGCAGAAGAAAGCGGAAGCGGCGGCTG
CGAAGAAAGCGCAACAGGAAGCGGAGAAAAAAGCCCAGCAGGAAGCGGCTAAGCAGGCGGCAGCTG
AAAAAGCGGCTGCCGAAAAAGCCGCTGAGAAAGCCGCCGCGCAAAAAGCGGCCGCTGAGAAGGCCG
CCGCCGAGAAAGCCGCAGCCGCTGAAAAAGCGGCGGCAGCGAAAGCGGCTGCAGCAGAGAAGGCT
GCAGCTGATAAAGCGGCCAAAGCGGCAGCAGCAAAAGCCGCGGCGGCGAAGAAAGCGGCGGCTGC
GAAAGAAGCGGACGGCGTTGACAACCTGCTCGGCGATCTGAGTTCTGGTAAGAATGCGCCTAAAACA
GGCGGTGGGGCCAAAGGAAACAATGCCTCCGCTGCCGGGAGTGGTAATACTAAAAACAGTGCCTCAG
GGGCTGATATCAACAACTATGCCGGACAGATAAAATCGGCGATTGAAAGTAAGTTTTATGACGCATCG
TCCTATGCGGGCAAAACATGTACCTTGCGTATCAAACTTGCTCCTGACGGCCTGTTGTTAAATATACAG
TCCGAAGGTGGTGATCCTGCTCTGTGCCAGGCCGCTCTTGCCGCAGCCCGACAGGCTAAGTTTCCGA
AACCACCTAGCCAGGCAGTATATGAAGTCTTCAAAAATGCGCCACTGGACTTCAAACCTCAGTGA

SEQ ID NO: 46

ATGTTTTTTTTAAGTATTTTTTACATGGAGATGACAAAAGTGAAATTAAGCGCTCTGTTTATTGCCCTGA
TTCCTCTACTGGGCTCGCCGGTTATTCATGCAGAAACTACTGCTGCGCCGGTTCTGGAAAATCGCGCT
GCGCAGGGAGATATCACCACTCCTGGCGGCGCGCGTCGTTTAACAGGCGATCAAACCGAAGCGCTGC
GCGCCTCGTTAATCAATAAGCCAGCTAAAAACGTTATTTTGCTGATTGGCGATGGCATGGGTGATTCG
GAAATTACCGCTGCGCGAAACTATGCCGAGGGGCGGGCGGTTTCTTTAAAGGAATTGATGCTCTGC
CGTTAACCGGGCAGTACACGCATTATTCGCTGGATAAAAAAACCGGGAAACCGGACTACGTGACCGA
CTCGGCGGCCTCCGCCACCGCCTGGACCACCGGCGTGAAGACTTATAACGGCGCGCTGGGCGTCGA
TATTCATGAGAATGCGCATCAGACCATCCTCGAGCTGGCGAAAGCGGCGGGGCTGGCCACCGGCAAC
GTTTCCACCGCCGAGCTGCAGGACGCCACCCCCGCGGCGTTGGTAGCGCATGTGACATCGCGTAAAT
GCTACGCCCCGACGGTCACCAGCGAAAAATGCCCCAGCAATGCGCTGGAAAAAGGGGGCAAAGGCT
CCATTACCGAACAGCTGCTGAACGCCCGACCGGATGTCACCTTGGGCGGCGGCGCGAAGACCTTTAC
CGAAACGGCGACGCGGGCGAGTGGCAGGGCAAAACCCTGCGCGAGCAGGCGCAAGCGCGCGGCT
ACCAGATTGTGACCGACGCGGCTTCTCTTGCCGCCGCGACGGAAGCCAGTCAGGATAAACCGCTGCT
GGGACTCTTTGCCGATGGCAATATGCCGGTACGCTGGGAAGGGCCGAAGGCGTCTTATCACGGTAAT
ATCGATAAGCGCCGGTGACCTGTACGCCAAACCCGAAGCGTGACGCCTCGGTGCCGACGCTGGCG
CAGATGACGGAGAAAGCGATTGACCTGCTCAGTCGCAACGAGAAAGGTTTCTTCCTGCAAGTCGAAG

-continued

```
GCGCTTCCATCGATAAGCAGGACCATGCGGCGAATCCGTGCGGCCAGATCGGCGAAACGGTTGATCT

TGACGAAGCGGTGCAGAAGGCGCTGGAATTCGCGCGAAAAGACGGTAATACCCTGGTGATCGTCACC

GCCGACCATGCGCATGCCAGCCAGATCATCCCGGCGGATAGCAAAGCCCCGGGGCTGACCCAGGCT

CTGAACACGCACGATGGCGCGGTGATGGTGATGAGCTACGGCAACTCTGAGGAAGAGTCGATGGAG

CACACCGGCACCCAACTGCGCATTGCGGCCTACGGTCCGCATGCGGCTAACGTCGTAGGCCTGACCG

ATCAGACCGACCTGTTCACGACCATGAAAGCTGCCCTGAGTCTCAAATAA
```

SEQ ID NO: 47
```
ATGTCACTGCCGTTCAAACCCCATATTATCGCCCTGCTCTGTAGCGCTGGCTTACTCGCGGCGGCAGG

AACACTCTATGTGCAAAGCCGAACCCCAGCGACGATCGCTGAACCGCCTGCGCAGCAAGCGCCAGCG

CCCGCAGCGTCGACGACACAGCCGGTGGCCGCCACTTACACCCAGGCGCAAATTGATCAGTGGGTCG

CCCCTATCGCGCTCTACCCGGACAGCCTGCTGTCGCAGGTGTTGATGGCCTCCACTTATCCCGACAAC

GTCCTGCAGGCGGTCCAGTGGTCCCAGGATAACCCCGCGATGAAAGGGGATGCGGCCGTGCAGGCG

GTTGCCAGCCAGCCGTGGGACCCTAGCGTCAAATCTCTTGTCGCTTTCCCTGCCCTGCTGGCGATGAT

GGGCGAGAATCCGCCCTGGGTGGAAAATCTTGGCAATGCGTTTTTGGCCCAGCCGCATGATGTGATG

GATTCAGTGCAGCGCCTGCGCGCCATTGCCCAACAAACCGGGACGCTGAAATCCACACCGCAGCAGA

AAGTGATTGTCACCCCTGCCGCACCGGTTTCAGCCAGCAGCAGCACGGCAGCAACCGCAACCGCCCA

CACAGCGGCGCCTGCGCCCACGCAGGTCATTAAAATAGAGCCGACCAATCCACAGGTGGTCTATGTT

CCCAGCTATAACCCCTCCACCGTCTATGGTACCTGGCCGAACAGCGCCTATCCGCCGGTCTATCTGCC

GCCCCCTCCCGGGGAGCAGTTTACCGATAGCTTCGTCAAAGGCTTCGGGTACAGCCTCGGCGTGGCC

ACCACCTGGGCGCTGTTCAGCAGTATCGACTGGGATGATGATGACCATCACCATCACGATGACGACTA

CCACCACGGCGATTACTCGCATAATGGCGATAACATCAATATTAATGTAAATAATTTCAATCATATAAC

AGGAGAAAACCTGCCGGGAAACCACGTTAACTGGCAGCACAATCCTGCCTATCGCGGACACACACCG

TATCCCGATAATACGGTAGCTCAGCGCTTCCATCAGACCAACGTTTCCGGCGGACTGAGCGCGACCCA

ACATGCGCCAGTCGATCGCGAAGCGCAGCGCCAGGCAGCGATGACCCAGCTGCAGCATAACGTACC

GACGGCCACAGCGGGCAACCTGGCGGCAAACAACGCCTCACGCGACGCCCAGCGTCAGGCGGCCTC

GGCGCAGCTGAAGCAAGCCACCCAACGCAGTAATTACCGCGGTTACGACAGTACGCCGACCCAACAG

CAGCGTCGCGAGGCGGCAAAAACGCAGCTGAAAAACCCCACGCCGCAGCAACAGCAGCGTCGAGAA

GCCGCCAGGAGCCACGAGCAGAACCGCACACCTCAGCAGCAGCAGCGCCGGCAGCAGTTCCAGTCC

GCCACGCCAGCCCAGCGTCAGCAGACGCTCAGCCATCTGCGCGCCAACGCCCTTAGCGGCAACGAAA

GCCGCGCCCCTCCTGGCAAGCGCAGCAGGAACGAGGACTGCAGAGCCGCCAGTTTTCCGGCGTAA

ACCGCGAGTTACGCGATGGCACCAGAGAACGTCTTTCCGAACACCATGAACTGCGTCGCCGCTAA
```

SEQ ID NO: 48
```
ATGTTTAAGTTTAAGGCTTCTTATGTCGCACTGGCGGCAGTATTAACCTCGTCGGTAGTTTATGCCGAC

CCCACAAGCTATACGCACTCTTCCGGCGCCACGGTTATCGATATTGAAAAGCCGAACGCCGCCGGTGT

CTCCCATAACCTGTACCGCGACTTCAACGTCGGCGCCAATGGCACCATCCTCAATAACAGCGGCGATG

ATGTCAGCCACAGCACATTTGGCAATATCGCCCGCAACAATAATCTGACCGCCGGCAGCGCTTCGGTG

ATTTTGAACGAGGTGACCTCCAAAAACGCCAGTAGCCTGAAGGGCTTTATCGAAGTCAACGGTCAGAA

AGCGGATGTGGTAATCGCCAACCCGAACGGCATCACCTGTTCCGGCTGTAGCTTTGTTAATACCAACA

AGGCTATCCTGACCACCGGCAAGGTTAATATGACCGACGATGGCGCTATCGGCAGCTATACCGTAAC

GGGCGGCACCCTCACCATCGGCGAAAATGGCATGAACGCCGCCAACGGCTATGCGGTTCTGCTCGCC

GACGCGATCAATATCAACGGTAAAGTGCAGGCCAACAACGCCCTGGTCAGCGCGGGCAACTTCACCA
```

-continued

```
TGGATAACAGCTCTGGCTCGGTGACCTCCGCTGGTAAAAAGGCCACCCTGATCCAGATGACGGTTAA

CCCGCAGTACAGCATCGACGTCAGCAGCCTTGGCGGCATTGAGGCCAACAGCATCAGCATGGTCGGC

AATAACATCGGCTTTGGCGTACGTAATAAAGGCTCTATCGTCGCGAATAGTTCGCTGCAGCTCACCAG

CAACGGTAATCTGCTGAACAAAGGCACGATCAAAAGCAACGGTCTGCTGAGTCAGGTCGCCACCGCC

TCGGGCATCACCAATGACGGTAGCATCGCCGGCGCCTATTATTTAATGCTCTCCAGTGGCGATTATAT

CGTTAACACCGGTTCTCTCTCCGGCGGCCAGCTGATTGCCACCGCTAACGGCAACATCACCAACGGC

GACTCAGGCACGATGACCGGCACCAGTGGATTAAGCCTGACCAGCGGCGGGAAAATCCGCAACGAA

GAAAAAGCCTCCCTGCTGTCAAATAACCAGATTGCCGCCACGGCAATCGGTGATTTCCTCAATGAAGG

CAAAATCAGCGCCAAACACACCAGCCTGACGTTTGTCGGCGACAGCTTTAAAAACACTGGCAATATTA

ACTCTACTGGCCAAACCACCATTCAGTCGCTTAAACAGGACGGCAGCGCCAATACGGGCGAGATCTAT

AACCTCGGCAATATCACCGGCGAAAATATCAATCTGCAGACCAATGGCACGCTGGCGCAAAGCAGCA

GTGGTCGTATTGAGGCAACCAACGCCATTACCGCCCACAGCTACTGGCTGAACCAAAATGGTTATATG

AATGCCGCCGATATCACCACCGATCACGGCGTAGTGAATAATTATGGCAATATTACTGCCAAAAATATT

TCAATCACGACCTACTCAGATATCACCAACGAAGGGCAGATCAGCAGCACCGGCGACCTGACCTTAAA

TACCAAAAATAAAGGCGCGATCTACAATTATTCAACCCTCAGCGCGGGCGGCAACATGACGTTAACCG

CCACCAAAGTGGTCAATGGTGGTAAAAGTTGCGGCATACTGGGCCTGGCGAAATGCGGCGTCGGGAC

GTTAACTGCTGACAAGCTGGTACTGAACTCATCGCAGAAATATGTTAGCGACATGGGTGGAAAACAGT

ATTTCAAGAGCACCGAAGTCAACACGGTGAAATAA
```

SEQ ID NO: 49
```
ATGATGGACAACCTACGCACGGCCGCCAACAGCGTCGTGCTCAAGATTATTTTCGGTATCATTATCGT

CTCGTTCATTTTGACCGGGGTGAGTGGTTACCTGATTGGCGGTGGCAAAAACTATGCCGCAAAAGTGA

ATGGCCAGGAGATTGGCCGTGGGCAGTTTGAAAACGCCGTCGCCAGCGAACGTAACCGTATGCAGCA

GCAGCTTGGCGATCAATTCTCCGAGCTGGCGGCGAACGAAAACTACATGAAAACCATGCGCCAGCAG

GTGCTGAACCGCCTGATCGATGAGTCGCTTCTGGATCAGTATGCCCGCGAGCTGGGCCTCAGCATCA

GCGATGAGCAGGTGAAGCAGGCGATCTTCCAGACCCAGGCGTTCCAGACGAACGGTAAGTTCGACAA

CCAGCGTTTCAGTGGTATTGTCGCCCAGATGGGGATGACCACCGATCAGTACGCCCAGGCGCTGCGT

AACCAGCTGACCACGCAGCAGCTGATTAACGCCATTGCGGGTACCGACTTCATGCTGCCGGGCGAGT

CCGATCAGCTGGCGGCGCTGGTATCTCAACAGCGGGTGGTCCGCGAAGCGACCATCAACGTAAATGC

CCTGGCGGCAAAACAGACCGCCAGCGATGAGGAAATCAACGCCTTCTGGCAGCAGAATCAGGCCCGT

TTTATGGCGCCGGAGCAGTTCCGCGTCAGCTACATCAAAATGGATGCCGCCAGCATGCAGGAGAGCG

CCTCTGACGAAGAGATTCAGTCATGGTACGACCAGCACAAGGATCAGTTCACTCAGCCGCAGCGCAA

CCGCTACAGCGTGATTCAGACCAAAACTGAAGCCGATGCGAAAGCGGTACTGGCCGAGCTGCAAAAA

GGAGCGGACTTCGCCACGCTGGCGAAAGAAAAATCGACCGATATTATCTCTGCCCGCAACGGTGGCG

ATATGGGGTGGATGGAAGATGCCTCTACCGTGCCTGAGCTGAAAGATGCCGGGCTGAAAGAGAAAG

GCCAGCTGTCTGGCGTGATCAAATCCTCGGTTGGCTTCCTGGTAGCTCGTCTGGACGACGTCCAGCC

GGCGCAGGTGAAGCCGCTGGCTGACGTGCGTAATGACATTGCGGCGAAAGTGAAGCAGGAAAAAGC

GTTGGATGCTTACTACGCGCTGCAGCAGAAGGTGAGCGATGCGGCCAGCAACGATAATGAATCGCTG

GCGAGCGCAGCGCAGGTCGCCGGGCTGAAGGTCGTAGAAACCGGCTGGTTTGGCCGCGATAACCTG

CCGGAGGAGCTGAACTTTAAACCGGTCGCTGACGCTATTTTCAACGGCGGTCTGGTGGGTGAGAACG

GCGCGCCGGGCAGCAACTCCGATATCATTACCGTTGACGGCGATCGCGCTTTTGTTCTGCGCATTAGC

GAACACAAAGCCGAGGCGGTGAAGCCGCTGGCCGAAGTGAAGGCACAGGTTAGCGATATCGTTAAG
```

-continued

CACAATAAAGCGGAACAGCAGGCGAAACTGGAGGCCGACAAGCTGCTGGCGGCGCTGAAAGACGGC

AAAGGCGATGAAGCGATGAAGGCGGCTGGCCTGAGCTTTGGCGCGCCGCAGACGCTTTCTCGTACC

GGCCAGGATCCGCTGAGCCAGCTGGCATTTACCCTGCCGCTGCCGCAGCAGGGTAAACCGGTCTACG

GCGTGGGCAGCAATATGCAAGGCGATGTGGTGCTGGTAGCGCTGGATGAGGTGAAAGCCGGCAGCA

TGCCGGAAGAGCAGAAGAAGGCCATGGTTCAGGGGATCACCCAGAACAATGCCCAAATCGCTTTCGA

AGCGCTGATGAGCAACCTGCGCAAGGCGGCGAAAATTAAGCTCGGCGACAGCATCGACCAGCAGCA

GTAA

SEQ ID NO: 50
ATGTTCAGGTTAAACCCTTTTATCCGGGCGGGATTGTCTGCGTCCGTCGTATCGTTGGCGTTTCCGGC

TCTGGCCGATGTGAATGAAGAAACGCTGGTGGTGACCGCCTCGGCCACTGAACAGAATGTCAAAGAC

GCGCCGGCGAGCATCAGCGTCATCACCCAACAGGATTTACAACGCAAGCCTGTTCAGAACCTGAAAG

ACGTGCTGCGCGATGTGCCTGGGGTCCAGCTCACCAACGAAGGGGATAACCGCAAGGGCGTTAGCAT

CCGCGGTCTGAGCAGCAGCTATACCCTGATCCTGGTCGACGGCAAGCGCGTTAACTCGCGGAACGCC

GTCTTCCGCCACAATGACTTCGACCTTAACTGGATCCCGGTGGATGCTATTGAGCGTATCGAAGTGGT

GCGCGGCCCGATGTCCTCCCTCTACGGCTCCGATGCGCTCGGTGGGGTGGTCAACATTATTACCAAA

AAAATCGGCCAGAAATGGACCGGGACGCTGAGTGCTGATACCACTATTCAGGAGCACCGCGATCGCG

GGGATACCTGGAACGGCCAGTTCTTCACCAGCGGCCCGCTGATCGACGGCGTACTTGGAATGAAGGC

CTACGGCAGCCTGGCAAAACGCGCCAAGGACGATCCGCAGTCATCCAGTAATGCCACCGGCGAGACG

CCGCGCATCGAGGGCTTCACCAGCCGCGATGGCAATGTTGAATTCGCCTGGACGCCGAACGAAAACC

ACGATTTTACCGCAGGCTACGGCTTTGACCGTCAGGATCGCGATTCCGATTCCCTTGACCGCAACCGC

CTTGAGCGGGAGAACTACTCTCTGAGCCATAACGGCCGCTGGGATATCGGCAATAGCGAGCTCAAGT

TCTACGGCGAAAAGGTGGATAACAAAAATCCAGGGCAGAGCGGGACTATTACCTCGGAAAGCAATGC

CATCGACGGCAAGTATGTCCTGCCGCTGGGCATGATTAACCAGCTGGTGACCTTCGGCGGCGAATGG

CGCCACGACAAACTTAAAGATCCGGTCAACCTGAGCAGCGGCGGCCAGTCAACGTCGGCCAGCCAGT

ACGCCCTGTTTATCGAAGACGAATGGCGCATCATCGAGCCGCTGGCGCTGACCACCGGCATTCGTAT

GGACGACCATCAGACCTATGGCGATCACTGGAGCCCGCGCGCCTATCTGGTGTATAACGCCACCGAT

ACCGTCACCGTCAAAGGCGGCTGGGCGACGGCGTTTAAAGCCCCGTCGCTGCTGCAGCTTAACCCCG

ACTGGACCACCAACTCCTGCCGCGGCTCGTGCAGCATCGTCGGTAACCCGGATCTGAAACCGGAAAC

CAGCGAAAGCTTCGAGCTCGGTCTCTACTACCGCGGGGAAGAGGGCTGGCTTGAAAATGTCGAAGGC

AGCATCACCACCTTCCAGAATAATGTCGACGACATGATCGACGTTCTGCGCACCTCCAGCGCCAGCGA

AGCGCCGGGCTACCCGAACTTTGTCGGCTGGAAAACTGTCAACGGCAAGCGCGTGCCGATCTTCCGC

TATTTCAACGTCAACAAAGCCCGCATCAAAGGGGTGGAGACGGAGGTGAAGATCCCGTTTGGCGATG

AGTGGAAGCTGACGGTGAACTACACCTACAACGATGGTCGCGATCTGAGCAATGGCGGCGACAAACC

GCTGCAGACGCTGCCGTTCCATACCGCCAACGGCACGCTCGACTGGAAACCGCTGGACGACTGGTCC

TTCTACGTGACGGCCAACTATACCGGCCAGCAGCGCGCGGTGAGCGCCACCGGCAAAACGCCGGGC

GGCTACACCCTGTTTGACGTTGGCGCGGCATGGCAGGTGACCAAAAACGTGAAACTGCGCTCCGGGG

TGCAGAACGTGGGTGATAAAGATCTGAGCCGGGACGACTACAGCTATACCGAAGAAGGCCGTCGCTA

CTTTATGGCGGTGGATTATCGCTTCTGA

SEQ ID NO: 51
ATGAACAGAGCCGCCACGCTGACCCTCAACGCGCCCCTGCTGATGCTCGTCGCTGCGCTGGCGCTTT

CAACCCCTTTCACCGCCGGCGCCGCGCCGGCCTTTCTTGATTACGCCCAACAGCAAACCCAGCAATCT

CAGGCGCAAGAAAAAAACGATGCCGCAAGCGCAAAACAAACACAAGAAAGCCGCCAGAGCGCAGATA

```
ATAAAAAAACCGGTACCAGCACCTCACAATTACAAAAAAGAATCACCAGCCAGCAGGCGGCGATTGCA

CAAAAAGATAAGCTTATACAGCAATTAAAAAAACAGCTTGCCGCTACGCCGCAAACGGATACTGCCGG

AGCGAATGAGCAAGCGGCGTTGAATAAGAGAATTAATGAATTACAGGTCGCCTTAAGCGCCGCTACT

GCAGAAAAAGAGGCATTAATAAAAAAAGCAGGCGTTGTGCAGAATAATAATCTACAGCAAAGCCAGGC

CGCGGCGCGTCAGCAGATCCAGCAATTAACGACGCAGATTCAGCAAGCCGAAGCTGAAAATAAACGC

CTCAGCGCCAGCTTTACCACGCTTAATAAAGATAAACACGCGCTAATGACCCAACTGGCCGCAACGGA

AAAAGAGAAACAGGCCGCTCTTGAGCAGGTCAAAGCGCTTAACGCTGACAAACAGCCGCTGACGACC

CGGCTGGCCGCCGCGGAAAAAGAGAAACAGGCCGTCCTCGAGCAGGTTAAGGCCCTTAACGCCGAT

AAACAGTCGCTGACTATTCGCCTCGCCGCTGCGGAGAAAGCGCAGCAGGCCGCTGTTGACCAGGCTA

AAGCGCTTAACGCTGACAAACAGCCGCTGGCTACCCGACTGGCCGCCGCGGAAAAAGAGAAACAGG

CCGTCCTCGAGCAGGTTAAGGCCCTTAGCGCCGATAAGCAGTCGCTGACTATTCGCCTCGCCGCTGC

GGAGAAGGCGCAGCAGGCCGCTCTTGACCAGGCTAAAGCGCTTAACGCTGACAAACAGCCGCTGGC

GACCCGGCTGGCCGCCGCGGAAAAAGAGAAACAGGCCGTCCTCGAGCAGGTTAAAGCCCTTAACGC

CGATAAGCAGTCGCTGACTATTCGCCTCGCCGCTGCGGAAAAGACGCAGCAGGCTGCCCTCGATCAG

GTCAAAGCCCTTAACGCCGATAAACAATCGCTGTCCACCCGGCTGGCCGCCGCGGATAAAGCGCCGC

ATGGCCCCGCTAACGACGCCGCTGCGCCAAAAAATGAGCCACCAGAGATGGCGGCCATAGTGGCAG

CCTATCGCCTGCAGGCGGATAAAGACAACGCCCAGCTACGGATGAAAGAAGATGAAATCGAACTGCT

GAGAACGCAGCTTTCTGTACAGTCCAAAACGCGCAGCGGCGAGAGCGCCGCCGCCAAACTCAGCGCA

TCGGGAGAACAGCAGGCTTATGCGATCGGCGCCTCGATGGGAAGCGAGGCGCTCAACGTCCTTACCA

CCCGTCGTACTCAGGGAGTTACCGTCGACGCAGGCCTGGTGCTGCAGGGCATCGAAGATGCCTTTCG

CGGCCAGCTTCGTCTCGGAGAGCAGGAACGTAACAAGGCGCTGTTTGATGTGTCGCAGCAGGTTTTT

CAGAACCTGAATAAAATAGAGCAGAAAAACATCAGTGCCGGCAAGAAATATCAGCAGGCGTTTGCGC

GCAAAAAAGATGTGGTCTTTAAAGAGGGCGTCTACAGCCGCGTCGATTACCTGGGTAAAGGAAAAAT

AAGCGGTAATGACCTGGTTACCGTGGTGATCAAAGAGATGCTGACGGACGGGACGGTGATCAACGAT

ATGGAAGCGAAAGATCAGGCGCTTACGCAAAAGCTGGATGCCTATCCCCCGGTGTTTCGCGAACCGC

TGAAGCGTCTACAGAACCACGGCTCCGTGACGCTCGTCGTCCCGCCTGAAAAGGCCTATGGCAGTAA

AGGATTACCGCCAAAAATCCCGCCAGGCGCCACCATGGTTTATTCCGTGCGGATAGTAGATAGCCAAC

CCGAGCCGGCAAAATAG
```

SEQ ID NO: 52
```
ATGAAAATCCTGTCCGTGCGTCACGCCGCCCTCCCGGCCCTGCTCTTGCCGCTCATTGCGGCAGCCCA

GGCCGCTGATGAACAAACCATGGTGGTGACCGCCGCGCCAACCACGGTTTCTGAACTGGATACCCCC

GCCGCCGTCAGCGTGGTGAATGGGGATGAGATGCGCCAGGCCGCGCCGCGCGTCAATCTCTCTGAA

TCGCTGGGCGCCGTGCCGGGCCTGCAGGTGCAGAACCGGCAAAACTATGCCCAGGATCTGCAGCTG

TCGATTCGCGGCTTTGGCTCGCGCTCAACCTATGGCGTGCGCGGACTGCGCATCTATGTGGATGGCA

TTCCGGCCACCATGCCCGACGGCCAGGGGCAGACCTCAAATATTGATATCGGCAGCGTTGACACCAT

TGAGGTGCTGCGCGGCCCCTTCTCTGCCCTGTACGGTAACTCGTCCGGCGGGGTGATCAACGTCACC

AGCCAGACCGGCACCCAGCCGCCCACCGTGGAAGCCAGCAGCTACTATGGCAGCTTCGGCACCTGG

CACTACGGGATGAAAGCCACTGGCGCCGTTGGCGACGGCAGCCACGCAGGCGATGTGGATTACACG

GTCTCAACCAATCGCTTCACCACCCATGGCTATCGCGATCACAGCGGCGCGCGCAAAAATCTGGCGA

ACGCCCGGCTGGGGGTGCGCATCAACGACGTCAGTAAGCTGACTCTGCTGCTGAATAGCGTGGATAT

CAAAGCCAATGACGCCGGTGGCCTGACCGCCGATGAATGGCGCGATAACCCGCGCCAGTCGCCGCG
```

```
CGGCGACCAGTATAATACCCGCAAGAATACCCGACAGACCCAGGCCGGCCTGCGCTATGAGCGCCAG

CTCAGTGCCCAGGACGATCTCAGCGTTATGATGTACGCTGGAGAACGTGAAACCACTCAGTTCCAGTC

GATCCCGCGCGCGCCGCAGCTGAAGCCGAGCCATGCCGGCGGGGTGATCGACCTTACCCGTCACTA

CCAGGGGATCGATACCCGGCTGACCCATCGCGGAGAGCTGCTGGTGCCCGTCACGCTCACCGCCGG

TCTCGACTACGAAAACATGAGCGAGCGGCGCAAAGGGTATGAAAACTTTGTGATGGTCAACGGCGCG

CCGCAGTATGGCGAACAGGGCGCGCTGCCGTAACGAACGCAACCTGATGTGGAACGTCGACCCC

TACCTGCAGACCCAGTGGCAGCTCACTGACAAACTCTCGCTCGATGCCGGGGTTCGCTACAGCTCGG

TATGGTTCGACTCGAACGACTACTACATCACCCCAGGCAATGGCGATGACAGCGGTGATGCCAGCTAT

CACAAATGGCTGCCCGCGGGCTCGCTGAAATATGCCCTGACCGACGCGTGGAACGTCTATCTTTCCG

CCGGCCGCGGCTTCGAGACGCCAACCATTAACGAACTCTCCTACCGCTCCGATAACCAGAGCGGCCT

CAACTTCGGCCTGAAACCCTCCACCAACGACACGGTGGAGATCGGCAGCAAGACGCGGATCGGCAAT

GGGCTGTTCACCGCCGCCCTGTTCCAGACCAATACCGATAATGAGATTGTGGTCGACAGCAGCAGCG

GCGGGCGCACCAGTTATAAAAACGCCGGCAAGACCCGCCGTCAGGGGATGGAGCTGGGGCTGGATC

AGCAGTTTGGCGAGAGCTGGCGTCTGAAGGCGGCCTGGACCTGGCTGGACGCGACCTATCGCACTA

ACGTCTGCGACGACGCCAGCTGCAATGGCAATCGCATTCCGGGGATCGCGCGCAATATGGGCTACGC

CTCCTTTGGCTATCAGCGGAGCAAGGTTGGTACGCCGGGAGCGATATTCGCTATATGAGCGATATCA

TGGCCAATGACGAAAACACCGCCAAAGCGCCCTCCTGGACGGTGGTTGGCCTGACGACTGGCTATAA

ATGGAGCTACGGCAGGATGGATATGGATCTGTTCGGTCGCATCGACAACCTGTTCGACCGGGAGTAC

GTCGGGTCTGTCATCGTTAACGAGTCTAACGGACGTTACTACGAGCCTGCCCCGGGACGTAACTACG

GCATCGGCCTGAACCTCGCCTGGCGCTTCGAATAA
```
SEQ ID NO: 53
```
ATGAAATACACGTCTCACTTCCCGCTGGGGATCGTCATTCCTCTGCTCGCCTGTAGCGTGCCGCTGCA

GGCGGCAGAGAACATGACCGAACAATCGACGCCTGACGAGAGCGCCGCCACTGCCGAAAATCACGA

GGAGACGATGGTCATAACCGCCGCCAGGCAGAACCTGCAGGCGCCGGGCGTGTCGACCATCACCGC

AGAAGAGATCCGCAAACATCCCCCCGCCCGCGATGTGTCGGAGTTAATTCGTACGCAGCCCGGGGTA

AACCTGACCGGCAACTCCACCAGCGGGCAGCGCGGCAACAACCGGCAAATTGATATCCGTGGCATGG

GGCCCGAGAATACGCTGGTGCTGGTCGATGGTAAACCGGTGACCAGCCGTAACTCGGTGCGGTATG

GCTGGCGCGGCGATCGTGACTCCCGCGGCGATACCAGTTGGGTGCCAGCGGAGATGATCGATCATAT

CGATGTGATCCGCGGCCCGGCGGCGGCGCGCTATGGTAATGGCGCGATGGGCGGGGTCGTCAACAT

CGTGACCAAACCGACCACGCGAGAATGGCACGGGTCGTGGAATACCTATATGAATGCTCCGCAGCAC

CGTAAAGAAGGGGCGACGAAACGTACTAACTTTAGCCTCAATGGTCCGCTGTCGGACAGTGTCAGCT

TCAATCTCTGGGGTAATCTGAGTAAAACCCAGGCCGATGCACAGGATATTAACGCCGGGCATGAAGC

GGAACGTACCGGTTCCTACGCCGGTTCTTATCCCGCCGGACGTGAAGGGGTGGTGAACAAAGATATT

CACAGTAAGCTGCGCTGGGAGTTTGCCCCGATGCAGGCCCTGGAGTTTGAGGCCGGTTACAGCCGCC

AGGGTAATCTCTATGCCGGCGACACACAAAACACCAATACCAGTACGCTGGTGAAGAGTATGTACGG

GAAAGAGACCAACCGTCTCTACCGGCAAACTTACGGCGTAACATGGACCGGCGGCTGGGATAATGGC

GTGACCAGCAACAGCTATGCCCAGTACGAACACACCCGTAACTCGCGAATGGATGAAGGGCTGGCGG

GCGGTACGGAAGGGATCTTCTCCAGTAGCGAGTTTTCAGATATCGATCTGGCCGATGTCCTGCTACAT

AGTGAAGTGAATATTCCGTTTACGCTGGGGGTCGATCAGAATCTGACGCTGGGGGCAGAATGGAATC

AGCAGCGGATGAAAGATGGCGTATCGACAACCCAGGCGCTCTCTTATGGCACTATCGATGGCGTATC

GGCTACCGGTCGTAGCCCGTACTCCAGTGCCGAGATCTTCTCGCTGTTTACCGAAGATAATATGGCGC
```

-continued

```
TAACGGACAGCACCATGCTGACACCCGCTCTGCGCTTCGATCACCACAGCATCGTCGGCAATAACTGG
AGCCCCTCACTGAACCTGTCTCAGGAGCTGACGGACGACTGGACGCTGAAGCTGGGCATTGCCCGTG
CTTACAAGGCGCCTAACCTCTACCAGTTGAACCCGAACTATATTCTCTACAGCAACGGTCAAGGCTGTT
ACGCCAGTAGTTCCGCCTGCTATCTGATGGGGAATAGCGATCTGAAAGCGGAGACCAGCGTTAATAA
AGAGATTGGTCTTGAGTACAAGCATGATGGCTATCAGGCGGGGATCACCTGGTTCCGTAACGACTATC
ACAATAAGATTGAGTCAGGGTATGCGGCGGTGGGTACCGCCAGCAACGGCACCACCAATATCTATCA
GTGGGAAAACGTACCAAAGGCGTTAGTGGAAGGCCTGGAAGGAACGCTGAATCTGCCGGTGGGGGA
GGCGGTTAACTGGAGCAATAACCTGACCTGGATGCTGCAGAGCAAGAATAAGACGACCGGCGACCG
GCTGTCAGTGATCCCGCAGTTTACCCTGAACTCGACTTTGAGCTGGCAGGTTCGTGAAGATCTCTCCC
TGCAGAGCACCTTTACCTGGTATGGCCGACAGAAACCAAAACGCTTCAATTATAAGGGCGAGGCGGT
CAGCGGCAGCGAACTAAACGAAGTCAGCCCATACAGCATTGTCGGCCTCAGTGCGACCTGGGATGTG
AACAAAAATCTGAGCTTCACCAGCGGGATAGATAACCTGTTTGATATTCGCCACTACCGGGCAGGGAA
TGCGCAAACGACCGGCAACGCGACGACGGGAGCTTATCTGTATGGCGCGGGTGCCGAGACCTATAAC
GAATCGGGGCGGACCTTCTTTATGAGCGTTAATACTCATTTCTGA
                                                                  SEQ ID NO: 54
ATGGAAAAAAACGCTTCTCTGCCTTTCGGCAGTTTCAACTCATTGGCATTGTTTACAGGTCTGTGTCTG
GGAGCCTCGCCGGCAGCAGGCATCGCAGCGGAAAATTCGGTCAAAAATAGTGAAGAGACGCTGGTA
GTGGAAGCCGCTCCGCCTTCACTCTACTCCCCCGGCGCTTCCGCCGATCCCAAGTTCAATAAACCGCT
GGTCGATACCACCCGCACCATCACCGTGATCCCGGAACAGGTGATTAAAGATCAGGGCGTCACCAAC
CTGACTGACGCCCTCAAAAACGTTCCCGGCGTCGGGGCGTTTTATGCCGGGGAGAATGGCAGCTCAA
CCACCGGGGATGCCATCTTTATGCGCGGCGTGGATACCTCTAACAGCATCTATGTGGACGGCATTCG
CGACATCGGTAGCGTGACGCGCGATACCTTCAATACCCAGCAGGTGGAAGTCATCAAAGGGCCCGCC
GGCACGGACTATGGCCGCAGCGCGCCCTCCGGCTCGATCAATATGATCAGCAAGCAGCCGCGCCTTG
ACTCCGGGATCGACGGCTCGGCCAGCATCGGCAGCGCCTGGTCGCGCCGGGGCACTCTCGACCTGA
ACCAGGCGTTTAGCGACAACGCTGCGTTCCGTCTGAACCTGATGGGGAAAAAACGCATGACGCTGG
TCGGGACCGCATTGAAAACGAACGCTATGGCATCGCACCGTCGCTGGCCTTCGGCCTTGATACCCCA
ACTCGTCTGTATCTGAACTATCTGCACGTCCGGCAGAACAACACCCCGGATGGCGGGATCCCTACCGT
CGGCCTGCCGGGCTATTCGGCGCCTTCGCCGAAGTATGCCGCACTCAACTCCGCCGGGAAGGTCGAT
ACCAGCAATTTCTATGGCACCGACTCCGATTACGATAAATCTACTACCGACAGCGGTACCCTGCGCTT
CGAACACGATCTGACGGAGAATACCACCGTGCGCAATACCACCCGCTGGTCGCGAGTGAAACAGGAG
TATCTTTTGACCGCGGTGATGGGCGGCGCGAACAATATCACCGCCCCCGATATCAATGACGTCAACAC
CTGGAGCTGGTCGCGTCTGGTTAATACCAAAGATGTCAGCAACCGTATTCTGACCAACCAGACCAATA
TCACCTCGACTTTCAATACTGGCTCGATAGGCCATGACGTCAGCGCCGGCGTGGAGTTTACCCGGGA
AAACCAGACCAACTATGGCGTTAACGCCAGGACCGCGCCGGCGGTGAATCTCTACCATCCGGTGAGC
AACCTGTCGATTGGCGGGCTGGACAGAAACGGGGCGAACGCCAACGGCCAGACCGATACCTTCGGG
ATTTATGCCTTTGATACGCTGACGCTGACCGAGCGGATTGAGATCAACGGCGGGCTGCGTCTCGACA
ATTACCATACCAAATATGACAGCGCCACCGCCTGCGGCGGCAGCGGACGCGGGGCTATCGCCTGCCC
GCCCGGACAGTCGACCGGCAGCCCGGTCACCACTGTCGATACCGCTAAATCCGGCAATCTGGTTAAC
TGGAAAGCCGGGGCGCTGTACCGCTTAACCGAGCAGGGCAATGTCTACGTCAACTACGCCATCTCAC
AGCAGCCGCCGGGAGGCAGCAGCTTCGCCCTGGCCGCCAGCGGCAGCGGCAACAGCGCTAACCGGA
CCGACTTTAAGCCACAGAAGGCGAAATCCAGCGAGCTGGGCACCAAGTGGCAAATCTTCGACAACCG
```

```
TCTGCTGCTCAGCGCGGCGTTATTCCGCACCGATATTGAAAACGAAGTGGCCGCCAACGATGACGGA

ACCTGGTCGCAGTACGGCAAAAAGCGCGTGGAGGGGTATGAACTCTCCGCGACCGGAAACCTGACCC

CGGACTGGACGATTATCGCCGGCTACACTCAGCAGCATGCGACAGTGACGGAGGGACAGAACGTTGC

ACAGGATGGATCTTCCGCCCTGGCCTACACCCCGAAACATGCCTTTACGCTGTGGACGCAGTATCAGG

CCACCAGCGATCTGTCCGTCGGCGGCGGTGTGCGCTATGTCGGAAGCCTGCGCCGGGGCAGCGATG

GTGCAGTCGGTACCCCGGATCACACCGAGGGCTACTGGGTTGCCGACGCCAAACTGGGCTATCGGGT

CAACAGCAACCTCGATCTGCAGCTCAATATGTATAACCTGTTTGATACCGATTACGTGGCCTCCATCAA

CAAGAGCGGCTATCGCTATCATCCGGGCGAACCCCGGACCTTTATGCTGACGGCGAACGTCCATTTCT

GA

SEQ ID NO: 55
ATGGCGACTATGTACAAATCGACTCCGTCAGCAGCATGGTGTAAAAAACGCCTGCTGGTGACCTCTTT

GTTTGCAGCAATTTATCAGACTTCTGCCATCGCAGCAGATACTTCCGCCGTTAGCGGCGAGGCGGTGG

ATGACACCTCGGAACAAATGACCGTCACCGCCCCCGCGCCGGTGCAGAAAGCCGGTAGCGAACACAG

CATCAGCGCCCGGGAGCTGGAGAATAAAGGCGCTAACGATTTCGGCTCAATCATGCGCTATGAGCCG

CTCATCAGCGCCACCGGGGCCAGCGGCGGCTCCGGCAACGGCAAAAGCGGCTTCGACCGCGGAGGT

TACACCGGCTACAACATTCGCGGTATGGAGAGCAACCGCGTAGGCATCGACGTGGACGGTATCGCGC

AACCCAACGCCACCGGCCGCGGCTACGTCGGCCGCGCCGGGCTCAACACCTTCGGCATCGGCCGCG

ATTATATCGACCCGTATATGTACGGCAGCGTTGATATCCAGTCCGGCGCCACCTCGACGGAAACGGCC

AACAGCGCTATCGGGGGAATGTCTCCTTCCGCCCGAAATCAGCGGATGATTACCTGCGCCCGGCA

AGACCAGCGCCTTCGGCTACCGCAGCGGTTACGACTCTGCGGATCGCAGCTGGCACAACGGGGTGA

CCGTCGCCGGCGGCGATGAGTTCCTGCGCGGGATTTTGGTCTATAGCCGCCGTGACGGCCAGGAAAC

TGAAAACAACAGCGGCACCGTCGACGCCTACCCGGCGAACTGGCACTCCGATGCTTTTCTGGCCTCC

GGGATCTGGCAGCCTAACGATGAGCACAAGCTGACCAGCACCTTCGACTATTACCATAAAACCAACCA

CACCCACTACGATACCTGGGACTCCAGCGGCAACAGCACCATCGGCACCGCCAACCAGACCAGCCAG

ACCCGGCGCTGGGGCCTGAGCCTGAAGGATGACTGGACGCCGATGAACGACTACCTCGACAGCGTC

TCCACAAAAATCTACTACCAGCATACCGAAGCCCATGACTGGACTTATATGCCGGACAGCGTCACCCG

CAAAATGCAGACGGTGAACTCTAACTACGATACCGACACCTGGGGCCTGCAGACCGCGCTGGCGAAA

ACCCTGGGCCGCCACGATCTGAGCGCCGGTTTCAACGCCAGCACCAGCAAAACCCAGCGGCCGTTCA

GCCAGTCGCCGATCCCCAGCGTTTACAGCGAGATCATGCAGCCGGAGGCAGACAGCCGCAGCTACAC

CCTCGGCGGCTTTGTCCAGGATAAGATCAACTTCGATCTCGACAGCCACAACTTCGCCGTTATTCCCG

GCGTGCGCGTGGTGCATCAATCGACTAAGCCGGAAAATCTGTCCGATCTCGCCGCCAACAGCAGCGT

GCTGAGCGAATCGTCGGTGGCGAATCTGTACGGCAAAAACAGCGATACCCAGGTTCTGCCGTCGTTG

ACCTTCCAGTACGACCTCACCCCGCGCCTGATGACCTACCTGCAGTACCAGCGCGGGGCGCAGTTCC

CCAACGCCAGCCAGCTGTATGGCTCCTGGAACCTCGGCTCCAGCTACGCCGGCAGCCAGCAGTATGC

CCTGATCGGCAATACCGATCTGAAGACGGAAACCAGCGATAATCTCGAGTGGGGGCTGAAAGGGGAA

GTTACCGAAGGCATCACCCTGCGCACGGCGCTGTTCTACAACAGCTATAAGAACTTTATCGCCTATAC

CCGCTATACCCGCGCCAACAATCCGGGCCAGTTCACGAATGTGCCGTCGAACATCTACACCATTTATC

AGGCGGAAAACCGCGATAAAGCCTATATCTACGGCGGTGAGATTAGCACCAAATTTAACTTTGGCACC

TGGTTTGAGCAGGTGGACGGCCTGAGCGCCACCCTCGCCCTCGGCTATAGCGAAGGGAAATCGAAAT

CCAGCTACAGCGGCGATAAATACGTCGACCTCGACAGCGTGGCGCCAATGAAAGCCATCGTCGGCGT

GGCGTGGGACGATCCGGCGAAACGCTACGGCACCGCCCTGACGGCGACCTTTGTCAAAGGGAAACA
```

-continued

GGCGACCGCCACCAACCGCGAAAGCTACAGCAACAGCGGATCCGCCATCACCGATGCCAGCAGCGA
CTATATGCGCGTGCCGGGCTACGGCATGCTGGACTGGACCGCGTACTGGCAGGTGGCGAAAAACGT
GCGCCTCAATGGCGGGGTCTACAACCTCACCGATCGTAAATACTGGGATTACCTGAGCAGCCGCAAT
ATCGAGACCGGCACCAACCAGGACGCCAACGATAAAGCGCTGGCGGTGATGCCGGGCCGCACCTGG
CAGCTGGGCGTCAACGTCGACTTCTGA

SEQ ID NO: 56

ATGGCGATGAAAAAGTTGCTCATAGCGTCGCTGCTGTTTAGCAGCGCGACTGTATACGGTGCTGAAG
GGTTCGTGGTGAAGGACATTCATTTCGAAGGCTTGCAGCGTGTCGCTGTTGGTGCGGCCCTCCTCAG
TATGCCAGTGCGTCCTGGCGATACGGTGACCGACGATGATATCAGTAACACTATTCGCGCGCTGTTTG
CCACTGGCAACTTCGAGGACGTCCGCGTCCTGCGCGATGGTGATACCCTGCTGGTTCAGGTGAAAGA
GCGTCCGACGATCGCCAGCATCACTTTCTCCGGCAACAAGTCGGTGAAAGATGACATGCTCAAGCAG
AACCTTGAGGCCTCAGGCGTTCGGGTGGGCGAGTCGCTTGACCGCACGACCATCGCGGATATCGAGA
AGGGTCTTGAAGACTTCTACTACAGCGTCGGTAAATACAGCGCCAGCGTCAAAGCAGTCGTTACGCC
GCTGCCGCGTAACCGTGTCGATTTGAAGCTGGTCTTCCAGGAAGGCGTCTCCGCAAAAATTCAACAGA
TCAACATCGTCGGCAACCATGCGTTTTCGACCGATGAGCTGATCTCCCACTTCCAGCTGCGCGATGAG
GTGCCGTGGTGGAACGTGGTCGGCGACCGTAAATACCAGAAGCAGAAGCTAGCGGGCGACCTTGAA
ACCCTGCGCAGCTACTACCTGGATCGCGGCTATGCCCGTTTCAACATCGATTCTACCCAGGTCAGCCT
GACGCCGGATAAGAAAGGGATCTACATCACCGTCAACATCACCGAAGGCGATCAGTACAAGTTTTCCG
GAGTGCAGGTGACGGGCAACCTCGCTGGCCATTCCGCGGAAATCGAAGCGCTGACTAAAGTTGAGCC
AGGCGAACTGTACAACGGCGCGAAAGTGACCAAGATGGAAAACGACATCAAGAAACTGTTGGGTCGT
TATGGTTACGCCTATCCGCGCGTGCAGTCGCAGCCGGAGATCAACGACAGCGATAAAACCGTTAAGC
TGCACGTTAACGTCGACGCAGGCAACCGTTATTACGTGCGTAAAATTCGCTTCGAAGGCAACGACACC
TCTAAAGATGCCGTACTGCGCCGCGAAATGCGCCAGATGGAAGGCGCATGGCTGGGCAGCGACCTC
GTCGATCAGGGTAAAGACCGTCTCAATCGTTTAGGTTTCTTTGAAACGGTGGATACTGATACCCAGCG
CGTGCCGGGCAGCCCGGACCAGGTCGACGTTGTCTACAAGGTGAAAGAGCGTAACACCGGTAGCTTC
AACTTCGGTATCGGCTACGGCACCGAGAGCGGCGTCAGCTTCCAGGCGGGCGTTCAGCAGGATAACT
GGTTAGGTACTGGCTATGCTGTCGGGATCAACGGTACCAAAAACGACTACCAGACCTATACCGAGCT
GTCGGTGACCAACCCGTACTTCACCGTAGACGGTGTAAGCCTCGGCGGTCGTGTCTTCTATAATGACT
TTGATGCGAACGATGCGGATCTGTCTGACTATACCAACAAAAGCTATGGTACAGACATTACGCTGGGC
TTCCCGGTCAACGAATACAACACGCTGCGCGCCGGCGTCGGTTATGTGCATAACTCCCTGTCCAATAT
GCAGCCGCAGGTGGCAATGTGGCGTTACCTTAACTCGATGGGCCAGTATCCGGACAACACCAACGAC
CGGAACTCGTTCAGTGCGAATGACTTCACCTTCAACTACGGTTGGACCTATAACAAGCTTGACCGCGG
CTTCTTCCCAACGGAAGGTTCGCGCGTCAACCTGAACGGTAAGGTGACCATTCCGGGCTCAGACAAC
GAGTACTACAAAGCGACGCTGGATACCGCGACCTACGTGCCGATCGACAACGATCATCAGTGGGTAG
TACTGGGTCGTACGCGCTTTGGTTATGGCGATGGTATCGGCGGCAAAGAGATGCCGTTCTATGAGAA
CTTCTATGCCGGTGGTTCCAGCACCGTGCGTGGCTTCCAGTCGAACACCATTGGTCCGAAGGCGGTG
TACTTCCCGGCAAGCAGTCGTCATGATGATGACGATAGTTACGATAATGAATGTAAGAGCACCGAATC
CGCACCGTGTAAATCCGATGATGCGGTGGGCGGTAACGCGATGGCGGTGGCCAGCCTTGAGCTGATT
ACCCCGACGCCGTTTATTAGTGACAAATATGCGAACTCGGTCCGTACTTCCGTCTTCTGGGATATGGG
TACCGTATGGGATACTCACTGGGATTCGAGCGCGTACGCTGGTTATCCGGATTACAGCGATCCGAGC
AACATCCGTATGTCTGCGGGTATTGCCGTGCAGTGGATGTCGCCGTTGGGGCCGTTGGTCTTCTCCTA

```
CGCCCAACCGTTCAAAAAGTACGATGGAGACAAAGCCGAACAGTTCCAGTTTAACATTGGTAAAACCT
GGTAA
```

SEQ ID NO: 57
```
ATGACAGATGTGACTATTAAAGCGCTGGCCTCAGAGATTCAGACCTCTGTGGATCGCCTGATACAGCA
ATTTGCTGACGCAGGCATCCGCAAATCGGCTGATGATTCTGTGACCTCGCAAGAGAAACAAACTTTGT
TGACGCACCTGAACCGTGAACACGGCTCGGCGCCAGACAAGCTGACGTTACAGCGTAAGACGCGCAG
TACGTTAAATATTCCAGGTACCGGTGGAAAGAGTAAATCGGTACAAATCGAAGTCCGCAAGAAACGCA
CCTTTGTGAAACGCGATCCGCAAGAGGCTGAACGCCTGGCCGCGGAAGAGCAGGCGCAGCGTGAAG
CGGAAGAGCAGGCCCGTCGTGAAGCTGAAGAAGCAGCGAAACGCGAGGCGCAATTAAAAGCTGAAC
GTGAGGCCGCAGAACAAGCTAAACGTGAAGTCGCTGATAAAGCGAAACGTGAAGCTGCGGAAAAAGA
CAAAGTGAGCAATCAACATACCGACGAAATGACCAAAACCGCCCAGGCTGAAAAGATCCGTCGCGAG
AACGAAGCCGCGGAATTGAAGCGCAAATCGGAAGAAGAAGCACGCCGCAAACTTGAAGAAGAAGCG
CGCCGTGTAGCGGAAGAAGCACGCCGTATGGCTGAAGAAAACGAAAAAAATTGGTCTGAAACCTCAG
ACAGCCCGGAAGATAGCAGCGACTATCACGTCACCACATCACAGCATGCTCGTCAGGCTGAAGATGA
TAACGATCGTGAAGTCGAAGGCGGTCGCGGCCGTAGCCGTAGCAGCAAAGCGGCTCGTCCGGCGAA
GAAAGGCAACAAACACGCTGAATCGAAAGCTGATCGTGAAGAAGCCCGCGCGGCCGTGCGCGGCGG
TAAAGGCGGTAAGCACCGTAAAGGTTCCGCTCTGCAGCAGGGCTTCCAGAAGCCAGCGCAGGCCGTT
AACCGTGACGTCGTAATCGGCGAAACCATCACCGTTGGCGAACTGGCTAACAAGATGGCGGTGAAAG
GTTCTCAGGTCATCAAAGCGATGATGAAGCTGGGCGCCATGGCGACCATCAACCAGGTCATCGACCA
GGAAACCGCACAGCTGGTTGCCGAAGAGATGGGCCACAAAGTTATCCTGCGTCGTGAAAACGAACTG
GAAGAAGCCGTAATGAGCGACCGTGACACCGGCGCGGCGGCTGAACCGCGCGCACCGGTCGTGACC
ATTATGGGTCACGTTGACCACGGTAAAACCTCGCTGCTGGACTACATTCGTTCTACCAAGGTTGCCTC
CGGCGAAGCGGGTGGTATTACCCAGCACATCGGTGCTTACCACGTCGAAACCGACAACGGCATGATC
ACCTTCCTGGATACCCCGGGCCACGCCGCGTTTACCTCCATGCGTGCTCGTGGCGCGCAGGCGACGG
ATATCGTGGTTCTGGTGGTGGCGGCAGACGACGGCGTGATGCCGCAGACTATCGAAGCTATCCAGCA
CGCTAAAGCGGCGCAGGTACCGGTGGTAGTGGCGGTGAACAAGATCGATAAGCCAGAAGCCGATCC
GGATCGCGTGAAGAACGAACTGTCCCAGTACGGCATCCTGCCGGAAGAGTGGGGCGGCGAGAGCCA
GTTCGTCCACGTTTCCGCGAAAGCGGGTACCGGCATCGACGACCTGCTGGACGCGATCCTGCTGCAG
GCTGAAGTTCTTGAGCTGAAAGCGGTCCGCAACGGTATGGCGAGCGGCGCGGTCATCGAATCCTTCC
TTGATAAAGGTCGTGGTCCGGTAGCTACCGTTCTGGTTCGCGAAGGTACTCTGCACAAGGGCGACATT
GTTCTGTGCGGCTTCGAATATGGCCGTGTGCGCGCGATGCGTGACGAACTGGGTCGCGAAGTGCTGG
AAGCGGGTCCGTCCATTCCGGTGGAAATCCTCGGCCTGTCCGGTGTGCCGGCTGCCGGTGATGAAGT
GACCGTAGTGCGTGACGAGAAAAAAGCGCGTGAAGTGGCGCTGTATCGTCAGGGCAAATTCCGTGAA
GTTAAGCTGGCGCGTCAGCAGAAATCTAAACTGGAAAACATGTTCGCTAACATGACCGAAGGCGAAG
TTCACGAAGTGAACATCGTACTGAAAGCGGACGTACAGGGTTCTGTCGAAGCGATTTCCGATTCCTTA
CTGAAACTGTCTACCGACGAAGTGAAAGTGAAGATCATCGGTTCCGGCGTAGGTGGTATCACCGAAA
CCGACGCTACCCTGGCAGCAGCATCCAACGCGATTCTGGTTGGCTTCAACGTTCGTGCCGATGCCTCT
GCGCGTAAAGTTATCGAAGCGGAAAGCCTGGATCTGCGTTACTACTCCGTCATCTATAACCTGATCGA
CGAAGTGAAAGCGGCGATGAGCGGCATGCTGTCTCCGGAACTGAAACAGCAGATCATCGGTCTGGCT
GAAGTGCGTGATGTCTTCAAATCGCCGAAATTCGGCGCCATCGCGGGCTGTATGGTTACCGAAGGGA
CGATCAAACGTCACAACCCAATCCGCGTTCTGCGTGACAACGTGGTTATCTATGAAGGCGAGCTGGAA
```

```
TCCCTGCGCCGCTTCAAAGATGACGTTAACGAAGTCCGTAACGGCATGGAATGTGGTATCGGCGTGA

AGAACTACAACGACGTTCGCGTTGGCGATATGATCGAAGTGTTCGAAATCATCGAAATCCAGCGTAGC

ATCGATTAA
```

SEQ ID NO: 58
```
ATGAAAAGAATGTTAATCAACGCAACTCAGCAGGAAGAGTTGCGCGTCGCCCTTGTTGATGGGCAGC

GCCTGTACGACCTGGATATCGAAAGCCCCGGGCACGAACAGAAAAAAGCGAACATCTACAAAGGCAA

AATCACCCGCATTGAACCCAGCCTTGAAGCCGCGTTTGTTGATTACGGCGCCGAGCGTCATGGTTTCC

TCCCCCTCAAAGAAATCGCCCGCGAATACTTCCCCGCCAACTACAATGCGCATGGTCGTCCTAATATC

AAAGACGTACTGCGGGAAGGTCAGGAAGTTATCGTGCAGATTGATAAAGAAGAACGCGGCAACAAAG

GCGCTGCGCTCACCACCTTTATCAGCCTCGCGGGCAGCTATCTGGTACTGATGCCGAACAACCCGCG

CGCCGGGGAATTTCCCGCCGTATCGAGGGCGACGACCGTACCGAACTGAAAGAAGCGCTGGCGAG

CCTGGAGCTTCCGGACGGCATGGGCCTGATCGTTCGCACCGCTGGCGTCGGCAAATCCGCCGAAGCC

CTGCAGTGGGACCTGAGCTTCCGCCTGAAGCACTGGGAAGCGATTCAGAAAGCCGCGGAAAGCCGTC

CGGCGCCGTTCCTGATCCACCAGGAAAGCAACGTCATTGTCCGCGCCTTCCGTGACTACCTGCGCCA

GGACATCGGCGAAATCCTGATCGATAACCCGAAAGTGCTTGAGCTGGCGCGCCAGCATATCGCCGCG

CTGGGTCGTCCGGATTTCAGCAGCAAAATAAAACTGTACACCGGTGAAATCCCGCTGTTCAGCCATTA

TCAGATCGAATCGCAAATTGAGTCCGCCTTCCAGCGCGAAGTGCGCCTGCCTTCCGGCGGGTCTATC

GTTATCGATAGCACCGAAGCGCTGACCGCGATCGATATCAACTCCGCCCGCGCCACCCGCGGCGGCG

ATATCGAAGAGACAGCCTTCAATACCAACCTCGAAGCGGCTGACGAAATTGCCCGCCAGCTGCGTCT

GCGCGACCTCGGCGGCCTGATCGTTATCGACTTCATCGATATGACCCCGGTTCGCCACCAGCGCGCC

GTGGAGAATCGTCTGCGCGAAGCCGTCCGTCAGGACCGTGCGCGCATTCAGATCAGCCATATTTCGC

GCTTCGGCCTGCTGGAGATGTCCCGTCAGCGCCTGAGCCCGTCGCTGGGCGAGTCCAGCCACCACGT

CTGCCCGCGCTGCTCCGGCACCGGCACCGTGCGTGATAACGAATCGCTGTCGCTCTCTATTCTGCGTC

TGATCGAAGAAGAAGCGCTGAAAGAGAATACCAAAGAAGTCCACGCCATTGTTCCGGTACCGATCGC

CTCCTATCTGCTGAACGAAAAACGTGCCGCAGTGAGCGCTATCGAATCCCGTCAGGGCGATGTGCGC

GTTATTATCGTGCCAAACGACGAAATGCAAACGCCGCACTACTCCGTCCTGCGCGTGCGCAAAGGTG

AAGAAACCTCAACGCTGAGCTATCTGCTGCCGAAGCTGCATGAAGAAGAAATGGCGCTGCCAGGCGA

CGATGAGCCGGCGGAGCGGAAACGTCCGGAACAGCCGGCCCTGGCCGCTTTTGTCATGCCAGATGC

GCCGCCAGCCCCGATGCTCGAAGAGCCTGCCGCCGCGCCTGTCGCCGCAGCGGCACCGGTCGCGGC

CGCCGCACCGGCGCAGCCTGGCCTGCTCTCACGCTTCTTCAGCGCGCTGAAGAATATCTTCTCTGGC

GCCGAAGAGGCCAAACCGGCTGAAGTTCAGGTCGAGAAGAAAGCGGAAGAAAAACCGGAGCGTCAG

CAGGAGCGTCGTAAACCGCGCGCCAACAACCGCCGCGACCGCAACGACCGCCGTGATAACCGCGAC

AATCGTGACAACCGCGATAACCGTGACAATCGCGACACCCGTGCGGACAATGCCGAGGGCCGTGAAC

CGCGCGAATCGCGTGAAGAGAACCGTCGCAACCGTCGCGAGAAGCCGTCGCAGAACGTGGAAGCCC

GTGATGTTCGCCAAACCTCAGGCGACGACGCGGAGAAAGCGAAATCCCGTGACGAGCAGCAGCCGC

GCCGCGAACGCACCCGCCGCCGCAGTGACGACAAACGTCAGGCGCAGCAGGAAGCCAAAGCGCAGA

CTCGCGAAGAGCCGGTTGTGCAGGAGACGGAGCAGGAAGAGCGTGTACAAACTCTGCCGCGTCGTA

AACCGCGCCAGCTGGCACAGAAAGTGCGCGTTGAGTCCGCTGTCGTCGAGCCAGTTGCCGAGATCGT

GCCAGAAGCCGTAGTGGCTGAAGTTATCGCTCCGCACAGCGAGCCGGTGAAAGCCGAGCTGCCGGC

AGGGGTGGAGAGCGTGGCGGACCAGGACGAAAATGGCGAATCCCGTGAAGCGAACGGTATGCCGCG

TCGCTCACGTCGCTCCCCGCGTCACCTGCGCGTCAGCGGTCAGCGTCGTCGTCGCTATCGTGACGAA
```

```
CGCTATCCGACCCAGTCGCCTATGCCGCTGACCGTAGCCTGCGCATCGCCGGAGATGGCTTCCGGTA

AAGTCTGGATCCGCTACCCGGTGGTTCGTCCGCAGGATCAGCAGCCGGAAGAGGTTCAGGTTCAGGA

CGCCAGCGTCGCGAAAACTGTCGAGGCCGTAGCGGCCCCGGTCGCCGTCGTTGAAACCGTTACCGCT

GCGCCGGTCACCGTCGAGCCGGCTACCATGGAACCAGTAACCGCTGAGCCGGTAGTCGTCGAGCCG

GTAGCGGCCGCCGAGCCGCTGGTCGTTGATGCTGCGGAAGTTGTCGCGCCAGCAGCCGTCGAGCCA

GCGCCTCAGGAGCCGGTCACCGAAGCACCGGCTGTCGAAGCGCCTCAGGCTATCGCCAGTGACG

CTCGACGCCGAGCCGGTGGTGGTAGAACCTGAAGCGGTGGAAACGACGCCTGTCGTTGCAGCGCCA

GTGGAAACTATCGCCCCGGTCGCAGAAACCGTGGAGCAAGCGCCAGTGACCGAAGCGGCCCCTGCC

GAACCGGTCAAAGCCGAGCCCCCGGTGAGCAAGCCGGTCGTAGTGGCGGGTCATCGCCATGCCACC

GCGCCAATGACCCGTGCGCCAGCTCCGGACTATGTCCCGGAAGCACCGCGTCATAGCACCTGGGTGC

GCCCGCCGTTCGCCTTTGAAGGTAAAGGCGCCGCCGGTGGTCATAGCGCGACCCATAAAGCCACCGC

TGAACCGACTCGCCCACAGCCCGTCGAGTAA
```

```
                                                          SEQ ID NO: 59
ATGCGCAAGCTCTCACTAAGTTTACTCACGCTGTCCCTCGGCGTTGCGCTGCTGCCGTTAGCGCAGGC

GGCGACGACGCCTGCCCAGGAGCATCTGCTGGAGCAGGTCCGCCTCGGCGAGGCCAGCAATCGTGA

AGACCTGGTGCGCCAGTCGCTGTACCGTCTGGAGCTGATTGATCCCAACAACCCGGAGCTGATTGCC

GCGCGGATGCGCTATCTGCTGCGTCAGGGGGATGCCGCCGGGGCGCAAAAAGAGCTGGAACGACTG

ACGAAGCAGGCGCCGGACTCCCCGGAGCTGAAGGCGTCGCGCAATGAGATGAAAAGCAACACCGGC

GAGGGCCGCCAGGCGCTGCAGCAGGCGCGACTGCTGGGCGTGGCCGGGAAGGTCGATGAAGCCAT

CGCCGCCTATGAAAAACTGTACGGCGGGGTGCCGGATGACGTTGACGTCGCCATTGAGTACTGGACG

CTGGTGGCGCGCCTGCCGGCCCGCCATAGCGAAGGCGTCAGCCAGTTGAAAAAACTGAACGCCAGC

GCGCCGGGCAACGTCAGCCTGCTGACTTCGCTGGCGAAGCAGATGTTCGCCGATAACAAACCGCAGG

AGGGGTTCGCCTATCTGGCGGAGATGGCCCGATCGGCCTCGGGACGCGGTATCGCCGCCGATATGT

GGTTCAGTGAGGTGAAAAGCATGCCGGTGAGTAAGGCCAGCGTGCAGGCGTTGCAGCAATTTCTTCT

GCAGTTTCCCACCGGCTCGGTGGCGGCGAACGCCCGCGTTCTGCTCGACCAACAGCAGGCGCAGCT

GCAGGATCCGACTTTCCGCGCCCGCTCGGAAGGGCTGGCGGCGGTCAAGTCCGGGAATACCACGCA

GGCGGTCGCGGATCTGCAGAAAGCCGTTCAGGCCGACAGCCGCGACAGCGACGCGGTGGGCGCTCT

CGGCCAGGCCTATTCCCAGCGCGGCGACCGCGCGCGGGCAGTGGCGCAGCTCAGTAAAGCGATTGC

TATGGACCCTGACAGCCCGAACCGCGGCAAGTGGGACAGCCTGCTGCAAACTAACCGCTACTGGCTG

CTGATAAAGCAGGGGGATAACGCCCTGAAAGCCGGCCAGCTTTCGCAGGCGCAGAACTATTATGCCC

AGGCGCAGCGGGTCGATCGCACCGACAGCTATGCCGTGCTGGGGCTGGGGGACGTCGCGGCGGCG

CGCAAAGAGGCGGCGGCGGCGGAGCGCTATTACCAGCAGGCGTTGCGCCTGGATCGCGGCAATAAC

CTGGCGGTGCGCGGCCTGGCCAACCTCTATCGCGCCGAATCGCCGGAGAAAGCCAGCGCCTGGATC

GCCGGCCTCCCTCCCGCTCAGCGGCGGAGCATCGATGATATTGAGCGCAGCCTGACTAACGACCGGC

TGGAGAAACAGGCGCAGGCTCTGGAGAGCCAGGGCAACTGGGCGCAGGCGGCGGAAGTTCAGCGT

CGGCGCCTGGCGCTGGATCCGGACAGCGTCTGGATAACCTACCGTCTGGCGCGGGATCTGGTCAGC

GCCGGCGAACGCCAGGAGGCCGACGCGCTGATGCGGACGATGGTCAACCGCCAGCCGCAGGACGC

CGAACGGGTCTACGCCTCGGGACTCTACCTGTCGGGGAACGACCAGGACGATCTGGCTCTGGCGCAA

ATCGCCGCTCTGCCGCGCAGCGCGTGGACGGATAACATTCGTGAGCTCGAAGCGCGTTTGCAAAGCG

ACCGGGTGCTGCGCCAGGCCAACCAGCTGCGCGACAGCGGTAACGAAGCGCAGGCGATCGCCCTTA

TCCGACAGCAGCCCGCCTCGGTGCGCTATGACCTGACGCTCGCCGACTGGGCGCAGCAGCGCGGCG
```

-continued

ACAGCCAGACGGCGATTGCCAACTATCAGCGGGTGCTGCGCCAGGAGGCCGACAACGGCGATGCGC

GCCTCGGCCTTGCGGAAGTCTACCTGGCCGAGGGCGATAAACCGGCCGCCCGGGCGCAGGTCATGC

AGCTGAAAGGCGCAGAGACCGAATCCATGAACATGCAGCGGCGGGTGGCGCTGGCGCGAGCTGGCC

TTGGCGATACCGCTGACGCGCAACGGATTTTTAATCAGATTGTGCCGCAGGCGAAGGCGCAGCCGCC

CTCGATGGAGAGCGCGCTGGTGCTGCGCGATGCCGCGCGCTTTGCCACCCAGAGCGGGGCGCCGCA

GCAGGCGCTGACGCACTACCGGGAAGCTATGGTGGCCTCCGGCATTACCCCGCGCAGCCGCAGGA

TAACGATACTTTTACGCGGCTGACGCGCAACGACAGCCATGATGACTGGCTGAAGCGCGGGATCCGC

AGCGATGCCGCCGACCTTTATCGTCAGCAGGATCTGAACGTCACCCTGGAACATGACTTCTGGGGTTC

CAGCGGCACCGGCGGCTATTCCGACCTGAAGGCGCATACCACCATGCTGCAGATGGATGCTCCGCTG

GCGGATGGCCGGATGTTCTTCCGCACCGACCTGGTCAATATGGATGCCGGCAGCTTTTCCACCCACA

GCGACGGGAGCTACTCGCCCAGCTGGGCACCTGCGGGAGATCGCCTGTACCAGCGGCAGTAAAA

ATCAGACCGACAGCGGGGCCAGCGTGGCGGTCGGCTGGAAGAATGACACCTGGAGCGGGGATATCG

GCACCACGCCGATGGGCTTCAATGTCGTCGATGTGGTGGGGGGCTGAGCTACAGCAGCGACGTCG

GGCCGGTGGGGTACACGGTCAACGTCCACCGGCGGCCTATCTCCAGCTCGCTGCTCTCCTTTGGCGG

GCAGAAGGACAGCAGCAGCCATACCGGCGCCACCTGGGGCGGCGTCCGCGCCGACGGCGGCGGCC

TGAGCCTGAGCTACGATCGCGGGGAGGCTCACGGCATCTGGTCCTCGCTGGGCGCCGACTCGCTGA

CCGGTAAAAACGTGGCGGATAACTGGCGCGTGCGCTGGATGACCGGGTACTACTACAAGGTCATCAA

CGAGAATAATCGTCGCGTCACCGTCGGCCTCAACAATATGATCTGGCACTACGACAAAGATCTCAGCG

GCTACACCCTCGGCCAGGGCGGCTATTACAGCCCACAGGAGTATCTCTCGTTCGCCGTGCCGGTGAC

CTGGCGTCAGCGCACCGAGAACTGGTCCTGGGAGCTCGGCGGGTCGGTGTCATGGTCCCATTCGCG

CACCCAGACGCAAGCCCGCTATCCGCTGCTGAACCTGATCCCGTCCGACTACCGGCAGCGCGCCAGC

GAGCTGACGGAGGAGGGGAGCAGCAGCCATGGATTCGGTTACACCGCCAGAGCGCTGGTGGAGCG

GCGGGTGACCAGCAACTGGTTCGTCGGCGCCGCGGTCGATATTCAGCAGGCGAAGGATTACACCCC

GAGCCATGCGCTGCTTTACGTCCGCTACTCGGCGGCCGGCTGGCAGGGGGATCTGGATATGCCGCC

CCAGCCGCTGGTGCCCTACGCCGACTGGTAG

SEQ ID NO: 60
ATGAGCCAGGAATACACCGAAGACAAAGAAGTCAAACTAACCAAACTCAGCAGCGGGCGCCGACTCC

TTGAGGCGATGCTCATCCTTTGCTCCCTCTTCGCCATCTGGCTGATGGCGGCACTACTGAGCTTTAAC

CCCTCGGACCCCAGCTGGTCGCAAACGGCATGGCATGAGCCTATTCATAATTTAGGCGGCGCCCCCG

GCGCGTGGCTTGCCGATACCCTCTTTTTCATTTTTGGCGTCATGGCCTACACCATCCCGGTGATCATCA

TCGGCGGATGCTGGTTTGCCTGGCGGCATCAGGAAAACGACGAATACATTGATTATTTTGCCGTTTCC

CTTCGCCTCATCGGTGCGTTAGCCCTGATCCTGACCTCCTGTGGTCTGGCGGCGATTAACGCCGATGA

TATCTGGTACTTCGCCTCCGGCGGGTGATCGGCAGCCTGCTGAGCACCACGCTGCAACCCCTGCTG

CACAGCAGCGGCGGCACCATCGCCCTGTTGTGTATCTGGGCGGCCGGGCTGACGCTGTTCACCGGCT

GGTCGTGGGTCAGCATTGCGGAAAAGCTGGGCGGCGGCATCCTGTCCGTTCTCACCTTTGCCAGCAA

CCGTACCCGTCGGGATGATACCTGGGTCGATGAAGGCGAATATGAAGACGACGAGGAAGAGTACGA

CGACGAAGAGGCGGCCAGGCCGCAGGAATCGCGTCGCGCCCGTATCTTACGCAGCGCGCTGGCGCG

GCGTAAGCGTCTGGCCGAGAAGTTTACCAACCCCTATGGGCGTAAAACCGACGCTGCGCTTTTCTCC

GGCAAACGGATGGATGACGGCGAAGAGGTGGTGCAATACAGCGCCAGCGGGGCGCCTGTTGCCGCC

GACGATGTACTGTTTTCCGGCGCCAGCGCCGCGCGTCCCGCAGAGGATGATGTGCTGTTCTCCGGCG

CCAGCGCCGTGCGCCCGGGCGATTTCGACCCTTACGATCCGTTGTTGAATGGCCACAGTATCGCTGA

-continued

```
GCCGGTAAGCGCAGCGGCGGCGGCTACAGCCGCGCCGCAGGCGTGGGCAGAATCACCGGTGGGCC

ATCACGGCGCTGCGCCAGCTTATCAGCCGGAAGCCAGCTATCCGCCGCAGCAGGCCTATCAGCCTGA

ACCCGCTCCGTTCCAGCAGGCCTATCAGCCTGAACCCGCTCCGTTCCAGCAGGCTGCTTATCAGCCGC

CAGCGGGGCAAACCGCACCGCAGGCGTATCAGCCTGAGCCAGCGCCGTATCAACAGCCGGTTTACGA

TCCGCGTGCCGGTCAACCTGCGCCGCAGGCCTATCAGCCTGAGCCAGCGCCGTATCAGCAGCCGGCT

TACGATCCGTATGCCGGTCAACCTGCGCCGCAGGCCTATCAGCCTGAACCTGCGCCGTATCAGCAGC

CGGCTTACGATCCGCATGCCGGTCAACCTGCACCGCAGGCCTATCAGCCTGAGCCAGCGCCGTATCA

GCAGCCGGCTTACGATCCCTATGCCGGTCAACCTGCGCCGCAGGCCTATCAGCCGGAGCCAGCGCCG

TATCAGCAGCCAACTTACGATCCCTATGCCGGTCAGCCTGCGCCTCAGACCTATCAGCAGCCGGCTTA

CGATCCGAATGCCGGTCAGCCCGCGCCGCAGCCGTATCAGCCGGAGCCAGCGGCGTATCAGCCGCA

AAGCGCGCCAGTTCCCCCACCGGAGCCAGAGCCCGAGGTCGTGCAGGAGGAAGTGAAACGTCCGCC

GCTCTATTATTTCGAGGAAGTGGAAGAGAAGCGGGCGCGCGAACGCGAGCTGTTGGCCTCCTGGTAT

CAGCCAATTCCTGAGCCGGAAAGTCCGATTGCCACTAAACCGCTGACGCCGCCGACCACTGCGTCCA

AACCGCCAGTGGAGACAACCGTAGTCTCTGCGGTAGCGGCTGGGGTGCATCAGGCTACCGCCGCCA

GCGGCGGCGCGGCGGCAGCAACCTCGTCCACTGCCGCATCCGCTGCGGCTACGCCATTGTTCAGCC

CGGCGTCCAGCGGCCCAAGGGTTCAGGTGAAAGAGGGCATCGGTCCAAAACTACCGCGGCCCAATC

GCGTGCGTGTTCCTACGCGTCGGGAACTGGCCTCCTACGGCATCAAGCTACCGTCGCAGCGGGAGGC

GGAACAGCGCGCGGCAGGCGGAGCGCGATCCGCATTATGATGATGAGCTGCTCTCGGATGAGGA

AGCGGATGCTATGGAGCAGGATGAACTGGCTCGCCAGTTCGCCGCCACCCAGCAGCAGCGCTACGG

TCATCGCTGGGAAGACGATAACGCGACTGATGACGATGAGGCCGACGCCGCGGCGGAAGCGGAGCT

GGCGCGTCAGTTTGCCGCTACCCAGCAGCAGCGGTACGCTACCGAGCAGCCGCCGGGCGCCAACCC

GTTCTCGCCGGCAGATTATGAATTCTCGCCGATGAAAACGTTGGTCAATGACGGCCCGAGCGAACCG

CTGTTTACGCCGACGCCGGAAGTCCAGCCGCAGCAGCCGGCCCAGCGCTATCAACAACCGGCGGCC

GCTCCGCAGCAGGGTTATCAACCTGCGCAGCATCAGCCGATACACCATCAGCCTGTGCCGCCACAGC

CGCAGTCCTATCCGACTGCGTCGCAGCCCGTACAGCCGCAACAACCGGTTGCCCCGCAGGGGCATCA

GCCTGCCGCCCCTGCGCCGCAGGAGAGCCTGATCCACCCGCTGCTGATGCGCAATGGCGATAGTCGA

CCGCTGCAAAAGCCGACCACGCCACTGCCGTCGCTGGATCTGCTTACCCCGCCGCCGAGTGAAGTCG

AGCCGGTGGATACCTTTGCTCTCGAGCAGATGGCACGCCTGGTGGAAGCGCGACTCGCTGATTTCCG

CATTAAAGCGGATGTGGTGAACTACTCACCGGGGCCGGTGATCACCCGCTTCGAACTGAATCTGGCG

CCTGGCGTTAAGGCCGCACGGATCTCTAACCTGTCACGGGACCTGGCGCGATCGCTGTCAACGGTCG

CCGTGCGCGTGGTGGAGGTGATCCCGGGCAAACCGTATGTCGGGCTTGAGCTGCCGAATAAAAAACG

CCAGACCGTCTACCTGCGTGAAGTGCTCGACAACGCCAAGTTCCGTGATAACCCATCTCCGCTCACCG

TGGTGTTGGGTAAAGACATCGCTGGCGATCCGGTAGTAGCCGATCTGGCGAAAATGCCGCATCTGCT

GGTGGCCGGTACCACCGGTTCCGGTAAGTCTGTTGGCGTCAACGCCATGATCCTCAGCATGCTCTAC

AAGGCGCAGCCGGAAGATGTGCGTTTCATTATGATCGACCCGAAAATGCTCGAGCTGTCGGTCTACG

AAGGAATTCCGCACCTGCTGACGGAAGTGGTCACCGACATGAAAGACGCCGCCAATGCGCTGCGCTG

GAGCGTCAATGAGATGGAGCGCCGCTACAAGCTGATGTCGGCGCTGGGCGTGCGTAACCTCGCGGG

CTACAACGAGAAGATCGCCGAAGCCGCGCGCATGGGACGTCCGATCCCGGATCCGTACTGGAAGCCT

GGCGACAGCATGGACGCCGTACATCCGGTGCTGGAAAAACTGCCGTACATCGTGGTGCTGGTGGATG

AATTCGCCGATCTGATGATGACCGTCGGCAAAAAGGTGGAAGAGCTGATCGCTCGCCTGGCGCAGAA
```

-continued

AGCGCGCGCGGCGGGGATCCACCTGGTGCTGGCGACACAGCGTCCGTCGGTAGATGTTATTACCGG

CCTGATTAAGGCCAACATCCCGACGCGCATCGCCTTTACCGTGTCGAGTAAAATTGACTCACGTACCA

TTCTCGATCAGGGCGGCGCGGAATCGCTGCTGGGTATGGGGGATATGCTTTACTCCGGGCCGAACTC

TACCACGCCGGTGCGTGTCCACGGGGCGTTTGTGCGCGACCAGGAAGTCCACGCCGTGGTTCAGGA

CTGGAAAGCCCGCGGTCGCCCGCAATATGTGGATGGCATTACCTCCGACAGCGAAAGCGAAGGCGG

CGGTGGCGGCTTCGACGGCGGGGAAGAGTTGGATCCGTTGTTCGATCAGGCAGTCAACTTTGTGACC

GAGAAGCGCAAAGCGTCGATTTCCGGGGTTCAGCGTCAGTTCCGCATCGGCTATAACCGTGCCGCGC

GTATTATCGAACAGATGGAAGCGCAGGGTATCGTCAGCGAGCAGGGCCATAACGGTAACCGCGAAGT

GCTGGCGCCGCCGCCCTTTGAATGA

SEQ ID NO: 61
AUGAAGAAGUUAGCUUUACUCUCCGCCGUAAUGACGCUUGGAAUGUCGUCAUGGGCUUUUGCUGC

CGACAACCCGCCGCCGCCGGAAAAAGGCGCGCAGCAUCAGGGUAAACCGCCGGUGAAAAACG

GCCAACACGAAGGUAAGCAAGCGCAAUACAACAGAAAACAGCCACAACGAGACGGCAAACAGCCGC

AGCACGACGGUAAACAGCCGCAGCACAACGGCAAGCAGCCGCCAAAAGGGAGCGAGCACAGCGGG

AAACCGCUGCCGCCGAAAGCGUAA

SEQ ID NO: 62
AUGAAACGUUACGCAACCGCACUGCUCUUUUGCACUCUGUCGCUGACCAGCCUGGCCGCUCGCGC

CGAUAUUAUCGAUGACGCGAUCGGCAAUAUUCAGCAAGCCAUUAACGACGCCUAUAACCCCGGCAG

CAGUCGCUCCGAUGACGACGACAGAUACGAUGACGAUGGCCGGUAUGAUGACGGGCGCUAUCAGG

GGAGCCGUCAGCAGAGCCGUGACAGUCAGCGCCAGUAUGACGAGCGGCAACGCCAGCUGGACGAG

CGCCGCCGCCAGCUGGAUGAACGCCAGCGUCAGCUCGACCGCGAUCGUCGUCAGUUAGAAAGCGA

CCAGCGUCGUCUGGAUGAUAGCUACUGA

SEQ ID NO: 63
AUGUUCAGGUCACUGAUUCUGGCAGCAGUACUGCUGGCCGCAGGGCCACUGGUCGCUAACGCUGG

UGAAAUCACCCUGCUGCCAUCGGUAAAAUUACAAAUAGGCGAUCGUGACAAUUACGGUAACUACUG

GGACGGUGGCAGCUGGCGCGACCGUGAUUACUGGCGUCGUCACUAUGAAUGGCGUGAUAACCGU

UGGCAUCGUCAUGACAACGGCUGGCACAAAGGCUGGUACAAAGGCAGAGAUAAAGCCUGGGAGCG

CGGCUAUCGUGCUGGCUGGAACGACCGCGAUGACCACCGCGGCGGCUGGGGUCGCGGCCCGGGC

GGGCGCGGUCACGGUCAUGGACAUGGCCAUCACUAA

SEQ ID NO: 64
AUGAAGGAAAUCGGCUUACCGUUAUUGCUACUGACCGCGCUGGCCAGUCCGGCUUUUGCUGCAGA

CUGUCAGCCAAACGGCAUUGGCGGCUCGUUUUGCAUUAACGAUGACGGUACGACUACCGACACGG

UGCCUAACGAAGUCAACGGCAUGGAUACGUACUCGAAUAAUGGCGGCUAUACCAGUUCCCUGCCC

GAUCGGUCAGGGGCGGAUGAAGCACUGGAAGGUUCAUCGCUGUCGACGCAGCAAGGCGUCGGCA

GCGGACAGAGCGACAGUGCGCUGGCGGGUCGCGACUGGCAUUCGCCCGCCAAUCUGAAUGAUGGC

GCCGCCACCUCCAGUAUGAGCCUGCUGGAUAAACCCUGA

SEQ ID NO: 65
AUGAAUAUGAAAAAACUGACGACCCUUUUGCUCACCGCCACCUUAGGUCUUGCCAGCGGCGCGGC

CCUGGCGGCAGACACCGGCGCCCAGUCCAAUAAUGGCCAGGCCAACUCUUCCGCGGAUGCCGGUC

AGGUGGCGCCGGAUGCCCGUGAGAACGUGGCGCCGAACAACGUGGACAAUAGUCAGAUCAACUCU

GGCUCUGGGGGCACCACGGGCUCGACGAUGACCCAGGAUAAUAUGUCGAGCAAUGAGGUACAUAA

AAACUCGAUGUGUAAAGACGGCCGCUGUCCGGACACCGGUAAAAAACUGGACAACGGUGGCAAUA

CGACCCAAGACAACAGCAAAACCGACGGCACCACCCAGUAA

-continued

SEQ ID NO: 66
AUGAAACACCGCAUCGCUCUGCUUCUGGUCCUGACUUCACUUAGCGCCAGCGCCCUAGCCGCCUC

UCCCUGCCAGGAAAAAGAGCAGGAUAUUCAACGAGAGAUCAGCUACGCCGAAAAGCAUCAUAAUCA

AAGUCGCAUUGAUGGGCUAAAUACCGCGCUACGUCAGGUUCGGGAAAACUGUAGCGACAGUAAAC

UCAAAGCCGAUCAUCAGCAAAAAAUUGCCAAACAGCGGGAAGAGAUCGCUGAACGUCAGCGCGAUC

UGCAGGAAGCCCGGAAGAAAGGCGAUGCGGACAAAAUUAACAAACGCCAGCAUAAACUCAAUGAAG

CGCAACAGGAGUUAAAAACGCUGGAGUCUCGGGAUUACUAA

SEQ ID NO: 67
AUGCGACUCAUAACACGACACGUGAGAGAGGAUAUUAUGAAAAAAGCAAUGAUUGCGUUAUCGGC

UAUUCUGGUUGCGGCUCCGGUUUUUGCUGCGACAACACAUGCAACAGAUGAUACCGUCGCGGCGG

CGAAUGCCAACGCCAACACCGCUAAAGAGAAGCUGCAUCAGGCCCAGCACGAGGGCGAAGAGCAGC

AGCUGAAGGCGAAACACGCCGCCGAAGGCAAGCAGGACAGCGUCGGCAGCCAGGUGAGCGAAGGC

GCGCAGAAAACCUGGAACAAGACCAAAGAAGGCACCGAGAAGGGGUGGGAUAAGACCAAAGAGGU

CAGUGAAAAGGCUGGAACGCCACCAAAUCCGGUGCGGAAAAGGGCUGGGAUAAAACCAAAACCG

GCGCCGAAGAGUUAAAAAAUAAAGUGACUGAAUAA

SEQ ID NO: 68
AUGAAAAAGAUGAUUUCUCUGGCAGUAAUUUUAUCCUGUGUGCUGAGCGUCCCGGCCUUUGCCGA

UGGCCCGAACGACGGCCAUCGCCCGGAGCAGCCCACGGUGUGGCAGAACGGUCCGGACCAUGACG

GGCAUGCACCGCAGGGCGGACCUGACGCGCAUCAUCAGGGCGACCAUGACCAGCGUGGCCCGGAU

CGCGACGGCCAUGACAAACGCGAUCUGGCACGUCAUGAGCAGGACCAUUUCGCCUGGCGCGGGAA

CGAUUUCCGCAAAGGCCACCCGGCUCCGGCGCCGUUCCGUGGCGAUGAAUAUCGCGUCCGCGACU

GGAGCGACCGCGGCCUGCCGCCCCGCCGGAAGGCCAUCACUGGUCCUAUAUCGACGGUAACUAU

GUGCUGAUCGCCGCGGCGACCGGGAUCAUCACCUCGAUUCGGUGAGCGGCGCCCUCGGCCACUA

A

SEQ ID NO: 69
AUGAAAAAACCGACAUCCGCCACCCGUGGCAAAUCCGGCCGCAAGUCGCGUGAAGAGUUAAAUCAG

GAAGCUCGCGAUCGCAAACGGCAGAAGAAACAUCGUGGCCACGCGGCAGGCAGUCGCGCGAACGG

CGGCGAUGCGGCUUCAGCGGGUAAAAAACAGCGUCAGGCGCAAGAUCCGCGCGUGGGUAGCAAAA

AACCGAUCCCGCUGGGCGUGAGCGAAAGCAGCGUUCCAGCUCCCAAGCAGCAUAAACCAAAGAGCG

AGAAACCUAUGCUUUCACCGCAGGCUGAGCUGGAGUUGCUGGAGAAUGAUGAGCGCCUGGACGCG

CUGCUGGAACGUCUGGAAGAGGGCGGCACCCUGAAUGCUGAAGAGCAGAGCUGGGUGGACGCCAA

ACUGGAUCGCAUUGAUGAGCUGAUGCAGCAGCUCGGCCUCUCUUACGAUGAUGAAGAUGAAGAAG

AGGAAGAGCGUCAGGAAGAUAUGAUGCGUCUGCUGAAGGGUGGAAACUAA

SEQ ID NO: 70
AUGGCGAGUAAGUUUCAGAACCGUUUAGUCGGGACAAUCGUGCUGGUGGCGCUGGGGGUGAUUA

UCCUGCCAGGGCUGCUGGACGGGCAGAAAAAGCAUUACCAGGAUGAGUUUGCCGCGAUCCCGCUG

GUACCGAAACCAGGCGAUCGCGAUGAACCGGAUAUGUUGCCGGCGGCAACCCAGGCGUUGCCUUC

GCAACCGCCGGAAGGGCGGCGGAAGAGGUGCGGGCGGGCGAUGCCGCCGCGCCAUCGUUAGAU

CCAUCGCGUAUUCCGGUGAACAGCAACAGCUUCGAUGACGUUCAGGAGCCGGUGGUGGCCGCGAA

ACCGCAGCCCAAGCCGCAGCCGAAACCGCAGCCGCAACAGCAGGCCUCGACGCCAACGCCGCCGCC

GGCUAAGCCACAGCAGCAACAGCCACCGCAGCAGCAGGCGGCCCUGCCGGCGCCGACCGGCAAAG

CCUAUGUGGUUCAGCUGGGCGCGUUGAAGAACGCCGAUAAGGUGAAUGAGAUUGUCGGUAAACUG

CGGGCCUCGGGUUUCAAAGUCUAUACGUCGCCUUCGACGCCGGUACAGGGUAAAAUUACCCGCAU

```
CCUCGUCGGCCCGGAUGCGUCAAAAGACAAGCUGAAAGGCCAGCUGGGCGAUCUGCAGCAGAUCU

CCGGGCUUAGCGGGGUGGUGAUGGGCUUCACCCCGAACUGA
```

SEQ ID NO: 71
```
AUGGCACAACGAGAUUAUGUACGCCGCAGCCAACCGGCUUCUUCGCGGCGCAAAAAGAGCACGACC

CGAAGCUCAAGGAAUAAGCAAAGCAGCCUUCCGGCGAUUUCACCGGCGAUGGUGGCGAUCGCGGC

GGCUGUGCUGGUGGCCUUUAUCGGUGGCCUCUAUUUCAUUACGCAUCAUAAGAAAGAAGAAGCGG

AAGCGAUGCAAAAUCGCCAGGCCGCCGGCAACGGCUUGCCGCCCAAACCGGAAGAGCGCUGGCGC

UAUAUUAAAGAGCUGGAAAGCCGCCAGCCUGGCGUCCGCGCGCCGACCGAACCGACCGCCGGUGG

CGAAGUCAUGAAACCGGAACAGCUGACCGACGAGCAGCGCCAGCUGCUCGCCCAGAUGCAGGCCG

AUAUGCGCCAGCAGCCGACCCAGCUGACCGAAGUGCCGUGGAACGAACAAACGCCGGCGCAGCGC

CAGCAGACGCUUCAGCGUCAGCGUUUAGCGCAGCAACAGCAGCAGGCGCAGCAGCAACAGUGGGC

GCAGACUCAGGCGCAGACCGUCCAACAGCAGCCGCCGCGCGUUCAGCAGCCGAAGCCGGUUCAGC

AGCAACAGCCGAAGCAGACCGCGUCAAACCAGCAGCCGUACCAGGAUCUGCUGCAGACGCCAGCGC

AUACCAAUACCACGCAGCCGCGUACCCAGGCCGCGGCGCCGGUAACUCGGGUGGAAGAAGCGCCG

AAAACCACCGCCGAGAAGAAAGACGAUCGUAGCUGGAUGAUCCAGUGCGGCUCUUUUAAAGGCGC

CGAGCAGGCCGAAACCGUCCGCGCUCAGCUGGCUUUCGAAGGGUUUGCUUCGCACAUUACCACUA

ACAACGGCUGGAACCGCGUGGUUAUUGGCCCGUUGAAAGGCAAAGAAAGCGCCAACGAGAUGAUC

ACCCGCCUGAAGAUGGCUGGACACGCGAACUGCAUUCGUCUCGCCGCCAGGGGUUGA
```

SEQ ID NO: 72
```
AUGAGCGCGGGAAGCACCAAAUUUACCGUCAGCCGUAUUGCGGCUCUUUCACUGGUUUCACUCUG

GCUGGCCGGGUGUACCAACACCAAUAAUCCGCCUGCGCCGGUUAGCUCUGCCGGCGGCGCCGCCU

CUUCCAGCACCAACUCCGGCAUGCUGAUUACGCCGCCACCCUCCGGCGUCAAGUCCGCUCCUCAGG

CGCAGCCGAUUCAGCCGAUGCAGACCCAGACCAUUCAGCCGGCGCCGGUGGCGCAGGAGCCGGUA

CAGACGGUAAAUGGCCGGAUCGUUUACAACCGCAAAUAUGGCGAUAUUCCGAAAGGUAGCUAUAC

CGGCGGCAGUACCUAUACGGUAAAACGCGGCGACACGCUAUUCUAUAUCGCCUGGGUCACCGGCA

ACGAUUUCCGCGACCUGGCGCAACGUAACAAUAUCCCGGCCCCGUACGCGCUGAACGUGGGGCAG

GUACUGCAGGUCGGUAACGCCUCAGGCCAGCCGAUCACCGGCGAAAACGCCGUUUCUCAGGCCAG

CGCAAGAGCGAGCGGCGGUGCGACGACCAGCACAACUUCUGCACAAAAAUCGACCGCGGUGGUUG

CUUCACAACCGACUAUUACGUAUUCUGAAUCUUCAGGUGAACAGAGUGCUACCAAGAUGUUGCCUA

AUAAUAAACCAGCGACCACAACCACAACGGUUGUCGCGCCGGUGACGGCACCAACAACGGUGAGCA

CAACCCAGCCGACUGCAAGCAGUACGUCAACCAGUUCGCCGAUCUCAGCAUGGCGCUGGCCGACU

GAUGGCAAGGUUAUCGAGAACUUUAGCGGCGCGGAAGGCGGCAAUAAAGGCAUCGAUAUUGCAGG

CAGUAAGGGACAGGCUAUUGUCGCGACCGCCGAUGGGCGCGUCGUCUAUGCCGGUAACGCACUGC

GCGGCUACGGUAAUCUUAUUAUCAUCAAACACAACGAUGAUUACCUGAGUGCCUACGCUCAUAACG

AUACCAUGCUGGUUCGGGAGCAACAGGAAGUCAAAGCGGGGCAGAAAAUCGCUACCAUGGGUAGC

ACCGGAACCAGCUCAACAAGAUUACAUUUUGAAAUUCGUUACAAGGGGAAAUCCGUCAACCCGCUG

CAGUACUUACCGCAGCGAUAA
```

SEQ ID NO: 73
```
AUGCGUAAGCAAUGGCUGGGGAUCUGCAUAGCAGCGGGGCUGCUGGCGGCAUGUUCGAGUGAUG

ACGUGCAACAAAAAACGGUCAGUACUCCACAGCCGGCCGUCUGUAAUGGCCCGACGGUUGAGAUC

AGCGGCGCCGAUCCGCAGUAUGAAACGCCGAACGCCACGGCGAAUCAGGAUUAUGAGCGCGACGG

UAAAAGCUACAAAAUCGUUCAGGAUCCGGCCAACUUUACUCAGGCCGGUUUCGCGGCGAUCUAUG
```

-continued

ACGCAGAACCCAACAGCAACCUGACCGCCAGCGGCGAAGCCUUCGAUCCGACUCAGUUGACCGCAG

CGCACCCGACGCUGCCGAUCCCGAGCUACGCGCGGAUCACUAACCUUGCCAACGGACGGAUGAUC

GUCGUGCGGAUUAACGAUCGCGGUCCCUAUGGCAACGAUCGGGUCAUCUCGCUUUCCCGCGCAUC

CGCUGACCGCCUGAACACCUCCAACAACACCAAAGUGCGCAUCGACCCCAUCAUCGUCGCGCCUGA

CGGUUCGCUUUCCGGCCCGGGGAUGGCCUGUACCACCGUCGCCAAACAGACUUACGCCCUGCCCG

CCCGUCCGAAUCUGGACGGUGGGGACGCCGCUGGCAUGAGCCAGCCCGCGCCCACUGACGUUCGC

CCGAUCAGCAACAGCACGCUGACGCCGGCAGACAGCGUGGGCGCGCCGGUGAACAGCGGCGGUUU

CCUCGGCGCGCCGACGCCCCUGAACAACGGCGUGCUGGAGAGUAGCGAACCAGCGGCAGCCGCCG

CGACGGCUCCUGCCGCCGGCGCCACGCCAACAGCGCCAGUGACCGCGCCUGGCUCCAUUCAGGGU

AAUGUGGUGCCCGCUGCGGCCACCGCCGCAGCCGCUGGCGCCGUGGCGGCCUCGUCCUCCGCGAC

CUCCAGCGCCAGCGGUAAUUUUGUUGUCCAGGUGGGCGCAGUAAGCGACCAGACGCGGGCGCAGC

AGUAUCAGCAGCGCCUGAGCCAGCAGUUUUCUGUGCCAGGCCGGGUCAUGCAAAACGGCGCGGUC

UGGCGUAUUCAGCUGGGUCCCUUUGCUGAUAAAGCACAGGCCAGCGCCGUGCAGCAGCGCCUGCA

AAGCGAAGCGCAGCUGCAGUCCUUUAUUACUCGCGCCAACUAA

SEQ ID NO: 74
AUGGAUGAUUUCAAACCAGAAGACGAUAUGAAAGCCGAUCGCAACGAUCGUCGUGCUGGUCGUUC

CCGUCAGUCUUCCGAGCUGAUGCCGAUCCGCAGAUCAAUUUUGACGAUGUUGAUCUUGAUGCCG

AUGAAGGCCGUCCGACGCGCGCUGGUAAGGCCCGUCGCGAGCGUGAAGAGGAAGAGUUCGAAGAA

GAACUGGAUGCGCAAGACGAGGAGAUGCUCGAAGAGCAGCCUGUAGAGCGUCGUCCGCGCAAGCG

UAAAAAAGCGCCGGCCAAACCGGCCUCCCGCCAGUACAUCAUGAUGGGUGUGGGGAUUCUGGUGC

UGCUGCUGUUGAUCGUGGGUAUCGGUUCCGCACUGAAAUCGCCAUCAUCUUCCAGCCAGCAGACC

GCUUCCGGCGAGAAGAGCAUUAAUCUGUCUGACGACCAGUCCGCCAGCAUGCCUGCUGCCGGCCA

GGACCAGACUGCCGCCGCUAACAGCACCUCACAGCAGGACGUAACGGUACCGCCUAUUGCCGCGAA

CCCGACGCAGGGCCAGGCAGCGGUUGCGCCGCAGGGCCAGCAGCGUAUCGAAGUUCAGGGCGAUC

UGAACAAUGCCUUGACCCAGCAGCAGGGCCAACUGGACGGCGCCGUGGCUAACUCGACGCUGCCG

ACUGAACCGGCUACCGUCGCGCCAAUCCGGAAUGGCGCCAAUGGCACCGCGGCGCCGCGCCAGGC

GACCGAGCGUCAGACAGCAGCGACCCCGCGUCCGGCUGAACGUAAGCAUACCGUUAUCGAAGCGA

AGCCGCAGUCGAAGCCACAGGCCGUGGCGAAAACGCCGGUAGAAUCGAAGCCGGUCCAGCCGAAG

CAUGUUGAAAGCACGGCGACCACCGCUCCGGCGAAAACGUCCGUCAGCGAAAGCAAACCGGUGGC

CACCGCUCAGAGCAAACCGACCACGACGACCGCAGCGCCAGCGGCAACGGCAGCUGCGGCAGCGC

CGGCAGCGAAGACCGGGAAGACGGCAGGUGACGUCAGCUCAAUGAAAACUGCGCCGUCGGGUCAC

UAUACUCUGCAGCUCAGCAGCUCCUCUAACUACGACAACCUCAACAACUGGGCGAAGAAAGAGAAG

CUGGAUAAAUAUGUUGUCUAUGAAACGUCGCGUAACGGCCAACCAUGGUACGUGCUGGUGAGCGG

UAUCUAUGCAUCGAAAGAUGAAGCGAAACGUGCUGUCACCUCGCUGCCGGCGGACGUGCAGGCGA

AAAAUCCAUGGGCAAAACCGCUGCAUCAGGUUCAGGCUGACCUGAAAUAA

SEQ ID NO: 75
AUGUCAAAGGCAACCGAACAAAACGACAAGCUUAAACGAGCGAUCAUCAUUUCAGUCGCGCUGCAC

AUCAUUCUGAUCGCGCUGCUGAUCGGAGUUCGUUUGACGAGCAUCGGAUGCCUCUGCCGGCGG

CGGCGGCGGAUCGUCGAUUGAUGCCGUCAUGGUCGAUCCGGGGGCGGUGGUAAAUAACUAUAACC

GUCAGCAACAGCAGCAGGCCAGCGCACGUCGCGCCGCUGAACAGCGUGAAAAACAGGCGCAGCAG

CAGGCGGAAGAGUUACGUGAGAAACAGGCGGCGGAACAGGAACGGCUGAAACAGCUCGAACAGGA

GCGGCUGCAGGCGCAGGAAGCGGCGAAAGAAGCGAAGGAGCAGCAGAAGCAGGCUGAAGAAGCGG

-continued

CUGCCAAGGCCGCCGCGGCGGCAAAAGCCAAAGCGGACGCACAGGCAAAAGAAGCGCAGGAAGCC

GCUGCCAAAGCGGCCGCCGAGGCGAAAGCGAAGGCGGAUGCCCAGGCGAAAGCGGCAGAACAGGC

GGCGGCCAAGGCGGCUGCUGACGCGAAAAAGCAGGCCGAAGCCGCUGCAGCGAAAGCCGCUGCCG

AGGCGAAGAAACAGGCGGAAGCUGAAGCGGCGAAAGCUGCGGCCGAGGCGCAGAAGAAAGCGGAA

GCGGCGGCUGCGAAGAAAGCGCAACAGGAAGCGGAGAAAAAAGCCCAGCAGGAAGCGGCUAAGCA

GGCGGCAGCUGAAAAAGCGGCUGCCGAAAAAGCCGCUGAGAAAGCCGCCGCGCAAAAAGCGGCCG

CUGAGAAGGCCGCCGCCGAGAAAGCCGCAGCCGCUGAAAAAGCGGCGGCAGCGAAAGCGGCUGCA

GCAGAGAAGGCUGCAGCUGAUAAAGCGGCCAAAGCGGCAGCAGCAAAAGCCGCGGCGGCGAAGAA

AGCGGCGGCUGCGAAAGAAGCGGACGGCGUUGACAACCUGCUCGGCGAUCUGAGUUCUGGUAAGA

AUGCGCCUAAAACAGGCGGUGGGGCCAAAGGAAACAAUGCCUCCGCUGCCGGGAGUGGUAAUACU

AAAAACAGUGCCUCAGGGGCUGAUAUCAACAACUAUGCCGGACAGAUAAAAUCGGCGAUUGAAAGU

AAGUUUUAUGACGCAUCGUCCUAUGCGGGCAAAACAUGUACCUUGCGUAUCAAACUUGCUCCUGA

CGGCCUGUUGUUAAAUAUACAGUCCGAAGGUGGUGAUCCUGCUCUGUGCCAGGCCGCUCUUGCCG

CAGCCCGACAGGCUAAGUUUCCGAAACCACCUAGCCAGGCAGUAUAUGAAGUCUUCAAAAAUGCGC

CACUGGACUUCAAACCUCAGUGA

SEQ ID NO: 76

AUGUUUUUUUUAAGUAUUUUUUACAUGGAGAUGACAAAAGUGAAAUUAAGCGCUCUGUUUAUUGC

CCUGAUUCCUCUACUGGGCUCGCCGGUUAUUCAUGCAGAAACUACUGCUGCGCCGGUUCUGGAAA

AUCGCGCUGCGCAGGGAGAUAUCACCACUCCUGGCGGCGCGCGUCGUUUAACAGGCGAUCAAACC

GAAGCGCUGCGCGCCUCGUUAAUCAAUAAGCCAGCUAAAAACGUUAUUUUGCUGAUUGGCGAUGG

CAUGGGUGAUUCGGAAAUUACCGCUGCGCGAAACUAUGCCGAGGGGCGGGCGGUUUCUUUAAA

GGAAUUGAUGCUCUGCCGUUAACCGGGCAGUACACGCAUUAUUCGCUGGAUAAAAAAACCGGGAA

ACCGGACUACGUGACCGACUCGGCGGCCUCCGCCACCGCCUGGACCACCGGCGUGAAGACUUAUA

ACGGCGCGCUGGGCGUCGAUAUUCAUGAGAAUGCGCAUCAGACCAUCCUCGAGCUGGCGAAAGCG

GCGGGGCUGGCCACCGGCAACGUUUCCACCGCCGAGCUGCAGGACGCCACCCCCGCGGCGUUGGU

AGCGCAUGUGACAUCGCGUAAAUGCUACGCCCGACGGUCACCAGCGAAAAAUGCCCCAGCAAUGC

GCUGGAAAAAGGGGCAAAGGCUCCAUUACCGAACAGCUGCUGAACGCCCGACCGGAUGUCACCU

UGGGCGGCGGCGCGAAGACCUUUACCGAAACGGCGACGGCGGGCGAGUGGCAGGGCAAAACCCU

GCGCGAGCAGGCGCAAGCGCGCGGCUACCAGAUUGUGACCGACGCGGCUUCUCUUGCCGCCGCGA

CGGAAGCCAGUCAGGAUAAACCGCUGCUGGGACUCUUUGCCGAUGGCAAUAUGCCGGUACGCUGG

GAAGGGCCGAAGGCGUCUUUAUCACGGUAAUAUCGAUAAGCCGCCGGUGACCUGUACGCCAAACCC

GAAGCGUGACGCCUCGGUGCCGACGCUGGCGCAGAUGACGGAGAAAGCGAUUGACCUGCUCAGUC

GCAACGAGAAAGGGUUUCUUCCUGCAAGUCGAAGGCGCUUCCAUCGAUAAGCAGGACCAUGCGGCG

AAUCCGUGCGGCCAGAUCGGCGAAACGGUUGAUCUUGACGAAGCGGUGCAGAAGGCGCUGGAAUU

CGCGCGAAAAGACGGUAAUACCCGGUGAUCGUCACCGCCGACCAUGCGCAUGCCAGCCAGAUCA

UCCCGGCGGAUAGCAAAGCCCCGGGGCUGACCCAGGCUCUGAACACGCACGAUGGCGCGGUGAUG

GUGAUGAGCUACGGCAACUCUGAGGAAGAGUCGAUGGAGCACACCGGCACCCAACUGCGCAUUGC

GGCCUACGGUCCGCAUGCGGCUAACGUCGUAGGCCUGACCGAUCAGACCGACCUGUUCACGACCA

UGAAAGCUGCCCUGAGUCUCAAAUAA

SEQ ID NO: 77

AUGUCACUGCCGUUCAAACCCCAUAUUAUCGCCCUGCUCUGUAGCGCUGGCUUACUCGCGGCGGC

-continued

AGGAACACUCUAUGUGCAAAGCCGAACCCCAGCGACGAUCGCUGAACCGCCUGCGCAGCAAGCGCC

AGCGCCCGCAGCGUCGACGACACAGCCGGUGGCCGCCACUUACACCCAGGCGCAAAUUGAUCAGU

GGGUCGCCCCUAUCGCGCUCUACCCGGACAGCCUGCUGUCGCAGGUGUUGAUGGCCUCCACUUAU

CCCGACAACGUCCUGCAGGCGGUCCAGUGGUCCCAGGAUAACCCCGCGAUGAAAGGGGAUGCGGC

CGUGCAGGCGGUUGCCAGCCAGCCGUGGGACCCUAGCGUCAAAUCUCUUGUCGCUUUCCCUGCCC

UGCUGGCGAUGAUGGGCGAGAAUCCGCCCUGGGUGGAAAAUCUUGGCAAUGCGUUUUUGGCCCA

GCCGCAUGAUGUGAUGGAUUCAGUGCAGCGCCUGCGCGCCAUUGCCCAACAAACCGGGACGCUGA

AAUCCACACCGCAGCAGAAAGUGAUUGUCACCCCUGCCGCACCGGUUUCAGCCAGCAGCAGCACGG

CAGCAACCGCAACCGCCCACACAGCGGCGCCUGCGCCCACGCAGGUCAUUAAAAUAGAGCCGACCA

AUCCACAGGUGGUCUAUGUUCCCAGCUAUAACCCCUCCACCGUCUAUGGUACCUGGCCGAACAGC

GCCUAUCCGCCGGUCUAUCUGCCGCCCCCUCCCGGGGAGCAGUUUACCGAUAGCUUCGUCAAAGG

CUUCGGGUACAGCCUCGGCGUGGCCACCACCUGGGCGCUGUUCAGCAGUAUCGACUGGGAUGAUG

AUGACCAUCACCAUCACGAUGACGACUACCACCACGGCGAUUACUCGCAUAAUGGCGAUAACAUCA

AUAUUAAUGUAAAUAAUUUCAAUCAUAUAACAGGAGAAAACCUGCCGGGAAACCACGUUAACUGGC

AGCACAAUCCUGCCUAUCGCGGACACACACCGUAUCCCGAUAAUACGGUAGCUCAGCGCUUCCAUC

AGACCAACGUUUCCGGCGGACUGAGCGCGACCCAACAUGCGCCAGUCGAUCGCGAAGCGCAGCGC

CAGGCAGCGAUGACCCAGCUGCAGCAUAACGUACCGACGGCCACAGCGGGCAACCUGGCGGCAAA

CAACGCCUCACGCGACGCCCAGCGUCAGGCGGCCUCGGCGCAGCUGAAGCAAGCCACCCAACGCA

GUAAUUACCGCGGUUACGACAGUACGCCGACCCAACAGCAGCGUCGCGAGGCGGCAAAAACGCAG

CUGAAAAACCCCACGCCGCAGCAACAGCAGCGUCGAGAAGCCGCCAGGAGCCACGAGCAGAACCGC

ACACCCUCAGCAGCAGCAGCGCCGGCAGCAGUUCCAGUCCGCCACGCCAGCCCAGCGUCAGCAGACG

CUCAGCCAUCUGCGCGCCAACGCCCUUAGCGGCAACGAAAGCCGCGCCCCCUCCUGGCAAGCGCAG

CAGGAACGAGGACUGCAGAGCCGCCAGUUUUCCGGCGUAAACCGCGAGUUACGCGAUGGCACCAG

AGAACGUCUUUCCGAACACCAUGAACUGCGUCGCCGCUAA

SEQ ID NO: 78

AUGUUUAAGUUUAAGGCUUCUUAUGUCGCACUGGCGGCAGUAUUAACCUCGUCGGUAGUUUAUGC

CGACCCCACAAGCUAUACGCACUCUUCCGGCGCCACGGUUAUCGAUAUUGAAAAGCCGAACGCCGC

CGGUGUCUCCCAUAACCUGUACCGCGACUUCAACGUCGGCGCCAAUGGCACCAUCCUCAAUAACAG

CGGCGAUGAUGUCAGCCACAGCACAUUUGGCAAUAUCGCCCGCAACAAUAAUCUGACCGCCGGCAG

CGCUUCGGUGAUUUUGAACGAGGUGACCUCCAAAAACGCCAGUAGCCUGAAGGGCUUUAUCGAAG

UCAACGGUCAGAAAGCGGAUGUGGUAAUCGCCAACCCGAACGGCAUCACCUGUUCCGGCUGUAGC

UUUGUUAAUACCAACAAGGCUAUCCUGACCACCGGCAAGGUUAAUAUGACCGACGAUGGCGCUAUC

GGCAGCUAUACCGUAACGGGCGGCACCCUCACCAUCGGCGAAAAUGGCAUGAACGCCGCCAACGG

CUAUGCGGUUCUGCUCGCCGACGCGAUCAAUAUCAACGGUAAAGUGCAGGCCAACAACGCCCUGG

UCAGCGCGGGCAACUUCACCAUGGAUAACAGCUCUGGCUCGGUGACCUCCGCUGGUAAAAAGGCC

ACCCUGAUCCAGAUGACGGUUAACCCGCAGUACAGCAUCGACGUCAGCAGCCUUGGCGGCAUUGA

GGCCAACAGCAUCAGCAUGGUCGGCAAUAACAUCGGCUUUGGCGUACGUAAUAAAGGCUCUAUCG

UCGCGAAUAGUUCGCUGCAGCUCACCAGCAACGGUAAUCUGCUGAACAAAGGCACGAUCAAAAGCA

ACGGUCUGCUGAGUCAGGUCGCCACCGCCUCGGGCAUCACCAAUGACGGUAGCAUCGCCGGCGCC

UAUUAUUUAAUGCUCUCCAGUGGCGAUUAUAUCGUUAACACCGGUUCUCUCUCCGGCGGCCAGCU

GAUUGCCACCGCUAACGGCAACAUCACCAACGGCGACUCAGGCACGAUGACCGGCACCAGUGGAUU

-continued

AAGCCUGACCAGCGGCGGGAAAAUCCGCAACGAAGAAAAAGCCUCCCUGCUGUCAAAUAACCAGAU

UGCCGCCACGGCAAUCGGUGAUUUCCUCAAUGAAGGCAAAAUCAGCGCCAAACACACCAGCCUGAC

GUUUGUCGGCGACAGCUUUAAAAACACUGGCAAUAUUAACUCUACUGGCCAAACCACCAUUCAGUC

GCUUAAACAGGACGGCAGCGCCAAUACGGGCGAGAUCUAUAACCUCGGCAAUAUCACCGGCGAAAA

UAUCAAUCUGCAGACCAAUGGCACGCUGGCGCAAAGCAGCAGUGGUCGUAUUGAGGCAACCAACG

CCAUUACCGCCCACAGCUACUGGCUGAACCAAAAUGGUUAUAUGAAUGCCGCCGAUAUCACCACCG

AUCACGGCGUAGUGAAUAAUUAUGGCAAUAUUACUGCCAAAAAUAUUUCAAUCACGACCUACUCAG

AUAUCACCAACGAAGGGCAGAUCAGCAGCACCGGCGACCUGACCUUAAAUACCAAAAAUAAAGGCG

CGAUCUACAAUUAUUCAACCCUCAGCGCGGGCGGCAACAUGACGUUAACCGCCACCAAAGUGGUCA

AUGGUGGUAAAAGUUGCGGCAUACUGGGCCUGGCGAAAUGCGGCGUCGGGACGUUAACUGCUGA

CAAGCUGGUACUGAACUCAUCGCAGAAAUAUGUUAGCGACAUGGGUGGAAAACAGUAUUUCAAGA

GCACCGAAGUCAACACGGUGAAAUAA

SEQ ID NO: 79

AUGAUGGACAACCUACGCACGGCCGCCAACAGCGUCGUGCUCAAGAUUAUUUCGGUAUCAUUAU

CGUCUCGUUCAUUUUGACCGGGGUGAGUGGUUACCUGAUUGGCGGUGGCAAAAACUAUGCCGCAA

AAGUGAAUGGCCAGGAGAUUGGCCGUGGGCAGUUUGAAAACGCCGUCGCCAGCGAACGUAACCGU

AUGCAGCAGCAGCUUGGCGAUCAAUUCUCCGAGCUGGCGGCGAACGAAAACUACAUGAAAACCAU

GCGCCAGCAGGUGCUGAACCGCCUGAUCGAUGAGUCGCUUCUGGAUCAGUAUGCCCGCGAGCUGG

GCCUCAGCAUCAGCGAUGAGCAGGUGAAGCAGGCGAUCUUCCAGACCCAGGCGUUCCAGACGAAC

GGUAAGUUCGACAACCAGCGUUUCAGUGGUAUUGUCGCCCAGAUGGGGAUGACCACCGAUCAGUA

CGCCCAGGCGCUGCGUAACCAGCUGACCACGCAGCAGCUGAUUAACGCCAUUGCGGGUACCGACU

UCAUGCUGCCGGGCGAGUCCGAUCAGCUGGCGGCGCUGGUAUCUCAACAGCGGGUGGUCCGCGA

AGCGACCAUCAACGUAAAUGCCCUGGCGGCAAAACAGACCGCCAGCGAUGAGGAAAUCAACGCCUU

CUGGCAGCAGAAUCAGGCCCGUUUUAUGGCGCCGGAGCAGUUCCGCGUCAGCUACAUCAAAAUGG

AUGCCGCCAGCAUGCAGGAGAGCGCCUCUGACGAAGAGAUUCAGUCAUGGUACGACCAGCACAAG

GAUCAGUUCACUCAGCCGCAGCGCAACCGCUACAGCGUGAUUCAGACCAAAACUGAAGCCGAUGCG

AAAGCGGUACUGGCCGAGCUGCAAAAAGGAGCGGACUUCGCCACGCUGGCGAAAGAAAAAUCGAC

CGAUAUUAUCUCUGCCCGCAACGGUGGCGAUAUGGGGUGGAUGGAAGAUGCCUCUACCGUGCCUG

AGCUGAAAGAUGCCGGGCUGAAAGAGAAAGGCCAGCUGUCUGGCGUGAUCAAAUCCUCGGUUGGC

UUCCUGGUAGCUCGUCUGGACGACGUCCAGCCGGCGCAGGUGAAGCCGCUGGCUGACGUGCGUA

AUGACAUUGCGGCGAAAGUGAAGCAGGAAAAAGCGUUGGAUGCUUACUACGCGCUGCAGCAGAAG

GUGAGCGAUGCGGCCAGCAACGAUAAUGAAUCGCUGGCGAGCGCAGCGCAGGUCGCCGGGCUGAA

GGUCGUAGAAACCGGCUGGUUUGGCCGCGAUAACCUGCCGGAGGAGCUGAACUUUAAACCGGUCG

CUGACGCUAUUUUCAACGGCGGUCUGGUGGGUGAGAACGGCGCGCCGGGCAGCAACUCCGAUAUC

AUUACCGUUGACGGCGAUCGCGCUUUUGUUCUGCGCAUUAGCGAACACAAAGCCGAGGCGGUGAA

GCCGCUGGCCGAAGUGAAGGCACAGGUUAGCGAUAUCGUUAAGCACAAUAAAGCGGAACAGCAGG

CGAAACUGGAGGCCGACAAGCUGCUGGCGGCGCUGAAAGACGGCAAAGGCGAUGAAGCGAUGAAG

GCGGCUGGCCUGAGCUUUGGCGCGCCGCAGACGCUUUCUCGUACCGGCCAGGAUCCGCUGAGCCA

GCUGGCAUUUACCCUGCCGCUGCCGCAGCAGGGUAAACCGGUCUACGGCGUGGGCAGCAAUAUGC

AAGGCGAUGUGGUGCUGGUAGCGCUGGAUGAGGUGAAAGCCGGCAGCAUGCCGGAAGAGCAGAA

GAAGGCCAUGGUUCAGGGGAUCACCCAGAACAAUGCCCAAAUCGCUUUCGAAGCGCUGAUGAGCA

-continued

ACCUGCGCAAGGCGGCGAAAAUUAAGCUCGGCGACAGCAUCGACCAGCAGCAGUAA

SEQ ID NO: 80

AUGUUCAGGUUAAACCCUUUUAUCCGGGCGGGAUUGUCUGCGUCCGUCGUAUCGUUGGCGUUUCC

GGCUCUGGCCGAUGUGAAUGAAGAAACGCUGGUGGUGACCGCCUCGGCCACUGAACAGAAUGUCA

AAGACGCGCCGGCGAGCAUCAGCGUCAUCACCCAACAGGAUUUACAACGCAAGCCUGUUCAGAACC

UGAAAGACGUGCUGCGCGAUGUGCCUGGGGUCCAGCUCACCAACGAAGGGGAUAACCGCAAGGGC

GUUAGCAUCCGCGGUCUGAGCAGCAGCUAUACCCUGAUCCUGGUCGACGGCAAGCGCGUUAACUC

GCGGAACGCCGUCUUCCGCCACAAUGACUUCGACCUUAACUGGAUCCCGGUGGAUGCUAUUGAGC

GUAUCGAAGUGGUGCGCGGCCCGAUGUCCUCCCUCUACGGCUCCGAUGCGCUCGGUGGGGUGGU

CAACAUUAUUACCAAAAAAAUCGGCCAGAAAUGGACCGGGACGCUGAGUGCUGAUACCACUAUUCA

GGAGCACCGCGAUCGCGGGGAUACCUGGAACGGCCAGUUCUUCACCAGCGGCCCGCUGAUCGACG

GCGUACUUGGAAUGAAGGCCUACGGCAGCCUGGCAAAACGCGCCAAGGACGAUCCGCAGUCAUCC

AGUAAUGCCACCGGCGAGACGCCGCGCAUCGAGGGCUUCACCAGCCGCGAUGGCAAUGUUGAAUU

CGCCUGGACGCCGAACGAAACCACGAUUUUACCGCAGGCUACGGCUUUGACCGUCAGGAUCGCG

AUUCCGAUUCCCUUGACCGCAACCGCCUUGAGCGGGAGAACUACUCUCUGACCAUAACGGCCGC

UGGGAUAUCGGCAAUAGCGAGCUCAAGUUCUACGGCGAAAAGGUGGAUAACAAAAAUCCAGGGCA

GAGCGGGACUAUUACCUCGGAAAGCAAUGCCAUCGACGGCAAGUAUGUCCUGCCGCUGGGCAUGA

UUAACCAGCUGGUGACCUUCGGCGGCGAAUGGCGCCACGACAAACUUAAAGAUCCGGUCAACCUG

AGCAGCGGCGGCCAGUCAACGUCGGCCAGCCAGUACGCCCUGUUUAUCGAAGACGAAUGGCGCAU

CAUCGAGCCGCUGGCGCUGACCACCGGCAUUCGUAUGGACGACCAUCAGACCUAUGGCGAUCACU

GGAGCCCGCGCGCCUAUCUGGUGUAUAACGCCACCGAUACCGUCACCGUCAAAGGCGGCUGGGCG

ACGGCGUUUAAAGCCCCGUCGCUGCUGCAGCUUAACCCCGACUGGACCACCAACUCCUGCCGCGG

CUCGUGCAGCAUCGUCGGUAAACCCGGAUCUGAAACCGGAAACCAGCGAAAGCUUCGAGCUCGGUC

UCUACUACCGCGGGGAAGAGGGCUGGCUUGAAAAUGUCGAAGGCAGCAUCACCACCUUCCAGAAU

AAUGUCGACGACAUGAUCGACGUUCUGCGCACCUCCAGCGCCAGCGAAGCGCCGGGCUACCCGAA

CUUUGUCGGCUGGAAAACUGUCAACGGCAAGCGCGUGCCGAUCUUCCGCUAUUUCAACGUCAACA

AAGCCCGCAUCAAAGGGGUGGAGACGGAGGUGAAGAUCCCGUUUGGCGAUGAGUGGAAGCUGAC

GGUGAACUACACCUACAACGAUGGUCGCGAUCUGAGCAAUGGCGGCGACAAACCGCUGCAGACGC

UGCCGUUCCAUACCGCCAACGGCACGCUCGACUGGAAACCGCUGGACGACUGGUCCUUCUACGUG

ACGGCCAACUAUACCGGCCAGCAGCGCGCGGUGAGCGCCACCGGCAAAACGCCGGGCGGCUACAC

CCUGUUUGACGUUGGCGCGGCAUGGCAGGUGACCAAAAACGUGAAACUGCGCUCCGGGGUGCAGA

ACGUGGGUGAUAAAGAUCUGAGCCGGGACGACUACAGCUAUACCGAAGAAGGCCGUCGCUACUUU

AUGGCGGUGGAUUAUCGCUUCUGA

SEQ ID NO: 81

AUGAACAGAGCCGCCACGCUGACCCUCAACGCGCCCCUGCUGAUGCUCGUCGCUGCGCUGGCGCU

UUCAACCCCUUUCACCGCCGGCGCCGCGCCGGCCUUUCUUGAUUACGCCCAACAGCAAACCCAGCA

AUCUCAGGCGCAAGAAAAAAACGAUGCCGCAAGCGCAAAACAAACACAAGAAAGCCGCCAGAGCGC

AGAUAAUAAAAAACCGGUACCAGCACCUCACAAUUACAAAAAGAAUCACCAGCCAGCAGGCGGC

GAUUGCACAAAAAGAUAAGCUUAUACAGCAAUUAAAAAAACAGCUUGCCGCUACGCCGCAAACGGA

UACUGCCGGAGCGAAUGAGCAAGCGGCGUUGAAUAAGAGAAUUAAUGAAUUACAGGUCGCCUUAA

GCGCCGCUACUGCAGAAAAAGAGGCAUUAAUAAAAAAAGCAGGCGUUGUGCAGAAUAAUAAUCUAC

AGCAAAGCCAGGCCGCGGCGCGUCAGCAGAUCCAGCAAUUAACGACGCAGAUUCAGCAAGCCGAA

-continued

```
GCUGAAAAUAAACGCCUCAGCGCCAGCUUUACCACGCUUAAUAAAGAUAAACACGCGCUAUGACC

CAACUGGCCGCAACGGAAAAAGAGAAACAGGCCGCUCUUGAGCAGGUCAAAGCGCUUAACGCUGAC

AAACAGCCGCUGACGACCCGGCUGGCCGCCGCGGAAAAAGAGAAACAGGCCGUCCUCGAGCAGGU

UAAGGCCCUUAACGCCGAUAAACAGUCGCUGACUAUUCGCCUCGCCGCUGCGGAGAAAGCGCAGC

AGGCCGCUGUUGACCAGGCUAAAGCGCUUAACGCUGACAAACAGCCGCUGGCUACCCGACUGGCC

GCCGCGAAAAAGAGAAACAGGCCGUCCUCGAGCAGGUUAAGGCCCUUAGCGCCGAUAAGCAGUC

GCUGACUAUUCGCCUCGCCGCUGCGGAGAAGGCGCAGCAGGCCGCUCUUGACCAGGCUAAAGCGC

UUAACGCUGACAAACAGCCGCUGGCGACCCGGCUGGCCGCCGCGGAAAAAGAGAAACAGGCCGUC

CUCGAGCAGGUUAAAGCCCUUAACGCCGAUAAGCAGUCGCUGACUAUUCGCCUCGCCGCUGCGGA

AAAGACGCAGCAGGCUGCCCUCGAUCAGGUCAAAGCCCUUAACGCCGAUAAACAAUCGCUGUCCAC

CCGGCUGGCCGCCGCGGAUAAAGCGCCGCAUGGCCCCGCUAACGACGCCGCUGCGCCAAAAAAUG

AGCCACCAGAGAUGGCGGCCAUAGUGGCAGCCUAUCGCCUGCAGGCGGAUAAAGACAACGCCCAG

CUACGGAUGAAAGAAGAUGAAAUCGAACUGCUGAGAACGCAGCUUUCUGUACAGUCCAAAACGCGC

AGCGGCGAGAGCGCCGCCGCCAAACUCAGCGCAUCGGGAGAACAGCAGGCUUAUGCGAUCGGCGC

CUCGAUGGGAAGCGAGGCGCUCAACGUCCUUACCACCCGUCGUACUCAGGGAGUUACCGUCGACG

CAGGCCUGGUGCUGCAGGGCAUCGAAGAUGCCUUUCGCGGCCAGCUUCGUCUCGGAGAGCAGGAA

CGUAACAAGGCGCUGUUUGAUGUGUCGCAGCAGGUUUUUCAGAACCUGAAUAAAAUAGAGCAGAA

AAACAUCAGUGCCGGCAAGAAAUAUCAGCAGGCGUUUGCGCGCAAAAAAGAUGUGGUCUUUAAAG

AGGGCGUCUACAGCCGCGUCGAUUACCUGGGUAAAGGAAAAAUAAGCGGUAAUGACCUGGUUACC

GUGGUGAUCAAAGAGAUGCUGACGGACGGGACGGUGAUCAACGAUAUGGAAGCGAAAGAUCAGGC

GCUUACGCAAAAGCUGGAUGCCUAUCCCCCGGUGUUUCGCGAACCGCUGAAGCGUCUACAGAACC

ACGGCUCCGUGACGCUCGUCGUCCCGCCUGAAAAGGCCUAUGGCAGUAAAGGAUUACCGCCAAAA

AUCCCGCCAGGCGCCACCAUGGUUUAUUCCGUGCGGAUAGUAGAUAGCCAACCCGAGCCGGCAAA

AUAG
```

SEQ ID NO: 82
```
AUGAAAAUCCUGUCCGUGCGUCACGCCGCCCUCCCGGCCCUGCUCUUGCCGCUCAUUGCGGCAGC

CCAGGCCGCUGAUGAACAAACCAUGGUGGUGACCGCCGCGCCAACCACGGUUUCUGAACUGGAUA

CCCCCGCCGCCGUCAGCGUGGUGAAUGGGGAUGAGAUGCGCCAGGCCGCGCCGCGCGUCAAUCUC

UCUGAAUCGCUGGGCGCCGUGCCGGGCCUGCAGGUGCAGAACCGGCAAAACUAUGCCCAGGAUCU

GCAGCUGUCGAUUCGCGGCUUUGGCUCGCGCUCAACCUAUGGCGUGCGCGGACUGCGCAUCUAUG

UGGAUGGCAUUCCGGCCACCAUGCCCGACGGCCAGGGGCAGACCUCAAAUAUUGAUAUCGGCAGC

GUUGACACCAUUGAGGUGCUGCGCGGCCCCUUCUCUGCCCUGUACGGUAACUCGUCCGGCGGGG

UGAUCAACGUCACCAGCCAGACCGGCACCCAGCCGCCCACCGUGGAAGCCAGCAGCUACUAUGGCA

GCUUCGGCACCUGGACUACGGGAUGAAAGCCACUGGCGCCGUUGGCGACGGCAGCCACGCAGGC

GAUGUGGAUUACACGGUCUCAACCAAUCGCUUCACCACCCAUGGCUAUCGCGAUCACAGCGGCGC

GCGCAAAAAUCUGGCGAACGCCCGGCUGGGGGUGCGCAUCAACGACGUCAGUAAGCUGACUCUGC

UGCUGAAUAGCGUGGAUAUCAAAGCCAAUGACGCCGGUGGCCUGACCGCCGAUGAAUGGCGCGAU

AACCCGCGCCAGUCGCCGCGCGGCGACCAGUAUAAUACCCGCAAGAAUACCCGACAGACCCAGGCC

GGCCUGCGCUAUGAGCGCCAGCUCAGUGCCCAGGACGAUCUCAGCGUUAUGAUGUACGCUGGAGA

ACGUGAAACCACUCAGUUCCAGUCGAUCCCGCGCGCGCCGCAGCUGAAGCCGAGCCAUGCCGGCG

GGGUGAUCGACCUUACCCGUCACUACCAGGGGAUCGAUACCCGGCUGACCCAUCGCGGAGAGCUG
```

-continued

CUGGUGCCCGUCACGCUCACCGCCGGUCUCGACUACGAAAACAUGAGCGAGCGGCGCAAAGGGUA
UGAAAACUUUGUGAUGGUCAACGGCGCGCCGCAGUAUGGCGAACAGGGCGCGCUGCGCCGUAACG
AACGCAACCUGAUGUGGAACGUCGACCCCUACCUGCAGACCCAGUGGCAGCUCACUGACAAACUCU
CGCUCGAUGCCGGGGUUCGCUACAGCUCGGUAUGGUUCGACUCGAACGACUACUACAUCACCCCA
GGCAAUGGCGAUGACAGCGGUGAUGCCAGCUAUCACAAAUGGCUGCCCGCGGGCUCGCUGAAAUA
UGCCCUGACCGACGCGUGGAACGUCUAUCUUUCCGCCGGCCGCGGCUUCGAGACGCCAACCAUUA
ACGAACUCUCCUACCGCUCCGAUAACCAGAGCGGCCUCAACUUCGGCCUGAAACCCUCCACCAACG
ACACGGUGGAGAUCGGCAGCAAGACGCGGAUCGGCAAUGGGCUGUUCACCGCCGCCCUGUUCCAG
ACCAAUACCGAUAAUGAGAUUGUGGUCGACAGCAGCAGCGGCGGGCGCACCAGUUAUAAAAACGC
CGGCAAGACCCGCCGUCAGGGGAUGGAGCUGGGGCUGGAUCAGCAGUUUGGCGAGAGCUGGCGU
CUGAAGGCGGCCUGGACCUGGCUGGACGCGACCUAUCGCACUAACGUCUGCGACGACGCCAGCUG
CAAUGGCAAUCGCAUUCCGGGGAUCGCGCGCAAUAUGGGCUACGCCUCCUUUGGCUAUCAGCCGG
AGCAAGGUUGGUACGCCGGGAGCGAUAUUCGCUAUAUGAGCGAUAUCAUGGCCAAUGACGAAAAC
ACCGCCAAAGCGCCCUCCUGGACGGUGGUUGGCCUGACGACUGGCUAUAAAUGGAGCUACGGCAG
GAUGGAUAUGGAUCUGUUCGGUCGCAUCGACAACCUGUUCGACCGGGAGUACGUCGGGUCUGUCA
UCGUUAACGAGUCUAACGGACGUUACUACGAGCCUGCCCCGGGACGUAACUACGGCAUCGGCCUG
AACCUCGCCUGGCGCUUCGAAUAA

SEQ ID NO: 83

AUGAAAUACACGUCUCACUUCCCGCUGGGGAUCGUCAUUCCUCUGCUCGCCUGUAGCGUGCCGCU
GCAGGCGGCAGAGAACAUGACCGAACAAUCGACGCCUGACGAGAGCGCCGCCACUGCCGAAAAUCA
CGAGGAGACGAUGGUCAUAACCGCCGCCAGGCAGAACCUGCAGGCGCCGGGCGUGUCGACCAUCA
CCGCAGAAGAGAUCCGCAAACAUCCCCCCGCCCGCGAUGUGUCGGAGUUAAUUCGUACGCAGCCC
GGGGUAAACCUGACCGGCAACUCCACCAGCGGGCAGCGCGGCAACAACCGGCAAAUUGAUAUCCG
UGGCAUGGGGCCCGAGAAUACGCUGGUGCUGGUCGAUGGUAAACCGGUGACCAGCCGUAACUCG
GUGCGGUAUGGCUGGCGCGGCGAUCGUGACUCCCGCGGCGAUACCAGUUGGGUGCCAGCGGAGA
UGAUCGAUCAUAUCGAUGUGAUCCGCGGCCCGGCGGCGGCGCGCUAUGGUAAUGGCGCGAUGGG
CGGGGUCGUCAACAUCGUGACCAAACCGACCACGCGAGAAUGGCACGGGUCGUGGAAUACCUAUA
UGAAUGCUCCGCAGCACCGUAAAGAAGGGGCGACGAAACGUACUAACUUUAGCCUCAAUGGUCCG
CUGUCGGACAGUGUCAGCUUCAAUCUCUGGGGUAAUCUGAGUAAAACCCAGGCCGAUGCACAGGA
UAUUAACGCCGGGCAUGAAGCGGAACGUACCGGUUCCUACGCCGGUUCUUAUCCCGCCGGACGUG
AAGGGGUGGUGAACAAAGAUAUUCACAGUAAGCUGCGCUGGGAGUUUGCCCCGAUGCAGGCCCUG
GAGUUUGAGGCCGGUUACAGCCGCCAGGGUAAUCUCUAUGCCGGCGACACACAAAACACCAAUACC
AGUACGCUGGUGAAGAGUAUGUACGGGAAAGAGACCAACCGUCUCUACCGGCAAACUUACGGCGU
AACAUGGACCGGCGGCUGGGAUAAUGGCGUGACCAGCAACAGCUAUGCCCAGUACGAACACACCC
GUAACUCGCGAAUGGAUGAAGGGCUGGCGGCGGUACGGAAGGGAUCUUCUCCAGUAGCGAGUU
UUCAGAUAUCGAUCUGGCCGAUGUCCUGCUACAUAGUGAAGUGAAUAUUCCGUUUACGCUGGGGG
UCGAUCAGAAUCUGACGCUGGGGGCAGAAUGGAAUCAGCAGCGGAUGAAAGAUGGCGUAUCGACA
ACCCAGGCGCUCUCUUAUGGCACUAUCGAUGGCGUAUCGGCUACCGGUCGUAGCCCGUACUCCAG
UGCCGAGAUCUUCUCGCUGUUUACCGAAGAUAAUAUGGCGCUAACGGACAGCACCAUGCUGACAC
CCGCUCUGCGCUUCGAUCACCACAGCAUCGUCGGCAAUAACUGGAGCCCCUCACUGAACCUGUCUC
AGGAGCUGACGGACGACUGGACGCUGAAGCUGGGGCAUUGCCCGUGCUUACAAGGCGCCUAACCUC

```
UACCAGUUGAACCCGAACUAUAUUCUCUACAGCAACGGUCAAGGCUGUUACGCCAGUAGUUCCGCC

UGCUAUCUGAUGGGGAAUAGCGAUCUGAAAGCGGAGACCAGCGUUAAUAAAGAGAUUGGUCUUGA

GUACAAGCAUGAUGGCUAUCAGGCGGGGAUCACCUGGUUCCGUAACGACUAUCACAAUAAGAUUG

AGUCAGGGUAUGCGGCGGUGGGUACCGCCAGCAACGGCACCACCAAUAUCUAUCAGUGGGAAAAC

GUACCAAAGGCGUUAGUGGAAGGCCUGGAAGGAACGCUGAAUCUGCCGGUGGGGAGGCGGUUA

ACUGGAGCAAUAACCUGACCUGGAUGCUGCAGAGCAAGAAUAAGACGACCGGCGACCGGCUGUCA

GUGAUCCCGCAGUUUACCCUGAACUCGACUUUGAGCUGGCAGGUUCGUGAAGAUCUCUCCCUGCA

GAGCACCUUUACCUGGUAUGGCCGACAGAAACCAAAACGCUUCAAUUAUAAGGGCGAGGCGGUCA

GCGGCAGCGAACUAAACGAAGUCAGCCCAUACAGCAUUGUCGGCCUCAGUGCGACCUGGGAUGUG

AACAAAAAUCUGAGCUUCACCAGCGGGAUAGAUAACCUGUUUGAUAUUCGCCACUACCGGGCAGG

GAAUGCGCAAACGACCGGCAACGCGACGACGGGAGCUUAUCUGUAUGGCGCGGGUGCCGAGACCU

AUAACGAAUCGGGGCGGACCUUCUUUAUGAGCGUUAAUACUCAUUUCUGA
```

SEQ ID NO: 84
```
AUGGAAAAAAACGCUUCUCUGCCUUUCGGCAGUUUCAACUCAUUGGCAUUGUUUACAGGUCUGUG

UCUGGGAGCCUCGCCGGCAGCAGGCAUCGCAGCGGAAAAUUCGGUCAAAAAUAGUGAAGAGACGC

UGGUAGUGGAAGCCGCUCCGCCUUCACUCUACUCCCCCGGCGCUUCCGCCGAUCCCAAGUUCAAU

AAACCGCUGGUCGAUACCACCCGCACCAUCACCGUGAUCCCGGAACAGGUGAUUAAAGAUCAGGGC

GUCACCAACCUGACUGACGCCCUCAAAAACGUUCCCGGCGUCGGGGCGUUUUAUGCCGGGGAGAA

UGGCAGCUCAACCACCGGGGAUGCCAUCUUUAUGCGCGGCGUGGAUACCUCUAACAGCAUCUAUG

UGGACGGCAUUCGCGACAUCGGUAGCGUGACGCGCGAUACCUUCAAUACCCAGCAGGUGGAAGUC

AUCAAAGGGCCCGCCGGCACGGACUAUGGCCGCAGCGCGCCCUCCGGCUCGAUCAAUAUGAUCAG

CAAGCAGCCGCGCCUUGACUCCGGGAUCGACGGCUCGGCCAGCAUCGGCAGCGCCUGGUCGCGCC

GGGGCACUCUCGACCUGAACCAGGCGUUUAGCGACAACGCUGCGUUCCGUCUGAACCUGAUGGGG

GAAAAAACGCAUGACGCUGGUCGGGACCGCAUUGAAAACGAACGCUAUGGCAUCGCACCGUCGCU

GGCCUUCGGCCUUGAUACCCCAACUCGUCUGUAUCUGAACUAUCUGCACGUCCGGCAGAACAACAC

CCCGGAUGGCGGGAUCCCUACCGUCGGCCUGCCGGGCUAUUCGGCGCCUUCGCCGAAGUAUGCCG

CACUCAACUCCGCCGGGAAGGUCGAUACCAGCAAUUUCUAUGGCACCGACUCCGAUUACGAUAAAU

CUACUACCGACAGCGGUACCCUGCGCUUCGAACACGAUCUGACGGAGAAUACCACCGUGCGCAAUA

CCACCCGCUGGUCGCGAGUGAAACAGGAGUAUCUUUUGACCGCGGUGAUGGGCGGCGCGAACAAU

AUCACCGCCCCGAUAUCAAUGACGUCAACACCUGGAGCUGGUCGCGUCUGGUUAAUACCAAAGAU

GUCAGCAACCGUAUUCUGACCAACCAGACCAAUAUCACCUCGACUUUCAAUACUGGCUCGAUAGGC

CAUGACGUCAGCGCCGGCGUGGAGUUUACCCGGGAAAACCAGACCAACUAUGGCGUUAACGCCAG

GACCGCGCCGGCGGUGAAUCUCUACCAUCCGGUGAGCAACCUGUCGAUUGGCGGGCUGGACAGAA

ACGGGGCGAACGCCAACGGCCAGACCGAUACCUUCGGGAUUUAUGCCUUUGAUACGCUGACGCUG

ACCGAGCGGAUUGAGAUCAACGGCGGGCUGCGUCUCGACAAUUACCAUACCAAAUAUGACAGCGC

CACCGCCUGCGGCGGCAGCGGACGCGGGGCUAUCGCCUGCCCGCCCGGACAGUCGACCGGCAGCC

CGGUCACCACUGUCGAUACCGCUAAAUCCGGCAAUCUGGUUAACUGGAAAGCCGGGGCGCUGUAC

CGCUUAACCGAGCAGGGCAAUGUCUACGUCAACUACGCCAUCUCACAGCAGCCGCCGGGAGGCAG

CAGCUUCGCCCUGGCCGCCAGCGGCAGCGGCAACAGCGCUAACCGGACCGACUUUAAGCCACAGA

AGGCGAAAUCCAGCGAGCUGGGCACCAAGUGGCAAAUCUUCGACAACCGUCUGCUGCUCAGCGCG

GCGUUAUUCCGCACCGAUAUUGAAAACGAAGUGGCCGCCAACGAUGACGGAACCUGGUCGCAGUA
```

-continued

CGGCAAAAAGCGCGUGGAGGGGUAUGAACUCUCCGCGACCGGAAACCUGACCCCGGACUGGACGA

UUAUCGCCGGCUACACUCAGCAGCAUGCGACAGUGACGGAGGGACAGAACGUUGCACAGGAUGGA

UCUUCCGCCCUGGCCUACACCCCGAAACAUGCCUUUACGCUGUGGACGCAGUAUCAGGCCACCAGC

GAUCUGUCCGUCGGCGGCGGUGUGCGCUAUGUCGGAAGCCUGCGCCGGGGCAGCGAUGGUGCAG

UCGGUACCCCGGAUCACACCGAGGGCUACUGGGUUGCCGACGCCAAACUGGGCUAUCGGGUCAAC

AGCAACCUCGAUCUGCAGCUCAAUAUGUAUAACCUGUUUGAUACCGAUUACGUGGCCUCCAUCAAC

AAGAGCGGCUAUCGCUAUCAUCCGGGCGAACCCCGGACCUUUAUGCUGACGGCGAACGUCCAUUU

CUGA

SEQ ID NO: 85

AUGGCGACUAUGUACAAAUCGACUCCGUCAGCAGCAUGGUGUAAAAAACGCCUGCUGGUGACCUC

UUUGUUUGCAGCAAUUUAUCAGACUUCUGCCAUCGCAGCAGAUACUUCCGCCGUUAGCGGCGAGG

CGGUGGAUGACACCUCGGAACAAAUGACCGUCACCGCCCCCGCGCCGGUGCAGAAAGCCGGUAGC

GAACACAGCAUCAGCGCCCGGGAGCUGGAGAAUAAAGGCGCUAACGAUUUCGGCUCAAUCAUGCG

CUAUGAGCCGCUCAUCAGCGCCACCGGGGCCAGCGGCGGCUCCGGCAACGGCAAAAGCGGCUUCG

ACCGCGGAGGUUACACCGGCUACAACAUUCGCGGUAUGGAGAGCAACCGCGUAGGCAUCGACGUG

GACGGUAUCGCGCAACCCAACGCCACCGGCCGCGGCUACGUCGGCCGCGCCGGGCUCAACACCUU

CGGCAUCGGCCGCGAUUAUAUCGACCCGUAUAUGUACGGCAGCGUUGAUAUCCAGUCCGGCGCCA

CCUCGACGGAAACGGCCAACAGCGCUAUCGGGGGGAAUGUCUCCUUCCGCCCGAAAUCAGCGGAU

GAUUACCUGCGCCCGGGCAAGACCAGCGCCUUCGGCUACCGCAGCGGUUACGACUCUGCGGAUCG

CAGCUGGCACAACGGGGUGACCGUCGCCGGCGGCGAUGAGUUCCUGCGCGGGAUUUUGGUCUAU

AGCCGCCGUGACGGCCAGGAAACUGAAAACAACAGCGGCACCGUCGACGCCUACCCGGCGAACUG

GCACUCCGAUGCUUUUCUGGCCUCCGGGAUCUGGCAGCCUAACGAUGAGCACAAGCUGACCAGCA

CCUUCGACUAUUACCAUAAAACCAACCACACCCACUACGAUACCGGGACUCCAGCGGCAACAGCA

CCAUCGGCACCGCCAACCAGACCAGCCAGACCCGGCGCUGGGGCCUGAGCCUGAAGGAUGACUGG

ACGCCGAUGAACGACUACCUCGACAGCGUCUCCACAAAAAUCUACUACCAGCAUACCGAAGCCCAU

GACUGGACUUAUAUGCCGGACAGCGUCACCCGCAAAAUGCAGACGGUGAACUCUAACUACGAUACC

GACACCUGGGGCCUGCAGACCGCGCUGGCGAAAACCCUGGGCCGCCACGAUCUGAGCGCCGGUUU

CAACGCCAGCACCAGCAAAACCCAGCGGCCGUUCAGCCAGUCGCCGAUCCCCAGCGUUUACAGCGA

GAUCAUGCAGCCGGAGGCAGACAGCCGCAGCUACACCCUCGCGGCUUUGUCCAGGAUAAGAUCA

ACUUCGAUCUCGACAGCCACAACUUCGCCGUUAUUCCCGGCGUGCGCGUGGUGCAUCAAUCGACU

AAGCCGGAAAAUCUGUCCGAUCUCGCCGCCAACAGCAGCGUGCUGAGCGAAUCGUCGGUGGCGAA

UCUGUACGGCAAAAACAGCGAUACCCAGGUUCUGCCGUCGUUGACCUUCCAGUACGACCUCACCCC

GCGCCUGAUGACCUACCUGCAGUACCAGCGCGGGGCGCAGUUCCCCAACGCCAGCCAGCUGUAUG

GCUCCUGGAACCUCGGCUCCAGCUACGCCGGCAGCCAGCAGUAUGCCCUGAUCGGCAAUACCGAU

CUGAAGACGGAAACCAGCGAUAAUCUCGAGUGGGGGCUGAAAGGGGAAGUUACCGAAGGCAUCAC

CCUGCGCACGGCGCUGUUCUACAACAGCUAUAAGAACUUUAUCGCCUAUACCCGCUAUACCCGCGC

CAACAAUCCGGGCCAGUUCACGAAUGUGCCGUCGAACAUCUACACCAUUUAUCAGGCGGAAAACCG

CGAUAAAGCCUAUAUCUACGGCGGUGAGAUUAGCACCAAAUUUAACUUUGGCACCUGGUUUGAGC

AGGUGGACGGCUGAGCGCCACCCUCGCCCUCGGCUAUAGCGAAGGGAAAUCGAAAUCCAGCUAC

AGCGGCGAUAAAUACGUCGACCUCGACAGCGUGGCGCCAAUGAAAGCCAUCGUCGGCGUGGCGUG

GGACGAUCCGGCGAAACGCUACGGCACCGCCCUGACGGCGACCUUUGUCAAAGGGAAACAGGCGA

CCGCCACCAACCGCGAAAGCUACAGCAACAGCGGAUCCGCCAUCACCGAUGCCAGCAGCGACUAUA

UGCGCGUGCCGGGCUACGGCAUGCUGGACUGGACCGCGUACUGGCAGGUGGCGAAAAACGUGCG

CCUCAAUGGCGGGGUCUACAACCUCACCGAUCGUAAAUACUGGGAUUACCUGAGCAGCCGCAAUA

UCGAGACCGGCACCAACCAGGACGCCAACGAUAAAGCGCUGGCGGUGAUGCCGGGCCGCACCUGG

CAGCUGGGCGUCAACGUCGACUUCUGA

SEQ ID NO: 86

AUGGCGAUGAAAAAGUUGCUCAUAGCGUCGCUGCUGUUUAGCAGCGCGACUGUAUACGGUGCUGA

AGGGUUCGUGGUGAAGGACAUUCAUUUCGAAGGCUUGCAGCGUGUCGCUGUUGGUGCGGCCCUC

CUCAGUAUGCCAGUGCGUCCUGGCGAUACGGUGACCGACGAUGAUAUCAGUAACACUAUUCGCGC

GCUGUUUGCCACUGGCAACUUCGAGGACGUCCGCGUCCUGCGCGAUGGUGAUACCCUGCUGGUUC

AGGUGAAAGAGCGUCCGACGAUCGCCAGCAUCACUUUCUCCGGCAACAAGUCGGUGAAAGAUGAC

AUGCUCAAGCAGAACCUUGAGGCCUCAGGCGUUCGGGUGGGCGAGUCGCUUGACCGCACGACCAU

CGCGGAUAUCGAGAAGGGUCUUGAAGACUUCUACUACAGCGUCGGUAAAUACAGCGCCAGCGUCA

AAGCAGUCGUUACGCCGCUGCCGCGUAACCGUGUCGAUUUGAAGCUGGUCUUCCAGGAAGGCGUC

UCCGCAAAAAUUCAACAGAUCAACAUCGUCGGCAACCAUGCGUUUUCGACCGAUGAGCUGAUCUCC

CACUUCCAGCUGCGCGAUGAGGUGCCGUGGUGGAACGUGGUCGGCGACCGUAAAUACCAGAAGCA

GAAGCUAGCGGGCGACCUUGAAACCCUGCGCAGCUACUACCUGGAUCGCGGCUAUGCCCGUUUCA

ACAUCGAUUCUACCCAGGUCAGCCUGACGCCGGAUAAGAAAGGGAUCUACAUCACCGUCAACAUCA

CCGAAGGCGAUCAGUACAAGUUUUCCGGAGUGCAGGUGACGGGCAACCUCGCUGGCCAUUCCGCG

GAAAUCGAAGCGCUGACUAAAGUUGAGCCAGGCGAACUGUACAACGGCGCGAAAGUGACCAAGAU

GGAAAACGACAUCAAGAAACUGUUGGGUCGUUAUGGUUACGCCUAUCCGCGCGUGCAGUCGCAGC

CGGAGAUCAACGACAGCGAUAAAACCGUUAAGCUGCACGUUAACGUCGACGCAGGCAACCGUUAUU

ACGUGCGUAAAAUUCGCUUCGAAGGCAACGACACCUCUAAAGAUGCCGUACUGCGCCGCGAAAUG

CGCCAGAUGGAAGGCGCAUGGCUGGGCAGCGACCUCGUCGAUCAGGGUAAAGACCGUCUCAAUCG

UUUAGGUUUCUUUGAAACGGUGGAUACUGAUACCCAGCGCGUGCCGGGCAGCCCGGACCAGGUCG

ACGUUGUCUACAAGGUGAAAGAGCGUAACACCGGUAGCUUCAACUUCGGUAUCGGCUACGGCACC

GAGAGCGGCGUCAGCUUCCAGGCGGGCGUUCAGCAGGAUAACUGGUUAGGUACUGGCUAUGCUG

UCGGGAUCAACGGUACCAAAAACGACUACCAGACCUAUACCGAGCUGUCGGUGACCAACCCGUACU

UCACCGUAGACGGGUGUAAGCCUCGGCGGUCGUGUCUUCUAUAAUGACUUUGAUGCGAACGAUGCG

GAUCUGUCUGACUAUACCAACAAAAGCUAUGGUACAGACAUUACGCUGGGCUUCCCGGUCAACGAA

UACAACACGCUGCGCGCCGGCGUCGGUUAUGUGCAUAACUCCCUGUCCAAUAUGCAGCCGCAGGU

GGCAAUGUGGCGUUACCUUAACUCGAUGGGCCAGUAUCCGGACAACACCAACGACCGGAACUCGU

UCAGUGCGAAUGACUUCACCUUCAACUACGGUUGGACCUAUAACAAGCUUGACCGCGGCUUCUUC

CCAACGGAAGGUUCGCGCGUCAACCUGAACGGUAAGGUGACCAUUCCGGGCUCAGACAACGAGUA

CUACAAAGCGACGCUGGAUACCGCGACCUACGUGCCGAUCGACAACGAUCAUCAGUGGGUAGUAC

UGGGUCGUACGCGCUUUGGUUAUGGCGAUGGUAUCGGCGGCAAAGAGAUGCCGUUCUAUGAGAA

CUUCUAUGCCGGUGGUUCCAGCACCGUGCGUGGCUUCCAGUCGAACACCAUUGGUCCGAAGGCGG

UGUACUUCCCGGCAAGCAGUCGUCAUGAUGAUGACGAUAGUUACGAUAAUGAAUGUAAGAGCACC

GAAUCCGCACCGUGUAAAUCCGAUGAUGCGGUGGGCGGUAACGCGAUGGCGGUGGCCAGCCUUG

AGCUGAUUACCCCGACGCCGUUUAUUAGUGACAAAUAUGCGAACUCGGUCCGUACUUCCGUCUUC

UGGGAUAUGGGUACCGUAUGGGAUACUCACUGGGAUUCGAGCGCGUACGCUGGUUAUCCGGAUU

```
ACAGCGAUCCGAGCAACAUCCGUAUGUCUGCGGGUAUUGCCGUGCAGUGGAUGUCGCCGUUGGG

GCCGUUGGUCUUCUCCUACGCCCAACCGUUCAAAAAGUACGAUGGAGACAAAGCCGAACAGUUCCA

GUUUAACAUUGGUAAAACCUGGUAA
```

SEQ ID NO: 87

```
AUGACAGAUGUGACUAUUAAAGCGCUGGCCUCAGAGAUUCAGACCUCUGUGGAUCGCCUGAUACA

GCAAUUUGCUGACGCAGGCAUCCGCAAAUCGGCUGAUGAUUCUGUGACCUCGCAAGAGAAACAAA

CUUUGUUGACGCACCUGAACCGUGAACACGGCUCGGCGCCAGACAAGCUGACGUUACAGCGUAAG

ACGCGCAGUACGUUAAAUAUUCCAGGUACCGGUGGAAAGAGUAAAUCGGUACAAAUCGAAGUCCG

CAAGAAACGCACCUUUGUGAAACGCGAUCCGCAAGAGGCUGAACGCCUGGCCGCGGAAGAGCAGG

CGCAGCGUGAAGCGGAAGAGCAGGCCCGUCGUGAAGCUGAAGAAGCAGCGAAACGCGAGGCGCAA

UUAAAAGCUGAACGUGAGGCCGCAGAACAAGCUAAACGUGAAGUCGCUGAUAAAGCGAAACGUGAA

GCUGCGGAAAAAGACAAAGUGAGCAAUCAACAUACCGACGAAAUGACCAAAACCGCCCAGGCUGAA

AAGAUCCGUCGCGAGAACGAAGCCGCGGAAUUGAAGCGCAAAUCGGAAGAAGAAGCACGCCGCAAA

CUUGAAGAAGAAGCGCGCCGUGUAGCGGAAGAAGCACGCCGUAUGGCUGAAGAAAACGAAAAAAA

UUGGUCUGAAACCUCAGACAGCCCGGAAGAUAGCAGCGACUAUCACGUCACCACAUCACAGCAUGC

UCGUCAGGCUGAAGAUGAUAACGAUCGUGAAGUCGAAGGCGGUCGCGGCCCGUAGCCGUAGCAGCA

AAGCGGCUCGUCCGGCGAAGAAAGGCAACAAACACGCUGAAUCGAAAGCUGAUCGUGAAGAAGCC

CGCGCGGCCGUGCGCGGCGGUAAAGGCGGUAAGCACCGUAAAGGUUCCGCUCUGCAGCAGGGCU

UCCAGAAGCCAGCGCAGGCCGUUAACCGUGACGUCGUAAUCGGCGAAACCAUCACCGUUGGCGAA

CUGGCUAACAAGAUGGCGGUGAAAGGUUCUCAGGUCAUCAAAGCGAUGAUGAAGCUGGGCGCCAU

GGCGACCAUCAACCAGGUCAUCGACCAGGAAACCGCACAGCUGGUUGCCGAAGAGAUGGGCCACA

AAGUUAUCCUGCGUCGUGAAAACGAACUGGAAGAAGCCGUAAUGAGCGACCGUGACACCGGCGCG

GCGGCUGAACCGCGCGCACCGGUCGUGACCAUUAUGGGUCACGUUGACCACGGUAAAACCUCGCU

GCUGGACUACAUUCGUUCUACCAAGGUUGCCUCCGGCGAAGCGGGUGGUAUUACCCAGCACAUCG

GUGCUUACCACGUCGAAACCGACAACGGCAUGAUCACCUUCCUGGAUACCCCGGGCCACGCCGCG

UUUACCUCCAUGCGUGCUCGUGGCGCGCAGGCGACGGAUAUCGUGGUUCUGGUGGUGGCGGCAG

ACGACGGCGUGAUGCCGCAGACUAUCGAAGCUAUCCAGCACGCUAAAGCGGCGCAGGUACCGGUG

GUAGUGGCGGUGAACAAGAUCGAUAAGCCAGAAGCCGAUCCGGAUCGCGUGAAGAACGAACUGUC

CCAGUACGGCAUCCUGCCGGAAGAGUGGGGCGGCGAGAGCCAGUUCGUCCACGUUUCCGCGAAAG

CGGGUACCGGCAUCGACGACCUGCUGGACGCGAUCCUGCUGCAGGCUGAAGUUCUUGAGCUGAAA

GCGGUCCGCAACGGUAUGGCGAGCGGCGCGGUCAUCGAAUCCUUCCUUGAUAAAGGUCGUGGUCC

GGUAGCUACCGUUCUGGUUCGCGAAGGUACUCUGCACAAGGGCGACAUUGUUCUGUGCGGCUUC

GAAUAUGGCCGUGUGCGCGCGAUGCGUGACGAACUGGGUCGCGAAGUGCUGGAAGCGGGUCCGU

CCAUUCCGGUGGAAAUCCUCGGCCUGUCCGGUGUGCCGGCUGCCGGUGAUGAAGUGACCGUAGU

GCGUGACGAGAAAAAGCGCGUGAAGUGGCGCUGUAUCGUCAGGGCAAAUUCCGUGAAGUUAAGC

UGGCGCGUCAGCAGAAAUCUAAACUGGAAAACAUGUUCGCUAACAUGACCGAAGGCGAAGUUCAC

GAAGUGAACAUCGUACUGAAAGCGGACGUACAGGGUUCGUCGAAGCGAUUUCCGAUUCCUUACU

GAAACUGUCUACCGACGAAGUGAAAGUGAAGAUCAUCGGUUCCGGCGUAGGUGGUAUCACCGAAA

CCGACGCUACCCUGGCAGCAGCAUCCAACGCGAUUCGGUUGGCUUCAACGUUCGUGCCGAUGCC

UCUGCGCGUAAAGUUAUCGAAGCGGAAAAGCCUGGAUCUGCGUUACUACUCCGUCAUCUAUAACCU

GAUCGACGAAGUGAAAGCGGCGAUGAGCGGCAUGCUGUCUCCGGAACUGAAACAGCAGAUCAUCG
```

```
GUCUGGCUGAAGUGCGUGAUGUCUUCAAAUCGCCGAAAUUCGGCGCCAUCGCGGGCUGUAUGGU

UACCGAAGGGACGAUCAAACGUCACAACCCAAUCCGCGUUCUGCGUGACAACGUGGUUAUCUAUGA

AGGCGAGCUGGAAUCCCUGCGCCGCUUCAAAGAUGACGUUAACGAAGUCCGUAACGGCAUGGAAU

GUGGUAUCGGCGUGAAGAACUACAACGACGUUCGCGUUGGCGAUAUGAUCGAAGUGUUCGAAAUC

AUCGAAAUCCAGCGUAGCAUCGAUUAA
```

SEQ ID NO: 88
```
AUGAAAAGAAUGUUAAUCAACGCAACUCAGCAGGAAGAGUUGCGCGUCGCCCUUGUUGAUGGGCA

GCGCCUGUACGACCUGGAUAUCGAAAGCCCCGGGCACGAACAGAAAAAAGCGAACAUCUACAAAGG

CAAAAUCACCCGCAUUGAACCCAGCCUUGAAGCCGCGUUUGUUGAUUACGGCGCCGAGCGUCAUG

GUUUCCUCCCCCUCAAAGAAAUCGCCCGCGAAUACUUCCCCGCCAACUACAAUGCGCAUGGUCGUC

CUAAUAUCAAAGACGUACUGCGGGAAGGUCAGGAAGUUAUCGUGCAGAUUGAUAAAGAAGAACGC

GGCAACAAAGGCGCUGCGCUCACCACCUUUAUCAGCCUCGCGGGCAGCUAUCUGGUACUGAUGCC

GAACAACCCGCGCGCCGGGGGAAUUUCCCGCCGUAUCGAGGGCGACGACCGUACCGAACUGAAAG

AAGCGCUGGCGAGCCUGGAGCUUCCGGACGGCAUGGGCCUGAUCGUUCGCACCGCUGGCGUCGG

CAAAUCCGCCGAAGCCCUGCAGUGGGACCUGAGCUUCCGCCUGAAGCACUGGGAAGCGAUUCAGA

AAGCCGCGGAAAGCCGUCCGGCGCCGUUCCUGAUCCACCAGGAAAGCAACGUCAUUGUCCGCGCC

UUCCGUGACUACCUGCGCCAGGACAUCGGCGAAAUCCUGAUCGAUAACCCGAAAGUGCUUGAGCU

GGCGCGCCAGCAUAUCGCCGCGCUGGGUCGUCCGGAUUUCAGCAGCAAAAUAAAACUGUACACCG

GUGAAAUCCCGCUGUUCAGCCAUUAUCAGAUCGAAUCGCAAAUUGAGUCCGCCUUCCAGCGCGAA

GUGCGCCUGCCUUCCGGCGGGUCUAUCGUUAUCGAUAGCACCGAAGCGCUGACCGCGAUCGAUAU

CAACUCCGCCCGCGCCACCCGCGGCGGCGAUAUCGAAGACAGCCUUCAAUACCAACCUCGAAGC

GGCUGACGAAAUUGCCCGCCAGCUGCGUCUGCGCGACCUCGGCGGCCUGAUCGUUAUCGACUUCA

UCGAUAUGACCCCGGUUCGCCACCAGCGCGCCGUGGAGAAUCGUCUGCGCGAAGCCGUCCGUCAG

GACCGUGCGCGCAUUCAGAUCAGCCAUAUUUCGCGCUUCGGCCUGCUGGAGAUGUCCCGUCAGCG

CCUGAGCCCGUCGCUGGGCGAGUCCAGCCACCACGUCUGCCCGCGCUGCUCCGGCACCGGCACCG

UGCGUGAUAACGAAUCGCUGUCGCUCUCUAUUCUGCGUCUGAUCGAAGAAGAAGCGCUGAAAGAG

AAUACCAAAGAAGUCCACGCCAUUGUUCCGGUACCGAUCGCCUCCUAUCUGCUGAACGAAAAACGU

GCCGCAGUGAGCGCUAUCGAAUCCCGUCAGGGCGAUGUGCGCGUUAUUAUCGUGCCAAACGACGA

AAUGCAAACGCCGCACUACUCCGUCCUGCGCGUGCGCAAAGGUGAAGAAACCUCAACGCUGAGCUA

UCUGCUGCCGAAGCUGCAUGAAGAAGAAAUGGCGCUGCCAGGCGACGAUGAGCCGGCGGAGCGGA

AACGUCCGGAACAGCCGGCCCUGGCCGCUUUUGUCAUGCCAGAUGCGCCGCCAGCCCCGAUGCUC

GAAGAGCCUGCCGCCGCGCCUGUCGCCGCAGCGGCACCGGUCGCGGCCGCCGCACCGGCGCAGCC

UGGCCUGCUCUCACGCUUCUUCAGCGCGCUGAAGAAUAUCUUCUCUGGCGCCGAAGAGGCCAAAC

CGGCUGAAGUUCAGGUCGAGAAGAAAGCGGAAGAAAAACCGGAGCGUCAGCAGGAGCGUCGUAAA

CCGCGCGCCAACAACCGCCGCGACCGCAACGACCGCCGUGAUAACCGCGACAAUCGUGACAACCGC

GAUAACCGUGACAAUCGCGACACCCGUGCGGACAAUGCCGAGGGCCGUGAACCGCGCGAAUCGCG

UGAAGAGAACCGUCGCAACCGUCGCGAGAAGCCGUCGCAGAACGUGGAAGCCCGUGAUGUUCGCC

AAACCUCAGGCGACGACGCGGAGAAAGCGAAAUCCCGUGACGAGCAGCAGCCGCGCCGCGAACGC

ACCCGCCGCCAGUGACGACAAACGUCAGGCGCAGCAGGAAGCCAAAGCGCAGACUCGCGAAGA

GCCGGUUGUGCAGGAGACGGAGCAGGAAGAGCGUGUACAAACUCUGCCGCGUCGUAAACCGCGCC

AGCUGGCACAGAAAGUGCGCGUUGAGUCCGCUGUCGUCGAGCCAGUUGCCGAGAUCGUGCCAGAA
```

```
GCCGUAGUGGCUGAAGUUAUCGCUCCGCACAGCGAGCCGGUGAAAGCCGAGCUGCCGGCAGGGG

UGGAGAGCGUGGCGGACCAGGACGAAAAUGGCGAAUCCCGUGAAGCGAACGGUAUGCCGCGUCGC

UCACGUCGCUCCCCGCGUCACCUGCGCGUCAGCGGUCAGCGUCGUCGUCGCUAUCGUGACGAACG

CUAUCCGACCCAGUCGCCUAUGCCGCUGACCGUAGCCUGCGCAUCGCCGGAGAUGGCUUCCGGUA

AAGUCUGGAUCCGCUACCCGGUGGUUCGUCCGCAGGAUCAGCAGCCGGAAGAGGUUCAGGUUCAG

GACGCCAGCGUCGCGAAAACUGUCGAGGCCGUAGCGGCCCCGGUCGCCGUCGUUGAAACCGUUAC

CGCUGCGCCGGUCACCGUCGAGCCGGCUACCAUGGAACCAGUAACCGCUGAGCCGGUAGUCGUCG

AGCCGGUAGCGGCCGCCGAGCCGCUGGUCGUUGAUGCUGCGGAAGUUGUCGCGCCAGCAGCCGU

CGAGCCAGCGCCUCAGGAGCCGGUCACCGAAGCACCGGCUGUCGAAGCGCCUCAGGCUAUCGCGC

CAGUGACGCUCGACGCCGAGCCGGUGGUGGUAGAACCUGAAGCGGUGGAAACGACGCCUGUCGUU

GCAGCGCCAGUGGAAACUAUCGCCCCGGUCGCAGAAACCGUGGAGCAAGCGCCAGUGACCGAAGC

GGCCCCUGCCGAACCGGUCAAAGCCGAGCCCCGGUGAGCAAGCCGGUCGUAGUGGCGGGUCAUC

GCCAUGCCACCGCGCCAAUGACCCGUGCGCCAGCUCCGGACUAUGUCCCGGAAGCACCGCGUCAU

AGCACCUGGGUGCGCCCGCCGUUCGCCUUUGAAGGUAAAGGCGCCGCCGGUGGUCAUAGCGCGAC

CCAUAAAGCCACCGCUGAACCGACUCGCCCACAGCCCGUCGAGUAA

SEQ ID NO: 89
AUGCGCAAGCUCUCACUAAGUUUACUCACGCUGUCCCUCGGCGUUGCGCUGCUGCCGUUAGCGCA

GGCGGCGACGACGCCUGCCCAGGAGCAUCUGCUGGAGCAGGUCCGCCUCGGCGAGGCCAGCAAUC

GUGAAGACCUGGUGCGCCAGUCGCUGUACCGUCUGGAGCUGAUUGAUCCCAACAACCCGGAGCUG

AUUGCCGCGCGGAUGCGCUAUCUGCUGCGUCAGGGGGAUGCCGCCGGGGCGCAAAAAGAGCUGG

AACGACUGACGAAGCAGGCGCCGGACUCCCCGGAGCUGAAGGCGUCGCGCAAUGAGAUGAAAAGC

AACACCGGCGAGGGCCGCCAGGCGCUGCAGCAGGCGCGACUGCUGGGCGUGGCCGGGAAGGUCG

AUGAAGCCAUCGCCGCCUAUGAAAAACUGUACGGCGGGGUGCCGGAUGACGUUGACGUCGCCAUU

GAGUACUGGACGCUGGUGGCGCGCCUGCCGGCCCGCCAUAGCGAAGGCGUCAGCCAGUUGAAAAA

ACUGAACGCCAGCGCGCCGGGCAACGUCAGCCUGCUGACUUCGCUGGCGAAGCAGAUGUUCGCCG

AUAACAAACCGCAGGAGGGGUUCGCCUAUCUGGCGGAGAUGGCCCGAUCGGCCUCGGGACGCGGU

AUCGCCGCCGAUAUGUGGUUCAGUGAGGUGAAAAGCAUGCCGGUGAGUAAGGCCAGCGUGCAGGC

GUUGCAGCAAUUUCUUCUGCAGUUUCCCACCGGCUCGGUGGCGGCGAACGCCCGCGUUCUGCUCG

ACCAACAGCAGGCGCAGCUGCAGGAUCCGACUUUCCGCGCCCGCUCGGAAGGGCUGGCGGCGGUC

AAGUCCGGGAAUACCACGCAGGCGGUCGCGGAUCUGCAGAAAGCCGUUCAGGCCGACAGCCGCGA

CAGCGACGCGGUGGGCGCUCUCGGCCAGGCCUAUUCCCAGCGCGGCGACCGCGCGCGGGCAGUG

GCGCAGCUCAGUAAAGCGAUUGCUAUGGACCCUGACAGCCCGAACCGCGGCAAGUGGGACAGCCU

GCUGCAAACUAACCGCUACUGGCUGCUGAUAAAGCAGGGGGAUAACGCCCUGAAAGCCGGCCAGC

UUUCGCAGGCGCAGAACUAUUAUGCCCAGGCGCAGCGGGUCGAUCGCACCGACAGCUAUGCCGUG

CUGGGGCUGGGGGACGUCGCGGCGGCGCGCAAAGAGGCGGCGGCGGCGGAGCGCUAUUACCAGC

AGGCGUUGCGCCUGGAUCGCGGCAAUAACCUGGCGGUGCGCGGCCUGGCCAACCUCUAUCGCGCC

GAAUCGCCGGAGAAAGCCAGCGCCUGGAUCGCCGGCCUCCCUCCCGCUCAGCGGCGGAGCAUCGA

UGAUAUUGAGCGCAGCCUGACUAACGACCGGCUGGAGAAACAGGCGCAGGCUCUGGAGAGCCAGG

GCAACUGGGCGCAGGCGGCGGAAGUUCAGCGUCGGCGCCUGGCGCUGGAUCCGGACAGCGUCUG

GAUAACCUACCGUCUGGCGCGGGAUCUGGUCAGCGCCGGCGAACGCCAGGAGGCCGACGCGCUGA

UGCGGACGAUGGUCAACCGCCAGCCGCAGGACGCCGAACGGGUCUACGCCUCGGGACUCUACCUG
```

```
UCGGGGAACGACCAGGACGAUCUGGCUCUGGCGCAAAUCGCCGCUCUGCCGCGCAGCGCGUGGAC
GGAUAACAUUCGUGAGCUCGAAGCGCGUUUGCAAAGCGACCGGGUGCUGCGCCAGGCCAACCAGC
UGCGCGACAGCGGUAACGAAGCGCAGGCGAUCGCCCUUAUCCGACAGCAGCCCGCCUCGGUGCGC
UAUGACCUGACGCUCGCCGACUGGGCGCAGCAGCGCGGCGACAGCCAGACGGCGAUUGCCAACUA
UCAGCGGGUGCUGCGCCAGGAGGCCGACAACGGCGAUGCGCGCCUCGGCCUUGCGGAAGUCUACC
UGGCCGAGGGCGAUAAACCGGCCGCCCGGGCGCAGGUCAUGCAGCUGAAAGGCGCAGAGACCGAA
UCCAUGAACAUGCAGCGGCGGGUGGCGCUGGCGCGAGCUGGCCUUGGCGAUACCGCUGACGCGC
AACGGAUUUUUAAUCAGAUUGUGCCGCAGGCGAAGGCGCAGCCGCCCUCGAUGGAGAGCGCGCUG
GUGCUGCGCGAUGCCGCGCGCUUUGCCACCCAGAGCGGGGCGCCGCAGCAGGCGCUGACGCACUA
CCGGGAAGCUAUGGUGGCCUCCGGCAUUACCCCCGCGCAGCCGCAGGAUAACGAUACUUUUACGC
GGCUGACGCGCAACGACAGCCAUGAUGACUGGCUGAAGCGCGGGAUCCGCAGCGAUGCCGCCGAC
CUUUAUCGUCAGCAGGAUCUGAACGUCACCCUGGAACAUGACUUCUGGGGUUCCAGCGGCACCGG
CGGCUAUUCCGACCUGAAGGCGCAUACCACCAUGCUGCAGAUGGAUGCUCCGCUGGCGGAUGGCC
GGAUGUUCUUCCGCACCGACCUGGUCAAUAUGGAUGCCGGCAGCUUUUCCACCCACAGCGACGGG
AGCUACUCGCCCAGCUGGGGCACCUGCGGGGAGAUCGCCUGUACCAGCGGCAGUAAAAAUCAGAC
CGACAGCGGGCCAGCGUGGCGGUCGGCUGGAAGAAUGACACCUGGAGCGGGGAUAUCGGCACC
ACGCCGAUGGGCUUCAAUGUCGUCGAUGUGGUGGGGGGCUGAGCUACAGCAGCGACGUCGGGC
CGGUGGGGUACACGGUCAACGUCCACCGGCGGCCUAUCUCCAGCUCGCUGCUCUCCUUUGGCGGG
CAGAAGGACAGCAGCAGCCAUACCGGCGCCACCUGGGGCGGCGUCCGCGCCGACGGCGGCGGCCU
GAGCCUGAGCUACGAUCGCGGGGAGGCUCACGGCAUCUGGUCCUCGCUGGGCGCCGACUCGCUG
ACCGGUAAAAACGUGGCGGAUAACUGGCGCGUGCGCUGGAUGACCGGGUACUACUACAAGGUCAU
CAACGAGAAUAAUCGUCGCGUCACCGUCGGCCUCAACAAUAUGAUCUGGCACUACGACAAAGAUCU
CAGCGGCUACACCCUCGGCCAGGGCGGCUAUUACAGCCCACAGGAGUAUCUCUCGUUCGCCGUGC
CGGUGACCUGGCGUCAGCGCACCGAGAACUGGUCCUGGGAGCUCGGCGGGUCGGUGUCAUGGUC
CCAUUCGCGCACCCAGACGCAAGCCCGCUAUCCGCUGCUGAACCUGAUCCCGUCCGACUACCGGCA
GCGCGCCAGCGAGCUGACGGAGGAGGGGAGCAGCAGCCAUGGAUUCGGUUACACCGCCAGAGCGC
UGGUGGAGCGGCGGGUGACCAGCAACUGGUUCGUCGCGCCGCGGUCGAUAUUCAGCAGGCGAA
GGAUUACACCCCGAGCCAUGCGCUGCUUUACGUCCGCUACUCGGCGGCCGGCUGGCAGGGGGAUC
UGGAUAUGCCGCCCCAGCCGCUGGUGCCCUACGCCGACUGGUAG
                                                    SEQ ID NO: 90
AUGAGCCAGGAAUACACCGAAGACAAAGAAGUCAAACUAACCAAACUCAGCAGCGGGCGCCGACUC
CUUGAGGCGAUGCUCAUCCUUUGCUCCCUCUUCGCCAUCGGCUGAUGGCGGCACUACUGAGCUU
UAACCCCUCGGACCCCAGCUGGUCGCAAACGGCAUGGCAUGAGCCUAUUCAUAAUUUAGGCGGCG
CCCCCGGCGCGUGGCUUGCCGAUACCCUCUUUUUCAUUUUUGGCGUCAUGGCCUACACCAUCCCG
GUGAUCAUCAUCGGCGGAUGCUGGUUUGCCUGGCGGCAUCAGGAAAACGACGAAUACAUUGAUUA
UUUUGCCGUUUCCCUUCGCCUCAUCGGUGCGUUAGCCCUGAUCCUGACCUCCUGUGGUCUGGCGG
CGAUUAACGCCGAUGAUAUCUGGUACUUCGCCUCCGGCGGGUGAUCGGCAGCCUGCUGAGCACC
ACGCUGCAACCCCUGCUGCACAGCAGCGGCGGCACCAUCGCCCUGUUGUGUAUCUGGGCGGCCGG
GCUGACGCUGUUCACCGGCUGGUCGUGGGUCAGCAUUGCGGAAAAGCUGGGCGGCGGCAUCCUG
UCCGUUCUCACCUUUGCCAGCAACCGUACCCGUCGGGAUGAUACCUGGGUCGAUGAAGGCGAAUA
UGAAGACGACGAGGAAGAGUACGACGACGAAGAGGCGGCCAGGCCGCAGGAAUCGCGUCGCGCCC
```

```
GUAUCUUACGCAGCGCGCUGGCGCGGCGUAAGCGUCUGGCCGAGAAGUUUACCAACCCUAUGGGG

CGUAAAACCGACGCUGCGCUUUUCUCCGGCAAACGGAUGGAUGACGGCGAAGAGGUGGUGCAAUA

CAGCGCCAGCGGGGCGCCUGUUGCCGCCGACGAUGUACUGUUUCCGGCGCCAGCGCCGCGCGU

CCCGCAGAGGAUGAUGUGCUGUUCUCCGGCGCCAGCGCCGUGCGCCCGGGCGAUUUCGACCCUUA

CGAUCCGUUGUUGAAUGGCCACAGUAUCGCUGAGCCGGUAAGCGCAGCGGCGGCGGCUACAGCCG

CGCCGCAGGCGUGGGCAGAAUCACCGGUGGGCCAUCACGGCGCUGCGCCAGCUUAUCAGCCGGAA

GCCAGCUAUCCGCCGCAGCAGGCCUAUCAGCCUGAACCCGCUCCGUUCCAGCAGGCCUAUCAGCCU

GAACCCGCUCCGUUCCAGCAGGCUGCUUAUCAGCCGCCAGCGGGGCAAACCGCACCGCAGGCGUA

UCAGCCUGAGCCAGCGCCGUAUCAACAGCCGGUUUACGAUCCGCGUGCCGGUCAACCUGCGCCGC

AGGCCUAUCAGCCUGAGCCAGCGCCGUAUCAGCAGCCGGCUUACGAUCCGUAUGCCGGUCAACCU

GCGCCGCAGGCCUAUCAGCCUGAACCUGCGCCGUAUCAGCAGCCGGCUUACGAUCCGCAUGCCGG

UCAACCUGCACCGCAGGCCUAUCAGCCUGAGCCAGCGCCGUAUCAGCAGCCGGCUUACGAUCCCUA

UGCCGGUCAACCUGCGCCGCAGGCCUAUCAGCCGGAGCCAGCGCCGUAUCAGCAGCCAACUUACG

AUCCCUAUGCCGGUCAGCCUGCGCCUCAGACCUAUCAGCAGCCGGCUUACGAUCCGAAUGCCGGU

CAGCCCGCGCCGCAGCCGUAUCAGCCGGAGCCAGCGGCGUAUCAGCCGCAAAGCGCGCCAGUUCC

CCCACCGGAGCCAGAGCCCGAGGUCGUGCAGGAGGAAGUGAAACGUCCGCCGCUCUAUUAUUUCG

AGGAAGUGGAAGAGAAGCGGGCGCGCGAACGCGAGCUGUUGGCCUCCUGGUAUCAGCCAAUUCCU

GAGCCGGAAAGUCCGAUUGCCACUAAACCGCUGACGCCGCCGACCACUGCGUCCAAACCGCCAGUG

GAGACAACCGUAGUCUCUGCGGUAGCGGCUGGGGUGCAUCAGGCUACCGCCGCCAGCGGCGGCG

CGGCGGCAGCAACCUCGUCCACUGCCGCAUCCGCUGCGGCUACGCCAUUGUUCAGCCCGGCGUCC

AGCGGCCCAAGGGUUCAGGUGAAAGAGGGCAUCGGUCCAAAACUACCGCGGCCCAAUCGCGUGCG

UGUUCCUACGCGUCGGGAACUGGCCUCCUACGGCAUCAAGCUACCGUCGCAGCGGGAGGCGGAAC

AGCGCGCGCGGCAGGCGGAGCGCGAUCCGCAUUAUGAUGAUGAGCUGCUCUCGGAUGAGGAAGC

GGAUGCUAUGGAGCAGGAUGAACUGGCUCGCCAGUUCGCCGCCACCCAGCAGCAGCGCUACGGUC

AUCGCUGGGAAGACGAUAACGCGACUGAUGACGAUGAGGCCGACGCCGCGGCGGAAGCGGAGCUG

GCGCGUCAGUUUGCCGCUACCCAGCAGCAGCGGUACGCUACCGAGCAGCCGCCGGGCGCCAACCC

GUUCUCGCCGGCAGAUUAUGAAUUCUCGCCGAUGAAAACGUUGGUCAAUGACGGCCCGAGCGAAC

CGCUGUUUACGCCGACGCCGGAAGUCCAGCCGCAGCAGCCGGCCCAGCGCUAUCAACAACCGGCG

GCCGCUCCGCAGCAGGGUUAUCAACCUGCGCAGCAUCAGCCGAUACACCAUCAGCCUGUGCCGCC

ACAGCCGCAGUCCUAUCCGACUGCGUCGCAGCCCGUACAGCCGCAACAACCGGUUGCCCCGCAGG

GGCAUCAGCCUGCCGCCCCUGCGCCGCAGGAGAGCCUGAUCCACCCGCUGCUGAUGCGCAAUGGC

GAUAGUCGACCGCUGCAAAAGCCGACCACGCCACUGCCGUCGCUGGAUCUGCUUACCCCGCCGCC

GAGUGAAGUCGAGCCGGUGGAUACCUUUGCUCUCGAGCAGAUGGCACGCCUGGUGGAAGCGCGA

CUCGCUGAUUCCGCAUUAAAGCGGAUGUGGUGAACUACUCACCGGGGCCGGUGAUCACCCGCUU

CGAACUGAAUCUGGCGCCUGGCGUUAAGGCCGACACGGAUCUCUAACCUGUCACGGGACCUGGCGC

GAUCGCUGUCAACGGUCGCCGUGCGCGUGGUGGAGGUGAUCCCGGGCAAACCGUAUGUCGGGCU

UGAGCUGCCGAAUAAAAAACGCCAGACCGUCUACCUGCGUGAAGUGCUCGACAACGCCAAGUUCCG

UGAUAACCCAUCUCCGCUCACCGUGGGUGUUGGGUAAAGACAUCGCUGGCGAUCCGGUAGUAGCCG

AUCUGGCGAAAAUGCCGCAUCUGCUGGUGGCCGGUACCACCGGUUCCGGUAAGUCUGUUGGCGUC

AACGCCAUGAUCCUCAGCAUGCUCUACAAGGCGCAGCCGGAAGAUGUGCGUUUCAUUAUGAUCGA
```

-continued

```
CCCGAAAAUGCUCGAGCUGUCGGUCUACGAAGGAAUUCCGCACCUGCUGACGGAAGUGGUCACCG

ACAUGAAAGACGCCGCCAAUGCGCUGCGCUGGAGCGUCAAUGAGAUGGAGCGCCGCUACAAGCUG

AUGUCGGCGCUGGGCGUGCGUAACCUCGCGGGCUACAACGAGAAGAUCGCCGAAGCCGCGCGCAU

GGGACGUCCGAUCCCGGAUCCGUACUGGAAGCCUGGCGACAGCAUGGACGCCGUACAUCCGGUGC

UGGAAAAACUGCCGUACAUCGUGGUGCUGGUGGAUGAAUUCGCCGAUCUGAUGAUGACCGUCGGC

AAAAAGGUGGAAGAGCUGAUCGCUCGCCUGGCGCAGAAAGCGCGCGCGGCGGGGAUCCACCUGGU

GCUGGCGACACAGCGUCCGUCGGUAGAUGUUAUUACCGGCCUGAUUAAGGCCAACAUCCCGACGC

GCAUCGCCUUUACCGUGUCGAGUAAAAUUGACUCACGUACCAUUCUCGAUCAGGGCGGCGCGGAA

UCGCUGCUGGGUAUGGGGGAUAUGCUUUACUCCGGGCCGAACUCUACCACGCCGGUGCGUGUCCA

CGGGGCGUUUGUGCGCGACCAGGAAGUCCACGCCGUGGUUCAGGACUGGAAAGCCCGCGGUCGC

CCGCAAUAUGUGGAUGGCAUUACCUCCGACAGCGAAAGCGAAGGCGGCGGUGGCGGCUUCGACGG

CGGGGAAGAGUUGGAUCCGUUGUUCGAUCAGGCAGUCAACUUUGUGACCGAGAAGCGCAAAGCGU

CGAUUUCCGGGGUUCAGCGUCAGUUCCGCAUCGGCUAUAACCGUGCCGCGCGUAUUAUCGAACAG

AUGGAAGCGCAGGGUAUCGUCAGCGAGCAGGGCCAUAACGGUAACCGCGAAGUGCUGGCGCCGCC

GCCCUUUGAAUGA
```

The polypeptides of the invention can also be designated as follows:

| SEQ ID NO: | Designation |
|---|---|
| 1 | KP1_2999 |
| 2 | KP1_0355 |
| 3 | KP1_3995 |
| 4 | KP1_3023 |
| 5 | KP1_1709 |
| 6 | KP1_4823 |
| 7 | KP1_1443 |
| 8 | KP1_1444 |
| 9 | KP1_0026 |
| 10 | KP1_3952 |
| 11 | KP1_0090 |
| 12 | KP1_4374 |
| 13 | KP1_1620 |
| 14 | KP1_5089 |
| 15 | KP1_1701 |
| 16 | KP1_1186 |
| 17 | KP1_0947 |
| 18 | KP1_1632 |
| 19 | KP1_1274 |
| 20 | KP1_3820 |
| 21 | KP1_0953 |
| 22 | KP1_2972 |
| 23 | KP1_0306 |
| 24 | KP1_2284 |
| 25 | KP1_4356 |
| 26 | KP1_1032 |
| 27 | KP1_4886 |
| 28 | KP1_2074 |
| 29 | KP1_5221 |
| 30 | KP1_1891 |
| 91 | KP1_1547 |
| 92 | KP1_1958 |
| 93 | KP1_4144 |
| 94 | KP1_4102 |

When designating a fragment of one of these proteins, this is done using the nomenclature KP1_XXXX-A-p1-p2, where XXXX is any of the 4 digit numbers following "KP1" in the table above, and p1 and p2 are the start and end amino acids relative to the entire sequence of the protein. For instance KP1_1891-50-200 is the fragment of KP1_1891 that has the amino acid sequence defined by residues 50 to 200 of KP1_1891, i.e. a (poly)peptide having the amino acid sequence of SEQ ID NO: 30, residues 50-200.

EXAMPLE

Challenge Studies in Mice

1. Challenge Study (*Klebsiella pneumonia*—Intranasal (IN) Model):

Challenge strain: *Klebsiella pneumoniae* NTUH-K2044 (Wu K M et al. (2009), J. Bacteriol, 191:4492-4501).
Mouse strain: BalbC/ByJ (inbred)
Dose: 25 μg in each immunization.
Immunization route: 3× subcutaneous
Immunization interval: 14 days
Inoculation route: intranasal (IN)
End point: Lethal challenge
Adjuvant choice: Priming immunization used Alum+IFA (incomplete Freund's adjuvant); $1^{st}$ and $2^{nd}$ booster immunizations used alum only
Bleeds: Bleed mouse 4 days before challenge for subsequent ELISA test.
Trial type: Double blinded
No of mice per group: At most 16 mice (see tables 1-6 for details)
Monitoring period: 7 days 2. Challenge Study (*Klebsiella pneumonia*—Intraperitoneal (IP Model)):

Challenge strain: *Klebsiella pneumoniae* NTUH-K2044)
Mouse strain: NMRI (outbred)
Dose: 25 μg in each immunization.
Immunization route: 3× subcutaneous
Immunization interval: 14 days
Inoculation route: intraperitoneal (IP)
End point: Lethal challenge
Adjuvant choice: Priming immunization used Alum+IFA (incomplete Freund's adjuvant); $1^{st}$ and $2^{nd}$ booster immunizations used alum only
Bleeds: Bleed mouse 4 days before challenge for subsequent ELISA test.

Trial type: Double blinded

No of mice per group: At most 16 mice (see tables 1-6 for details)

Monitoring period: 7 days

A total 6 experiments was carried out. Only experiment 2 utilised the IP model whereas the remaining experiments utilised the IN model.

A number of the tested proteins proved insoluble in saline. Instead they were solubilized in 4 M urea to avoid precipitation before adding aluminum hydroxide. After adding aluminum hydroxide the urea is removed completely. The remaining proteins are solubilized in physiological saline.

The protocol for immunization is described below.

$1^{st}$ Immunization:
- 25 μg protein (per mice) are mixed with 100 μl aluminum hydroxide (Alhydrogel 2.0%, Brenntag) per 125 μg protein and incubated with end-over-end rotation for 1 hour.
- The compositions is centrifuged at 1000 rpm for 2 minutes and the supernatant is removed
- The alu-beads are washed once (slowly) in 0.9% (0.15 M) NaCl to remove excess urea
- Freund's incomplete adjuvant (Sigma) is added 1:1 (v/v) and the resulting mixture is vortexed thoroughly for 1 hour.
- Subsequently the final composition is injected subcutaneously $2^{nd}$ and $3^{rd}$ Immunization
- The mice receive booster immunization with 2 weeks interval, using the same amount of protein mixed with aluminum hydroxide and physiological saline solution.
- Subsequently the final composition is injected subcutaneously The following table A lists the immunogens used in each of the immunization studies in 6 different experiments as well as the p-value for the survival in each group when compared to mice vaccinated with phosphate buffered saline alone.

The corresponding survival plots are shown in FIGS. 1-6, which show the results for Experiments 1-6, respectively. The survival data are also indicated for each group of mice in each experiment in Tables 1-6.

TABLE A

Kaplan-Meier survival curve overview

| Challenge: | | P-value | |
|---|---|---|---|
| EXPERIMENT # 1 (IN model) | Immunization agent - Protein ID(s) | Log rank test | Fisher's exact test |
| Group 1 vs PBS | (KP1_1547-26-742; NCBI-ProteinID: BAH62300) SEQ ID NO: 91, residues 26-742 Positive control | 0.2321 | 0.5000 |
| Group 2 vs PBS | (KP1_1958-22-356, NCBI-ProteinID: BAH62679) SEQ ID NO: 92, residues 22-356 Postive control | 0.9346 | 0.7419 |
| Group 3 vs PBS | (KP1_4144-1-245, NCBI-ProteinID: BAH64685) SEQ ID NO: 93, residues 1-245 Postive control | 0.0004 | 0.0030 |
| Group 4 vs PBS | (KP1_1632-23-597 + KP1_1632-276-597 + KP1_1632-23-275) Mixture of 3 peptides: SEQ ID NO: 18, residues 23-597 + SEQ ID NO: 18 residues 276-597 + SEQ ID NO: 18, residues 23-275 | <0.0001 | <0.0001 |
| EXPERIMENT # 2 (IP model) | Protein ID | Log rank test | Fisher's exact test |
| Group 1 vs PBS | (KP1_5089-121-428 + KP1_0947-1-535 + KP1_0947-21-535) Mixture of 3 peptides: SEQ ID NO: 14, residues 121-428 + SEQ ID NO: 17, residues 1-535 + SEQ ID NO: 17, residues 21-535 | 0.6869 | 0.32700 |
| Group 2 vs PBS | (KP1_1620-1-382 + KP1_1620-21-382 + KP1_4374-27-376) Mixture of 3 peptides: SEQ ID NO: 13, residues 1-382 + SEQ ID NO: 13, residues 21-382 + SEQ ID NO: 12, residues 27-376 | 0.0249 | 0.02690 |
| Group 3 vs PBS | (KP1_0953-31-500 + KP_0953-31-675 + KP1_0355-22-117) Mixture of 3 peptides: SEQ ID NO: 21, residues 31-500 + SEQ ID NO: 21, residues 31-675 + SEQ ID NO: 2, residues 22-117. | 0.0153 | 0.01170 |
| Group 4 vs PBS | (KP1_4356-35-790 + KP1_4356-450-790 + KP1_4356-35-450 + KP1_0306-25-752 + KP1_0306-470-752 + KP1_0306-25-469) Mixture of 6 peptides: SEQ ID NO: 25, residues 35-790 + SEQ ID NO: 25, residues 450-790 + SEQ ID NO: 25, residues 35-450 + SEQ ID NO: 23, residues 25-752 + SEQ ID NO: 23, residues 470-752 + SEQ ID NO: 23, residues 25-4690 | 0.2216 | 0.02690 |
| EXPERIMENT # 3 (IN model) | Protein ID | Log rank test | Fisher's exact test |
| Group 1 vs PBS | (KP1_5221-23-650 (NaCl) + KP1_5221-651-1159 (Urea)) Mixture of 2 peptides: SEQ ID NO. 29, residues 23-650 (in saline) + SEQ ID NO: 29, residues 651-1159 (in Urea) | 0.0156 | 0.2759 |
| Group 2 vs PBS | (KP1_1186-35-484 (NaCl)) 1 peptide: SEQ ID NO: 16, residues 25-484 | 0.3488 | 1.0000 |
| Group 3 vs PBS | (KP1_3995-22-119 (NaCl) + KP1_3995-22-119 (Urea)) Mixture of 2 peptides: SEQ ID NO: 3, residues 22-119 (in saline) + SEQ ID NO: 3, residues 22-119 (in Urea) | 0.8585 | 0.4839 |
| Group 4 vs PBS | (KP1_1032-21-809 (Urea) + KP1_1032-451-809 (Urea) + KP1_1032-21-450 (NaCl)) Mixture of 3 peptides: SEQ ID NO: 26, residues 21-809 (in Urea) + SEQ | 0.0576 | 0.1129 |

TABLE A-continued

Kaplan-Meier survival curve overview

| Challenge: | | | P-value | |
|---|---|---|---|---|
| | ID NO: 26, residues 451-809 (in Urea) + SEQ ID NO: 26, residues 21-450 (in saline) | | | |
| EXPERIMENT # 4 (IN model) | Protein ID | | Log rank test | Fisher's exact test |
| Group 1 vs PBS | (KP1__1709-1-121 (NaCl))<br>1 peptide: SEQ ID NO: 5, residues 1-121 (in saline) | | 0.2473 | 1.0000 |
| Group 2 vs PBS | (KP1__2999-22-94 (NaCl))<br>1 peptide: SEQ ID NO: 1, residues 22-94 (in saline) | | 0.7392 | 1.0000 |
| Group 3 vs PBS | (KP1__1274-36-624 (NaCl))<br>1 peptide: SEQ ID NO: 19, residues 36-624 (in saline) | | 0.5190 | 1.0000 |
| Group 4 vs PBS | (KP1__0026-1-168 (NaCl))<br>1 peptide: SEQ ID NO: 9, residues 1-168 (in saline) | | 0.3482 | 1.0000 |
| EXPERIMENT # 5 (IN model) | Protein ID | | Log rank test | Fisher's exact test |
| Group 1 vs PBS | (KP1__4102-582-1099 + KP1__4102-1100-1649, i.e. two fragments of NCBI-ProteinID: BAH64645)<br>Mixture of 2 peptides: SEQ ID NO: 94, residues 582-1099 + SEQ ID NO: 94, residues 1100-1649<br>Postive control | | 0.0012 | 0.0217 |
| Group 2 vs PBS | (KP1__3820-26-657 + KP1__3820-392-657 + KP1__3820-26-391 + KP1__3820-26-153 + KP1__0306-61-177)<br>Mixture of 5 peptides: SEQ ID NO: 20, residues 26-657 + SEQ ID NO: 20, residues 392-657 + SEQ ID NO: 20, residues 26-391 + SEQ ID NO: 20, residues 26-153 + SEQ ID NO: 23, residues 61-177 | | <0.0001 | <0.0001 |
| Group 3 vs PBS | (KP1__2284-1-761 + KP1__2284-515-761 + KP1__2284-1-514 + KP1__2284-61-176)<br>Mixture of 4 peptides: SEQ ID NO: 24, residues 1-761 + SEQ ID NO: 24, residues 515-761 + SEQ ID NO: 24, residues 1-514 + SEQ ID NO: 24, residues 61-176 | | 0.0019 | 0.0217 |
| Group 4 vs PBS | (KP1__2972-25-701 + KP1__2972-450-696 + KP1__2972-25-449 + KP1__2972-20-154)<br>Mixture of 4 peptides: SEQ ID NO: 22, residues 25-701 + SEQ ID NO: 22, residues 450-696 + SEQ ID NO: 22, residues 25-449 + SEQ ID NO: 22, residues 20-154 | | <0.0001 | 0.0088 |
| EXPERIMENT # 6 (IN model) | Protein ID | | Log rank test | Fisher's exact test |
| Group 1 vs PBS | (KP1__5089-121-428 + KP1__0947-1-535 + KP1__0947-21-535)<br>Mixture of 3 peptides: SEQ D NO: 14, residues 121-428 + SEQ ID NO: 17, residues 1-535 + SEQ ID NO: 17, residues 21-535 | | 0.0148 | 0.1129 |
| Group 2 vs PBS | (KP1__1620-1-382 + KP1__1620-21-382 + KP1__4374-27-376)<br>Mixture of 3 peptides: SEQ ID NO: 13, residues 1-382 + SEQ ID NO: 13, residues 21-382 + SEQ ID NO: 12, residues 27-376 | | 0.0006 | 0.0506 |
| Group 3 vs PBS | (KP1__0953-31-500 + KP1__0953-31-675 + KP1__0355-22-117)<br>Mixture of 3 peptides: SEQ ID NO: 21, residues 31-500 + SEQ ID NO: 21, residues 31-675 + SEQ ID NO: 2, residues 22-117 | | <0.0001 | 0.0004 |
| Group 4 vs PBS | (KP1__4356-35-790 + KP1__4356-450-790 + KP1__4356-35-450 + KP1__0306-25-752 + KP1__0306-470-752 + KP1__0306-25-469)<br>Mixture of 6 peptides: SEQ ID NO: 25, residues 35-790 + SEQ ID NO: 25, residues 450-790 + SEQ ID NO: 25, residues 35-450 + SEQ ID NO: 23, residues 25-752 + SEQ ID NO: 23, residues 470-752 + SEQ ID NO: 23, residues 25-469 | | 0.0012 | 0.0004 |

TABLE 1 survival in Experiment 1

| Group | Survival | Day 0 | Day 1 | Day 2 | Day 3 | Day 4 | Day 5 | Day 6 | Day 7 |
|---|---|---|---|---|---|---|---|---|---|
| 1 | # Alive | 16 | 16 | 16 | 16 | 7 | 0 | 0 | 0 |
|   | % Survival | 100.0 | 100.0 | 100.0 | 100.0 | 43.8 | 0.0 | 0.0 | 0.0 |
| 2 | # Alive | 15 | 15 | 15 | 15 | 8 | 3 | 1 | 1 |
|   | % Suivival | 100.0 | 100.0 | 100.0 | 100.0 | 53.3 | 20.0 | 6.7 | 6.7 |
| 3 | # Alive | 16 | 16 | 16 | 16 | 14 | 12 | 11 | 9 |
|   | % Survival | 100.0 | 100.0 | 100.0 | 100.0 | 87.5 | 75.0 | 68.8 | 56.3 |
| 4 | # Alive | 16 | 16 | 16 | 16 | 16 | 16 | 15 | 14 |
|   | % Survival | 100.0 | 100.0 | 100.0 | 100.0 | 100.0 | 100.0 | 93.8 | 87.5 |

TABLE 1-continued survival in Experiment 1

| Group | Survival | Day 0 | Day 1 | Day 2 | Day 3 | Day 4 | Day 5 | Day 6 | Day 7 |
|---|---|---|---|---|---|---|---|---|---|
| 5 | # Alive | 16 | 16 | 16 | 16 | 7 | 4 | 1 | 1 |
|   | % Survival | 100.0 | 100.0 | 100.0 | 100.0 | 43.8 | 25.0 | 6.3 | 6.3 |

TABLE 2 survival in Experiment 2

| Group | | Day 0 | Day 1 | Day 2 | Day 3 | Day 4 | Day 5 | Day 6 | Day 7 |
|---|---|---|---|---|---|---|---|---|---|
| 1 | # Alive | 16 | 13 | 4 | 4 | 4 | 4 | 4 | 4 |
|   | % Survival | 100 | 81.3 | 25.0 | 25.0 | 25.0 | 25.0 | 25.0 | 25.0 |
| 2 | # Alive | 16 | 15 | 9 | 9 | 9 | 9 | 8 | 8 |
|   | % Suivival | 100 | 94 | 56 | 56 | 56 | 56 | 50 | 50 |
| 3 | # Alive | 16 | 15 | 9 | 9 | 9 | 9 | 9 | 9 |
|   | % Survival | 100 | 94 | 56 | 56 | 56 | 56 | 56 | 56 |
| 4 | # Alive | 16 | 11 | 8 | 8 | 8 | 8 | 8 | 8 |
|   | % Survival | 100 | 69 | 50 | 50 | 50 | 50 | 50 | 50 |
| 5 | # Alive | 16 | 14 | 2 | 2 | 2 | 2 | 2 | 2 |
|   | % Survival | 100 | 87.5 | 12.5 | 12.5 | 12.5 | 12.5 | 12.5 | 12.5 |

TABLE 3 survival in Experiment 3

| Group | | Day 0 | Day 1 | Day 2 | Day 3 | Day 4 | Day 5 | Day 6 | Day 7 |
|---|---|---|---|---|---|---|---|---|---|
| 1 | # Alive | 16 | 16 | 16 | 16 | 10 | 5 | 3 | 1 |
|   | % Survival | 100.0 | 100.0 | 100.0 | 100.0 | 62.5 | 31.3 | 18.8 | 6.3 |
| 2 | # Alive | 15 | 15 | 15 | 15 | 7 | 1 | 0 | |
|   | % Suivival | 100.0 | 100.0 | 100.0 | 100.0 | 46.7 | 6.7 | 0.0 | |
| 3 | # Alive | 15 | 15 | 15 | 15 | 3 | 1 | 1 | 1 |
|   | % Survival | 100.0 | 100.0 | 100.0 | 100.0 | 20.0 | 6.7 | 6.7 | 6.7 |
| 4 | # Alive | 16 | 16 | 16 | 16 | 7 | 4 | 3 | 3 |
|   | % Survival | 100.0 | 100.0 | 100.0 | 100.0 | 43.8 | 25.0 | 18.8 | 18.8 |
| 5 | # Alive | 16 | 16 | 16 | 16 | 4 | 1 | 0 | 0 |
|   | % Survival | 100.0 | 100.0 | 100.0 | 100.0 | 25.0 | 6.3 | 0.0 | 0.0 |

TABLE 4 survival in Experiment 4

| Group | | Day 0 | Day 1 | Day 2 | Day 3 | Day 4 | Day 5 | Day 6 | Day 7 |
|---|---|---|---|---|---|---|---|---|---|
| 1 | # Alive | 10 | 10 | 10 | 10 | 1 | 0 | 0 | 0 |
|   | % Survival | 100.0 | 100.0 | 100.0 | 100.0 | 10.0 | 0.0 | 0.0 | 0.0 |
| 2 | # Alive | 15 | 15 | 15 | 15 | 6 | 0 | 0 | 0 |
|   | % Suivival | 93.8 | 93.8 | 93.8 | 93.8 | 37.5 | 0.0 | 0.0 | 0.0 |
| 3 | # Alive | 14 | 14 | 14 | 14 | 3 | 0 | 0 | 0 |
|   | % Survival | 100.0 | 100.0 | 100.0 | 100.0 | 21.4 | 0.0 | 0.0 | 0.0 |
| 4 | # Alive | 15 | 15 | 14 | 14 | 3 | 0 | 0 | 0 |
|   | % Survival | 100.0 | 100.0 | 93.3 | 93.3 | 20.0 | 0.0 | 0.0 | 0.0 |
| 5 | # Alive | 16 | 15 | 15 | 15 | 6 | 0 | 0 | 0 |
|   | % Survival | 100.0 | 93.8 | 93.8 | 93.8 | 37.5 | 0.0 | 0.0 | 0.0 |

TABLE 5 survival in Experiment 5

| Group | | Day 0 | Day 1 | Day 2 | Day 3 | Day 4 | Day 5 | Day 6 | Day 7 |
|---|---|---|---|---|---|---|---|---|---|
| 1 | # Alive | 16 | 16 | 16 | 16 | 14 | 8 | 7 | 5 |
|   | % Survival | 100.0 | 100.0 | 100.0 | 100.0 | 87.5 | 50.0 | 43.8 | 31.3 |
| 2 | # Alive | 16 | 16 | 16 | 16 | 15 | 14 | 13 | 12 |
|   | % Suivival | 100.0 | 100.0 | 100.0 | 100.0 | 93.8 | 87.5 | 81.3 | 75.0 |
| 3 | # Alive | 16 | 16 | 16 | 16 | 14 | 8 | 6 | 5 |
|   | % Survival | 100.0 | 100.0 | 100.0 | 100.0 | 87.5 | 50.0 | 37.5 | 31.3 |

TABLE 5-continued

| | | \multicolumn{8}{c}{survival in Experiment 5} | | | | | | | |
|---|---|---|---|---|---|---|---|---|
| Group | | Day 0 | Day 1 | Day 2 | Day 3 | Day 4 | Day 5 | Day 6 | Day 7 |
| 4 | # Alive | 16 | 16 | 16 | 16 | 16 | 11 | 9 | 6 |
| | % Survival | 100.0 | 100.0 | 100.0 | 100.0 | 100.0 | 68.8 | 56.3 | 37.5 |
| 5 | # Alive | 16 | 16 | 16 | 16 | 8 | 2 | 0 | |
| | % Survival | 100.0 | 100.0 | 100.0 | 100.0 | 50.0 | 12.5 | 0.0 | |

TABLE 6

| | | \multicolumn{8}{c}{survival in Experiment 6} | | | | | | | |
|---|---|---|---|---|---|---|---|---|
| Group | | Day 0 | Day 1 | Day 2 | Day 3 | Day 4 | Day 5 | Day 6 | Day 7 |
| 1 | # Alive | 16 | 16 | 16 | 15 | 10 | 7 | 5 | 3 |
| | % Survival | 100.0 | 100.0 | 100.0 | 93.8 | 62.5 | 43.8 | 31.3 | 18.8 |
| 2 | # Alive | 16 | 16 | 15 | 15 | 13 | 9 | 8 | 4 |
| | % Suivival | 100.0 | 100.0 | 93.8 | 93.8 | 81.3 | 56.3 | 50.0 | 25.0 |
| 3 | # Alive | 16 | 16 | 16 | 16 | 16 | 12 | 10 | 9 |
| | % Survival | 100.0 | 100.0 | 100.0 | 100.0 | 100.0 | 75.0 | 62.5 | 56.3 |
| 4 | # Alive | 16 | 15 | 15 | 14 | 13 | 9 | 9 | 9 |
| | % Survival | 100.0 | 93.8 | 93.8 | 87.5 | 81.3 | 56.3 | 56.3 | 56.3 |
| 5 | # Alive | 16 | 16 | 16 | 16 | 6 | 0 | | |
| | % Survival | 100.0 | 100.0 | 100.0 | 100.0 | 37.5 | 0.0 | | |

The invention claimed is:

1. A method for treatment or amelioration of infection with *K. pneumoniae*, in particular infection with multi-resistant *K. pneumoniae*, comprising administering to an individual in need thereof a therapeutically effective amount of a monoclonal antibody which specifically binds to a polypeptide consisting of
   a) an amino acid sequence SEQ ID NO: 2, or
   b) an amino acid sequence, which is a fragment of SEQ ID NO: 2 consisting of amino acid residues 22-117.

2. The method according to claim 1, wherein the monoclonal antibody specifically binds to SEQ ID NO:2 residues 22-117.

3. The method according to claim 1, wherein the monoclonal antibody is selected from a multi-domain antibody and a single-domain antibody of a llama or a camel.

4. The method according to claim 3, wherein the multi-domain antibody is selected from a murine antibody, a humanized antibody, and a fully human antibody.

5. The method according to claim 1, wherein the monoclonal antibody specifically binds to SEQ ID NO: 2.

6. A method for treatment or amelioration of infection with *K. pneumoniae*, in particular infection with multi-resistant *K. pneumoniae*, comprising administering to an individual in need thereof a therapeutically effective amount of an antibody analogue, which specifically binds to a polypeptide consisting of
   a) an amino acid sequence SEQ ID NO: 2, or
   b) an amino acid sequence, which is a fragment of SEQ ID NO: 2 consisting of amino acid residues 22-117, wherein the antibody analogue is selected from an Fab or an F(ab')2, and an scFV.

7. The method according to claim 6, wherein the antibody analogue specifically binds to SEQ ID NO: 2.

8. The method according to claim 6, wherein the antibody analogue specifically binds to amino acid residues 22-117 of SEQ ID NO: 2.

* * * * *